United States Patent
Macielag et al.

(10) Patent No.: US 9,682,940 B2
(45) Date of Patent: Jun. 20, 2017

(54) INDAZOLE DERIVATIVES USEFUL AS CB-1 INVERSE AGONISTS

(71) Applicant: Janssen Pharmaceutica NV, Beerse (BE)

(72) Inventors: Mark J. Macielag, Gwynedd Valley, PA (US); Rui Zhang, Belle Mead, NJ (US); Michael H. Parker, Chalfont, PA (US); Bart L. DeCorte, Southampton, PA (US); Michael N. Greco, Lansdale, PA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 15/239,348

(22) Filed: Aug. 17, 2016

(65) Prior Publication Data

US 2017/0057925 A1    Mar. 2, 2017

Related U.S. Application Data

(60) Provisional application No. 62/209,383, filed on Aug. 25, 2015.

(51) Int. Cl.
| | |
|---|---|
| *C07D 231/56* | (2006.01) |
| *C07D 401/04* | (2006.01) |
| *C07D 417/14* | (2006.01) |
| *C07D 405/14* | (2006.01) |
| *C07D 409/14* | (2006.01) |
| *C07D 401/14* | (2006.01) |

(52) U.S. Cl.
CPC ......... *C07D 231/56* (2013.01); *C07D 401/04* (2013.01); *C07D 401/14* (2013.01); *C07D 405/14* (2013.01); *C07D 409/14* (2013.01); *C07D 417/14* (2013.01)

(58) Field of Classification Search
None
See application file for complete search history.

(56) References Cited

U.S. PATENT DOCUMENTS

| | | |
|---|---|---|
| 2004/0142922 A1 | 7/2004 | Alanine et al. |
| 2009/0069284 A1 | 3/2009 | Baker et al. |
| 2009/0099143 A1 | 4/2009 | Lagu et al. |
| 2009/0247499 A1 | 10/2009 | Fletcher et al. |
| 2015/0239845 A1 | 8/2015 | DeCorte et al. |

FOREIGN PATENT DOCUMENTS

| | | | |
|---|---|---|---|
| WO | 2004022544 | * | 3/2004 |
| WO | WO 2004 022544 A1 | | 3/2004 |
| WO | WO 2009/106980 | | 9/2009 |
| WO | WO 2014 038623 A1 | | 3/2014 |

OTHER PUBLICATIONS

Felder, C. C., et al., "Cannabinoid agonists stimulate both receptor- and non-receptor-mediated signal transdiction pathways in cells transfected with and expressing cannabinoid receptor clones", *Molecular Pharmacology*, 1992, pp. 838-845, vol. 42.

Reggio, P.H., "Toward the Design of Cannabinoid CB1 Receptor Inverse Agonists and Neutral Antagonists", *Drug Dev. Res.*, 2009, pp. 585-600, vol. 70.

International Search Report re: PCT/US16/47293 dated Oct. 6, 2016.

* cited by examiner

*Primary Examiner* — Karl J Puttlitz
(74) *Attorney, Agent, or Firm* — Thomas J. Dodd

(57) ABSTRACT

The present invention is directed to indazole derivatives, pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

21 Claims, No Drawings

INDAZOLE DERIVATIVES USEFUL AS CB-1 INVERSE AGONISTS

CROSS REFERENCE TO RELATED APPLICATIONS

This application claims the benefit of U. S. Provisional Application 62/209,383, filed on Aug. 25, 2015, which is incorporated by reference herein in its entirety.

FIELD OF THE INVENTION

The present invention is directed to indazole derivatives, pharmaceutical compositions containing them and their use in the treatment of disorders and conditions mediated by the CB-1 receptor; more particularly, use in the treatment of disorders and conditions responsive to inverse agonism of the CB-1 receptor. More particularly, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated with serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/or skeletal muscle, to avoid these adverse effects.

Thus, there is a need for peripherally restricted cannabanoid-1 receptor (CB1R) inverse agonists for the treatment of, for example metabolic disorders, such as obesity, Type II diabetes mellitus, metabolic syndrome, Syndrome X, and the like.

SUMMARY OF THE INVENTION

The present invention is directed to compounds of formula (I)

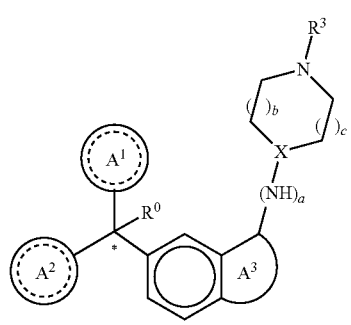

(I)

wherein $R^0$ is selected from the group consisting of hydrogen and hydroxy;

is selected from the group consisting of cyclopropyl, cyclobutyl, cyclopentyl, cyclohexyl, phenyl, furyl, thienyl, pyridyl, thiazolyl, benzothiazolyl and benzo[d][1,3]dioxolyl;

wherein the phenyl, furyl, thienyl, pyridyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl, —C(O)NR$^A$R$^B$ and NR$^A$R$^B$;

and wherein R$^A$ and R$^B$ are each independently selected from the group consisting of hydrogen, $C_{1-4}$alkyl, hydroxy substituted $C_{1-2}$alkyl and carboxy substituted $C_{1-2}$alkyl; provided that each substituent is bound to a carbon atom of the ring;

is selected from the group consisting of cyclopropyl, cyclobutyl, cyclopentyl, cyclohexyl, phenyl, furyl, thienyl, pyridyl, thiazolyl, benzothiazolyl and benzo[d][1,3]dioxolyl;

wherein the phenyl, furyl, thienyl, pyridyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl, —C(O)NR$^C$R$^D$ and NR$^C$R$^D$;

and wherein R$^C$ and R$^D$ are each independently selected from the group consisting of hydrogen, $C_{1-4}$alkyl, hydroxy substituted $C_{1-2}$alkyl and carboxy substituted $C_{1-2}$alkyl; provided that each substituent is bound to a carbon atom of the ring;

is selected from the group consisting of (a)

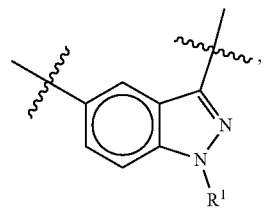

, wherein R¹ is selected from the group consisting of hydrogen, $C_{1-4}$alkyl, hydroxy substituted $C_{1-4}$alkyl, —C(O)—($C_{1-4}$ alkyl), —($C_{1-2}$alkyl)-C(O)OH, —($C_{1-2}$alkyl)-C(O)—O—($C_{1-4}$alkyl), —($C_{1-2}$alkyl)-O—($C_{1-2}$alkyl)-C(O)OH, —($C_{1-2}$alkyl)-C(O)—NR$^E$R$^F$, —SO$_2$-(fluorinated $C_{1-2}$alkyl), $C_{3-6}$cycloalkyl and benzyl;

wherein the benzyl is optionally substituted with one substituent selected from the group consisting of —C(O)OH, —C(O)O—($C_{1-4}$alkyl) and —C(O)—NR$^E$R$^F$;

and wherein R$^E$ and R$^F$ are each independently selected from the group consisting of hydrogen and $C_{1-2}$alkyl;

and (b)

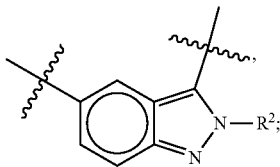

wherein R² is selected from the group consisting of $C_{3-6}$cycloalkyl and $C_{1-4}$alkyl;

a is an integer from 0 to 1;

b is an integer from 0 to 1; c is an integer from 0 to 1;

X is selected from the group consisting of CH and N;

provided that when one or both of b or c is 0, then X is CH;

such that

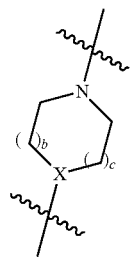

is selected from the group consisting of piperazin-1,4-diyl (where b is 1, c is 1 and X is N), piperidin-1,4-diyl (where b is 1, c is 1 and X is CH), pyrroldin-1,3-diyl (where b is 1, c is 0 and X is CH or b is 0, c is 1 and X is CH) and azetidin-1,3-diyl (where b is 0, c is 0 and X is CH);

R³ is selected from the group consisting of $C_{1-4}$alkyl, halogenated $C_{1-4}$alkyl, —C(O)-(fluorinated $C_{1-2}$alkyl), —C(O)-(hydroxy substituted $C_{1-4}$alkyl), —C(O)—($C_{1-2}$ alkyl)-C(O)OH, —C(O)—($C_{1-2}$alkyl)-C(O)O—($C_{1-4}$ alkyl), —C(O)—($C_{1-4}$alkyl)-C(O)—NR$^G$R$^H$, —C(O)O—($C_{1-4}$ alkyl), —C(O)O—($C_{3-6}$cycloalkyl), —C(O)—NR$^G$R$^H$, —SO$_2$—($C_{1-4}$alkyl), —SO$_2$-(halogenated $C_{1-4}$alkyl), —SO$_2$—($C_{1-2}$alkyl)-C(O)OH, —SO$_2$—($C_{1-2}$ alkyl)-C(O)O—($C_{1-4}$alkyl), —SO$_2$—NR$^G$R$^H$, —SO$_2$—($C_{1-2}$alkyl)-C(O)—NR$^G$R$^H$, phenyl, pyridyl (provided that the pyridyl is bound through a carbon atom) and -L¹-R⁴;

wherein phenyl or pyridyl is optionally substituted with one or more (preferably one to two) substituents independently selected from the group consisting of halogen, $C_{1-4}$alkyl, halogenated $C_{1-2}$alkyl, $C_{1-4}$alkoxy, —($C_{1-2}$alkyl)-C(O)OH, —($C_{1-2}$alkyl)-C(O)O—($C_{1-4}$alkyl), —($C_{1-2}$alkyl)-C(O)—NR$^J$R$^K$, —O—($C_{1-2}$alkyl)-C(O)OH, —O—($C_{1-2}$alkyl)-C(O)O—($C_{1-4}$alkyl), —O—($C_{1-2}$alkyl)-C(O)—NR$^J$R$^K$, —C(O)OH, —C(O)O—($C_{1-4}$alkyl) and —C(O)—NR$^J$R$^K$;

wherein R$^G$ and R$^H$ are each independently selected from the group consisting of hydrogen and $C_{1-4}$alkyl; and wherein R$^J$ and R$^K$ are each independently selected from the group consisting of hydrogen and $C_{1-2}$alkyl;

L¹ is selected from the group consisting of —CH$_2$—, CH$_2$CH$_2$—, —CH(CH$_3$)—, —C(O)—, —C(O)—CH$_2$—, —C(O)O—, —C(O)O—CH$_2$—, —C(O)—NH—, —C(O)—NH—CH$_2$— and —SO$_2$—;

R⁴ is selected from the group consisting of $C_{3-6}$cycloalkyl, phenyl, furanyl, thienyl, pyridyl, pyrazolyl, triazolyl, and tetrazolyl;

wherein the phenyl, furanyl, thienyl, pyridyl, pyrazolyl and triazolyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, —C(O)OH, —C(O)O—($C_{1-4}$alkyl), —C(O)—NR$^L$R$^M$ and —SO$_2$—NR$^L$R$^M$;

and wherein R$^L$ and R$^M$ are each independently selected from the group consisting of hydrogen and $C_{1-2}$alkyl;

and stereoisomers, tautomers and pharmaceutically acceptable salts thereof.

The present invention is further directed to processes for the preparation of the compounds of formula (I). The present invention is further directed to a product prepared according to any of the process(es) described herein.

The present invention is further directed to intermediate compounds useful in the synthesis of the compounds of formula (I), as described and defined in the synthesis schemes and examples which follow herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain). In another embodiment, the present invention is directed to a composition comprising a compound of formula (I) for the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain).

Another example of the invention is the use of any of the compounds described herein in the preparation of a medicament for treating: (a) obesity, (b) Type I diabetes, (c) Type II diabetes, (d) gestational diabetes, (e) latent autoimmune diabetes of adults (LADA), (f) pre-diabetes, (g) insulin resistance, (h) inadequate glucose tolerance, (i) dyslipidemia (including, but not limited to elevated triglycerides and LDL, and low HDL), (j) nonalcoholic steatohepatitis (NASH), (k) cirrhosis, (l) fatty liver disease, (m) atherosclerosis, (n) hypertension, (o) inflammatory bowel disease, (p) Alzheimer's disease, (q) osteoporosis, (r) multiple sclerosis, (s) traumatic brain injury, (t) arthritis, or (u) neuropathic pain, in a subject in need thereof. In another example, the present invention is directed to a compound as described herein for use in method for treating a disorder selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain, in a subject in need thereof.

In additional embodiments the present invention is as described herein.

DETAILED DESCRIPTION OF THE INVENTION

The present invention is directed to compounds of formula (I)

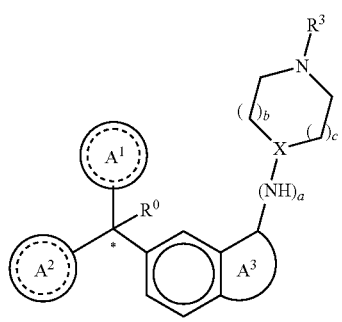

(I)

wherein $R^0$,

a, b, c, X and R are as herein defined.

The compounds of formula (I) of the present invention are CB-1 receptor inverse agonists, useful in the treatment of metabolic disorders, including but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

In an embodiment, the present invention is directed to compounds of formula (I-A)

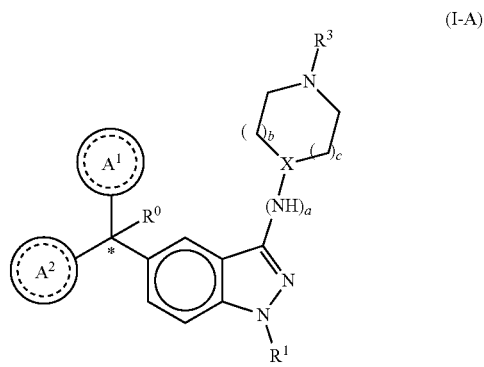

(I-A)

and stereoisomers, tautomers and pharmaceutically acceptable salts thereof. In another embodiment, the present invention is directed to compounds of formula (I-B)

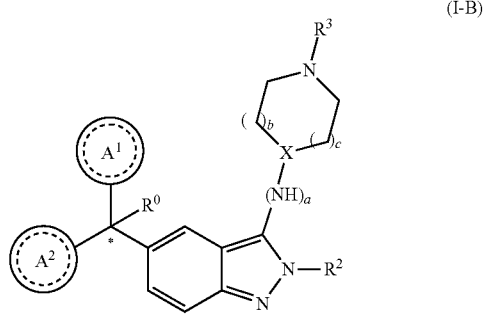

(I-B)

and stereoisomers, tautomers and pharmaceutically acceptable salts thereof.

In an embodiment, the present invention is directed to compounds of formula (I) wherein the stereocenter designated with the "*" symbol is present in the S-configuration. In another embodiment, the present invention is directed to compounds of formula (I) wherein the stereocenter designated with the "*" symbol is present in the R-configuration.

In an embodiment, the present invention is directed to compounds of formula (I) wherein $R^O$ is hydrogen. In another embodiment, the present invention is directed to compounds of formula (I) wherein $R^O$ is hydroxy.

In an embodiment, the present invention is directed to compounds of formula (I) wherein

is selected from the group consisting of cyclopropyl, cyclopentyl, cyclohexyl, phenyl, furyl, thienyl, pyridyl and thiazolyl; wherein the phenyl, furyl, thienyl, pyridyl or thiazolyl is optionally substituted with one to three substituents independently selected from the group consisting of halogen, hydroxy, $C_{1-2}$alkyl, $C_{1-2}$alkoxy, fluorinated $C_{1-2}$alkyl, fluorinated $C_{1-2}$alkoxy, —C(O)OH, —C(O)O—$C_{1-4}$alkyl, —C(O)—$NR^A R^B$ and —$NR^A R^B$ wherein $R^A$ and $R^B$ are each independently selected from the group consisting of hydrogen, $C_{1-2}$alkyl, hydroxy substituted $C_{1-2}$alkyl and carboxy substituted $C_{1-2}$alkyl; provided that each substituent is bound to a carbon atom of the ring.

In another embodiment, the present invention is directed to compounds of formula (I) wherein

is phenyl; wherein the phenyl is substituted with a substituent selected from the group consisting of halogen, $C_{1-2}$alkyl and $C_{1-2}$alkoxy.

In another embodiment, the present invention is directed to compounds of formula (I) wherein

is selected from the group consisting of 4-chlorophenyl, 4-fluorophenyl, 4-methylphenyl and 4-methoxyphenyl. In another embodiment, the present invention is directed to compounds of formula (I) wherein

is selected from the group consisting of 4-chlorophenyl, 4-methylphenyl and 4-methoxyphenyl. In another embodiment, the present invention is directed to compounds of formula (I) wherein

is selected from the group consisting of 4-chlorophenyl and 4-methoxyphenyl. In another embodiment, the present invention is directed to compounds of formula (I) wherein

is 4-chlorophenyl.

In an embodiment, the present invention is directed to compounds of formula (I) wherein

is selected from the group consisting of cyclopropyl, cyclopentyl, cyclohexyl, phenyl, furyl, thienyl, pyridyl and thiazolyl; wherein the phenyl, furyl, thienyl, pyridyl or thiazolyl is optionally substituted with one to three substituents independently selected from the group consisting of halogen, hydroxy, $C_{1-2}$alkyl, $C_{1-2}$alkoxy, fluorinated $C_{1-2}$alkyl, fluorinated $C_{1-2}$alkoxy, —C(O)OH, —C(O)O—$C_{1-4}$alkyl, —C(O)—$NR^A R^B$ and —$NR^A R^B$ wherein $R^A$ and $R^B$ are each independently selected from the group consisting of hydrogen, $C_{1-2}$alkyl, hydroxy substituted $C_{1-2}$alkyl and carboxy substituted $C_{1-2}$alkyl; provided that each substituent is bound to a carbon atom of the ring.

In another embodiment, the present invention is directed to compounds of formula (I) wherein

is selected from the group consisting of cyclopropyl, cyclopentyl, cyclohexyl, phenyl, pyridyl and thiazolyl; wherein the phenyl, pyridyl or thiazolyl is optionally substituted with one to two substituents independently selected from the group consisting of halogen, $C_{1-2}$alkyl, $C_{1-2}$alkoxy, fluorinated $C_{1-2}$alkyl, fluorinated $C_{1-2}$alkoxy, —C(O)OH and —C(O)—$NR^A R^B$; wherein $R^A$ and $R^B$ are each independently selected from the group consisting of hydrogen, hydroxy substituted $C_{1-2}$alkyl and carboxy substituted $C_{1-2}$alkyl; provided that each substituent is bound to a carbon atom of the ring.

In another embodiment, the present invention is directed to compounds of formula (I) wherein

is selected from the group consisting of cyclopropyl, cyclopentyl, cyclohexyl, phenyl, 2-chlorophenyl, 3-chlorophenyl, 4-chlorophenyl, 4-fluorophenyl, 3,4-dichlorophenyl, 4-methylphenyl, 4-methoxyphenyl, 3-trifluoromethylphenyl, 4-trifluoromethylphenyl, 4-trifluoromethoxyphenyl, 4-carboxyphenyl, S*-4-carboxyphenyl, R*-4-carboxyphenyl, 4-aminocarbonylphenyl, 4-(2-hydroxyethyl-aminocarbonyl)-phenyl, 4-(2-carboxyethyl-aminocarbonyl)-phenyl, 6-carboxy-pyrid-3-yl, 6-(aminocarbonyl)-pyrid-3-yl, thiazol-2-yl and 5-methyl-thiazol-2-yl.

In another embodiment, the present invention is directed to compounds of formula (I) wherein

is selected from the group consisting of cyclopropyl, phenyl, 2-chlorophenyl, 3-chlorophenyl, 4-chlorophenyl, 4-fluorophenyl, 3,4-dichlorophenyl, 4-methylphenyl, 4-methoxyphenyl, 3-trifluoromethylphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl.

In another embodiment, the present invention is directed to compounds of formula (I) wherein

is selected from the group consisting of cyclopropyl, phenyl, 2-chlorophenyl, 3-chlorophenyl, 4-chlorophenyl, 4-fluorophenyl, 3,4-dichlorophenyl, 4-methylphenyl, 4-methoxyphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl.

In another embodiment, the present invention is directed to compounds of formula (I) wherein

is selected from the group consisting of cyclopropyl, phenyl, 2-chlorophenyl, 4-chlorophenyl, 4-fluorophenyl, 3,4-dichlorophenyl, 4-methylphenyl, 4-methoxyphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl.

In another embodiment, the present invention is directed to compounds of formula (I) wherein

is selected from the group consisting of 4-chlorophenyl, 3,4-dichlorophenyl, 4-methoxyphenyl, 4-aminocarbonylphenyl, 6-(aminocarbonyl)-pyrid-3-yl, thiazol-2-yl and 5-methyl-thiazol-2-yl.

In another embodiment, the present invention is directed to compounds of formula (I) wherein

is selected from the group consisting of 4-chlorophenyl, 4-carboxyphenyl and 4-aminocarbonylphenyl. In another embodiment, the present invention is directed to compounds of formula (I) wherein

is selected from the group consisting of 4-chlorophenyl and 4-aminocarbonylphenyl. In another embodiment, the present invention is directed to compounds of formula (I) wherein

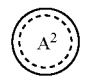

is selected from the group consisting of 4-chlorophenyl and S*-(3-carboxyphenyl). In another embodiment, the present invention is directed to compounds of formula (I) wherein

is 4-chlorophenyl.

In an embodiment, the present invention is directed to compounds of formula (I) wherein is

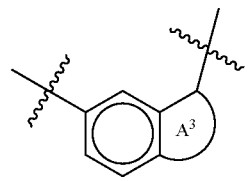

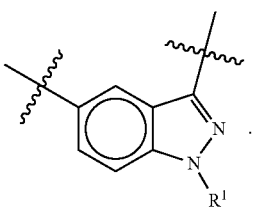

In an embodiment, the present invention is directed to compounds of formula (I) wherein $R^1$ is selected from the group consisting of hydrogen, $C_{1-4}$alkyl, hydroxy substituted $C_{1-4}$alkyl, —C(O)—($C_{1-4}$alkyl), —($C_{1-2}$alkyl)-C(O)OH, —($C_{1-2}$alkyl)-C(O)—O—($C_{1-4}$alkyl), —($C_{1-2}$alkyl)-O—($C_{1-2}$alkyl)-C(O)OH, —($C_{1-2}$alkyl)-C(O)—$NR^E R^F$, —$SO_2$-(fluorinated $C_{1-2}$alkyl) and benzyl; wherein the benzyl is optionally substituted with one substituent selected from the group consisting of —C(O)OH, —C(O)O—($C_{1-4}$ alkyl) and —C(O)—$NR^E R^F$; and wherein $R^E$ and $R^F$ are each independently selected from the group consisting of hydrogen and $C_{1-2}$alkyl. In another embodiment, the present invention is directed to compounds of formula (I) wherein $R^1$ is selected from the group consisting of hydrogen, $C_{1-4}$alkyl, hydroxy substituted $C_{1-4}$alkyl, —C(O)—($C_{1-2}$ alkyl), —($C_{1-2}$alkyl)-C(O)OH, —($C_{1-2}$alkyl)-C(O)O—($C_{1-2}$ alkyl), —($C_{1-2}$alkyl)-O—($C_{1-2}$alkyl)-C(O)OH), —($C_{1-2}$ alkyl)-C(O)—NH$_2$, —SO$_2$-(fluorinated $C_{1-2}$alkyl) and benzyl; wherein the benzyl is optionally substituted with one substituent selected from the group consisting of —C(O)OH, —C(O)O—($C_{1-2}$alkyl) and —C(O)—NH$_2$.

In another embodiment, the present invention is directed to compounds of formula (I) wherein $R^1$ is selected from the group consisting of hydrogen, methyl, 2-hydroxy-ethyl, 2-hydroxy-1-methyl-ethyl-, 2-hydoxy-1,1-dimethyl-ethyl-, 2-(carboxy-methoxy)-ethyl, —C(O)—CH$_3$, —CH$_2$—C(O)OH, —CH$_2$—C(O)O—CH$_2$CH$_3$, —CH$_2$—C(O)—NH$_2$, —SO$_2$—CF$_3$, cyclopropyl, 2-(methoxycarbonyl)-benzyl, 2-carboxy-benzyl and 2-(aminocarbonyl)-benzyl. In another embodiment, the present invention is directed to compounds of formula (I) wherein $R^1$ is selected from the group consisting of hydrogen, methyl, 2-hydroxy-ethyl, 2-hydroxy-1-methyl-ethyl-, 2-(carboxy-methoxy)-ethyl, —C(O)—CH$_3$, —CH$_2$—C(O)O—CH$_2$CH$_3$, —CH$_2$—C(O)—NH$_2$ and cyclopropyl. In another embodiment, the present invention is directed to compounds of formula (I) wherein $R^1$ is selected from the group consisting of hydrogen, methyl, 2-hydroxy-ethyl, —C(O)—CH$_3$, —CH$_2$—C(O)—NH$_2$ and cyclopropyl. In another embodiment, the present invention is directed to compounds of formula (I) wherein $R^1$ is selected from the group consisting of hydrogen, methyl, 2-hydroxy-ethyl, —C(O)—CH$_3$ and cyclopropyl. In another embodiment, the present invention is directed to compounds of formula (I) wherein $R^1$ is selected from the group consisting of hydrogen and cyclopropyl.

In an embodiment, the present invention is directed to compounds of formula (I) wherein

is

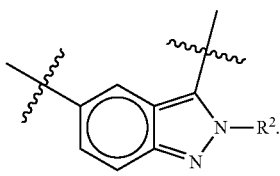

In an embodiment, the present invention is directed to compounds of formula (I) wherein $R^2$ is selected from the group consisting of $C_{3-6}$cycloalkyl and $C_{1-2}$alkyl. In another embodiment, the present invention is directed to compounds of formula (I) wherein $R^2$ is $C_{3-6}$cycloalkyl. In another embodiment, the present invention is directed to compounds of formula (I) wherein $R^2$ is cyclopropyl.

In an embodiment, the present invention is directed to compounds of formula (I) wherein a is 0. In another embodiment, the present invention is directed to compounds of formula (I) wherein a is 1.

In an embodiment, the present invention is directed to compounds of formula (I) wherein b is 0. In another embodiment, the present invention is directed to compounds of formula (I) wherein b is 1.

In an embodiment, the present invention is directed to compounds of formula (I) wherein c is 0. In another embodiment, the present invention is directed to compounds of formula (I) wherein c is 1.

In an embodiment, the present invention is directed to compounds of formula (I) wherein b is 0 and c is 0. In another embodiment, the present invention is directed to compounds of formula (I) wherein b is 0 and c is 1 or alternatively, b is 1 and c is 0. In another embodiment, the present invention is directed to compounds of formula (I) wherein b is 1 and c is 1.

In an embodiment, the present invention is directed to compounds of formula (I) wherein X is CH. In another embodiment, the present invention is directed to compounds of formula (I) wherein X is N.

In an embodiment, the present invention is directed to compounds of formula (I) wherein

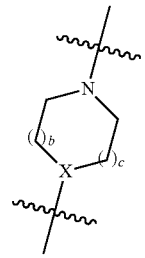

is selected from the group consisting of piperazin-1,4-diyl, piperidin-1,4-diyl and pyrroldin-1,3-diyl. In another embodiment, the present invention is directed to compounds of formula (I0 wherein

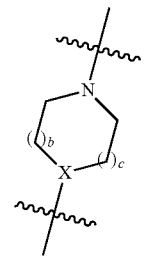

is selected from the group consisting of piperazin-1,4-diyl and piperidin-1,4-diyl. In another embodiment, the present invention is directed to compounds of formula (I) wherein

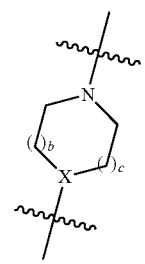

is piperidin-1,4-diyl.

In an embodiment, the present invention is directed to compounds of formula (I) wherein $R^3$ is selected from the group consisting of $C_{1-4}$alkyl, halogenated $C_{1-2}$alkyl, —C(O)-(fluorinated $C_{1-2}$alkyl), —C(O)-(hydroxy substituted $C_{1-4}$alkyl), —C(O)—($C_{1-2}$alkyl)-C(O)OH, —C(O)—($C_{1-2}$alkyl)-C(O)O—($C_{1-4}$alkyl), —C(O)—($C_{1-4}$alkyl)-C(O)—$NR^GR^H$, —C(O)O—($C_{1-4}$alkyl), —C(O)—$NR^GR^H$, —$SO_2$—($C_{1-4}$alkyl), —$SO_2$-(halogenated $C_{1-4}$alkyl), —$SO_2$—($C_{1-2}$alkyl)-C(O)OH, —$SO_2$—($C_{1-2}$alkyl)-C(O)O—($C_{1-4}$alkyl), —$SO_2$—$NR^GR^H$, —$SO_2$—($C_{1-2}$alkyl)-C(O)—$NR^GR^H$, phenyl and -$L^1$-$R^4$; wherein phenyl is optionally substituted with one to two substituents independently selected from the group consisting of halogen, $C_{1-2}$alkyl, halogenated $C_{1-2}$alkyl, $C_{1-2}$alkoxy, —($C_{1-2}$alkyl)-C(O)OH, —($C_{1-2}$alkyl)-C(O)O—($C_{1-4}$alkyl), —($C_{1-2}$alkyl)-C(O)—$NR^JR^K$, —O—($C_{1-2}$alkyl)-C(O)OH, —O—($C_{1-2}$alkyl)-C(O)O—($C_{1-4}$alkyl), —O—($C_{1-2}$alkyl)-C(O)—$NR^JR^K$, —C(O)OH, —C(O)O—($C_{1-4}$alkyl) and —C(O)—$NR^JR^K$; wherein $R^G$ and $R^H$ are each independently selected from the group consisting of hydrogen and $C_{1-4}$alkyl; and wherein $R^J$ and $R^K$ are each independently selected from the group consisting of hydrogen and $C_{1-2}$alkyl; wherein $L^1$ is selected from the group consisting of —$CH_2$—, $CH_2CH_2$—, —CH($CH_3$)—, —C(O)—, —C(O)O—, —C(O)—NH—, —C(O)—NH—$CH_2$— and —$SO_2$—; wherein $R^4$ is selected from the group consisting of $C_{3-6}$cycloalkyl, phenyl, furanyl, thienyl, pyridyl, triazolyl, and tetrazolyl; wherein the phenyl, furanyl, thienyl, pyridyl, pyrazolyl and triazolyl is optionally substituted with one to two substituents independently selected from the group consisting of halogen, hydroxy, $C_{1-2}$alkyl, fluorinated $C_{1-4}$alkyl, $C_{1-4}$alkoxy, fluorinated $C_{1-5}$alkoxy, —C(O)OH, —C(O)O—($C_{1-4}$alkyl), —C(O)—$NR^LR^M$ and —$SO_2$—$NR^LR^M$; and wherein $R^L$ and $R^M$ are each independently selected from the group consisting of hydrogen and $C_{1-2}$alkyl.

In another embodiment, the present invention is directed to compounds of formula (I) wherein $R^3$ is selected from the group consisting of —C(O)-(fluorinated $C_{1-2}$alkyl), —C(O)-(hydroxy substituted $C_{1-2}$alkyl), —C(O)—($C_{1-2}$alkyl)-C(O)OH, —C(O)—($C_{1-2}$alkyl)-C(O)O—($C_{1-2}$alkyl), —C(O)—($C_{1-2}$alkyl)-C(O)—$NR^GR^H$, —C(O)O—($C_{1-4}$alkyl), —C(O)—$NR^GR^H$, —$SO_2$—($C_{1-4}$alkyl), —$SO_2$-(fluorinated $C_{1-2}$alkyl), —$SO_2$—($C_{1-2}$alkyl-C(O)OH, —$SO_2$—C(O)O—($C_{1-2}$alkyl), —$SO_2$—$NR^GR^H$, —$SO_2$—($C_{1-2}$alkyl)-C(O)—$NR^GR^H$, phenyl and -$L^1$-$R^4$; wherein the phenyl is optionally substituted with a substituent selected from the group consisting of —C(O)OH, —($C_{1-2}$alkyl)-C(O)OH, —O—($C_{1-2}$alkyl)-C(O)OH, —C(O)—$NH_2$, —($C_{1-2}$alkyl)-C(O)—$NH_2$ and —O—($C_{1-2}$alkyl)-C(O)—$NH_2$; wherein $R^G$ and $R^H$ are each independently selected from the group consisting of hydrogen and $C_{1-2}$alkyl; wherein $L^1$ is selected from the group consisting of —$CH_2$—, —CH($CH_3$)—, —C(O)—, —C(O)O—, —C(O)O—$CH_2$—, —C(O)—NH—, —C(O)—NH—$CH_2$— and —$SO_2$—; wherein $R^4$ is selected from the group consisting of cyclopropyl, cyclopentyl, phenyl, furan-2-yl, thien-2-yl, pyrid-2-yl, pyrid-3-yl, 1,2,3-triazol-4-yl, 1,3,4-triazol-2-yl, and 1,2,3,4-tetrazol-5-yl; wherein the phenyl, furan-2-yl, thien-2-yl, pyrid-2-yl or pyrid-3-yl is optionally substituted with one to two substituents independently selected from the group consisting of halogen, hydroxy, $C_{1-2}$alkyl, fluorinated $C_{1-2}$alkyl, $C_{1-2}$alkoxy, fluorinated $C_{1-2}$alkoxy, —C(O)OH, —C(O)O—($C_{1-2}$alkyl), —C(O)—$NR^LR^M$ and —$SO_2$—$NR^LR^M$; and wherein $R^L$ and $R^M$ are each independently selected from the group consisting of hydrogen and $C_{1-2}$alkyl.

In another embodiment, the present invention is directed to compounds of formula (I) wherein $R^3$ is selected from the group consisting of —C(O)—$CH_2OH$, —C(O)—$CH_2CH_2OH$, —C(O)—$CH_2CF_3$, —C(O)—$CH_2$—C(O)OH, —C(O)—$CH_2CH_2$—C(O)OH, —C(O)—$CH_2$—C(O)O—$CH_3$, —C(O)—$CH_2$—C(O)—$NH_2$, —C(O)—$CH_2CH_2$—C(O)—$NH_2$, —C(O)O—C($CH_3$)$_3$, —C(O)O—$CH_2CH_3$, —C(O)—NH—$CH_2CH_3$, —$SO_2$—$CH_3$, —$SO_2$—CH($CH_2$)$_2$, —$SO_2$—$CF_3$, —$SO_2$—$CH_2CF_3$, —$SO_2$—$CH_2$—C(O)OH, —$SO_2$—$CH_2$—C(O)O—$CH_2CH_3$, —$SO_2$—$NH_2$, —$SO_2$—$CH_2$—C(O)—$NH_2$, —$SO_2$—$CH_2CH_2$—C(O)—$NH_2$, 3-carboxyphenyl, 4-carboxyphenyl, 3-(carboxy-methyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl and -$L^1$-$R^4$; wherein $L^1$ is selected from the group consisting of —$CH_2$—, —CH($CH_3$)—, —C(O)—, —C(O)O—, —C(O)O—$CH_2$—, —C(O)—NH—, —C(O)—NH—$CH_2$— and —$SO_2$—; and wherein $R^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 4-carboxy-pyrid-2-yl, 5-carboxy-pyrid-2-yl, 6-carboxy-pyrid-2-yl, 5-carboxy-pyrid-3-yl, 6-carboxy-pyrid-3-yl, 1,2,3-triazol-4-yl, 1,3,4-triazol-2-yl, and 1,2,3,4-tetrazol-5-yl.

In another embodiment, the present invention is directed to compounds of formula (I) wherein $R^3$ is selected from the group consisting of —C(O)—$CH_2OH$, —C(O)—$CH_2CH_2OH$, —C(O)—$CH_2CF_3$, —C(O)—$CH_2$—C(O)OH, —C(O)—$CH_2$—C(O)O—$CH_3$, —C(O)—$CH_2$—C(O)—$NH_2$, —C(O)—$CH_2CH_2$—C(O)—$NH_2$, —C(O)O—C($CH_3$)$_3$, —C(O)O—$CH_2CH_3$, —C(O)—NH—$CH_2CH_3$, —$SO_2$—$CH_3$, —$SO_2$—CH($CH_2$)$_2$, —$SO_2$—$CF_3$, —$SO_2$—$CH_2CF_3$, —$SO_2$—$CH_2$—C(O)OH, —$SO_2$—$CH_2$—C(O)O—$CH_2CH_3$, —$SO_2$—$CH_2CH_2$—C(O)—$NH_2$, 3-carboxyphenyl, 4-carboxyphenyl, 3-(carboxy-methyl)-phenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -$L^1$-$R^4$; wherein $L^1$ is selected from the group consisting of —$CH_2$—, —C(O)—, —C(O)O—, —C(O)O—$CH_2$—, —C(O)—NH— and —$SO_2$—; and wherein $R^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-chloro-phenyl, 3-(methylaminocarbonyl)-4-methoxy-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl, 6-carboxy-pyrid-3-yl and 1,2,3-triazol-4-yl.

In another embodiment, the present invention is directed to compounds of formula (I) wherein $R^3$ is selected from the group consisting of —C(O)—CH$_2$OH, —C(O)—CH$_2$CH$_2$OH, —C(O)O—CH$_2$CH$_2$—C(O)—NH$_2$, —C(O)—CH$_2$CF$_3$, —C(O)O—CH$_2$CH$_3$, —SO$_2$—CF$_3$, —SO$_2$—CH$_2$CF$_3$, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L$^1$-R$^4$; wherein L$^1$ is selected from the group consisting of —CH$_2$—, —C(O)—, —C(O)O— and —SO$_2$—; and wherein R$^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 4-(trifluoromethyl)-phenyl, 3-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 6-carboxy-pyrid-2-yl, 5-carboxy-pyrid-3-yl, 6-carboxy-pyrid-3-yl and 1,2,3-triazol-4-yl;

In another embodiment, the present invention is directed to compounds of formula (I) wherein $R^3$ is selected from the group consisting of —SO$_2$—CF$_3$ and -L$^1$-R$^4$; wherein L$^1$ is selected from the group consisting of —CH$_2$—, —C(O)—, and —SO$_2$—; and wherein R$^4$ is selected from the group consisting of 2-hydroxyphenyl, 3-hydroxyphenyl, 4-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-chloro-4-carboxy-phenyl, 3-chloro-4-(methylaminocarbonyl)-phenyl, 3-methoxy-4-(aminocarbonyl)-phenyl 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 5-carboxy-furan-2-yl, 5-(aminocarbonyl)-furan-2-yl, 4-(aminocarbonyl)-thien-2-yl, 6-(methylaminocarbonyl)-pyrid-3-yl, 6-carboxy-pyrid-2-yl, 6-carboxy-pyrid-3-yl and 6-(aminocarbonyl)-pyrid-3-yl.

In another embodiment, the present invention is directed to compounds of formula (I) wherein $R^3$ is selected from the group consisting of —C(O)—CH$_2$OH, —C(O)—CH$_2$CH$_2$OH, —C(O)—CH$_2$CF$_3$, —C(O)—CH$_2$—C(O)OH, —C(O)—CH$_2$CH$_2$—C(O)OH, —C(O)—CH$_2$—C(O)O—CH$_3$, —C(O)—CH$_2$—C(O)—NH$_2$, —C(O)—CH$_2$CH$_2$—C(O)—NH$_2$, —C(O)O—C(CH$_3$)$_3$, —C(O)O—CH$_2$CH$_3$, —C(O)—NH—CH$_2$CH$_3$, —SO$_2$—CH$_3$, —SO$_2$—CF$_3$, —SO$_2$—CH$_2$CF$_3$, —SO$_2$—CH$_2$—C(O)OH, —SO$_2$—CH$_2$CH$_2$—C(O)OH, —SO$_2$—CH$_2$—C(O)O—CH$_2$CH$_3$, —SO$_2$—NH$_2$, —SO$_2$—CH$_2$—C(O)—NH$_2$, —SO$_2$—CH$_2$CH$_2$—C(O)—NH$_2$, 3-carboxyphenyl, 4-carboxyphenyl, 3-(carboxy-methyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl and -L$^1$-R$^4$; wherein L$^1$ is selected from the group consisting of —CH$_2$—, —CH(CH$_3$)—, —C(O)—, —C(O)O—, —C(O)

O—CH$_2$—, —C(O)—NH—, —C(O)—NH—CH$_2$— and —SO$_2$—; and wherein R$^4$ is selected from the group consisting of cyclopropyl, cyclopentyl, phenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 4-carboxy-pyrid-2-yl, 1,2,3-triazol-4-yl, 1,3,4-triazol-2-yl, and 1,2,3,4-tetrazol-5-yl.

In another embodiment, the present invention is directed to compounds of formula (I) wherein R$^3$ is selected from the group consisting of —C(O)—CH$_2$OH, —C(O)—CH$_2$CH$_2$OH, —C(O)O—CH$_2$CH$_2$—C(O)—NH$_2$, —C(O)—CH$_2$CF$_3$, —C(O)O—CH$_2$CH$_3$, —SO$_2$—CF$_3$, —SO$_2$—CH$_2$CF$_3$, 3-(aminocarbonyl)-phenyl, 4-(aminocarbonyl)-phenyl, and -L$^1$-R$^4$; wherein L$^1$ is selected from the group consisting of —CH$_2$—, —C(O)—, —C(O)O— and —SO$_2$—; and wherein R$^4$ is selected from the group consisting of cyclopropyl, cyclopentyl, phenyl, 4-hydroxyphenyl 2-(trifluoromethyl)-phenyl, 4-(trifluoromethyl)-phenyl, 3-(methoxycarbonyl)-phenyl, 3-carboxy-phenyl, 4-carboxy-phenyl, 3-(aminocarbonyl)-phenyl, 4-(aminocarbonyl)-phenyl 4-(aminosulfonyl)-phenyl, 5-carboxy-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl and 1,2,3-triazol-4-yl.

In another embodiment, the present invention is directed to compounds of formula (I) wherein R$^3$ is selected from the group consisting of —SO$_2$—CF$_3$ and -L$^1$-R$^4$; wherein L$^1$ is selected from the group consisting of —CH$_2$—, —C(O)—, and —SO$_2$—; and wherein R$^4$ is selected from the group consisting of 4-hydroxyphenyl, 3-carboxy-phenyl, 3-(aminocarbonyl)-phenyl and 4-(am inocarbonyl)-phenyl.

In another embodiment, the present invention is directed to compounds of formula (I) wherein R$^3$ is selected from the group consisting of —C(O)—CH$_2$OH, —C(O)—CH$_2$CH$_2$OH, —C(O)—CH$_2$—C(O)OH, —C(O)—CH$_2$CH$_2$—C(O)OH, —C(O)—CH$_2$—C(O)—NH$_2$, —C(O)—CH$_2$CH$_2$—C(O)—NH$_2$, —SO$_2$—CF$_3$, —SO$_2$—CH$_2$—C(O)OH, —SO$_2$—CH$_2$CH$_2$—C(O)OH, —SO$_2$—CH$_2$—C(O)—NH$_2$, —SO$_2$—CH$_2$CH$_2$—C(O)—NH$_2$, 3-carboxyphenyl, 4-carboxyphenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L$^1$-R$^4$; wherein L$^1$ is selected from the group consisting of —CH$_2$—, —C(O)— and —SO$_2$—; and wherein R$^4$ is selected from the group consisting of 2-hydroxyphenyl, 3-hydroxyphenyl, 2-methoxyphenyl, 3-methoxyphenyl, 4-methoxyphenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-(aminocarbonyl)-furan-2-yl, 5-carboxy-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl.

In another embodiment, the present invention is directed to compounds of formula (I) wherein R$^3$ is selected from the group consisting of —SO$_2$—CF$_3$, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L$^1$-R$^4$; wherein L$^1$ is selected from the group consisting of —CH$_2$—, —C(O)— and —SO$_2$—; and wherein R$^4$ is selected from the group consisting of 2-hydroxyphenyl, 3-hydroxyphenyl, 2-methoxyphenyl, 3-methoxyphenyl, 4-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-carboxy-furan-2-yl, 5-(aminocarbonyl)-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl.

In another embodiment, the present invention is directed to compounds of formula (I) wherein R$^3$ is selected from the group consisting of —SO$_2$—CF$_3$ and -L$^1$-R$^4$; wherein L$^1$ is selected from the group consisting of —CH$_2$— and —SO$_2$—; and wherein R$^4$ is selected from the group consisting of 2-hydroxyphenyl, 3-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(methylaminocarbonyl)-phenyl, 3-methoxy-4-(aminocarbonyl)-phenyl, 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 5-carboxy-furan-2-yl, 5-(aminocarbonyl)-furan-2-yl, 4-(aminocarbonyl)-thien-2-yl, 6-(aminocarbonyl)-pyrid-3-yl, 6-(methylaminocarbonyl)-pyrid-3-yl, 6-carboxy-pyrid-2-yl and 6-carboxy-pyrid-3-yl.

In another embodiment, the present invention is directed to compounds of formula (I) wherein R$^3$ is -L$^1$-R$^4$; wherein L$^1$ is selected from the group consisting of —CH$_2$— and —SO$_2$—; and wherein R$^4$ is selected from the group consisting of 2-methoxyphenyl, 4-(aminocarbonyl)-phenyl, 3-fluoro-4-carboxy-phenyl, 3-chloro-4-carboxy-phenyl, 3-chloro-4-(methylamninocarbonyl)-phenyl, 3-methoxy-4- carboxy-phenyl, 3-carboxy-4-fluoro-phenyl, 3-carboxy-4-chloro-phenyl, 3-(aminocarbonyl)-4-methoxy-phenyl, 3-(methylaminocabronyl)-4-methoxy-phenyl, 5-carboxy-furan-2-yl, 5-(aminocarbonyl)-furan-2-yl and 4-(aminocarbonyl)-thien-2-yl.

In an embodiment, the present invention is directed to compounds of formula (I) wherein $R^3$ is selected from the group consisting of $R^3$ is selected from the group consisting of $C_{1-4}$alkyl, halogenated $C_{1-4}$alkyl, —C(O)-(fluorinated $C_{1-2}$alkyl), —C(O)-(hydroxy substituted $C_{1-4}$alkyl), —C(O)—($C_{1-2}$alkyl)-C(O)OH, —C(O)—($C_{1-2}$alkyl)-C(O)O—($C_{1-4}$alkyl), —C(O)—($C_{1-4}$alkyl)-C(O)—$NR^GR^H$, —C(O)O—($C_{1-4}$alkyl), —C(O)O—($C_{3-6}$cycloalkyl), —C(O)—$NR^GR^H$, —$SO_2$—($C_{1-4}$alkyl), —$SO_2$-(halogenated $C_{1-4}$alkyl), —$SO_2$—($C_{1-2}$alkyl)-C(O)OH, —$SO_2$—($C_{1-2}$alkyl)-C(O)O—($C_{1-4}$alkyl), —$SO_2$—$NR^GR^H$, —$SO_2$—($C_{1-2}$alkyl)-C(O)—$NR^GR^H$, phenyl, pyridyl (provided that the pyridyl is bound through a carbon atom) and -$L^1$-$R^4$; wherein phenyl or pyridyl is optionally substituted with one or more (preferably one to two) substituents independently selected from the group consisting of halogen, $C_{1-4}$alkyl, halogenated $C_{1-2}$alkyl, $C_{1-4}$alkoxy, —($C_{1-2}$alkyl)-C(O)OH, —($C_{1-2}$alkyl)-C(O)O—($C_{1-4}$alkyl), —($C_{1-2}$alkyl)-C(O)—$NR^JR^K$, —O—($C_{1-2}$alkyl)-C(O)OH, —O—($C_{1-2}$alkyl)-C(O)O—($C_{1-4}$alkyl), —O—($C_{1-2}$alkyl)-C(O)—$NR^JR^K$, —C(O)OH, —C(O)O—($C_{1-4}$alkyl) and —C(O)—$NR^JR^K$; wherein $R^G$ and $R^H$ are each independently selected from the group consisting of hydrogen and $C_{1-4}$alkyl; and wherein $R^J$ and $R^K$ are each independently selected from the group consisting of hydrogen and $C_{1-2}$alkyl.

In another embodiment, the present invention is directed to compounds of formula (I) wherein $R^3$ is selected from the group consisting of $C_{1-4}$alkyl, halogenated $C_{1-2}$alkyl, —C(O)-(fluorinated $C_{1-2}$alkyl), —C(O)-(hydroxy substituted $C_{1-4}$alkyl), —C(O)—($C_{1-2}$alkyl)-C(O)OH, —C(O)—($C_{1-2}$alkyl)-C(O)O—($C_{1-4}$alkyl), —C(O)—($C_{1-4}$alkyl)-C(O)—$NR^GR^H$, —C(O)O—($C_{1-4}$alkyl), —C(O)—$NR^GR^H$, —$SO_2$—($C_{1-4}$alkyl), —$SO_2$-(halogenated $C_{1-4}$alkyl), —$SO_2$—($C_{1-2}$alkyl)-C(O)OH, —$SO_2$—($C_{1-2}$alkyl)-C(O)O—($C_{1-4}$alkyl), —$SO_2$—$NR^GR^H$, —$SO_2$—($C_{1-2}$alkyl)-C(O)—$NR^GR^H$ and phenyl; wherein phenyl is optionally substituted with one to two substituents independently selected from the group consisting of halogen, $C_{1-2}$alkyl, halogenated $C_{1-2}$alkyl, $C_{1-2}$alkoxy, —($C_{1-2}$alkyl)-C(O)OH, —($C_{1-2}$alkyl)-C(O)O—($C_{1-4}$alkyl), —($C_{1-2}$alkyl)-C(O)—$NR^JR^K$, —O—($C_{1-2}$alkyl)-C(O)OH, —O—($C_{1-2}$alkyl)-C(O)O—($C_{1-4}$alkyl), —O—($C_{1-2}$alkyl)-C(O)—$NR^JR^K$, —C(O)OH, —C(O)O—($C_{1-4}$alkyl) and —C(O)—$NR^JR^K$; wherein $R^G$ and $R^H$ are each independently selected from the group consisting of hydrogen and $C_{1-4}$alkyl; and wherein $R^J$ and $R^K$ are each independently selected from the group consisting of hydrogen and $C_{1-2}$alkyl.

In another embodiment, the present invention is directed to compounds of formula (I) wherein $R^3$ is selected from the group consisting of —C(O)-(fluorinated $C_{1-2}$alkyl), —C(O)-(hydroxy substituted $C_{1-2}$alkyl), —C(O)—($C_{1-2}$alkyl)-C(O)OH, —C(O)—($C_{1-2}$alkyl)-C(O)O—($C_{1-2}$alkyl), —C(O)—($C_{1-2}$alkyl)-C(O)—$NR^GR^H$, —C(O)O—($C_{1-4}$alkyl), —C(O)—$NR^GR^H$, —$SO_2$—($C_{1-4}$alkyl), —$SO_2$-(fluorinated $C_{1-2}$alkyl), —$SO_2$—($C_{1-2}$alkyl-C(O)OH, —$SO_2$—C(O)O—($C_{1-2}$alkyl), —$SO_2$—$NR^GR^H$, —$SO_2$—($C_{1-2}$alkyl)-C(O)—$NR^GR^H$, phenyl and -$L^1$-$R^4$; wherein the phenyl is optionally substituted with a substituent selected from the group consisting of —C(O)OH, —($C_{1-2}$alkyl)-C(O)OH, —O—($C_{1-2}$alkyl)-C(O)OH, —C(O)—$NH_2$, —($C_{1-2}$alkyl)-C(O)—$NH_2$ and —O—($C_{1-2}$alkyl)-C(O)—$NH_2$; and wherein $R^G$ and $R^H$ are each independently selected from the group consisting of hydrogen and $C_{1-2}$alkyl.

In another embodiment, the present invention is directed to compounds of formula (I) wherein $R^3$ is selected from the group consisting of —C(O)—$CH_2OH$, —C(O)—$CH_2CH_2OH$, —C(O)—$CH_2CF_3$, —C(O)—$CH_2$—C(O)OH, —C(O)—$CH_2CH_2$—C(O)OH, —C(O)—$CH_2$—C(O)O—$CH_3$, —C(O)—$CH_2$—C(O)—$NH_2$, —C(O)—$CH_2CH_2$—C(O)—$NH_2$, —C(O)O—C($CH_3$)$_3$, —C(O)O—$CH_2CH_3$, —C(O)—NH—$CH_2CH_3$, —$SO_2$—$CH_3$, —$SO_2$—CH($CH_2$)$_2$, —$SO_2$—$CF_3$, —$SO_2$—$CH_2CF_3$, —$SO_2$—$CH_2$—C(O)OH, —$SO_2$—$CH_2$—C(O)O—$CH_2CH_3$, —$SO_2$—$NH_2$, —$SO_2$—$CH_2$—C(O)—$NH_2$, —$SO_2$—$CH_2CH_2$—C(O)—$NH_2$, 3-carboxyphenyl, 4-carboxyphenyl, 3-(carboxy-methyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is selected from the group consisting of —C(O)—$CH_2OH$, —C(O)—$CH_2CH_2OH$, —C(O)—$CH_2CF_3$, —C(O)—$CH_2$—C(O)OH, —C(O)—$CH_2$—C(O)O—$CH_3$, —C(O)—$CH_2$—C(O)—$NH_2$, —C(O)—$CH_2CH_2$—C(O)—$NH_2$, —C(O)O—C($CH_3$)$_3$, —C(O)O—$CH_2CH_3$, —C(O)—NH—$CH_2CH_3$, —$SO_2$—$CH_3$, —$SO_2$—CH($CH_2$)$_2$, —$SO_2$—$CF_3$, —$SO_2$—$CH_2CF_3$, —$SO_2$—$CH_2$—C(O)OH, —$SO_2$—$CH_2$—C(O)O—$CH_2CH_3$, —$SO_2$—$CH_2CH_2$—C(O)—$NH_2$, 3-carboxyphenyl, 4-carboxyphenyl, 3-(carboxy-methyl)-phenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is selected from the group consisting of —C(O)—$CH_2OH$, —C(O)—$CH_2CH_2OH$, —C(O)O—$CH_2CH_2$—C(O)—$NH_2$, —C(O)—$CH_2CF_3$, —C(O)O—$CH_2CH_3$, —$SO_2$—$CF_3$, —$SO_2$—$CH_2CF_3$, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is selected from the group consisting of —C(O)—$CH_2OH$, —C(O)—$CH_2CH_2OH$, —C(O)O—$CH_2CH_2$—C(O)—$NH_2$, —C(O)O—$CH_2CH_3$, —$SO_2$—$CF_3$, —$SO_2$—$CH_2CF_3$, 4-(carboxy-methyl)-phenyl, 3-(aminocarbonyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is —$SO_2$—$CF_3$.

In another embodiment, the present invention is directed to compounds of formula (I) wherein $R^3$ is selected from the group consisting of —C(O)—$CH_2OH$, —C(O)—$CH_2CH_2OH$, —C(O)—$CH_2CF_3$, —C(O)—$CH_2$—C(O)OH, —C(O)—$CH_2CH_2$—C(O)OH, —C(O)—$CH_2$—C(O)O—$CH_3$, —C(O)—$CH_2$—C(O)—$NH_2$, —C(O)—$CH_2CH_2$—C(O)—$NH_2$, —C(O)O—C($CH_3$)$_3$, —C(O)O—$CH_2CH_3$, —C(O)—NH—$CH_2CH_3$, —$SO_2$—$CH_3$, —$SO_2$—$CF_3$, —$SO_2$—$CH_2CF_3$, —$SO_2$—$CH_2$—C(O)OH, —$SO_2$—$CH_2$—C(O)O—$CH_3$, —$SO_2$—$NH_2$, —$SO_2$—$CH_2$—C(O)—$NH_2$, —$SO_2$—$CH_2CH_2$—C(O)—$NH_2$, 3-carboxyphenyl, 4-carboxyphenyl, 3-(carboxy-methyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl and 4-(aminocarbonyl-methoxy)-phenyl. In another embodiment, the present invention is directed to compounds of formula (I) wherein $R^3$ is selected from the group consisting of —C(O)—$CH_2$OH, —C(O)—$CH_2CH_2$OH, —C(O)O—$CH_2CH_2$—C(O)—$NH_2$, —C(O)—$CH_2CF_3$, —C(O)O—$CH_2CH_3$, —$SO_2$—$CF_3$, —$SO_2$—$CH_2CF_3$, 3-(aminocarbonyl)-phenyl and 4-(aminocarbonyl)-phenyl.

In another embodiment, the present invention is directed to compounds of formula (I) wherein $R^3$ is selected from the group consisting of —C(O)—$CH_2$OH, —C(O)—$CH_2CH_2$OH, —C(O)—$CH_2$—C(O)OH, —C(O)—$CH_2CH_2$—C(O)OH, —C(O)—$CH_2$—C(O)—$NH_2$, —C(O)—$CH_2CH_2$—C(O)—$NH_2$, —$SO_2$—$CF_3$, —$SO_2$—$CH_2$—C(O)OH, —$SO_2$—$CH_2CH_2$—C(O)OH, —$SO_2$—$CH_2$—C(O)—$NH_2$, —$SO_2$—$CH_2CH_2$—C(O)—$NH_2$, 3-carboxyphenyl, 4-carboxyphenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is selected from the group consisting of —$SO_2$—$CF_3$, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl and 4-(aminocarbonyl-methoxy)-phenyl.

In another embodiment, the present invention is directed to compounds of formula (I) wherein $R^3$ is -$L^1$-$R^4$; wherein $L^1$ is selected from the group consisting of —$CH_2$—, $CH_2CH_2$—, —CH($CH_3$)—, —C(O)—, —C(O)—$CH_2$—, —C(O)O—, —C(O)O—$CH_2$—, —C(O)—NH—, —C(O)—NH—$CH_2$— and —$SO_2$—; wherein $R^4$ is selected from the group consisting of $C_{3-6}$cycloalkyl, phenyl, furanyl, thienyl, pyridyl, pyrazolyl, triazolyl, and tetrazolyl; wherein the phenyl, furanyl, thienyl, pyridyl, pyrazolyl and triazolyl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, —C(O)OH, —C(O)O—($C_{1-4}$alkyl), —C(O)—$NR^LR^M$ and —$SO_2$—$NR^LR^M$; and wherein $R^L$ and $R^M$ are each independently selected from the group consisting of hydrogen and $C_{1-2}$alkyl.

In an embodiment, the present invention is directed to compounds of formula (I) wherein $L^1$ is selected from the group consisting of —$CH_2$—, $CH_2CH_2$—, —CH($CH_3$)—, —C(O)—, —C(O)O—, —C(O)—NH—, —C(O)—NH—$CH_2$— and —$SO_2$—.

In another embodiment, the present invention is directed to compounds of formula (I) wherein $L^1$ is selected from the group consisting of —$CH_2$—, $CH_2CH_2$—, —CH($CH_3$)—, —C(O)—, —C(O)O—, —C(O)—NH— and —$SO_2$—. In another embodiment, the present invention is directed to compounds of formula (I) wherein $L^1$ is selected from the group consisting of —$CH_2$—, —CH($CH_3$)—, —C(O)—, —C(O)O—, —C(O)O—$CH_2$—, —C(O)—NH—, —C(O)—NH—$CH_2$— and —$SO_2$—. In another embodiment, the present invention is directed to compounds of formula (I) wherein $L^1$ is selected from the group consisting of —$CH_2$—, —C(O)—, —C(O)O—, —C(O)O—$CH_2$—, —C(O)—NH— and —$SO_2$—. In another embodiment, the present invention is directed to compounds of formula (I) wherein $L^1$ is selected from the group consisting of —$CH_2$—, —C(O)—, —C(O)O— and —$SO_2$—. In another embodiment, the present invention is directed to compounds of formula (I) wherein $L^1$ is selected from the group consisting of —$CH_2$—, —C(O)—, and —$SO_2$—. In another embodiment, the present invention is directed to compounds of formula (I) wherein $L^1$ is selected from the group consisting of —$CH_2$— and —$SO_2$—. In another embodiment, the present invention is directed to compounds of formula (I) wherein $L^1$ is —$CH_2$—. In another embodiment, the present invention is directed to compounds of formula (I) wherein $L^1$ is —C(O)—. In another embodiment, the present invention is directed to compounds of formula (I) wherein $L^1$ is —$SO_2$—.

In an embodiment, the present invention is directed to compounds of formula (I) wherein $R^4$ is selected from the group consisting of $C_{3-6}$cycloalkyl, phenyl, furanyl, thienyl, pyridyl, triazolyl, and tetrazolyl; wherein the phenyl, furanyl, thienyl, pyridyl, pyrazolyl and triazolyl is optionally substituted with one to two substituents independently selected from the group consisting of halogen, hydroxy, $C_{1-2}$alkyl, fluorinated $C_{1-4}$alkyl, $C_{1-4}$alkoxy, fluorinated $C_{1-5}$alkoxy, —C(O)OH, —C(O)O—($C_{1-4}$alkyl), —C(O)—$NR^LR^M$ and —$SO_2$—$NR^LR^M$; wherein $R^L$ and $R^M$ are each independently selected from the group consisting of hydrogen and $C_{1-2}$alkyl. In another embodiment, the present invention is directed to compounds of formula (I) wherein $R^4$ is selected from the group consisting of cyclopropyl, cyclopentyl, phenyl, furan-2-yl, thien-2-yl, pyrid-2-yl, pyrid-3-yl, 1,2,3-triazol-4-yl, 1,3,4-triazol-2-yl, and 1,2,3,4-tetrazol-5-yl; wherein the phenyl, furan-2-yl, thien-2-yl, pyrid-2-yl or pyrid-3-yl is optionally substituted with one to two substituents independently selected from the group consisting of halogen, hydroxy, $C_{1-2}$alkyl, fluorinated $C_{1-2}$alkyl, $C_{1-2}$alkoxy, fluorinated $C_{1-2}$alkoxy, —C(O)OH, —C(O)O—($C_{1-2}$alkyl), —C(O)—$NR^LR^M$ and —$SO_2$—$NR^LR^M$; and wherein $R^L$ and $R^M$ are each independently selected from the group consisting of hydrogen and $C_{1-2}$alkyl.

In another embodiment, the present invention is directed to compounds of formula (I) wherein $R^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 4-carboxy-pyrid-2-yl, 5-carboxy-pyrid-2-yl, 6-carboxypyrid-2-yl, 5-carboxy-pyrid-3-yl, 6-carboxy-pyrid-3-yl, 1,2, 3-triazol-4-yl, 1,3,4-triazol-2-yl, and 1,2,3,4-tetrazol-5-yl.

In another embodiment, the present invention is directed to compounds of formula (I) wherein $R^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-chloro-phenyl, 3-(methylaminocarbonyl)-4-methoxy-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl, 6-carboxy-pyrid-3-yl and 1,2,3-triazol-4-yl.

In another embodiment, the present invention is directed to compounds of formula (I) wherein $R^4$ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 4-(trifluoromethyl)-phenyl, 3-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-chloro-phenyl, 3-(methylaminocarbonyl)-4-methoxy-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl, 6-carboxy-pyrid-3-yl and 1,2,3-triazol-4-yl.

In another embodiment, the present invention is directed to compounds of formula (I) wherein $R^4$ is selected from the group consisting of cyclopropyl, cyclopentyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-chloro-phenyl, 3-(methylaminocarbonyl)-4-methoxy-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 6-carboxy-pyrid-2-yl, 5-carboxy-pyrid-3-yl, 6-carboxy-pyrid-3-yl and 1,2,3-triazol-4-yl.

In another embodiment, the present invention is directed to compounds of formula (I) wherein $R^4$ is selected from the group consisting of 2-hydroxyphenyl, 3-hydroxyphenyl, 4-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-chloro-4-carboxy-phenyl, 3-chloro-4-(methylaminocarbonyl)-phenyl, 3-methoxy-4-(aminocarbonyl)-phenyl, 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 5-carboxy-furan-2-yl, 5-(aminocarbonyl)-furan-2-yl, 4-(aminocarbonyl)-thien-2-yl, 6-(methylaminocarbonyl)-pyrid-3-yl, 6-carboxy-pyrid-2-yl, 6-carboxy-pyrid-3-yl and 6-(aminocarbonyl)-pyrid-3-yl.

In another embodiment, the present invention is directed to compounds of formula (I) wherein $R^4$ is selected from the group consisting of cyclopropyl, cyclopentyl, phenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 4-carboxy-pyrid-2-yl, 1,2,3-triazol-4-yl, 1,3,4-triazol-2-yl, and 1,2,3,4-tetrazol-5-yl.

In another embodiment, the present invention is directed to compounds of formula (I) wherein $R^4$ is selected from the group consisting of cyclopropyl, cyclopentyl, phenyl, 4-hydroxyphenyl 2-(trifluoromethyl)-phenyl, 4-(trifluoromethyl)-phenyl, 3-(methoxycarbonyl)-phenyl, 3-carboxy-phenyl, 4-carboxy-phenyl, 3-(aminocarbonyl)-phenyl, 4-(aminocarbonyl)-phenyl 4-(aminosulfonyl)-phenyl, 5-carboxy-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl and 1,2,3-triazol-4-yl.

In another embodiment, the present invention is directed to compounds of formula (I) wherein $R^4$ is selected from the group consisting of 4-hydroxyphenyl, 3-carboxy-phenyl, 3-(aminocarbonyl)-phenyl and 4-(aminocarbonyl)-phenyl.

In another embodiment, the present invention is directed to compounds of formula (I) wherein $R^4$ is selected from the group consisting of 2-hydroxyphenyl, 3-hydroxyphenyl, 2-methoxyphenyl, 3-methoxyphenyl, 4-methoxyphenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-(aminocarbonyl)-furan-2-yl, 5-carboxy-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl.

In another embodiment, the present invention is directed to compounds of formula (I) wherein $R^4$ is selected from the group consisting of 2-hydroxyphenyl, 3-hydroxyphenyl, 2-methoxyphenyl, 3-methoxyphenyl, 4-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-carboxy-furan-2-yl, 5-(aminocarbonyl)-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl.

In another embodiment, the present invention is directed to compounds of formula (I) wherein $R^4$ is selected from the group consisting of 2-hydroxyphenyl, 3-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(methylaminocarbonyl)-phenyl, 3-methoxy-4-(aminocarbonyl)-phenyl, 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 5-carboxy-furan-2-yl, 5-(aminocarbonyl)-furan-2-yl, 4-(aminocarbonyl)-thien-2-yl, 6-(aminocarbonyl)-pyrid-3-yl, 6-(methylaminocarbonyl)-pyrid-3-yl, 6-carboxy-pyrid-2-yl and 6-carboxy-pyrid-3-yl.

In another embodiment, the present invention is directed to compounds of formula (I) wherein $R^4$ is selected from the group consisting of 2-methoxyphenyl, 4-(aminocarbonyl)-phenyl, 3-fluoro-4-carboxy-phenyl, 3-chloro-4-carboxy-phenyl, 3-chloro-4-(methylamninocarbonyl)-phenyl, 3-methoxy-4-carboxy-phenyl, 3-carboxy-4-fluoro-phenyl, 3-carboxy-4-chloro-phenyl, 3-(aminocarbonyl)-4-methoxy-phenyl, 3-(methylaminocabronyl)-4-methoxy-phenyl, 5-carboxy-furan-2-yl, 5-(aminocarbonyl)-furan-2-yl and 4-(aminocarbonyl)-thien-2-yl.

In another embodiment, the present invention is directed to compounds of formula (I) wherein $R^3$ is selected from the group consisting of trifluoromethylsulfonyl, 3-(aminocarbonyl)-phenyl, 3-hydroxyphenyl-sulfonyl-, 3-methoxy-4-carboxyphenyl-sulfonyl-, 3-(aminocarbonyl)-4-chloro-phenylsulfonyl-, 3-(aminocarbonyl)-benzyl, 3-carboxy-benzyl and 4-(aminocarbonyl)-thien-2-yl-methyl-. In another embodiment, the present invention is directed to compounds of formula (I) wherein $R^3$ is selected from the group consisting of 3-(aminocarbonyl)-phenyl, 3-hydroxyphenyl-sulfonyl-, 3-methoxy-4-carboxyphenyl-sulfonyl-, 3-(aminocarbonyl)-4-chloro-phenyl-sulfonyl- and 4-(aminocarbonyl)-thien-2-yl-methyl-. In another embodiment, the present invention is directed to compounds of formula (I) wherein $R^3$ is selected from the group consisting of trifluoromethylsulfonyl 3-(aminocarbonyl)-benzyl and 3-carboxy-benzyl.

Additional embodiments of the present invention, include those wherein the substituents selected for one or more of the variables defined herein (e.g. $R^0$,

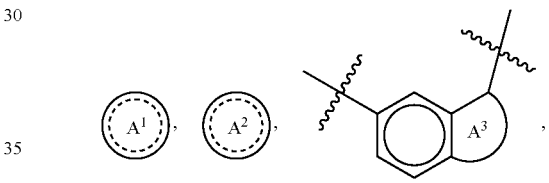

a, b, c, X and $R^3$, etc.) are independently selected to be any individual substituent or any subset of substituents selected from the complete list as defined herein.

Additional embodiments of the present invention, include those wherein the substituents selected for one or more of the variables defined herein (e.g. $R^0$,

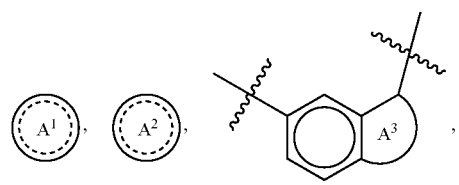

a, b, c, X, $R^3$, etc.) are independently selected to be individual substituent or subset of substituents selected from those exemplified in the Tables which follow herein.

In additional embodiments, the present invention is directed to any single compound or subset of compounds selected from the representative compounds listed in Tables 1 and 2, below.

Representative compounds of the present invention are as listed in Tables 1 and 2, below. In Tables 1 and 2, the substituent group listed in the column headed

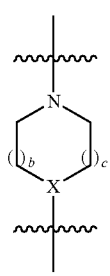

includes recitation of the bonding position of said group to the indazole core, but omits recitation of the bonding position of the R³ group, as this is defined in the structure heading the Table itself. (For example, piperidin-4-yl denotes that the 4-position of the piperidinyl group is bound to the indazole core, optionally though the —NH— linker group, and therefore the $R^3$ group is bound to the N atom at the 1-position of said piperidinyl group. In another example, piperazin-1-yl denotes that the 1-position of the piperazinyl group is bound to the indazole core, optionally though the —NH— linker group, and therefore the $R^3$ group is bound to the N atom at the 4-position of said piperazinyl group.) Unless otherwise noted, wherein a stereogenic center is present in the listed compound, the compound was prepared as a mixture of stereo-configurations. Where a stereogenic center is present, the S*- and R* designations are intended to indicate that compound was isolated as a single stereoisomer, although the exact stereo-configuration of the stereogenic center (isolated stereoisomer) was not determined.

TABLE 1

Representative Compounds of Formula (I-A)

| ID No. | $R^0$ | $A^1$ | $A^2$ | $R^1$ | $(NH)_a$ | X-ring | $R^3$ |
|---|---|---|---|---|---|---|---|
| 17 | H | 4-chlorophenyl | 4-chlorophenyl | H | a = 0 | piperazin-1-yl | trifluoromethyl-sulfonyl- |
| 19 | H | 4-chlorophenyl | 4-chlorophenyl | aminocarbonyl-methyl- | a = 0 | piperazin-1-yl | trifluoromethyl-sulfonyl- |
| 20 | H | 4-chlorophenyl | 4-chlorophenyl | ethoxy-carbonyl-methyl- | a = 0 | piperazin-1-yl | trifluoromethyl-sulfonyl- |
| 21 | H | 4-chlorophenyl | 4-chlorophenyl | H | a = 0 | piperidin-4-yl | ethoxy-carbonyl-methyl-sulfonyl- |
| 22 | H | 4-chlorophenyl | 4-chlorophenyl | H | a = 0 | piperidin-4-yl | carboxy-methyl-sulfonyl- |
| 23 | H | 4-chlorophenyl | 4-chlorophenyl | H | a = 0 | piperidin-4-yl | amino-sulfonyl- |
| 24 | H | 4-chlorophenyl | 4-chlorophenyl | H | a = 0 | piperidin-4-yl | 4-(methoxy-carbonyl)-phenyl-sulfonyl- |
| 25 | H | 4-chlorophenyl | 4-chlorophenyl | H | a = 0 | piperidin-4-yl | amino-carbonyl-methyl-sulfonyl- |

TABLE 1-continued

Representative Compounds of Formula (I-A)

(I-A)

| ID No. | R⁰ | A¹ | A² | R¹ | (NH)ₐ | [X ring] | R³ |
|---|---|---|---|---|---|---|---|
| 26 | H | 4-chloro-phenyl | 4-chloro-phenyl | methyl | a = 0 | piperazin-1-yl | trifluoro-methyl-sulfonyl- |
| 27 | H | 4-chloro-phenyl | 4-chloro-phenyl | H | a = 0 | piperidin-4-yl | 4-carboxy-phenyl-sulfonyl- |
| 28 | H | 4-chloro-phenyl | 4-chloro-phenyl | H | a = 0 | piperidin-4-yl | 4-(amino-carbonyl)-phenyl-sulfonyl- |
| 29 | H | 4-chloro-phenyl | 4-chloro-phenyl | trifluoro-methyl-sulfonyl- | a = 0 | piperazin-1-yl | trifluoro-methyl-sulfonyl |
| 30 | H | 4-chloro-phenyl | 4-chloro-phenyl | 2-(methoxy-carbonyl)-benzyl- | a = 0 | piperazin-1-yl | trifluoro-methyl-sulfonyl- |
| 31 | H | 4-chloro-phenyl | 4-chloro-phenyl | H | a = 0 | piperidin-4-yl | 2-(methoxy-carbonyl)-phenyl-sulfonyl- |
| 32 | H | 4-chloro-phenyl | 4-chloro-phenyl | H | a = 0 | piperidin-4-yl | 4-trifluoro-methyl-phenyl-sulfonyl- |
| 33 | H | 4-chloro-phenyl | 4-chloro-phenyl | H | a = 0 | piperidin-4-yl | 2-trifluoro-methyl-phenyl-sulfonyl- |
| 34 | H | 4-chloro-phenyl | 4-chloro-phenyl | H | a = 0 | piperidin-4-yl | 2-carboxy-phenyl-sulfonyl- |
| 35 | H | 4-chloro-phenyl | 4-chloro-phenyl | H | a = 0 | piperidin-4-yl | trifluoro-methyl-sulfonyl- |
| 37 | H | 4-chloro-phenyl | thiazol-2-yl | H | a = 0 | piperidin-4-yl | trifluoro-methyl-sulfonyl- |
| 38 | H | 4-chloro-phenyl | 5-methyl-thiazol-2-yl | H | a = 0 | piperidin-4-yl | trifluoro-methyl-sulfonyl- |
| 39 | H | 4-chloro-phenyl | 4-chloro-phenyl | H | a = 0 | piperidin-4-yl | tert-butoxy-carbonyl |
| 40 | H | 4-chloro-phenyl | 4-chloro-phenyl | H | a = 0 | piperidin-4-yl | 2-(amino-carbonyl)-phenyl-sulfonyl |

TABLE 1-continued

Representative Compounds of Formula (I-A)

(I-A)

| ID No. | $R^0$ | $A^1$ | $A^2$ | $R^1$ | $(NH)_a$ | [X ring] | $R^3$ |
|---|---|---|---|---|---|---|---|
| 41 | H | 4-chloro-phenyl | 4-chloro-phenyl | H | a = 0 | piperidin-4-yl | carboxy-methyl-carbonyl- |
| 42 | H | 4-chloro-phenyl | 4-chloro-phenyl | 2-hydroxy-ethyl | a = 0 | piperazin-1-yl | trifluoro-methyl-sulfonyl- |
| 43 | H | 4-chloro-phenyl | 4-chloro-phenyl | H | a = 0 | piperidin-4-yl | 2-(amino-carbonyl)-ethyl-carbonyl- |
| 44 | H | 4-chloro-phenyl | 4-chloro-phenyl | methyl-carbonyl- | a = 0 | piperazin-1-yl | trifluoro-methyl-sulfonyl- |
| 45 | H | 4-chloro-phenyl | 4-chloro-phenyl | 2-carboxy-benzyl- | a = 0 | piperazin-1-yl | trifluoro-methyl-sulfonyl- |
| 46 | H | 4-chloro-phenyl | 4-trifluoro-methyl-phenyl | H | a = 0 | piperidin-4-yl | trifluoro-methyl-sulfonyl- |
| 47 | H | 4-chloro-phenyl | 3-chloro-phenyl | H | a = 0 | piperidin-4-yl | trifluoro-methyl-sulfonyl- |
| 48 | H | 4-chloro-phenyl | 2-chloro-phenyl | H | a = 0 | piperidin-4-yl | trifluoro-methyl-sulfonyl- |
| 49 | H | 4-chloro-phenyl | 4-trifluoro-methoxy-phenyl | H | a = 0 | piperidin-4-yl | trifluoro-methyl-sulfonyl- |
| 50 | H | 4-fluoro-phenyl | 4-fluoro-phenyl | H | a = 0 | piperidin-4-yl | trifluoro-methyl-sulfonyl- |
| 51 | H | 4-chloro-phenyl | 4-chloro-phenyl | H | a = 0 | piperidin-4-yl | methoxy-carbonyl-methyl-carbonyl- |
| 52 | H | 4-chloro-phenyl | 4-chloro-phenyl | 2-(carboxy-methoxy)-ethyl- | a = 0 | piperazin-1-yl | trifluoro-methyl-sulfonyl- |
| 53 | H | 4-chloro-phenyl | 4-chloro-phenyl | H | a = 0 | piperidin-4-yl | 2,2,2-trifluoro-ethyl-sulfonyl- |
| 54 | H | 4-chloro-phenyl | 4-chloro-phenyl | H | a = 0 | piperidin-4-yl | cyclopropyl-sulfonyl |

TABLE 1-continued

Representative Compounds of Formula (I-A)

| ID No. | R⁰ | A¹ | A² | R¹ | (NH)ₐ | [piperazine/piperidine] | R³ |
|---|---|---|---|---|---|---|---|
| 55 | H | 4-chloro-phenyl | 4-chloro-phenyl | 2-(amino-carbonyl)-benzyl- | a = 0 | piperazin-1-yl | trifluoro-methyl-sulfonyl- |
| 56 | H | 4-chloro-phenyl | 4-chloro-phenyl | H | a = 0 | piperidin-4-yl | 2,2,2-trifluoro-ethyl-carbonyl- |
| 57 | H | 4-chloro-phenyl | 3-trifluoro-methyl-phenyl | H | a = 0 | piperidin-4-yl | trifluoro-methyl-sulfonyl- |
| 58 | H | 4-chloro-phenyl | 3,4-dichloro-phenyl | H | a = 0 | piperidin-4-yl | trifluoro-methyl-sulfonyl- |
| 59 | H | 4-chloro-phenyl | 4-chloro-phenyl | H | a = 0 | piperidin-4-yl | 3-trifluoro-methyl-phenyl-sulfonyl |
| 60 | H | 4-chloro-phenyl | 4-chloro-phenyl | H | a = 0 | piperidin-4-yl | 3-(methoxy-carbonyl)-phenyl-sulfonyl |
| 61 | H | 4-chloro-phenyl | 4-chloro-phenyl | H | a = 0 | piperidin-4-yl | 3-carboxy-phenyl-sulfonyl |
| 62 | H | 4-chloro-phenyl | 4-chloro-phenyl | methyl | a = 0 | piperidin-4-yl | 4-carboxy-phenyl-sulfonyl- |
| 63 | H | 4-chloro-phenyl | 4-chloro-phenyl | methyl | a = 0 | piperidin-4-yl | 3-carboxy-phenyl-sulfonyl |
| 64 | H | 4-chloro-phenyl | 4-chloro-phenyl | methyl | a = 0 | piperidin-4-yl | 4-(amino-carbonyl)-phenyl-sulfonyl- |
| 65 | H | 4-chloro-phenyl | 4-chloro-phenyl | methyl | a = 0 | piperidin-4-yl | 3-(amino-carbonyl)-phenyl-sulfonyl- |
| 66 | H | 4-chloro-phenyl | 4-chloro-phenyl | H | a = 0 | piperidin-4-yl | 3-(amino-carbonyl)-phenyl-sulfonyl- |
| 67 | H | 4-methoxy-phenyl | 4-methoxy-phenyl | H | a = 0 | piperidin-4-yl | trifluoro-methyl-sulfonyl- |

TABLE 1-continued

Representative Compounds of Formula (I-A)

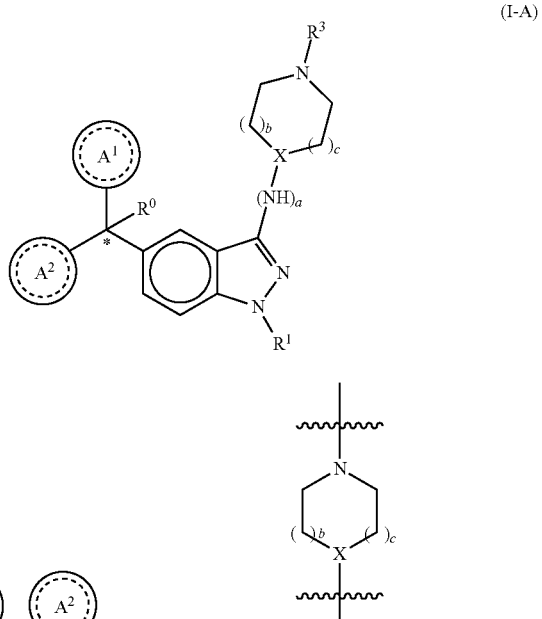

(I-A)

| ID No. | R⁰ | A¹ | A² | R¹ | (NH)ₐ | X | R³ |
|---|---|---|---|---|---|---|---|
| 68 | H | 4-chloro-phenyl | 4-chloro-phenyl | 2-hydroxy-ethyl | a = 0 | piperidin-4-yl | 3-carboxy-phenyl-sulfonyl |
| 69 | H | 4-chloro-phenyl | 4-chloro-phenyl | 2-hydroxy-ethyl | a = 0 | piperidin-4-yl | 4-(amino-carbonyl)-phenyl-sulfonyl- |
| 70 | H | 4-chloro-phenyl | 4-chloro-phenyl | 2-hydroxy-ethyl | a = 0 | piperidin-4-yl | 2-(amino-carbonyl)-phenyl-sulfonyl |
| 71 | H | 4-chloro-phenyl | 4-chloro-phenyl | 2-hydroxy-ethyl | a = 0 | piperidin-4-yl | 3-(amino-sulfonyl)-phenyl-carbonyl- |
| 72 | H | 4-chloro-phenyl | 4-chloro-phenyl | 2-hydroxy-ethyl | a = 0 | piperidin-4-yl | 4-(amino-sulfonyl)-phenyl-carbonyl- |
| 73 | H | 4-chloro-phenyl | 4-chloro-phenyl | carboxy-methyl- | a = 0 | piperidin-4-yl | trifluoro-methyl-sulfonyl- |
| 74 | H | 4-chloro-phenyl | 4-chloro-phenyl | H | —NH— (a = 1) | piperidin-4-yl | tert-butoxy-carbonyl |
| 75 | H | 4-chloro-phenyl | 4-chloro-phenyl | ethoxy-carbonyl-methyl- | a = 0 | piperidin-4-yl | trifluoro-methyl-sulfonyl- |
| 76 | H | 4-chloro-phenyl | 4-chloro-phenyl | 2-hydroxy-ethyl | a = 0 | piperidin-4-yl | tert-butoxy-carbonyl |
| 77 | H | 4-chloro-phenyl | 4-chloro-phenyl | H | —NH— (a = 1) | piperidin-4-yl | trifluoro-methyl-sulfonyl- |
| 78 | H | 4-chloro-phenyl | 4-chloro-phenyl | H | —NH— (a = 1) | piperidin-4-yl | isopropyl-sulfonyl- |
| 79 | H | 4-chloro-phenyl | 4-chloro-phenyl | 2-hydroxy-ethyl | a = 0 | piperidin-4-yl | trifluoro-methyl-sulfonyl- |
| 80 | H | 4-chloro-phenyl | 4-chloro-phenyl | 2-hydroxy-ethyl | a = 0 | piperidin-4-yl | 4-carboxy-phenyl-sulfonyl- |
| 81 | H | 4-chloro-phenyl | 4-chloro-phenyl | 2-hydroxy-ethyl | a = 0 | piperidin-4-yl | 2-carboxy-phenyl-sulfonyl- |

TABLE 1-continued

Representative Compounds of Formula (I-A)

(I-A)

| ID No. | R⁰ | A¹ | A² | R¹ | (NH)ₐ | [piperidine] | R³ |
|---|---|---|---|---|---|---|---|
| 82 | H | 4-chloro-phenyl | 4-chloro-phenyl | 2-hydroxy-ethyl | a = 0 | piperidin-4-yl | 3-(amino-carbonyl)-phenyl-sulfonyl- |
| 83 | H | 4-chloro-phenyl | 4-chloro-phenyl | 2-hydroxy-ethyl | a = 0 | piperidin-4-yl | 2-carboxy-ethyl-sulfonyl |
| 86 | H | 4-chloro-phenyl | 4-chloro-phenyl | cyclo-propyl | a = 0 | piperidin-4-yl | carboxy-methyl-sulfonyl- |
| 87 | H | 4-chloro-phenyl | 4-chloro-phenyl | cyclo-propyl | a = 0 | piperidin-4-yl | 2-carboxy-phenyl-sulfonyl- |
| 88 | H | 4-chloro-phenyl | 4-chloro-phenyl | cyclo-propyl | a = 0 | piperidin-4-yl | 3-carboxy-phenyl-sulfonyl |
| 89 | H | 4-chloro-phenyl | 4-chloro-phenyl | cyclo-propyl | a = 0 | piperidin-4-yl | 4-carboxy-phenyl-sulfonyl- |
| 90 | H | 4-chloro-phenyl | 4-chloro-phenyl | cyclo-propyl | a = 0 | piperidin-4-yl | amino-carbonyl-methyl-carbonyl- |
| 91 | H | 4-chloro-phenyl | 4-chloro-phenyl | cyclo-propyl | a = 0 | piperidin-4-yl | hydroxy-methyl-carbonyl- |
| 92 | H | 4-chloro-phenyl | 4-chloro-phenyl | cyclo-propyl | a = 0 | piperidin-4-yl | 2-(amino-carbonyl)-ethyl-carbonyl- |
| 93 | H | 4-chloro-phenyl | 4-chloro-phenyl | cyclo-propyl | a = 0 | piperidin-4-yl | 2-(amino-carbonyl)-phenyl-sulfonyl |
| 94 | H | 4-chloro-phenyl | 4-chloro-phenyl | cyclo-propyl | a = 0 | piperidin-4-yl | 3-(amino-carbonyl)-phenyl-sulfonyl- |
| 95 | H | 4-chloro-phenyl | 4-chloro-phenyl | cyclo-propyl | a = 0 | piperidin-4-yl | 4-(amino-carbonyl)-phenyl-sulfonyl- |
| 96 | H | 4-chloro-phenyl | 4-chloro-phenyl | cyclo-propyl | a = 0 | piperidin-4-yl | 2-(amino-carbonyl)-phenyl-carbonyl- |

TABLE 1-continued

Representative Compounds of Formula (I-A)

| ID No. | R⁰ | A¹ | A² | R¹ | (NH)$_a$ | X | R³ |
|---|---|---|---|---|---|---|---|
| 97 | H | 4-chlorophenyl | 4-chlorophenyl | cyclopropyl | a = 0 | piperidin-4-yl | 3-carboxyphenylcarbonyl- |
| 98 | H | 4-chlorophenyl | 4-chlorophenyl | cyclopropyl | a = 0 | piperidin-4-yl | 3-(aminocarbonyl)-phenylcarbonyl- |
| 99 | H | 4-chlorophenyl | 4-chlorophenyl | cyclopropyl | a = 0 | piperidin-4-yl | 4-carboxyphenylcarbonyl- |
| 100 | H | 4-chlorophenyl | 4-chlorophenyl | H | —NH— (a = 1) | piperidin-4-yl | 2-methoxyphenylsulfonyl- |
| 101 | H | 4-chlorophenyl | 4-chlorophenyl | H | —NH— (a = 1) | piperidin-4-yl | 3-methoxyphenylsulfonyl- |
| 102 | H | 4-chlorophenyl | 4-chlorophenyl | cyclopropyl | a = 0 | piperidin-4-yl | carboxymethylcarbonyl- |
| 103 | H | 4-chlorophenyl | 4-chlorophenyl | cyclopropyl | a = 0 | piperidin-4-yl | 2-carboxyphenylcarbonyl- |
| 104 | H | 4-chlorophenyl | 4-chlorophenyl | cyclopropyl | a = 0 | piperidin-4-yl | 4-(aminocarbonyl)-phenylcarbonyl- |
| 105 | H | 4-chlorophenyl | 4-chlorophenyl | cyclopropyl | a = 0 | piperidin-4-yl | trifluoromethylsulfonyl- |
| 106 | H | 4-chlorophenyl | 4-chlorophenyl | cyclopropyl | a = 0 | piperidin-4-yl | 2-carboxyethylsulfonyl- |
| 107 | H | 4-chlorophenyl | 4-chlorophenyl | cyclopropyl | a = 0 | piperidin-4-yl | 2-carboxyethylcarbonyl- |
| 108 | H | 4-chlorophenyl | 4-chlorophenyl | cyclopropyl | a = 0 | piperidin-4-yl | 2-hydroxyethylcarbonyl- |
| 109 | H | 4-chlorophenyl | 4-chlorophenyl | cyclopropyl | a = 0 | piperidin-4-yl | 2-(aminocarbonyl)-ethylsulfonyl- |
| 115 | H | 4-chlorophenyl | 4-chlorophenyl | cyclopropyl | a = 0 | piperidin-4-yl | aminocarbonylmethylsulfonyl- |

TABLE 1-continued

Representative Compounds of Formula (I-A)

| ID No. | R⁰ | A¹ | A² | R¹ | (NH)ₐ | X | R³ |
|---|---|---|---|---|---|---|---|
| 119 | H | 4-chlorophenyl | 4-chlorophenyl | H | —NH— (a = 1) | piperidin-4-yl | 4-methoxy-phenyl-sulfonyl- |
| 120 | H | 4-chlorophenyl | 4-chlorophenyl | H | —NH— (a = 1) | piperidin-4-yl | 4-(aminocarbonyl)-phenyl-sulfonyl- |
| 121 | H | 4-chlorophenyl | 4-chlorophenyl | H | —NH— (a = 1) | piperidin-4-yl | 2-(aminocarbonyl)-phenyl-sulfonyl- |
| 122 | H | 4-chlorophenyl | 4-chlorophenyl | H | —NH— (a = 1) | piperidin-4-yl | 3-(aminocarbonyl)-phenyl-sulfonyl- |
| 125 | H | 4-chlorophenyl | 4-chlorophenyl | H | 1 | piperidin-4-yl | methyl-sulfonyl- |
| 128 | H | 4-chlorophenyl | 4-chlorophenyl | H | —NH— (a = 1) | piperidin-4-yl | 3-carboxy-phenyl-sulfonyl- |
| 129 | H | 4-chlorophenyl | 4-chlorophenyl | H | —NH— (a = 1) | piperidin-4-yl | 4-carboxy-phenyl-sulfonyl- |
| 130 | H | 4-chlorophenyl | 4-chlorophenyl | H | —NH— (a = 1) | piperidin-4-yl | 4-hydroxy-phenyl-sulfonyl- |
| 143 | H | 4-chlorophenyl | 4-chlorophenyl | H | a = 0 | piperidin-4-yl | 1,2,3,4-tetrazol-5-yl-carbonyl- |
| 144 | H | 4-chlorophenyl | 4-chlorophenyl | H | a = 0 | piperidin-4-yl | 1,3,4-triazol-2-yl-sulfonyl- |
| 145 | H | 4-chlorophenyl | 4-chlorophenyl | H | a = 0 | piperidin-4-yl | 1,2,3-triazol-4-yl-carbonyl- |
| 173 | H | 4-chlorophenyl | 4-chlorophenyl | H | a = 0 | piperidin-4-yl | trifluoro-methyl-sulfonyl- |
| 175 | H | 4-chlorophenyl | 4-chlorophenyl | cyclopropyl | a = 0 | piperidin-4-yl | 4-(aminocarbonyl-methoxy)-phenyl |
| 178 | H | 4-chlorophenyl | 4-chlorophenyl | cyclopropyl | a = 0 | piperidin-4-yl | 3-carboxy-phenyl- |
| 179 | H | 4-chlorophenyl | 4-chlorophenyl | cyclopropyl | a = 0 | piperidin-4-yl | 3-(aminocarbonyl)-phenyl- |

TABLE 1-continued

Representative Compounds of Formula (I-A)

(I-A)

| ID No. | R⁰ | A¹ | A² | R¹ | (NH)$_a$ | X (piperidinyl/morpholinyl) | R³ |
|---|---|---|---|---|---|---|---|
| 180 | H | 4-chloro-phenyl | 4-chloro-phenyl | cyclo-propyl | a = 0 | piperidin-4-yl | 3-(carboxy-methyl)-phenyl- |
| 181 | H | 4-chloro-phenyl | 4-chloro-phenyl | cyclo-propyl | a = 0 | piperidin-4-yl | 4-(carboxy-methyl)-phenyl- |
| 182 | H | 4-chloro-phenyl | 4-chloro-phenyl | cyclo-propyl | a = 0 | piperidin-4-yl | 4-(amino-carbonyl-methyl)-phenyl- |
| 187 | OH | 4-chloro-phenyl | 4-carboxy-phenyl | H | a = 0 | piperidin-1-yl | trifluoro-methyl-sulfonyl- |
| 189 | H | 4-chloro-phenyl | 4-chloro-phenyl | cyclo-propyl | a = 0 | piperidin-4-yl | 4-(amino-carbonyl)-phenyl- |
| 190 | H | 4-chloro-phenyl | 4-chloro-phenyl | cyclo-propyl | a = 0 | piperidin-4-yl | 3-(amino-carbonyl-methyl)-phenyl- |
| 191 | H | 4-chloro-phenyl | 4-chloro-phenyl | cyclo-propyl | a = 0 | piperidin-4-yl | 3-(carboxy-methoxy)-phenyl- |
| 192 | H | 4-chloro-phenyl | 4-chloro-phenyl | cyclo-propyl | a = 0 | piperidin-4-yl | 4-(carboxy-methoxy)-phenyl- |
| 198 | H | 4-chloro-phenyl | 4-chloro-phenyl | cyclo-propyl | a = 0 | piperidin-4-yl | 4-carboxy-phenyl- |
| 199 | H | 4-chloro-phenyl | 4-chloro-phenyl | cyclo-propyl | a = 0 | piperidin-4-yl | 3-(amino-carbonyl-methoxy)-phenyl- |
| 201 | H | 4-chloro-phenyl | 4-chloro-phenyl | 2-hydroxy-1,1-dimethyl-ethyl- | a = 0 | piperidin-4-yl | trifluoro-methyl-sulfonyl- |
| 202 | H | 4-chloro-phenyl | 4-chloro-phenyl | 2-hydroxy-1-methyl-ethyl- | a = 0 | piperidin-4-yl | trifluoro-methyl-sulfonyl- |
| 204 | H | 4-chloro-phenyl | 4-carboxy-phenyl | H | a = 0 | piperidin-4-yl | trifluoro-methyl-sulfonyl- |
| 205 | H | 4-chloro-phenyl | 4-amino-carbonyl-phenyl | H | a = 0 | piperidin-4-yl | trifluoro-methyl-sulfonyl- |

TABLE 1-continued

Representative Compounds of Formula (I-A)

| ID No. | R⁰ | A¹ | A² | R¹ | (NH)ₐ | X | R³ |
|---|---|---|---|---|---|---|---|
| 206 | H | 4-chlorophenyl | 4-chlorophenyl | cyclopropyl | a = 0 | piperidin-4-yl | 3-(aminocarbonyl)benzyl- |
| 207 | H | 4-chlorophenyl | 4-chlorophenyl | cyclopropyl | a = 0 | piperidin-4-yl | 3-carboxybenzyl- |
| 208 | H | 4-chlorophenyl | 4-chlorophenyl | H | a = 0 | piperidin-4-yl | 4-(aminocarbonyl)phenyl- |
| 209 | H | 4-chlorophenyl | 4-chlorophenyl | cyclopropyl | a = 0 | piperidin-4-yl | 4-carboxybenzyl- |
| 210 | H | 4-chlorophenyl | 4-chlorophenyl | cyclopropyl | a = 0 | piperidin-4-yl | 4-(aminocarbonyl)benzyl- |
| 211 | H | 4-chlorophenyl | 4-chlorophenyl | H | a = 0 | piperidin-4-yl | 4-(carboxymethoxy)phenyl- |
| 212 | H | 4-chlorophenyl | 4-chlorophenyl | H | a = 0 | piperidin-4-yl | 3-carboxyphenyl- |
| 213 | H | 4-chlorophenyl | 4-chlorophenyl | H | a = 0 | piperidin-4-yl | 4-carboxyphenyl- |
| 214 | H | 4-chlorophenyl | 4-chlorophenyl | H | a = 0 | piperidin-4-yl | 3-(carboxymethyl)phenyl- |
| 215 | H | 4-chlorophenyl | 4-chlorophenyl | H | a = 0 | piperidin-4-yl | 4-(carboxymethyl)phenyl- |
| 216 | H | 4-chlorophenyl | 4-chlorophenyl | H | a = 0 | piperidin-4-yl | 3-(carboxymethoxy)phenyl- |
| 217 | H | 4-chlorophenyl | 4-chlorophenyl | H | a = 0 | piperidin-4-yl | 3-(aminocarbonylmethoxy)phenyl- |
| 218 | H | 4-chlorophenyl | 4-chlorophenyl | H | a = 0 | piperidin-4-yl | 3-(aminocarbonyl)phenyl- |
| 219 | H | 4-chlorophenyl | 4-chlorophenyl | H | a = 0 | piperidin-4-yl | 3-(aminocarbonylmethyl)phenyl- |
| 220 | H | 4-chlorophenyl | 4-chlorophenyl | H | a = 0 | piperidin-4-yl | 3-(aminocarbonyl)benzyl- |
| 221 | H | 4-chlorophenyl | 4-chlorophenyl | H | a = 0 | piperidin-4-yl | 4-carboxybenzyl- |

TABLE 1-continued

Representative Compounds of Formula (I-A)

| ID No. | R⁰ | A¹ | A² | R¹ | (NH)ₐ | X | R³ |
|---|---|---|---|---|---|---|---|
| 222 | H | 4-chloro-phenyl | 4-chloro-phenyl | H | a = 0 | piperidin-4-yl | 4-(amino-carbonyl)-benzyl- |
| 223 | H | 4-chloro-phenyl | 4-chloro-phenyl | H | a = 0 | piperidin-4-yl | 4-(amino-carbonyl-methyl)-phenyl- |
| 224 | H | 4-chloro-phenyl | 4-chloro-phenyl | H | a = 0 | piperidin-4-yl | 4-(amino-carbonyl-methoxy)-phenyl- |
| 225 | H | 4-chloro-phenyl | 4-chloro-phenyl | H | a = 0 | piperidin-4-yl | 3-carboxy-benzyl- |
| 226 | H | 4-chloro-phenyl | 4-amino-carbonyl-phenyl | H | a = 0 | piperazin-1-yl | trifluoro-methyl-sulfonyl- |
| 227 | H | 4-chloro-phenyl | 4-chloro-phenyl | cyclo-propyl | a = 0 | piperidin-4-yl | 4-carboxy-thien-2-yl-methyl- |
| 229 | H | 4-chloro-phenyl | 4-(2-hydroxy-ethyl-amino-carbonyl)-phenyl | H | a = 0 | piperidin-4-yl | trifluoro-methyl-sulfonyl- |
| 230 | H | 4-chloro-phenyl | 4-(2-carboxy-ethyl-amino-carbonyl)-phenyl | H | a = 0 | piperidin-4-yl | trifluoro-methyl-sulfonyl- |
| 231 | H | 4-chloro-phenyl | R*-(4-carboxy-phenyl) | H | a = 0 | piperidin-4-yl | trifluoro-methyl-sulfonyl- |
| 232 | H | 4-chloro-phenyl | S*-(4-carboxy-phenyl) | H | a = 0 | piperidin-4-yl | trifluoro-methyl-sulfonyl- |
| 233 | H | 4-chloro-phenyl | R*-(4-carboxy-phenyl) | H | a = 0 | piperazin-1-yl | trifluoro-methyl-sulfonyl- |
| 234 | H | 4-chloro-phenyl | S*-(4-carboxy-phenyl) | H | a = 0 | piperazin-1-yl | trifluoro-methyl-sulfonyl- |
| 235 | H | 4-chloro-phenyl | 4-chloro-phenyl | cyclo-propyl | a = 0 | piperidin-4-yl | 4-(amino-carbonyl)-thien-2-yl-methyl- |

TABLE 1-continued

Representative Compounds of Formula (I-A)

| ID No. | R⁰ | A¹ | A² | R¹ | (NH)ₐ | X | R³ |
|---|---|---|---|---|---|---|---|
| 236 | H | 4-chloro-phenyl | 4-chloro-phenyl | cyclo-propyl | a = 0 | piperidin-4-yl | 5-carboxy-thien-2-yl-methyl- |
| 240 | OH | 4-chloro-phenyl | 6-carboxy-pyrid-3-yl | H | a = 0 | piperidin-4-yl | trifluoro-methyl-sulfonyl- |
| 241 | H | 4-chloro-phenyl | 6-carboxy-pyrid-3-yl | H | a = 0 | piperidin-4-yl | trifluoro-methyl-sulfonyl- |
| 243 | H | 4-fluoro-phenyl | 4-fluoro-phenyl | cyclo-propyl | a = 0 | piperidin-4-yl | 3-carboxy-benzyl- |
| 244 | H | 4-methyl-phenyl | 4-methyl-phenyl | cyclo-propyl | a = 0 | piperidin-4-yl | 3-carboxy-benzyl- |
| 245 | H | 4-chloro-phenyl | phenyl | cyclo-propyl | a = 0 | piperidin-4-yl | 3-carboxy-benzyl- |
| 246 | H | 4-chloro-phenyl | 4-fluoro-phenyl | cyclo-propyl | a = 0 | piperidin-4-yl | 3-carboxy-benzyl- |
| 247 | H | 4-chloro-phenyl | 4-methyl-phenyl | cyclo-propyl | a = 0 | piperidin-4-yl | 3-carboxy-benzyl- |
| 248 | H | 4-chloro-phenyl | 4-trifluoro-methyl-phenyl | cyclo-propyl | a = 0 | piperidin-4-yl | 3-carboxy-benzyl- |
| 250 | H | 4-chloro-phenyl | 4-chloro-phenyl | cyclo-propyl | a = 0 | piperidin-4-yl | 5-carboxy-furan-2-yl-methyl- |
| 253 | H | 4-chloro-phenyl | 6-(amino-carbonyl)-pyrid-3-yl | H | a = 0 | piperidin-4-yl | trifluoro-methyl-sulfonyl- |
| 254 | H | 4-chloro-phenyl | 4-chloro-phenyl | cyclo-propyl | a = 0 | piperidin-4-yl | 5-(amino-carbonyl)-thien-2-yl-methyl- |
| 258 | H | 4-chloro-phenyl | 4-chloro-phenyl | H | a = 0 | piperidin-4-yl | 4-(methoxy-carbonyl)-benzyl- |
| 259 | H | 4-chloro-phenyl | 4-chloro-phenyl | H | a = 0 | piperidin-4-yl | 3-(methoxy-carbonyl)-benzyl- |
| 260 | H | 4-chloro-phenyl | 4-chloro-phenyl | H | a = 0 | piperidin-4-yl | 5-(methoxy-carbonyl)-furan-2-yl-sulfonyl- |

TABLE 1-continued

Representative Compounds of Formula (I-A)

(I-A)

| ID No. | R⁰ | A¹ | A² | R¹ | (NH)ₐ | [X linker] | R³ |
|---|---|---|---|---|---|---|---|
| 261 | H | 4-chloro-phenyl | 4-chloro-phenyl | H | a = 0 | piperidin-4-yl | 5-carboxy-thien-2-yl-sulfonyl- |
| 262 | H | 4-chloro-phenyl | 4-chloro-phenyl | H | a = 0 | piperidin-4-yl | benzyl-amino-carbonyl- |
| 263 | H | 4-chloro-phenyl | 4-chloro-phenyl | H | a = 0 | piperidin-4-yl | cyclopentyl-amino-carbonyl- |
| 264 | H | 4-chloro-phenyl | 4-chloro-phenyl | H | a = 0 | piperidin-4-yl | ethyl-amino-carbonyl- |
| 265 | H | 4-chloro-phenyl | 4-chloro-phenyl | H | a = 0 | piperidin-4-yl | benzyloxy-carbonyl- |
| 267 | H | 4-chloro-phenyl | 4-chloro-phenyl | H | a = 0 | piperidin-4-yl | phenyloxy-carbonyl- |
| 268 | H | 4-chloro-phenyl | 4-chloro-phenyl | H | a = 0 | piperidin-4-yl | ethoxy-carbonyl- |
| 269 | H | 4-chloro-phenyl | 4-chloro-phenyl | H | a = 0 | pyrrolidin-3-yl | 4-carboxy-phenyl-sulfonyl- |
| 270 | H | 4-chloro-phenyl | 4-chloro-phenyl | H | a = 0 | pyrrolidin-3-yl | 5-carboxy-furan-2-yl-sulfonyl- |
| 271 | H | 4-chloro-phenyl | 4-chloro-phenyl | H | a = 0 | piperidin-4-yl | cyclopentyl-oxy-carbonyl- |
| 272 | H | 4-chloro-phenyl | 4-chloro-phenyl | H | a = 0 | pyrrolidin-3-yl | 3-carboxy-benzyl- |
| 273 | H | 4-chloro-phenyl | 4-chloro-phenyl | H | a = 0 | pyrrolidin-3-yl | 3-carboxy-phenyl-sulfonyl- |
| 274 | H | 4-chloro-phenyl | 4-chloro-phenyl | H | a = 0 | piperidin-4-yl | phenyl-amino-carbonyl- |
| 275 | H | 4-chloro-phenyl | cyclo-propyl | H | a = 0 | piperidin-4-yl | trifluoro-methyl-sulfonyl |
| 277 | H | 4-chloro-phenyl | 4-chloro-phenyl | H | a = 0 | pyrrolidin-3-yl | 3-carboxy-phenyl-CH(CH₃)— |
| 278 | H | 4-chloro-phenyl | 4-chloro-phenyl | H | a = 0 | pyrrolidin-3-yl | 4-carboxy-pyrid-2-yl-CH(CH₃)— |
| 279 | H | 4-chloro-phenyl | cyclo-pentyl | H | a = 0 | piperidin-4-yl | trifluoro-methyl-sulfonyl |

TABLE 1-continued

Representative Compounds of Formula (I-A)

(I-A)

| ID No. | R⁰ | A¹ | A² | R¹ | (NH)ₐ | [piperidine] | R³ |
|---|---|---|---|---|---|---|---|
| 280 | H | 4-chloro-phenyl | cyclohexyl | H | a = 0 | piperidin-4-yl | trifluoro-methyl-sulfonyl |

TABLE 2

Representative Compounds of Formula (I-B)

(I-B)

| ID No. | R⁰ | A¹ | A² | R² | (NH)ₐ | [piperidine] | R³ |
|---|---|---|---|---|---|---|---|
| 110 | H | 4-chloro-phenyl | 4-chloro-phenyl | cyclo-propyl | a = 0 | piperidin-4-yl | hydroxy-methyl-carbonyl- |
| 111 | H | 4-chloro-phenyl | 4-chloro-phenyl | cyclo-propyl | a = 0 | piperidin-4-yl | 3-carboxy-phenyl-carbonyl- |

TABLE 2-continued

Representative Compounds of Formula (I-B)

| ID No. | R⁰ | A¹ | A² | R² | (NH)ₐ | X ring | R³ |
|---|---|---|---|---|---|---|---|
| 112 | H | 4-chloro-phenyl | 4-chloro-phenyl | cyclo-propyl | a = 0 | piperidin-4-yl | 3-(amino-carbonyl)-phenyl-carbonyl- |
| 113 | H | 4-chloro-phenyl | 4-chloro-phenyl | cyclo-propyl | a = 0 | piperidin-4-yl | 4-carboxy-phenyl-carbonyl- |
| 114 | H | 4-chloro-phenyl | 4-chloro-phenyl | cyclo-propyl | a = 0 | piperidin-4-yl | 4-(amino-carbonyl)-phenyl-carbonyl- |
| 116 | H | 4-chloro-phenyl | 4-chloro-phenyl | cyclo-propyl | a = 0 | piperidin-4-yl | 3-carboxy-phenyl-sulfonyl- |
| 117 | H | 4-chloro-phenyl | 4-chloro-phenyl | cyclo-propyl | a = 0 | piperidin-4-yl | 4-carboxy-phenyl-sulfonyl- |
| 118 | H | 4-chloro-phenyl | 4-chloro-phenyl | cyclo-propyl | a = 0 | piperidin-4-yl | 4-(amino-carbonyl)-phenyl-sulfonyl- |
| 123 | H | 4-chloro-phenyl | 4-chloro-phenyl | cyclo-propyl | a = 0 | piperidin-4-yl | 2-carboxy-phenyl-sulfonyl- |
| 124 | H | 4-chloro-phenyl | 4-chloro-phenyl | cyclo-propyl | a = 0 | piperidin-4-yl | 2-(amino-carbonyl)-phenyl-carbonyl- |
| 126 | H | 4-chloro-phenyl | 4-chloro-phenyl | cyclo-propyl | a = 0 | piperidin-4-yl | carboxy-methyl-carbonyl- |
| 127 | H | 4-chloro-phenyl | 4-chloro-phenyl | cyclo-propyl | a = 0 | piperidin-4-yl | 2-carboxy-ethyl-carbonyl- |
| 131 | H | 4-chloro-phenyl | 4-chloro-phenyl | cyclo-propyl | a = 0 | piperidin-4-yl | carboxy-methyl-sulfonyl- |
| 132 | H | 4-chloro-phenyl | 4-chloro-phenyl | cyclo-propyl | a = 0 | piperidin-4-yl | 2-hydroxy-ethyl-carbonyl- |
| 133 | H | 4-chloro-phenyl | 4-chloro-phenyl | cyclo-propyl | a = 0 | piperidin-4-yl | 2-carboxy-ethyl-sulfonyl- |
| 134 | H | 4-chloro-phenyl | 4-chloro-phenyl | cyclo-propyl | a = 0 | piperidin-4-yl | 2-(amino-carbonyl)-ethyl-sulfonyl- |
| 135 | H | 4-chloro-phenyl | 4-chloro-phenyl | cyclo-propyl | a = 0 | piperidin-4-yl | 2-(amino-carbonyl)-ethyl-carbonyl- |
| 136 | H | 4-chloro-phenyl | 4-chloro-phenyl | cyclo-propyl | a = 0 | piperidin-4-yl | trifluoro-methyl-sulfonyl- |

TABLE 2-continued

Representative Compounds of Formula (I-B)

(I-B)

| ID No. | R⁰ | A¹ | A² | R² | (NH)ₐ | | R³ |
|---|---|---|---|---|---|---|---|
| 137 | H | 4-chloro-phenyl | 4-chloro-phenyl | cyclo-propyl | a = 0 | piperidin-4-yl | amino-carbonyl-methyl-sulfonyl- |
| 138 | H | 4-chloro-phenyl | 4-chloro-phenyl | cyclo-propyl | a = 0 | piperidin-4-yl | amino-carbonyl-methyl-carbonyl- |
| 139 | H | 4-chloro-phenyl | 4-chloro-phenyl | cyclo-propyl | a = 0 | piperidin-4-yl | 2-(amino-carbonyl)-phenyl-sulfonyl- |
| 140 | H | 4-chloro-phenyl | 4-chloro-phenyl | cyclo-propyl | a = 0 | piperidin-4-yl | 3-(amino-carbonyl)-phenyl-sulfonyl- |
| 141 | H | 4-chloro-phenyl | 4-chloro-phenyl | cyclo-propyl | a = 0 | piperidin-4-yl | 2-carboxy-phenyl-carbonyl- |
| 146 | H | 4-chloro-phenyl | 4-chloro-phenyl | cyclo-propyl | a = 0 | piperidin-4-yl | 3-methoxy-4-(amino-carbonyl)-phenyl-sulfonyl- |
| 147 | H | 4-chloro-phenyl | 4-chloro-phenyl | cyclo-propyl | a = 0 | piperidin-4-yl | 3-methoxy-4-(methyl-amino-carbonyl)-phenyl-sulfonyl- |
| 149 | H | 4-chloro-phenyl | 4-chloro-phenyl | cyclo-propyl | a = 0 | piperidin-4-yl | 2-hydroxy-phenyl-sulfonyl- |
| 150 | H | 4-chloro-phenyl | 4-chloro-phenyl | cyclo-propyl | a = 0 | piperidin-4-yl | 3-methoxy-phenyl-sulfonyl- |
| 151 | H | 4-chloro-phenyl | 4-chloro-phenyl | cyclo-propyl | a = 0 | piperidin-4-yl | 3-hydroxy-phenyl-sulfonyl- |
| 152 | H | 4-chloro-phenyl | 4-chloro-phenyl | cyclo-propyl | a = 0 | piperidin-4-yl | 4-methoxy-phenyl-sulfonyl- |
| 153 | H | 4-chloro-phenyl | 4-chloro-phenyl | cyclo-propyl | a = 0 | piperidin-4-yl | 3-chloro-4-(amino-carbonyl)-phenyl-sulfonyl- |
| 154 | H | 4-chloro-phenyl | 4-chloro-phenyl | cyclo-propyl | a = 0 | piperidin-4-yl | 3-chloro-4-(methyl-amino- |

TABLE 2-continued

Representative Compounds of Formula (I-B)

(I-B)

| ID No. | R⁰ | A¹ | A² | R² | (NH)ₐ | | R³ |
|---|---|---|---|---|---|---|---|
| 155 | H | 4-chloro-phenyl | 4-chloro-phenyl | cyclo-propyl | a = 0 | piperidin-4-yl | carbonyl)-phenyl-sulfonyl- |
| 156 | H | 4-chloro-phenyl | 4-chloro-phenyl | cyclo-propyl | a = 0 | piperidin-4-yl | 6-(methyl-amino-carbonyl)-pyrid-3-yl-sulfonyl--2-methoxy-phenyl-sulfonyl- |
| 157 | H | 4-chloro-phenyl | 4-chloro-phenyl | cyclo-propyl | a = 0 | piperidin-4-yl | 3-methoxy-4-carboxy-phenyl-sulfonyl- |
| 158 | H | 4-chloro-phenyl | 4-chloro-phenyl | cyclo-propyl | a = 0 | piperidin-4-yl | 3-(amino-carbonyl)-4-methoxy-phenyl-sulfonyl- |
| 159 | H | 4-chloro-phenyl | 4-chloro-phenyl | cyclo-propyl | a = 0 | piperidin-4-yl | 3-(methyl-amino-carbonyl)-4-methoxy-phenyl-sulfonyl- |
| 160 | H | 4-chloro-phenyl | 4-chloro-phenyl | cyclo-propyl | a = 0 | piperidin-4-yl | 6-carboxy-pyrid-3-yl-sulfonyl- |
| 161 | H | 4-chloro-phenyl | 4-chloro-phenyl | cyclo-propyl | a = 0 | piperidin-4-yl | 3-chloro-4-carboxy-phenyl-sulfonyl- |
| 162 | H | 4-chloro-phenyl | 4-chloro-phenyl | cyclo-propyl | a = 0 | piperidin-4-yl | 3-carboxy-4-fluoro-phenyl-sulfonyl- |
| 163 | H | 4-chloro-phenyl | 4-chloro-phenyl | cyclo-propyl | a = 0 | piperidin-4-yl | 3-(amino-carbonyl)-4-fluoro-phenyl-sulfonyl- |
| 164 | H | 4-chloro-phenyl | 4-chloro-phenyl | cyclo-propyl | a = 0 | piperidin-4-yl | 3-carboxy-4-methoxy-phenyl-sulfonyl- |
| 165 | H | 4-chloro-phenyl | 4-chloro-phenyl | cyclo-propyl | a = 0 | piperidin-4-yl | 6-(amino-carbonyl)-pyrid-3-yl-sulfonyl- |
| 166 | H | 4-chloro-phenyl | 4-chloro-phenyl | cyclo-propyl | a = 0 | piperidin-4-yl | 3-fluoro-4-carboxy- |

TABLE 2-continued

Representative Compounds of Formula (I-B)

| ID No. | R⁰ | A¹ | A² | R² | (NH)ₐ | | R³ |
|---|---|---|---|---|---|---|---|
| 167 | H | 4-chloro-phenyl | 4-chloro-phenyl | cyclo-propyl | a = 0 | piperidin-4-yl | phenyl-sulfonyl-3-fluoro-4-(amino-carbonyl)-phenyl-sulfonyl- |
| 168 | H | 4-chloro-phenyl | 4-chloro-phenyl | cyclo-propyl | a = 0 | piperidin-4-yl | 3-carboxy-4-chloro-phenyl-sulfonyl- |
| 169 | H | 4-chloro-phenyl | 4-chloro-phenyl | cyclo-propyl | a = 0 | piperidin-4-yl | 3-(amino-carbonyl)-4-chloro-phenyl-sulfonyl- |
| 170 | H | 4-chloro-phenyl | 4-chloro-phenyl | cyclo-propyl | a = 0 | piperidin-4-yl | 3-(methyl-amino-carbonyl)-4-chloro-phenyl-sulfonyl- |
| 171 | H | 4-chloro-phenyl | 4-chloro-phenyl | cyclo-propyl | a = 0 | piperidin-4-yl | 5-carboxy-furan-2-yl-sulfonyl- |
| 172 | H | 4-chloro-phenyl | 4-chloro-phenyl | cyclo-propyl | a = 0 | piperidin-4-yl | 5-(amino-carbonyl)-furan-2-yl-sulfonyl- |
| 176 | H | 4-chloro-phenyl | 4-chloro-phenyl | cyclo-propyl | a = 0 | piperidin-4-yl | 3-fluoro-4-(methyl-amino-carbonyl)-phenyl-sulfonyl- |
| 183 | H | 4-chloro-phenyl | 4-chloro-phenyl | cyclo-propyl | a = 0 | piperidin-4-yl | 3-carboxy-phenyl- |
| 184 | H | 4-chloro-phenyl | 4-chloro-phenyl | cyclo-propyl | a = 0 | piperidin-4-yl | 3-(amino-carbonyl)-phenyl- |
| 185 | H | 4-chloro-phenyl | 4-chloro-phenyl | cyclo-propyl | a = 0 | piperidin-4-yl | 3-(carboxy-methyl)-phenyl- |
| 186 | H | 4-chloro-phenyl | 4-chloro-phenyl | cyclo-propyl | a = 0 | piperidin-4-yl | 4-(amino-carbonyl-methyl)-phenyl- |
| 193 | H | 4-chloro-phenyl | 4-chloro-phenyl | cyclo-propyl | a = 0 | piperidin-4-yl | 4-carboxy-phenyl- |
| 194 | H | 4-chloro-phenyl | 4-chloro-phenyl | cyclo-propyl | a = 0 | piperidin-4-yl | 4-(amino-carbonyl)-phenyl- |
| 195 | H | 4-chloro-phenyl | 4-chloro-phenyl | cyclo-propyl | a = 0 | piperidin-4-yl | 3-(amino-carbonyl- |

TABLE 2-continued

Representative Compounds of Formula (I-B)

| ID No. | R⁰ | A¹ | A² | R² | (NH)ₐ | [X piperidine] | R³ |
|---|---|---|---|---|---|---|---|
| 196 | H | 4-chloro-phenyl | 4-chloro-phenyl | cyclo-propyl | a = 0 | piperidin-4-yl | methoxy)-phenyl-4-(carboxy-methoxy)-phenyl- |
| 197 | H | 4-chloro-phenyl | 4-chloro-phenyl | cyclo-propyl | a = 0 | piperidin-4-yl | 4-(amino-carbonyl-methoxy)-phenyl- |
| 200 | H | 4-chloro-phenyl | 4-chloro-phenyl | cyclo-propyl | a = 0 | piperidin-4-yl | 3-(carboxy-methoxy)-phenyl- |
| 203 | H | 4-chloro-phenyl | 4-chloro-phenyl | cyclo-propyl | a = 0 | piperidin-4-yl | 4-(carboxy-methyl)-phenyl- |
| 228 | H | 4-chloro-phenyl | 4-chloro-phenyl | cyclo-propyl | a = 0 | piperidin-4-yl | 5-carboxy-furan-2-yl-methyl- |
| 237 | H | 4-chloro-phenyl | 4-chloro-phenyl | cyclo-propyl | a = 0 | piperidin-4-yl | 4-(amino-carbonyl)-thien-2-yl-methyl- |
| 238 | H | 4-chloro-phenyl | 4-carboxy-phenyl | cyclo-propyl | a = 0 | piperidin-4-yl | trifluoro-methyl-sulfonyl- |
| 239 | H | 4-chloro-phenyl | 4-chloro-phenyl | cyclo-propyl | a = 0 | piperidin-4-yl | 4-carboxy-thien-2-yl-methyl- |
| 242 | H | 4-chloro-phenyl | 4-chloro-phenyl | cyclo-propyl | a = 0 | piperidin-4-yl | 5-carboxy-thien-2-yl-methyl- |
| 249 | H | 4-chloro-phenyl | 4-amino-carbonyl-phenyl | cyclo-propyl | a = 0 | piperidin-4-yl | trifluoro-methyl-sulfonyl- |
| 251 | H | 4-chloro-phenyl | 4-chloro-phenyl | cyclo-propyl | a = 0 | piperidin-4-yl | 6-carboxy-pyrid-2-yl-methyl- |
| 252 | H | 4-chloro-phenyl | 4-chloro-phenyl | cyclo-propyl | a = 0 | piperidin-4-yl | 5-carboxy-pyrid-2-yl-methyl- |
| 255 | H | 4-chloro-phenyl | 4-chloro-phenyl | cyclo-propyl | a = 0 | piperidin-4-yl | 5-carboxy-pyrid-3-yl-methyl- |
| 256 | H | 4-chloro-phenyl | 4-chloro-phenyl | cyclo-propyl | a = 0 | piperidin-4-yl | 4-carboxy-benzyl- |
| 257 | H | 4-chloro-phenyl | 4-chloro-phenyl | cyclo-propyl | a = 0 | piperidin-4-yl | 3-carboxy-benzyl- |

Definitions

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$alkyl" shall mean any straight or branched chain composition of between 1 and 4 carbon atoms (including methyl, ethyl, n-propyl, isopropyl, n-butyl, isobutyl and t-butyl).

One skilled in the art will recognize that the term "—($C_{X-Y}$alkyl)-" shall denote any $C_{X-Y}$alkyl straight or branched chain composition as defined above, wherein said $C_{X-Y}$alkyl straight or branched chain composition is divalent and is therefore bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CH_2F$, —$CH_2I$, —$CH_2Br$, —$CH_2Cl$, —$CF_3$, —$CCl_3$, —$CH_2$—$CF_3$, $CH_2$—$CCl_3$, —$CF_2$—$CF_2$—$CF_2$—$CF_3$, and the like. Similarly, the term "fluorinated $C_{1-4}$alkyl" shall mean any $C_{1-4}$alkyl group as defined above substituted with at least one fluoro atom, preferably one to three fluoro atoms. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{X-Y}$alkyl" shall mean any $C_{X-Y}$alkyl group as defined above, substituted with at least one hydroxy group, preferably one to two hydroxy groups, more preferably one hydroxy group; provided that when the "hydroxy substituted $C_{X-Y}$alkyl" is bound to a N or O atom of a substituent group as defined herein, then the hydroxy group(s) on the "hydroxy substituted $C_{X-Y}$alkyl" are not bound to C-1 carbon atom of the $C_{X-Y}$alkyl portion of the "hydroxy substituted $C_{X-Y}$alkyl" (i.e. the hydroxy group(s) are not bound to the carbon atom which is directly bound to the N or O atom of said substituent group). Suitable examples include but are not limited to —$CH_2OH$, —$CH_2CH_2OH$, —$CH(OH)CH_3$, —$CH_2CH_2CH_2OH$, —$CH_2CH(OH)CH_3$, —$CH_2CH_2CH_2CH_2OH$, —$C(CH_2CH_2OH)_2$—$CH_2CH_2OH$, and the like. In an embodiment, the $C_{X-Y}$alkyl is substituted with the hydroxy group(s) at terminal carbon atom(s).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched chain carbon chain composition of between X and Y carbon atoms. For example, "$C_{1-4}$alkoxy" shall mean any oxygen ether radical of the above described straight or branched chain composition of between 1 and 4 carbon atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom.

Suitable examples include but are not limited to —$OCH_2F$, —$OCH_2I$, —$OCH_2Br$, —$OCH_2Cl$, —$OCF_3$, —$OCCl_3$, —$OCH_2$—$CF_3$, —$OCH_2$—$CCl_3$, —$OCF_2$—$CF_2$—$CF_2$—$CF_3$, and the like. Similarly, the term "fluorinated $C_{1-4}$alkoxy" shall mean any $C_{1-4}$alkoxy group as defined above substituted with at least one fluoro atom, preferably one to three fluoro atoms. Suitable examples include but are not limited to —$OCF_3$, —$OCH_2$—$CF_3$, —$OCF_2$—$CF_2$—$CF_2$—$CF_3$, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl. Unless otherwise noted, "$C_{X-Y}$cycloalkyl" wherein X and Y are integers, shall mean a cycloalkyl ring structure as herein defined wherein the ring structure contains between X and Y carbon atoms. For example, $C_{3-6}$cycloalkyl shall include cyclopropyl, cyclobutyl, cyclopentyl and cyclohexyl.

When a particular group is "substituted" (e.g., alkyl, cycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

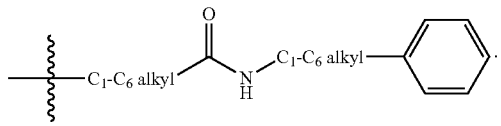

Abbreviations used in the specification, particularly the Schemes and Examples, are as follows:
AcOH=Acetic acid
AIBN=Azobisisobutyronitrile
aq.=Aqueous
BINAP=(2,2'-Bis(diphenylphosphino)-1,1'-binaphthyl)
BLOQ=Below Limit of Quantitation
Boc or BOC=tert-Buroxycarbonyl-
Boc$_2$O=Boc anhydride (i.e. di-tert-butyl dicarbonate)
BSA=Bovine Serum Albumin
cAMP=Cyclic Adenosine Monophosphate
CB1 or CB1R or $CB_1R$=Cannabanoid 1 Receptor
CB2 or CB2R or $CB_2R$=Cannabanoid 2 Receptor
CBz=Carboxybenzyl
Cu(OAc)$_2$=Copper Acetate
DBU=1,8-Diazabicyclo[5.4.0]undec-7-ene
DCC=N, N'-Dicyclohexylcarbodiimide
DCE=1,1-Dichloroethane
DCM=Dichloromethane
DIC=N,N'-diisopropylcarbodiimide
DIPEA or DIEA=Diisopropylethylamine
DME=Dimethoxyethane
DMEM=Dulbecco's Modified Eagle Medium
DMF=N,N-Dimethylformamide
DMSO=Dimethylsulfoxide
dppf=1,1'-Bis(diphenylphosphino)ferrocene
EDCl=1-Ethyl-3-(3-dimethylaminopropyl)carbodiimide
Et$_2$O=Diethyl ether
Et$_3$N or TEA=Triethylamine
Et$_3$SiH=Triethylsilane
EtOAc or EA=Ethyl acetate
FBS=Fetal Bovine Serum
GPCR=G-coupled Receptor HATU=O-(7-Azabenzotriazol-1-yl)-N, N, N",N"-Tetramethyl Uronium Hexafluorophosphate
HBSS=Hank's Balanced Salt Solution
HBTU=N N,N,N',N'-Tetramethyl-O-(1H-benzotriazol-1-yl) uronium hexafluorophosphate
HDL=High Density Lipoprotein
HEPES=4-(2-Hydroxyethyl)-1-Piperazine Ethane Sulfonic Acid
HPLC=High Performance Liquid Chromatography
Hunig's Base Diisopropylethylamine
KHMDS=Potassium bis(trimethylsilyl)amide
LADA=Latent Autoimmune Diabetes of Adults
LCMS=Liquid Chromatography-Mass Spectrometry
LDL=Low Density Lipoprotein
LiHMDS=Lithium bis(trimethylsilyl)amide
MeCN=Acetonitrile
MeOH=Methanol
Mesyl=Methylsulfonyl
Mesyl Chloride=Methylsulfonyl chloride
MTBE=Methyl t-butyl ether
Na(OAc)$_3$BH or =Sodium triacetoxyborohydride NaBH(OAc)$_3$
NaHDMS=Sodium bis(trimethylsilyl)amide
NASH=NonAlcoholic Steatohepatitis
NBS=N-Bromosuccinimide
n-BuLi=n-Butyl Lithium
NMR=Nuclear magnetic Resonance
NSB=Non-Specific Binding
PBS=Phosphate Buffered Saline
Pd(dppf)Cl$_2$=[1,1'-Bis(diphenylphosphino) ferrocene]dichloropalladium(II)
Pd(PPh$_3$)$_4$=Tetrakistriphenylphosphine palladium (0)
Pd$_2$(dba)$_3$=Tris(dibenzylidene acetone)dipalladium(0)
Pd(OAc)$_2$=Palladium acetate
Pd—C or Pd/C=Palladium on Carbon Catalyst
PE=Petroleum ether
Ph=Phenyl
sec-BuLi=sec-Butyl lithium
t-BuLi or tert-BuLi=tert-Butyl lithium
TEA=Triethylamine
Tf=Trifluoromethane sulfonyl
TFA=Trifluoroacetic Acid
Tf$_2$O=Trifluoromethane sulfonic anhydride
THF=Tetrahydrofuran
THP=Tetrahydropyranyl
Tosyl=p-Toluenesulfonyl
Tris HCl or Tris-Cl=Tris[hydroxymethyl]aminomethyl hydrochloride
Trityl Triphenylmethyl-
TsOH or p-TsOH=p-Toluene sulfonic acid
XANTPhos=4,5-Bis(diphenylphosphino)-9,9-dimethylxanthene
XPhos or X-Phos=2-Dicyclohexylphosphino-2',4',6'-triisopropylbiphenyl The compounds of the present invention are CB-1 inverse agonists useful for the treatment and/or prevention of metabolic disorders, including obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain. Preferably, the metabolic disorder is selected from the group consisting of obesity, Type II diabetes, and dyslipidemias. More preferably, the metabolic disorder is obesity or Type II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of one or more additional symptoms; and/or (d) delay or avoidance of the development or progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named. One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one Step of a process, the individual reagents are independently selected for each reaction Step and may be the same or different from each other. For example wherein two steps of a process recite an organic or inorganic base as a reagent, the organic or inorganic base selected for the first Step may be the same or different than the organic or inorganic base of the second step. Further, one skilled in the art will recognize that wherein a reaction Step of the present invention may be carried out in a variety of solvents or solvent systems, said reaction Step may also be carried out in a mixture of the suitable solvents or solvent systems. Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

One skilled in the art will recognize that during any of the processes for preparation of the compounds of the present invention, as herein described in more detail, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T.W. Greene & P.G.M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($R$moles−$S$moles)/($R$moles+$S$moles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee=([\alpha-obs]/[\alpha-max])\times100$.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

General Synthesis Schemes

Compounds of formula (I-A), wherein a is 0 (—NH— is absent) and wherein

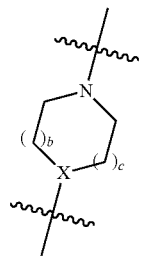

is azetidin-1,3-diyl, pyrrolidin-1,3-diyl or piperidin-1,4-diyl may be prepared from the corresponding, suitably substituted intermediate compound of formula (II)

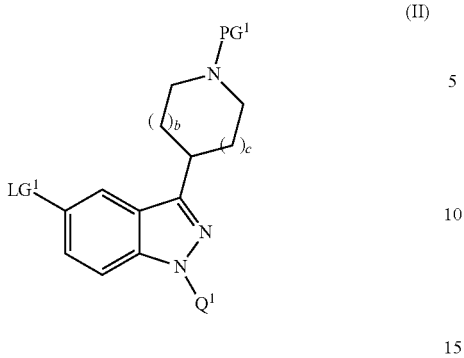

(II)

wherein PG¹ is a suitably selected nitrogen protecting group such as Tf, Boc, Cbz, and the like; wherein LG¹ is a suitably selected leaving group such as Br, I, and the like; and wherein Q¹ is R¹ or is a suitably selected nitrogen protecting group such as THP, trityl, Boc, CBz, phenylsulfonyl-, and the like.

Compounds of formula (II) wherein LG¹ is Br, and the like, may be prepared according to the process as outlined in Scheme 1, below.

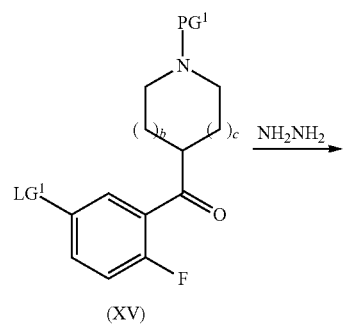

(XV)

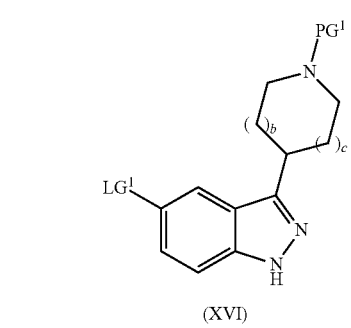

(XVI)

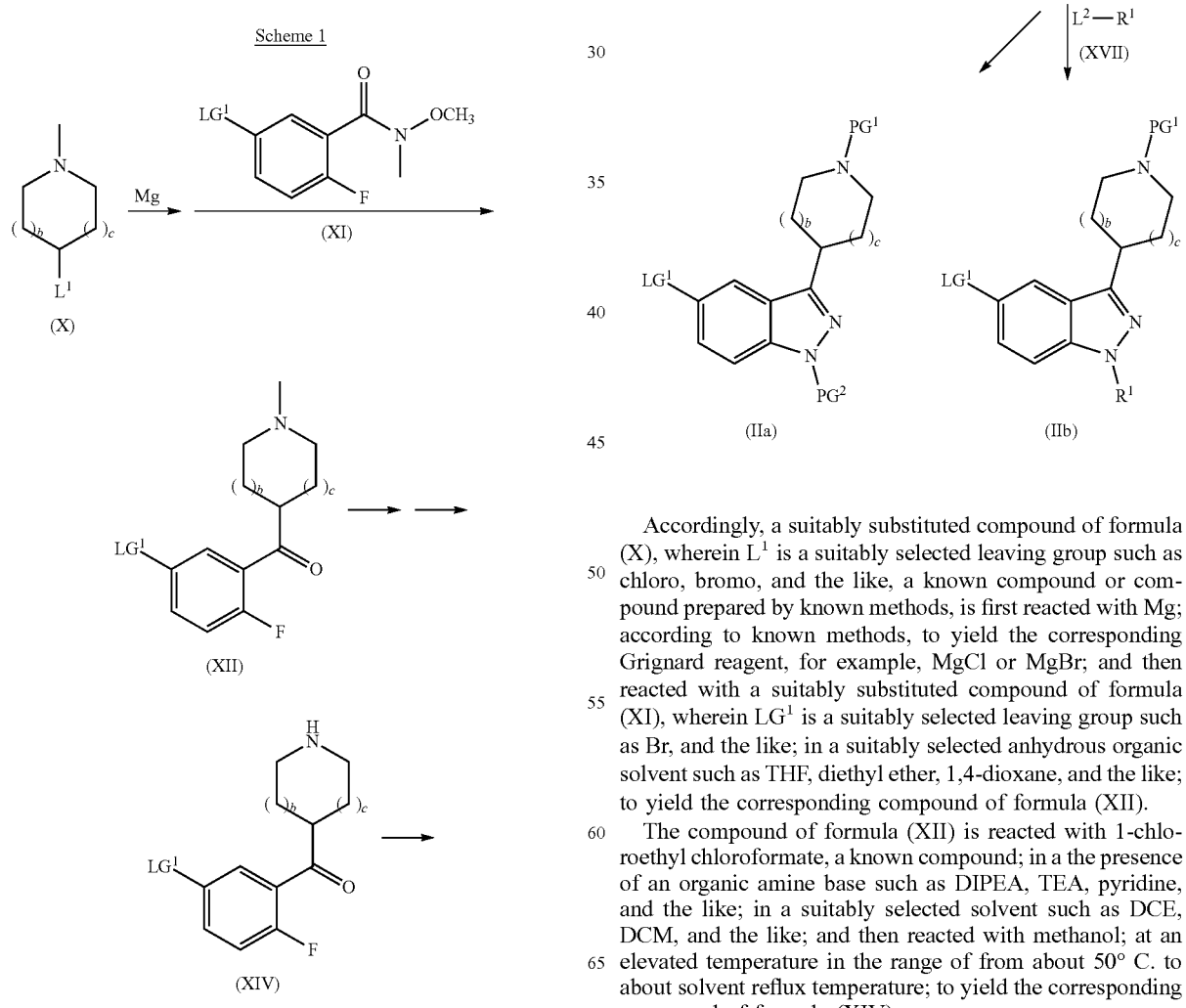

Accordingly, a suitably substituted compound of formula (X), wherein $L^1$ is a suitably selected leaving group such as chloro, bromo, and the like, a known compound or compound prepared by known methods, is first reacted with Mg; according to known methods, to yield the corresponding Grignard reagent, for example, MgCl or MgBr; and then reacted with a suitably substituted compound of formula (XI), wherein LG¹ is a suitably selected leaving group such as Br, and the like; in a suitably selected anhydrous organic solvent such as THF, diethyl ether, 1,4-dioxane, and the like; to yield the corresponding compound of formula (XII).

The compound of formula (XII) is reacted with 1-chloroethyl chloroformate, a known compound; in a the presence of an organic amine base such as DIPEA, TEA, pyridine, and the like; in a suitably selected solvent such as DCE, DCM, and the like; and then reacted with methanol; at an elevated temperature in the range of from about 50° C. to about solvent reflux temperature; to yield the corresponding compound of formula (XIV).

The compound of formula (XIV) is protected at the nitrogen atom with a suitably selected nitrogen protecting group such as Tf, Boc, and the like, according to known methods to yield the corresponding compound of formula (XV). For example, the compound of formula (XIV) is reacted with Boc$_2$O.Tf$_2$O in the presence of a suitably selected organic amine base such as TEA, in a suitably selected organic solvent such as DCM, to yield the corresponding compound of formula (XV), wherein PG$^1$ is Boc or Tf, respectively. One skilled in the art will recognize that in some compounds of the present invention, the Tf protecting group corresponds to the desired substituent group.

The compound of formula (XV) is reacted with hydrazine, a known compound; optionally in the presence of a suitably selected base such as DIPEA, TEA, pyridine, and the like; optionally in a suitably selected solvent such as DME, 1,4-dioxane, ethanol, and the like; preferably at about reflux temperature; to yield the corresponding compound of formula (XVI).

One skilled in the art will recognize that the compound of formula (XVI) corresponds to the compound of formula (II) wherein Q$^1$ is R$^1$ and R$^1$ is hydrogen.

The compound of formula (XVI) is protected at the 1-indazole nitrogen according to known methods; to yield the corresponding compound of formula (IIa), the compound of formula (II) wherein Q$^1$ is a suitably selected nitrogen protecting group, PG$^2$. For example, the compound of formula (XVI) is reacted with trityl chloride, in the presence of a suitably selected base such as TEA, K$_2$CO$_3$, and the like; in a suitably selected solvent such as acetonitrile, DCM, DMF, and the like; to yield the corresponding compound of formula (IIa) wherein PG$^2$ is trityl.

Alternatively, the compound of formula (XVI) is reacted with a suitably substituted compound of formula (XVII), wherein L$^2$ is a suitably selected leaving group such as Br, I, and the like, a known compound or compound prepared by known methods; in the presence of a suitably selected base such as K$_2$CO$_3$, Cs$_2$CO$_3$, TEA, and the like; in a suitably selected solvent such as acetonitrile, DMF, DCM, and the like; to yield the corresponding compound of formula (IIb), the compound of formula (II) wherein Q$^1$ is R$^1$.

Compounds of formula (I-A), wherein a is 0 (—NH— is absent) and wherein

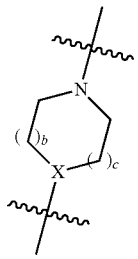

is pyrrolidin-1,3-diyl or piperidin-1,4-diyl may alternatively be prepared from the corresponding, suitably substituted intermediate compound of formula (III)

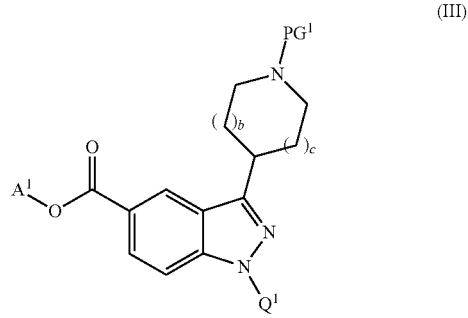

(III)

wherein A$^1$ is a C1-4alkyl (preferably methyl); wherein PG$^1$ is a suitably selected nitrogen protecting group such as Tf, Boc, CBz, and the like; and wherein Q$^1$ is R$^1$ or is PG$^2$, a suitably selected nitrogen protecting groups such as THP, trityl, Boc, CBz, phenyl-sulfonyl- and the like.

Compounds of formula (III) may be prepared according to the process outlined in Scheme 2, below.

Scheme 2

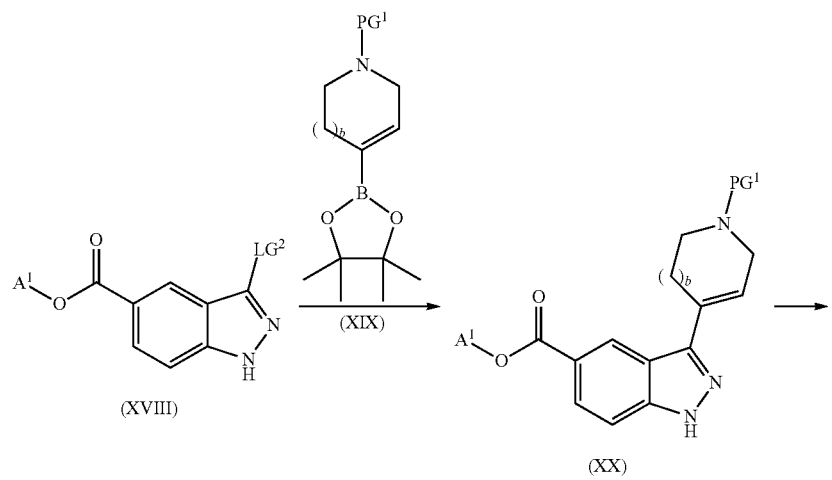

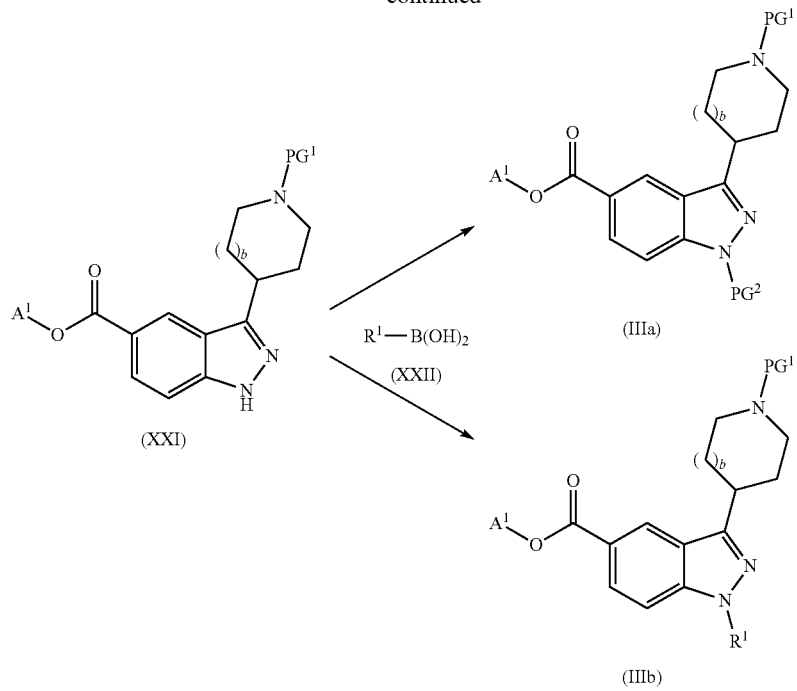

Accordingly, a suitably substituted compound of formula (XVIII), wherein $A^1$ is a $C_{1-4}$alkyl, preferably methyl or ethyl, more preferably methyl, and wherein $LG^2$ is a suitably selected leaving groups such as Br, I, and the like; a known compound or compound prepared by known methods, is reacted with a suitably substituted compound of formula (XIX), wherein b is in integer from 0 to 1, and wherein $PG^1$ is a suitably selected nitrogen protecting group such as Boc, CBz, Tf, and the like; in the presence of a suitably selected catalyst such as $Pd(OAc)_2$, $Pd_2(dba)_3$, and the like; in the presence of a suitably selected ligand such as S-Phos, X-Phos, BINAP, and the like; in the presence of a suitably selected base such as $K_3PO_4$, $Cs_2CO_3$, $K_2CO_3$, and the like; in a suitably selected solvent such as toluene, 1,4-dioxane, DME, water, and the like; to yield the corresponding compound of formula (XX).

The compound of formula (XX) is reacted with ammonium formate, a known compound; in the presence of a Pd/C catalyst; in a suitably selected solvent such as methanol, ethanol, and the like; at about reflux temperature; to yield the corresponding compound of formula (XXI). Alternatively, the compound of formula (XX) is hydrogenated according to known methods, for example by reacting with hydrogen in the presence of a catalyst such as Pd/C.

One skilled in the art will recognize that the compound of formula (XXI) corresponds to the compound of formula (III) wherein $Q^1$ is $R^1$ and wherein $R^1$ is hydrogen.

The compound of formula (XXI) is reacted with a suitably substituted boronic acid, a compound of formula (XXII), a known compound or compound prepared by known methods; in the presence of a suitably selected catalyst such as $Cu(OAc)_2$, and the like; in the presence of pyridine or TEA; and in the presence of a suitably selected inorganic base such as $Na_2CO_3$, $K_2CO_3$, $Cs_2CO_3$, and the like; optionally in a suitably selected solvent such as THF, DCE, and the like; to yield the corresponding compound of formula (IIIb)—a compound of formula (III) wherein $Q^1$ is $R^1$ other than hydrogen.

Alternatively, the compound of formula (XXI) is protected at the 1-indazole nitrogen according to known methods; to yield the corresponding compound of formula (IIIa)—a compound of formula (III) wherein $Q^1$ is $PG^2$, a suitably selected nitrogen protecting group such as THP, trityl, Boc, Cbz, phenyl-sulfonyl-, and the like.

Alternatively, the compound of formula (XXI) is reacted with a suitably selected alkylating agent, a compound of the formula $R^1$—I, $R^1$—Br, and the like; to yield the corresponding compound of formula (III) where $R^1$ is alkyl. Alternatively the compound of formula (XXI) can be reacted with a suitably substituted reactive ester (for example an alpha-bromo-ester such as ethyl bromo acetate, alpha-dimethyl bromo acetate, alpha-methyl alpha bromo acetate) to yield the corresponding compound of formula (III) wherein $R^1$ is the corresponding alkyl ester; and wherein the $R^1$ alkyl ester substituent group may be further functionalized according to known methods (for example, as described in the Examples which follow hereinafter). One skilled in the art will further recognize that the 1-position on the indazole core may be alternatively reacted according to known methods; to yield the corresponding acylated or sulfonylated substituent group.

Compounds of formula (I-A) wherein a is 0 and

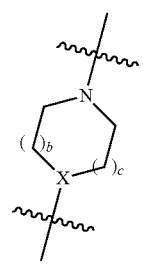

is piperazin-1,4-diyl, and compounds of formula (I-A) wherein a is 1 (i.e. wherein —NH— is present) and wherein

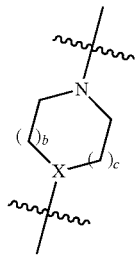

is selected from the group consisting of azetidin-1,3-diyl, pyrrolidin-1,3-diyl, piperidin-1,4-diyl and piperazin-1,4-diyl, may be prepared from the corresponding, suitably substituted intermediate compound of formula (IVa)

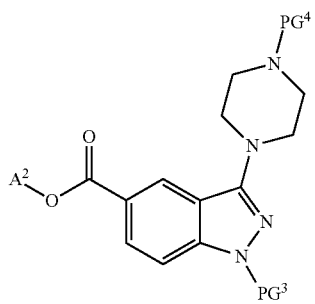

(IVa)

wherein $A^2$ is a $C_{1-4}$alkyl (preferably methyl); and wherein $PG^3$ and $PG^4$ are each an independently selected nitrogen protecting group; or intermediate compound of formula (IVb)

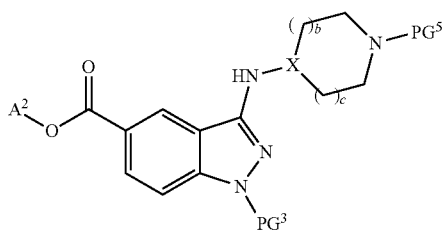

(IVb)

wherein $A^2$ is a $C_{1-4}$alkyl (preferably methyl;) and wherein $PG^3$ and $PG^5$ are each an independently selected nitrogen protecting group.

Compounds of formula (IVa) and (IVb) may be prepared according to the process outlined in Scheme 3, below.

Scheme 3

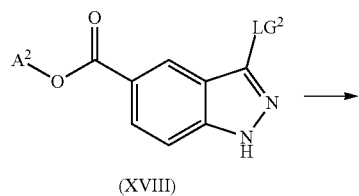

(XVIII)

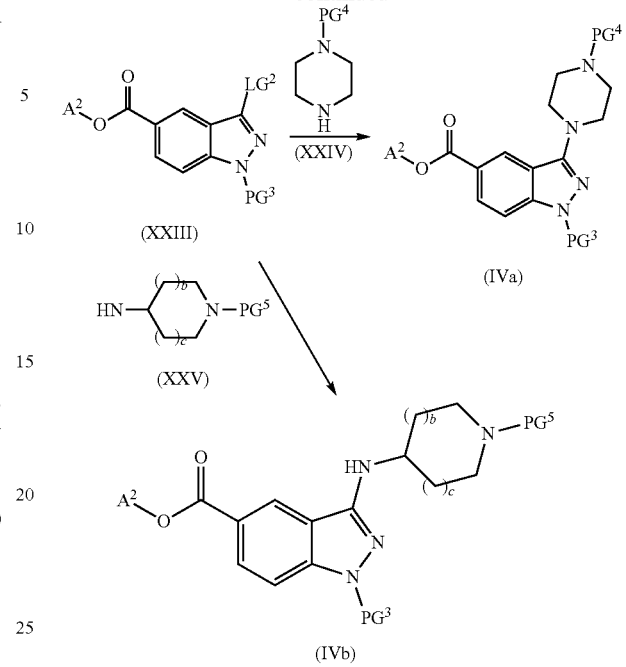

Accordingly, a suitably substituted compound of formula (XVIII), wherein $LG^2$ is a suitably selected leaving group such as Br, I, and the like, a known compound or compound prepared by known methods, is protected at the 1-indazolyl nitrogen atom according to known methods; to yield the corresponding compound of formula (XXIII). In an example, the compound of formula (XVIII) is reacted with trityl chloride, phenyl-sulfonyl chloride, and the like; in a suitably selected solvent; to yield the corresponding compound of formula (XXIII), wherein $PG^3$ is trityl or phenyl-sulfonyl-, respectively. Alternatively, the compound of formula (XXVIII) is reacted 3,4-dihydro-2H-pyran, a known compound, in the presence of TsOH, in an organic solvent such as DCM; to yield the corresponding compound of formula (XXIII) wherein $PG^3$ is THP (tetrahydropyranyl).

The compound of formula (XXIII) is reacted with a suitably substituted compound of formula (XXIV), wherein $PG^4$ is a suitably selected nitrogen protecting group such as Tf, Boc, Cbz, and the like; in the presence of a suitably selected coupling agent such as $Pd(OAc)_2$, $Pd_2(dba)_3$, and the like; in the presence of a suitably selected ligand such as BINAP, S-Phos, XantPhos, X-Phos, and the like; in the presence of a suitably selected base such as $Cs_2CO_3$, $K_2CO_3$, and the like; in a suitably selected solvent such as toluene, 1,4-dioxane, DMF, and the like; to yield the corresponding compound of formula (IVa).

Alternatively, the compound of formula (XXIII) is reacted with a suitably substituted compound of formula (XXV), wherein $PG^5$ is a suitably selected nitrogen protecting group such as Tf, Boc, Cbz, and the like; in the presence of a suitably selected coupling agent such as $Pd(OAc)_2$, $Pd_2(dba)_3$, and the like; in the presence of a suitably selected ligand such as BINAP, S-Phos, XantPhos, X-Phos, and the like; in the presence of a suitably selected base such as $Cs_2CO_3$, $K_2CO_3$, and the like; in a suitably selected solvent such as toluene, 1,4-dioxane, DMF, and the like; to yield the corresponding compound of formula (IVb).

One skilled in the art will recognize that the compounds of formula (IVa) may be further optionally reacted according to known methods, to remove the PG³ protecting group (according to known methods) and then further reacted with a suitably substituted compound of formula (XVII) or a suitably substituted compound of formula (XXII), to yield the corresponding compound of formula wherein the 1-indazole nitrogen is substituted with the desired R¹ group.

Compounds of formula (II), formula (III), formula (IVa) and formula (IVb) may be reacted as described in Schemes 4-6 below, to yield the corresponding intermediate compound of formula (V)

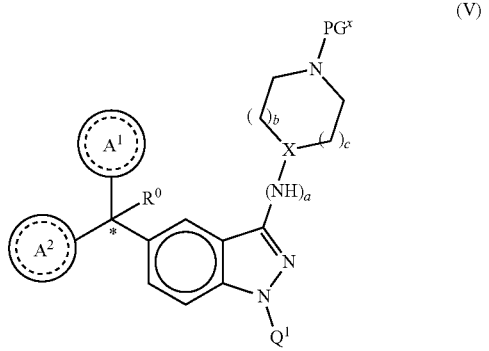

(V)

wherein PG^X is a suitably selected nitrogen protecting group and wherein Q¹ is PG^Y (a suitably selected nitrogen protecting group) or is R¹ (wherein R¹ is preferably other than hydrogen).

Compounds of formula (V) may be prepared according to the procedure as outlined in Scheme 4 below.

Scheme 4

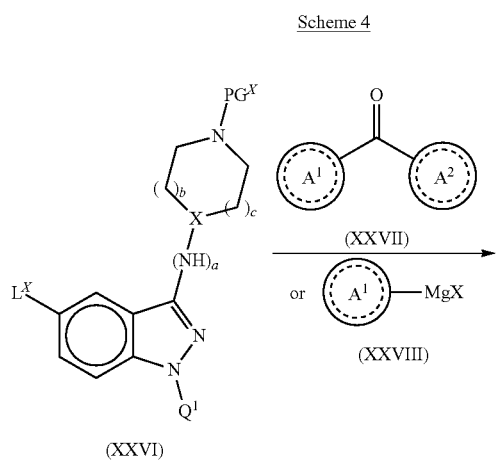

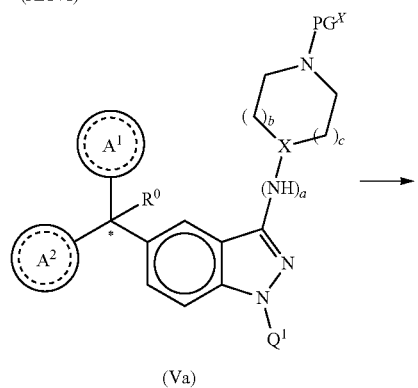

(Va)

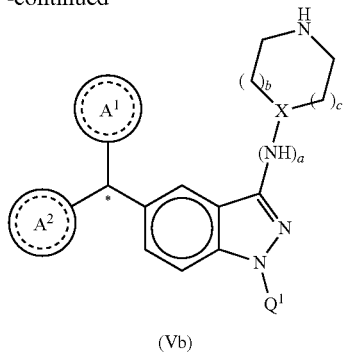

(Vb)

Accordingly, a suitably substituted compound of formula (XXVI), wherein L^X is a suitably selected leaving group such as Br, I, $C_{1-4}$alkyl-O—C(O)—, and the like, wherein PG^X is a suitably selected nitrogen protecting group and wherein Q¹ is R¹ or is a suitably selected nitrogen protecting group, such as Tf, Boc, and the like; a known compound or compound prepared as herein described, is reacted first with a suitably substituted alkyl lithium reagent such as n-BuLi, sec-BuLi, t-BuLi, and the like; and then reacted with a suitably substituted compound of formula (XXVII), wherein

and

are the same or are different, a known compound or compound prepared by known methods; in a suitably selected organic solvent such as THF, diethyl ether, and the like; to yield the corresponding compound of formula (Va). Wherein the compound of formula (XXVI), a is 1 (i.e. wherein the —NH— group is present), then the compound of formula (XXVI) is first reacted with a suitably selected base such as KHMDS, LiHMDS, NaHMDS, NaH, and the like; prior to reacting with the suitably selected alkyl lithium reagent and the compound of formula (XXVII), wherein

and

are the same or are different; to yield the corresponding compound of formula (Va). One skilled in the art will recognize that when the compound of formula (XXVI) a is 1 (i.e. wherein the —NH— group is present), then L^X is selected from the group consisting of $C_{1-4}$alkyl-OC(O)—, preferably $L^X$ is $CH_3$—OC(O)— or $CH_3CH_2$—OC(O)—.

Alternatively, a suitably substituted compound of formula (XXVI), wherein $L^X$ is selected from the group consisting of $C_{1-4}$alkyl-OC(O)—, preferably, LX is $CH_3OC(O)$—, wherein $PG^X$ is a suitably selected nitrogen protecting group and wherein $Q^1$ is $R^1$ or is a suitably selected nitrogen protecting group, a known compound or compound prepared as herein described is reacted with an excess of (preferably greater than at least two molar equivalents of) a suitably substituted compound of formula (XXVIII), wherein X is Br or CI, a known compound or compound prepared by known methods; under Grignard conditions, in a suitably selected anhydrous organic solvent such as THF, diethyl ether, and the like; to yield the corresponding compound of formula (Va), wherein (A¹)

and (A²)

are the same.

The compound of formula (Va) is then further optionally reacted with $Et_3SiH$ in combination with TFA, or $SnCl_2$ in combination with HCl or $TiCl_4$ in combination with $Et_3SiH$; in a suitably selected organic solvent such as DCM, DCE, and the like; to yield the corresponding compound of formula (Vb).

One skilled in the art will recognize that wherein the compound of formula (Va), $Q^1$ is a nitrogen protecting group, said nitrogen protecting group may be removed when reacting the compound of formula (Va) with for example $Et_3SiH/TFA$, such that in the resulting compound of formula (Vb), $Q^1$ is hydrogen.

Compounds of formula (V) may alternatively be prepared according to the process outlined in Scheme 5, below.

Scheme 5

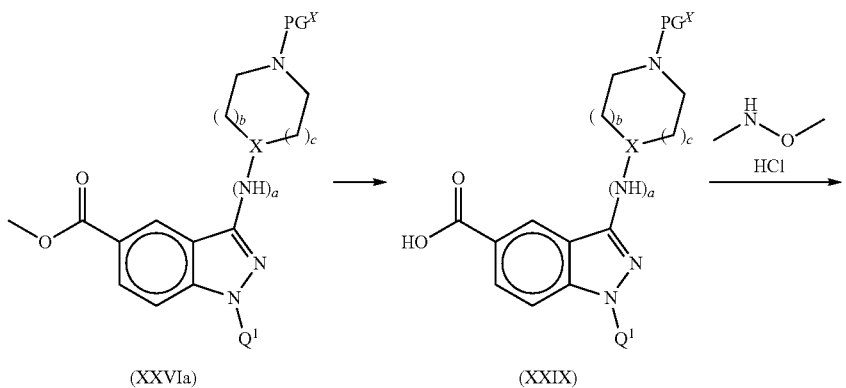

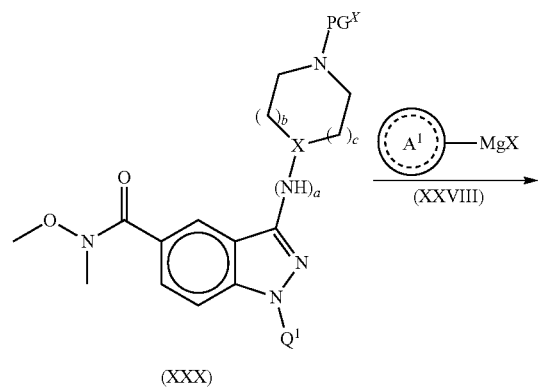

-continued

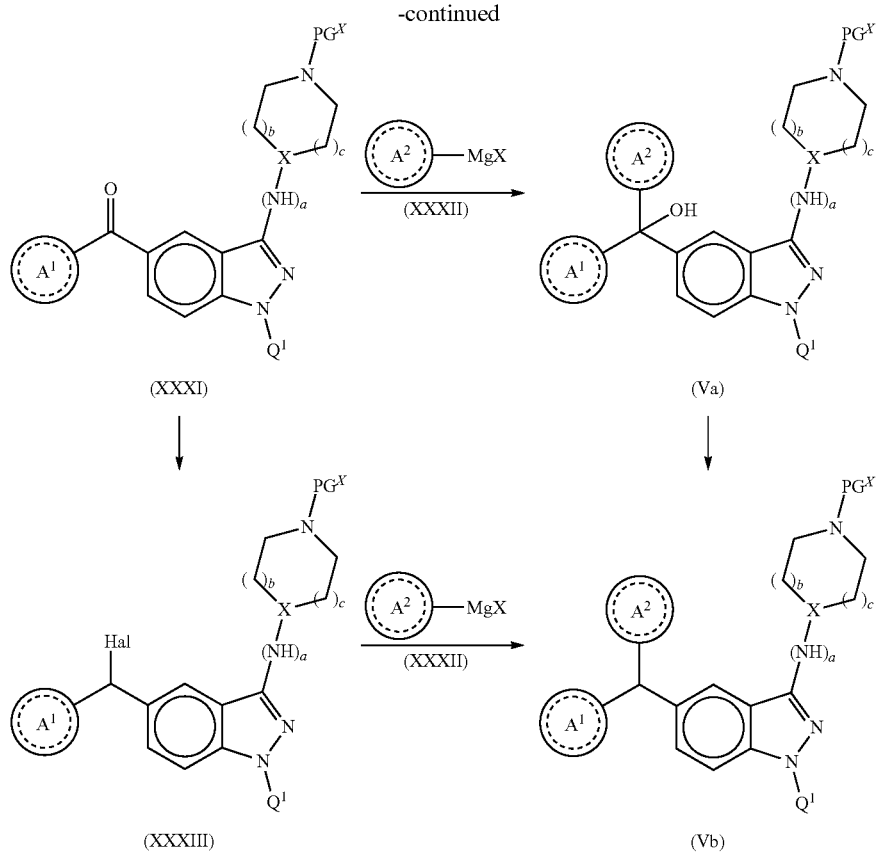

(XXXI)

(Va)

(XXXIII)

(Vb)

Accordingly, a suitably substituted compound of formula (XXVIa) (a compound of formula (XXVI wherein $L^X$ is —C(O)OCH$_3$) wherein PG$^X$ is a suitably selected nitrogen protecting group and wherein $Q^1$ is $R^1$ or is a suitably selected nitrogen protecting group, is reacted with a suitably selected base such as LiOH, NaOH, and the like; in a suitably selected solvent or mixture of solvent and water such as 1,4-dioxane/water, THF/water, methanol/water, ethanol/water, and the like; to yield the corresponding compound of formula (XXIX).

The compound of formula (XXIX) is reacted with N,O-dimethylhydroxylamine hydrochloride (also known as methoxymethylamine hydrochloride or Weinreb amide), a known compound, in the presence of a suitably selected coupling agent such as HATU, DIC, EDCl, and the like; in the presence of a suitably selected organic amine base such as DIPEA, TEA, pyridine, and the like; in a suitably selected solvent such as DCM, DMF, and the like; to yield the corresponding compound of formula (XXX).

The compound of formula (XXX) is reacted with a suitably substituted compound of formula (XXVIII) wherein X is Br or Cl, a known compound or compound prepared by known methods; under Grignard conditions, in a suitably selected anhydrous organic solvent such as diethyl ether, THF, and the like; to yield the corresponding compound of formula (XXXI).

The compound of formula (XXXI) is reacted with a suitably substituted compound of formula (XXXII), wherein X is Br or Cl, a known compound or compound prepared by known methods; under Grignard conditions, in a suitably selected anhydrous organic solvent such as diethyl ether, THF, and the like; to yield the corresponding compound of formula (Va).

The compound of formula (Va) is reacted with Et$_3$SiH in combination with TFA, or SnCl$_2$ in combination with HCl or TiCl$_4$ in combination with Et$_3$SiH; in a suitably selected organic solvent such as DCM, DCE, and the like; to yield the corresponding compound of formula (Vb).

Alternatively, the compound of formula (XXXI) is reacted with sodium borohydride in a suitably selected solvent such as methanol, ethanol, and the like; and the resulting intermediate is then reacted a suitably selected halogenating (preferably chlorinating) agent such as SOCl$_2$, mesyl chloride, and the like; in a suitably selected solvent such as DCM, and the like; at about reflux temperature; to yield the corresponding compound of formula (XXXIII).

The compound of formula (XXXIII) is reacted with a suitably substituted compound of formula (XXXII), X is Br or Cl, a known compound or compound prepared by known methods; under Grignard conditions, in the presence of a suitably selected zinc compound, such as Zn Cl, and the like; in a suitably selected anhydrous organic solvent such as diethyl ether, THF, and the like; to yield the corresponding compound of formula (Vb).

One skilled in the art will recognize that in the process as described in Scheme 5 above, the

and

groups may be incorporated into the desired compound in either order. Accordingly, the compound of formula (XXX) may alternatively be reacted first with a suitably substituted compound of formula (XXXII) and the resulting intermediate then reacted with a suitably substituted compound of formula (XXVIII), as described above, to yield the corresponding compound of formula (Va).

Compounds of formula (Va) and (Vb) wherein a is 0 (i.e wherein the —NH— group is absent), may alternatively be prepared according to the process outlined in Scheme 6, below.

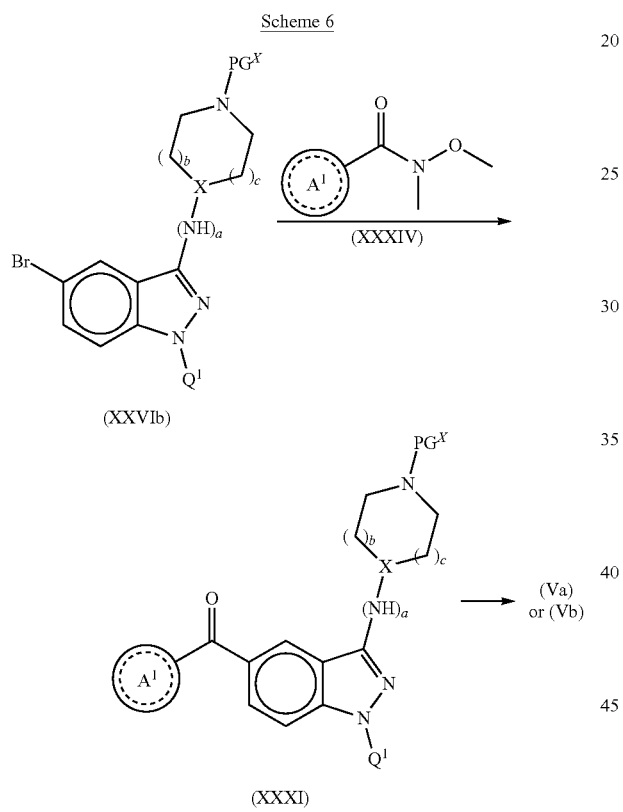

Accordingly, a suitably substituted compound of formula (XXVIb) (a compound of formula (XXVII) wherein $L^X$ is Br) wherein $PG^X$ is a suitably selected nitrogen protecting group and wherein $Q^1$ is $R^1$ or is a suitably selected nitrogen protecting group, is reacted with a suitably substituted compound of formula (XXXIV), a known compound or compound prepared by known methods; in the presence of a suitably selected organolithium reagent such as n-BuLi, t-BuLi, and the like; in a suitably selected solvent such as THF, DME, 1,4-dioxane, and the like; to yield the corresponding compound of formula (XXXI).

The compound of formula (XXXI) is then reacted as described in Scheme 5 above, to yield the corresponding compound of formula (Va) or formula (Vb), as desired.

Compounds of formula (I-A) may be prepared from the corresponding suitably substituted intermediate compound of formula (Vb) as outlined in Scheme 7, below.

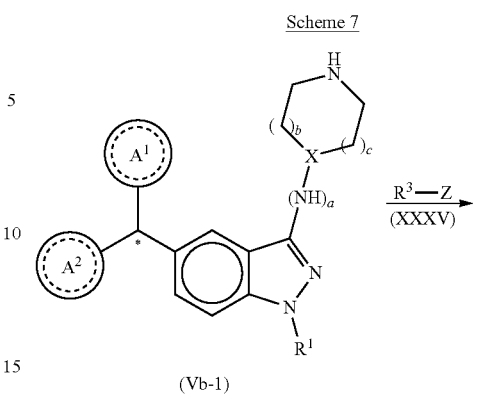

Accordingly, a suitably substituted compound of formula (Vb-1), a compound of formula (Vb) wherein $Q^1$ is $R^1$, is reacted with a suitably substituted compound of formula (XXXV), wherein Z is a suitably selected group such as Cl, Br, I, OH, and the like, a known compound or compound prepared by known methods; according to known methods; to yield the corresponding compound of formula (I-A).

For example, wherein $R^3$ is bound through a —$SO_2$— group, the compound of formula (XXXV) is the corresponding sulfonyl chloride and the compound of formula (Vb-1) is reacted with the compound of formula (XXXV) in the presence of a suitably selected tertiary organic base such as TEA, Hunig's base, and the like; in a suitably selected solvent such as DCM, THF, and the like.

In another example, wherein $R^3$ is bound through a —C(O)— group, the compound of formula (XXXV) is the corresponding acid chloride, and the compound of formula (Vb-1) is reacted with the compound of formula (XXXV) in the presence of a suitably selected tertiary organic base such as TEA, Hunig's base, and the like; in a suitably selected solvent such as DCM, THF, and the like. Alternatively, wherein $R^3$ is bound through a —C(O)— group, the compound of formula (XXXV) is the corresponding carboxylic acid, and the compound of formula (Vb-1) is reacted with the compound of formula (XXXV) in the presence of a suitably selected peptide coupling agent such as DCC, HATU, HBTU, EDCl, and the like; optionally in the presence of a suitably selected base such as Hunig's base, TEA, and the like; in a suitably selected solvent such as DMF, DCM, and the like.

In another example, wherein $R^3$ is an optionally substituted phenyl or pyridyl, and the like, the compound of formula (XXXV) is the corresponding bromo-substituted phenyl or bromo-substituted pyridyl, and the compound of formula (Vb-1) is reacted with the compound of formula (XXXV) in the presence of a suitably selected catalyst such as Pd$_2$(dba)$_3$, Pd(OAc)$_2$, and the like; in the presence of a suitably selected ligand such as BINAP, dppf, XantPhos, XPhos, and the like; in the presence of a suitably selected base such as Cs$_2$CO$_3$, K$_2$CO$_3$, K$_3$PO$_4$, and the like; in a suitably selected organic solvent such as 1,4-dioxane, toluene, THF, DME, and the like.

In another example, wherein R$^3$ is -L$^1$R$^4$ and L$^1$ is an alkyl chain such as —CH$_2$—, —CH(CH$_2$)—, and the like, the compound of formula (I-A) may be prepared by reacting a suitably substituted compound of formula (Vb-1) with a suitably substituted, optionally protected aldehyde (a compound of the formula (R$^4$—C(O)H, wherein the R$^4$ group may be optionally protected at reactive N or O atom(s)), in the presence of a suitably selected reducing agent such as NaBH(OAc)$_3$, sodium cyanoborohydride, and the like; optionally in the presence of a suitably selected organic amine base such as TEA, and the like; in a suitably selected solvent such as DCM, and the like.

In another example, wherein R$^3$ is -L$^1$R$^4$ and L$^1$ is —C(O)NH—, the compound of formula (I-A) may be prepared by reacting a suitably substituted compound of formula (Vb-1) with a suitably substituted compound of the formula O=C=N—R$^4$, a known compound or compound prepared by known methods, in the presence of a suitably selected organic base such as TEA, DIPEA, pyridine, and the like; in a suitably selected solvent such as DCM, DMF, and the like.

In another example, wherein R$^3$ is -L$^1$R$^4$ and L$^1$ is an ester such as —C(O)O—CH$_2$CH$_2$—, and the like, the compound of formula (I-A) may be prepared by reacting a suitably substituted compound of formula (Vb-1) with a suitably substituted compound of the formula Cl—C(O)O—R$^4$, a known compound or compound prepared by known methods, in the presence of a suitably selected organic base such as TEA, DIPEA, pyridine, and the like; in a suitably selected solvent such as DCM, THF, and the like.

Compounds of formula (I-A) wherein R$^1$ is other than hydrogen may be prepared from the corresponding suitably substituted compound of formula (I-A) wherein R$^1$ is hydrogen as outlined in Scheme 8, below.

Scheme 8

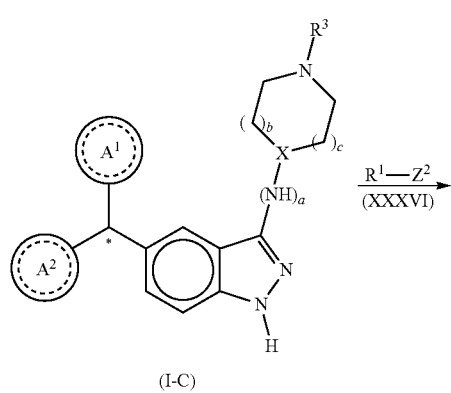

(I-C)

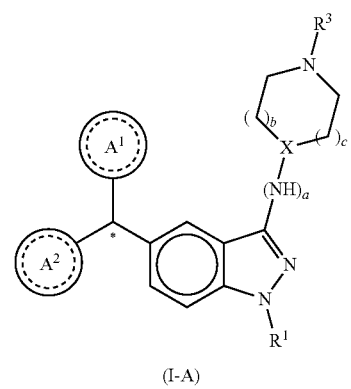

(I-A)

Accordingly, a suitably substituted compound of formula (I-A) wherein R$^1$ is hydrogen is reacted with a suitably substituted compound of formula (XXXVI), wherein Z$^2$ is a suitably selected leaving group such as Br, Cl, and the like, according to known methods, for example as described in Scheme 7 above; to yield the corresponding compound of formula (I-A) wherein R$^1$ is other than hydrogen.

As outlined in Scheme 7 and 8 above, one skilled in the art will recognize that the R$^1$ substituent group may be incorporated into the compounds of formula (I-A) before or after coupling of the R$^3$ group and/or before or after coupling of the

and

groups.

One skilled in the art will further recognize that in the processes as described in the Schemes above, when the desired R$^1$ substituent group is hydrogen, then the 1-indazole nitrogen atom in each of the intermediate compounds is preferably protected with a suitably selected nitrogen protecting groups. The nitrogen protecting group on the 1-indazole is then removed according to known methods, as the final Step of the synthesis of the desired compound of formula (I-A).

One skilled in the art will further recognize that wherein the R$^1$ substituent group is other than hydrogen and is incorporated after the coupling of the R$^3$ group and/or the

and

groups, then the 1-indazole nitrogen atom is preferably protected with a suitably selected nitrogen protecting group prior to coupling of the $R^3$ group and/or the

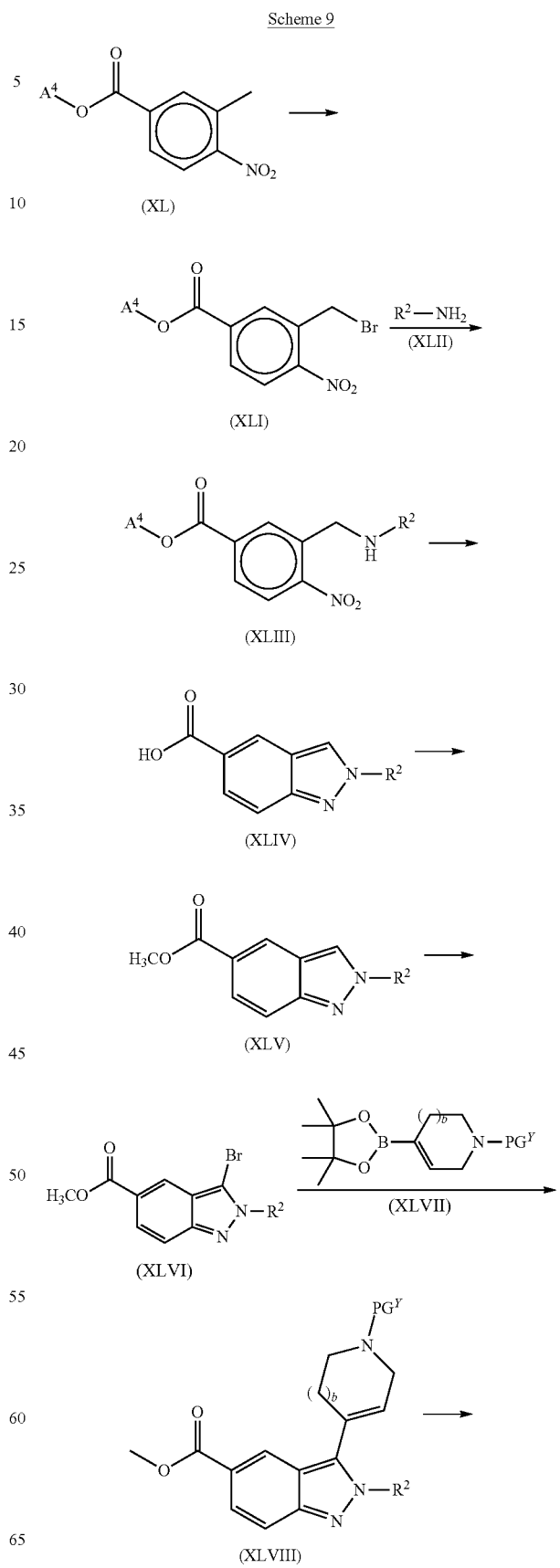

Scheme 9 and groups, de-protected following the coupling and then further reacted to functionalize with the desired $R^1$ substituent group.

Compounds of formula (I-B) may be prepared from the corresponding, suitably substituted intermediate compound of formula (VI)

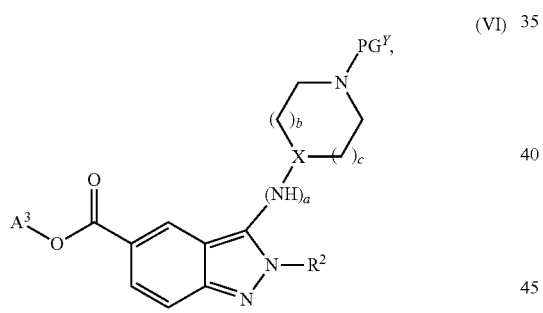

(VI)

wherein $A^3$ is selected from the group consisting of $C_{1-4}$alkyl, preferably methyl or ethyl, more preferably methyl.

Compounds of formula (VI) wherein a is 0 (i.e. wherein the —NH— group is absent) and wherein

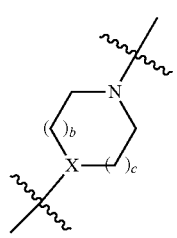

is pyrrolidin-1,3-diyl or piperidin-1,4-diyl, may be prepared as outlined in Scheme 9 below.

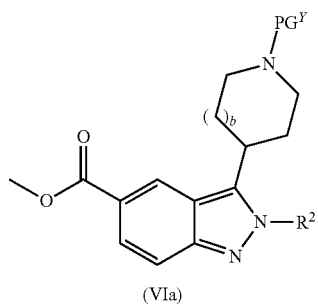

(VIa)

Accordingly, a suitably substituted compound of formula (XL), a known compound or compound prepared by known methods, is reacted with a suitably selected brominating agent such as NBS, and the like; in the presence of a suitably selected initiator such as benzyl peroxide, AIBN, and the like; in a suitably selected solvent such as $CCl_4$, DCM, and the like; to yield the corresponding compound of formula (XLI).

The compound of formula (XLI) is reacted with a suitably substituted compound of formula (XLII), a known compound or compound prepared by known methods; in the presence of a suitably selected base such as $K_2CO_3$, $Cs_2CO_3$, and the like; in the presence of a suitably selected organic base such as TEA, DIPEA, and the like; in a suitably selected solvent such as acetonitrile, DMF, and the like; to yield the corresponding compound of formula (XLIII).

The compound of formula (XLIII) is reacted with zinc; in the presence of a suitably selected base such as NaOH, KOH, and the like; in a suitably selected solvent such as a mixture of 1,4-dioxane and water, and the like; to yield the corresponding compound of formula (XLIV).

The compound of formula (XLIV) is reacted with $CH_3I$, in the presence of a suitably selected base such as $K_2CO_3$, $Na_2CO_3$, $Cs_2CO_3$, and the like; in a suitably selected solvent such as DMF, acetonitrile, and the like; to yield the corresponding compound of formula (XLV).

The compound of formula (XLV) is reacted with a suitably selected brominating agent such as NBS, $Br_2$, and the like; in the presence of a suitably selected solvent such as acetic acid, and the like; to yield the corresponding compound of formula (XLVI).

The compound of formula (XLVI) is reacted with a suitably substituted compound of formula (XLVII), a known compound or compound prepared by known methods; in the presence of a suitably selected catalyst such as $Pd(OAc)_2$, $Pd(PPh_3)_4$, $Pd_2(dba)_3 \cdot CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XLVIII).

The compound of formula (XLVIII) is reacted with ammonium formate, a known compound; in the presence of a Pd/C catalyst; in a suitably selected solvent such as methanol, ethanol, and the like; at about reflux temperature; to yield the corresponding compound of formula (VIa). Alternatively, the compound of formula (XLVIII) is hydrogenated according to known methods, for example by reacting with hydrogen in the presence of a catalyst such as Pd/C.

Compounds of formula (VI) wherein

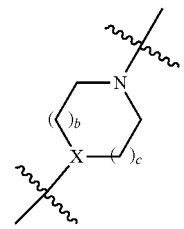

is piperazin-1,4-diyl, and compounds of formula (VI) wherein a is 1 (—NH— is present) may be prepared as outlined in Scheme 10, below.

Scheme 10

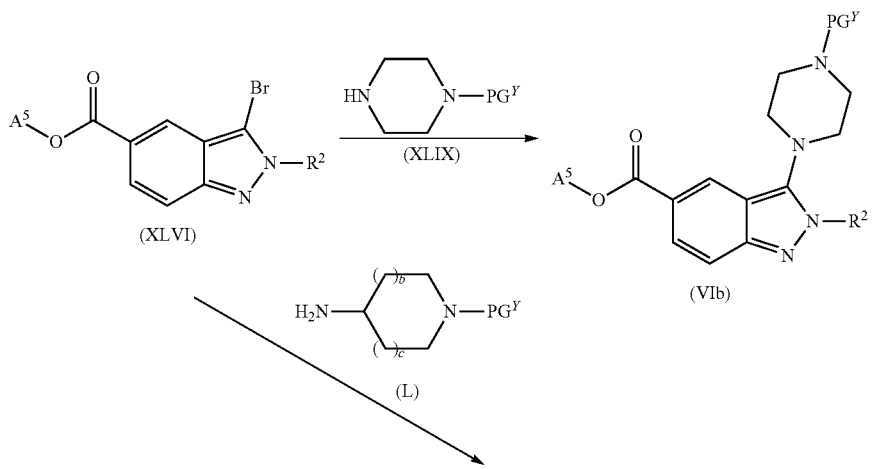

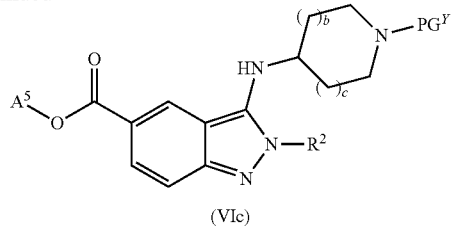

(VIc)

Accordingly, a suitably substituted compound of formula (XLVI), wherein $A^5$ is selected from the group consisting of $C_{1-4}$alkyl, preferably methyl or ethyl, more preferably, methyl, a known compound or compound prepared by known methods or prepared as described herein, is reacted with a suitably substituted compound of formula (XLIX), a known compound or compound prepared by known methods, wherein $PG^Y$ is a suitably selected nitrogen protecting group such as Tf, Boc, Cbz, and the like; in the presence of a suitably selected coupling agent such as $Pd(OAc)_2$, $Pd_2(dba)_3$, and the like; in the presence of a suitably selected ligand such as BINAP, S-Phos, XantPhos, X-Phos, and the like; in the presence of a suitably selected base such as $Cs_2CO_3$, $K_2CO_3$, and the like; in a suitably selected solvent such as toluene, 1,4-dioxane, DMF, and the like; to yield the corresponding compound of formula (VIb).

Alternatively, a suitably substituted compound of (XLVI) is reacted with a suitably substituted compound of formula (L), wherein $PG^Y$ is a suitably selected nitrogen protecting group such as Tf, Boc, Cbz, and the like; in the presence of a suitably selected coupling agent such as $Pd(OAc)_2$, $Pd_2(dba)_3$, and the like; in the presence of a suitably selected ligand such as BINAP, S-Phos, XantPhos, X-Phos, and the like; in the presence of a suitably selected base such as $Cs_2CO_3$, $K_2CO_3$, and the like; in a suitably selected solvent such as toluene, 1,4-dioxane, DMF, and the like; to yield the corresponding compound of formula (VIc).

Compounds of formula (I-B) may be prepared, for example, as outlined in Schemes 4-5 by substituting a suitably substituted compound of formula (VI) for the compound of formula (XXVI) and reacting as described therein, to yield the corresponding compound of formula (VII)

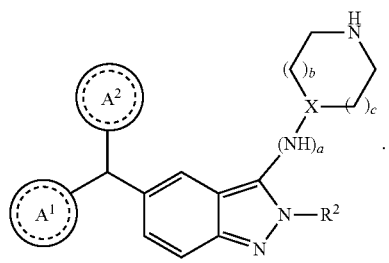

The compound of formula (VII) is then substituted for the compound of formula (Vb-1) in Scheme 7, and reacted as described therein, to yield the corresponding compound of formula (I-B).

One skilled in the art will recognize that in certain compounds of formula (I), the nitrogen protecting group(s) may constitute the desired $R^1$, $R^2$ and/or $R^3$ substituent groups. One skilled in the art will further recognize that for such compounds, the nitrogen protecting group is either not removed or is coupled onto the desired position, according to known nitrogen-protecting conditions, to the yield desired the compound of formula (I).

One skilled in the art will further recognize that in any of the processes described herein, the

and

rings (as substituent groups or in reagents containing said substituent groups) may be interchanged, and the synthesis completed as described, to yield the corresponding desired compound.

One skilled in the art will further recognize that the reaction steps and processes described herein (in the Synthesis Schemes and Examples) may be adapted and/or applied to the synthesis of any of the compounds of the present invention.

Pharmaceutical Compositions and Method of Treatment

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation.

Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.5 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may contain suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of metabolic disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.01 to about 50.0 mg/kg of body weight per day, or any amount or range therein. More preferably, from about 0.05 to about 15.0 mg/kg of body weight per day, or any amount or range therein. More preferably, from about 0.07 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Synthesis Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example PH-1

5-(bis(4-chlorophenyl)methyl)-3-(1-(trifluoromethyl-sulfonyl)piperidin-4-yl)-1H-indazole

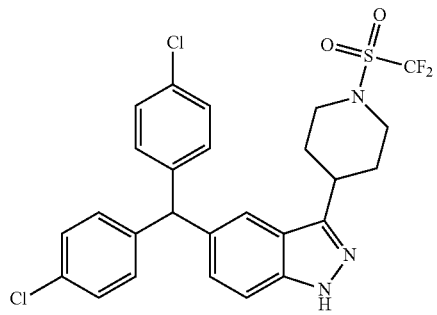

Step 1: Synthesis of
5-bromo-2-fluoro-N-methoxy-N-methylbenzamide

Into a 500-mL oven-dried round-bottom flask, was placed a solution of 5-bromo-2-fluorobenzoic acid (100 g, 456.6 mmol) in thionyl chloride (250 mL). After the reaction was stirred for 3 h under reflux under nitrogen, a solution of methoxy(methyl)amine hydrochloride (53.4 g, 547.4 mmol) in pyridine (200 mL), triethylamine (139 g, 1.37 mol) were added successively at 0° C. The resulting solution was stirred for 5 h at room temperature, and then concentrated under vacuum. The residue was purified on a silica gel column eluted with ethyl acetate/petroleum ether (0:100-2:1) to yield 5-bromo-2-fluoro-N-methoxy-N-methylbenzamide as yellow oil. LC/MS (ES, m/z): 386 [M+H]$^+$.

Step 2: Synthesis of 4-[(5-bromo-2-fluorophenyl)carbonyl]-1-methylpiperidine

Into a 1000-mL oven-dried 3-necked round-bottom flask purged and maintained under nitrogen, were added a solution of Mg (8.8 g, 366.7 mmol) in tetrahydrofuran (100 mL), 4-chloro-1-methylpiperidine (40.7 g, 304.6 mmol). After the reaction solution was refluxed for 2 h, a solution of 5-bromo-2-fluoro-N-methoxy-N-methylbenzamide (40 g, 152.6 mmol) in tetrahydrofuran (400 mL) was added, and the resulting solution was stirred overnight at room temperature, and then saturated sodium bicarbonate solution (200 mL) was carefully added, and extracted with ethyl acetate (3×200 mL). The combined organic extract was dried over sodium sulfate and concentrated under vacuum. The residue was purified on a silica gel column eluted with dichloromethane/methanol (20:1) to yield 4-[(5-bromo-2-fluorophenyl)carbonyl]-1-methylpiperidine as a yellow solid. LC/MS (ES, m/z): 300 [M+H]$^+$ Step 3: Synthesis of 1-chloroethyl 4-[(5-bromo-2-fluorophenyl)carbonyl]piperidine-1-carboxylate Into a 250-mL oven-dried round-bottom flask, were placed a solution of 4-[(5-bromo-2-fluorophenyl)carbonyl]-1-methylpiperidine (6.0 g, 20.0 mmol) in DCE (120 mL), 1-chloroethyl chloroformate (11.4 g, 80.3 mmol) and DIEA (12.9 g, 99.8 mmol). The resulting solution was stirred for 2 h at room temperature, and then concentrated under vacuum to yield 1-chloroethyl 4-[(5-bromo-2-fluorophenyl)carbonyl]piperidine-1-carboxylate as a yellow oil. LC/MS (ES, m/z): 393 [M+H]$^+$ Step 4: Synthesis of 4-[(5-bromo-2-fluorophenyl)carbonyl]piperidine Into a 250-mL oven-dried round-bottom flask, was placed a solution of 1-chloroethyl 4-[(5-bromo-2-fluorophenyl)carbonyl]piperidine-1-carboxylate (8 g, 16.3 mmol) in methanol (150 mL). The resulting solution was stirred for 2 h at 75° C. in an oil bath under nitrogen, and then concentrated under vacuum. The residue was suspended in ethyl acetate and the insoluble material was collected by filtration to yield 4-[(5-bromo-2-fluorophenyl)carbonyl]piperidine as a white solid. LC/MS (ES, m/z): 286 [M+H]$^+$ Step 5: Synthesis of 4-[(5-bromo-2-fluorophenyl)carbonyl]-1-(trifluoromethane)sulfonylpiperidine Into a 1000-mL oven-dried round-bottom flask, were placed a solution of 4-[(5-bromo-2-fluorophenyl)carbonyl]piperidine (25 g, 87.4 mmol) in dichloromethane (800 mL), triethylamine (44.4 g, 439.2 mmol). To the mixture was then added Tf$_2$O (27.2 g, 96.4 mmol) dropwise at −10° C. The resulting solution was stirred overnight at room temperature under nitrogen, and then washed with water (3×100 mL). The combined organic extract was dried over anhydrous sodium sulfate and then concentrated under vacuum. Flash chromatography of the residue on a silica gel column eluted with ethyl acetate/petroleum ether (1:20) yielded 4-[(5-bromo-2-fluorophenyl)carbonyl]-1-(trifluoromethane)sulfonylpiperidine as a yellow solid. LC/MS (ES, m/z): 418 [M+H]$^+$ Step 6: Synthesis of 5-bromo-3-[1-(trifluoromethane)sulfonylpiperidin-4-yl]-1H-indazole Into a 250-mL oven-dried round-bottom flask, was placed a solution of 4-[(5-bromo-2-fluorophenyl)carbonyl]-1-(trifluoromethane)sulfonylpiperidine (8.5 g, 20.3 mmol) in hydrazine monohydrate (150 mL). The resulting solution was heated to reflux under nitrogen overnight in an oil bath, and then concentrated under vacuum. The residue was purified on a silica gel column eluted with ethyl acetate/petroleum ether (0:100-1:1) to yield 5-bromo-3-[1-(trifluoromethane)sulfonylpiperidin-4-yl]-1H-indazole as a white solid. LC/MS (ES, m/z): 412 [M+H]$^+$ Step 7: Synthesis of 5-bromo-3-[1-(trifluoromethane)sulfonylpiperidin-4-yl]-1-(triphenylmethyl)-1H-indazole Into a 250-mL round-bottom flask, were placed a solution of 5-bromo-3-[1-(trifluoromethane)sulfonylpiperidin-4-yl]-1H-indazole (2.0 g, 4.8 mmol) in CH$_3$CN (100 mL), potassium carbonate (3.4 g, 24.3 mmol) and (chlorodiphenylmethyl)benzene (5.4 g, 19.4 mmol). The resulting solution was stirred under nitrogen for 3.5 h at room temperature, and then concentrated under vacuum. The residue was suspended in H$_2$O (100 mL), and then extracted with DCM (3×80 mL). The combined organic extract was dried over anhydrous sodium sulfate and then concentrated under vacuum. Precipitation of the residue in diethyl ether yielded 5-bromo-3-[1-(trifluoromethane)sulfonylpiperidin-4-yl]-1-(triphenylmethyl)-1H-indazole as a white solid. LC/MS (ES, m/z): 654.5 [M+H]$^+$ Step 8: Synthesis of (4-chlorophenyl)[4-(trifluoromethoxy)phenyl]methanone Into a 250-mL oven-dried round-bottom flask purged and maintained nitrogen, was placed a solution of 1-bromo-4-(trifluoromethoxy)benzene (5.0 g, 20.8 mmol) in tetrahydrofuran (60 mL), followed by dropwise addition of 2.5 M solution of n-BuLi in hexanes (9.2 mL, 23.0 mmol) at −78° C. After 30 min, a solution of 4-chloro-N-methoxy-N-methylbenzamide (4.15 g, 20.8 mmol) in tetrahydrofuran (20 mL) was added. The resulting solution was stirred for 5 h at room temperature, and then saturated sodium bicarbonate solution (150 mL) was added. The mixture was extracted with ethyl acetate (3×150 mL). The combined organic extract was dried over sodium sulfate and concentrated under vacuum. The residue was purified on a silica gel column eluted with ethyl acetate/petroleum ether (0:100-1:20) to yield (4-chlorophenyl)[4-(trifluoromethoxy)phenyl]methanone as a white solid.

Step 9: Synthesis of bis(4-chlorophenyl)([3-[1-(trifluoromethane)sulfonylpiperidin-4-yl]-1-(triphenylmethyl)-1H-indazol-5-yl])methanol Into a 50-mL oven-dried round-bottom flask purged and maintained under nitrogen, was placed a solution of 5-bromo-3-[1-(trifluoromethane)sulfonylpiperidin-4-yl]-1-(triphenylmethyl)-1H-indazole (200.0 mg, 0.31 mmol) in tetrahydrofuran (15 mL) followed by dropwise addition of 2.5 M solution of n-BuLi in hexanes (0.154 mL, 0.38 mmol) at −78° C. After 30 min, a solution of bis(4-chlorophenyl)methanone (76.1 mg, 0.30 mmol) in tetrahydrofuran (5 mL) was added. The resulting solution was stirred for 4 h at room temperature and then saturated sodium bicarbonate solution (150 mL) was added. The mixture was extracted with ethyl acetate (3×150 mL). The combined organic extract was dried over sodium sulfate and concentrated under vacuum to yield bis(4-chlorophenyl)([3-[1-(trifluoromethane)sulfonylpiperidin-4-yl]-1-(triphenylmethyl)-1H-indazol-5-yl])methanol as a yellow oil. LC/MS (ES, m/z): 827 [M+H]$^+$.

Step 10: Synthesis of bis(4-chlorophenyl)([3-[1-(trifluoromethane)sulfonylpiperidin-4-yl]-1H-indazol-5-yl])methanol Into a 25-mL round-bottom flask, were placed a solution of bis(4-chlorophenyl)([3-[1-(trifluoromethane)sulfonylpiperidin-4-yl]-1-(triphenylmethyl)-1H-indazol-5-yl])methanol (300.0 mg, 0.11 mmol) in dichloromethane (2 mL) and trifluoroacetic acid (1 mL). The resulting solution was stirred under nitrogen for 5 h at room temperature, and then concentrated under vacuum. The residue was purified on a silica gel column eluted with ethyl acetate/petroleum ether (0:100-100:0) to yield bis(4-chlorophenyl)([3-[1-(trifluoromethane)sulfonylpiperidin-4-yl]-1H-indazol-5-yl])methanol as a white solid. LC/MS (ES, m/z): 584 [M+H]$^+$.

Step 11: Synthesis of 5-[bis(4-chlorophenyl)methyl]-3-[1-(trifluoromethane)sulfonylpiperidin-4-yl]-1H-indazole Into a 25-mL round-bottom flask, were placed a solution of bis(4-chlorophenyl)([3-[1-(trifluoromethane)sulfonylpiperidin-4-yl]-1H-indazol-5-yl])methanol (40.0 mg, 0.07 mmol) in dichloromethane (5 mL), Et$_3$SiH (39.5 mg, 0.34 mmol) and trifluoroacetic acid (135.7 mg, 1.19 mmol). The resulting solution was stirred for 0.5 h at room temperature. After diluted with DCM (15 mL), the resulting mixture was washed with water (3×10 mL). The organic layer was dried over anhydrous sodium sulfate and concentrated under vacuum. The residue was purified on a silica gel column eluted with ethyl acetate/petroleum ether (0:100-100:0) to yield 5-[bis(4-chlorophenyl)methyl]-3-[1-(trifluoromethane)sulfonylpiperidin-4-yl]-1H-indazole as a white solid.

$^1$HNMR (300 MHz, CDCl$_3$) δ: 7.47 (d, J=8.7 Hz, 1H), 7.19-7.35 (m, 5H), 7.03 (d, J=8.4 Hz, 4H), 5.62 (s, 1H), 4.04-4.08 (m, 2H), 3.29 (brm, 3H), 2.05-2.13 (m, 4H). LC/MS (ES, m/z): 568 [M+H]$^+$.

Example PH-2

5-((4-chlorophenyl)(4-(trifluoromethoxy)phenyl)methyl)-3-(1-(trifluoromethylsulfonyl)piperidin-4-yl)-1H-indazole

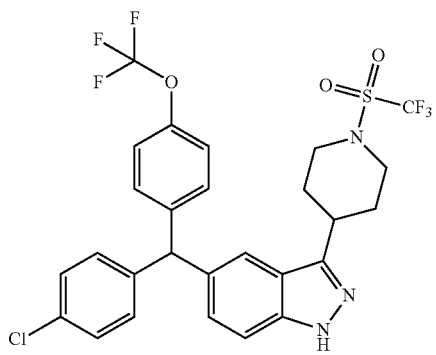

Step 1: Synthesis of (4-chlorophenyl)[4-(trifluoromethoxy)phenyl]methanone

Into a 250-mL oven-dried round-bottom flask purged and maintained under nitrogen, was placed a solution of 1-bromo-4-(trifluoromethoxy)benzene (5.0 g, 20.8 mmol) in tetrahydrofuran (60 mL), followed by dropwise addition of 2.5M solution of n-BuLi in hexanes (9.2 mL, 23.0 mmol) at −78° C. In 30 min a solution of 4-chloro-N-methoxy-N-methylbenzamide (4.15 g, 20.8 mmol) in tetrahydrofuran (20 mL) was added. The resulting solution was stirred for 5 h at room temperature, and then saturated sodium bicarbonate solution (150 mL) was added. The mixture was extracted with ethyl acetate (3×150 mL). The combined organic extract was dried over sodium sulfate and concentrated under vacuum. The residue was purified on a silica gel column with ethyl acetate/petroleum ether (0:100-1:20) to yield (4-chlorophenyl)[4-(trifluoromethoxy)phenyl]methanone as a white solid.

Step 2: Synthesis of (4-chlorophenyl)([3-[1-(trifluoromethane)sulfonylpiperidin-4-yl]-1-(triphenylmethyl)-1H-indazol-5-yl])[4-(trifluoromethoxy)phenyl]methanol Into a 50-mL oven-dried round-bottom flask purged and maintained under nitrogen, was placed a solution of 5-bromo-3-[1-(trifluoromethane)sulfonylpiperidin-4-yl]-1-(triphenylmethyl)-1H-indazole (200 mg, 0.31 mmol) in tetrahydrofuran (15 mL), followed by dropwise addition of 2.5 M solution of n-BuLi in hexanes (0.306 mL, 0.76 mmol) at −78° C. In 30 min a solution of (4-chlorophenyl)[4-(trifluoromethoxy)phenyl]methanone (182.9 mg, 0.61 mmol) in tetrahydrofuran (5 mL) was added. The resulting solution was stirred for 2 h at room temperature, and then saturated sodium bicarbonate solution (50 mL) was added. The mixture was extracted with ethyl acetate (3×50 mL). The combined organic extract was dried over sodium sulfate and concentrated under vacuum concentrated under vacuum to yield (4-chlorophenyl)([3-[1-(trifluoromethane)sulfonylpiperidin-4-yl]-1-(triphenylmethyl)-1H-indazol-5-yl])[4-(trifluoromethoxy)phenyl]methanol as yellow oil. LC/MS (ES, m/z): 876 [M+H]$^+$ Step 3: Synthesis of 5-[(4-chlorophenyl)[4-(trifluoromethoxy)phenyl]methyl]-3-[1-(trifluoromethane)sulfonylpiperidin-4-yl]-1H-indazole Into a 50-mL round-bottom flask, were placed a solution of (4-chlorophenyl)([3-[1-(trifluoromethane)sulfonylpiperidin-4-yl]-1-(triphenylmethyl)-1H-indazol-5-yl])[4-(trifluoromethoxy)phenyl]methanol (400 mg, 0.18 mmol) in dichloromethane (20 mL), Et$_3$SiH (57.0 mg, 0.49 mmol) and trifluoroacetic acid (192 mg, 1.70 mmol). The resulting solution was stirred overnight at room temperature, and then concentrated under vacuum. The residue was purified on a silica gel column eluted with ethyl acetate/petroleum ether (0:100-2:1). The impure product was further purified by Prep-HPLC under the following conditions (Waters 2767-1): Column, SunFire Prep C18, 5 um, 19×100 mm; mobile phase, water and MeCN both with 0.05% TFA (52% to 85% CH$_3$CN over 10 min); Detection wavelength, UV 254 nm. The title compound 5-[(4-chlorophenyl)[4-(trifluoromethoxy)phenyl]methyl]-3-[1-(trifluoromethane)sulfonylpiperidin-4-yl]-1H-indazole was obtained as a white solid.

$^1$HNMR (300 MHz, CDCl$_3$) δ: 7.42 (d, J=8.7 Hz, 1H), 7.26-7.33 (m, 3H), 7.10-7.18 (m, 5H), 7.03-7.06 (m, 2H), 5.65 (s, 1H), 4.03-4.07 (m, 2H), 3.21-3.32 (m, 3H), 1.99-2.11 (m, 4H). LC/MS (ES, m/z): 618 [M+H]$^+$.

Example PH-3

5-((4-chlorophenyl)(4-(trifluoromethyl)phenyl)methyl)-3-(1-(trifluoromethylsulfonyl)piperidin-4-yl)-1H-indazole

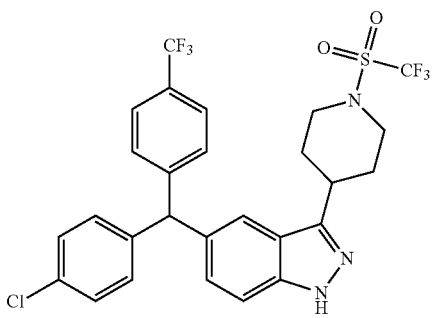

The title compound was prepared according to the procedure as described in Example PH-2 above substituting 1-bromo-4-(trifluoromethyl)benzene for 1-bromo-4-(trifluoromethoxy)benzene in Step 1.

$^1$HNMR (300 MHz, CDCl$_3$) δ: 7.56 (d, J=8.1 Hz, 2H), 7.42 (d, J=8.7 Hz, 1H), 7.35 (s, 1H), 7.21-7.28 (m, 4H), 7.15 (d, J=8.7 Hz, 1H), 7.04 (d, J=8.1 Hz, 2H), 5.69 (s, 1H), 4.02-4.07 (m, 2H), 3.25-3.32 (m, 3H), 2.04-2.14 (m, 4H). LC/MS (ES, m/z): 620 [M+H]$^+$.

Example PH-4

5-((3-chlorophenyl)(4-chlorophenyl)methyl)-3-(1-(trifluoromethylsulfonyl)piperidin-4-yl)-1H-indazole

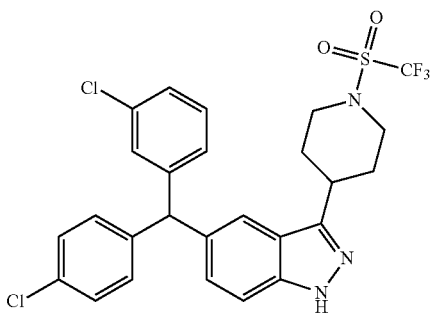 [SMILES: O=S(=O)(N1CCC(c2n[nH]c3ccc(C(c4ccc(Cl)cc4)c4cccc(Cl)c4)cc23)CC1)C(F)(F)F]

The title compound was prepared according to the procedure as described in Example PH-2 above substituting 1-bromo-3-chlorobenzene for 1-bromo-4-(trifluoromethoxy)benzene in Step 1.

$^1$HNMR (300 MHz, CDCl$_3$) δ: 7.41 (d, J=8.7 Hz, 1H), 7.23-7.30 (m, 5H), 7.15 (d, J=8.9 Hz, 1H), 6.98-7.08 (m, 4H), 5.61 (s, 1H), 4.02-4.07 (m, 2H), 3.21-3.33 (m, 3H), 1.99-2.16 (m, 4H). LC/MS (ES, m/z): 568 [M+H]$^+$.

Example PH-5

5-((2-chlorophenyl)(4-chlorophenyl)methyl)-3-(1-(trifluoromethylsulfonyl)piperidin-4-yl)-1H-indazole

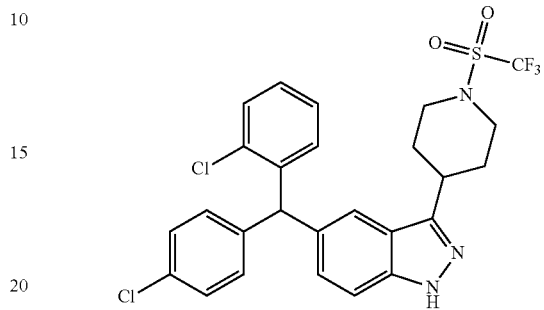

The title compound was prepared according to the procedure as described in Example PH-2 above substituting 1-bromo-2-chlorobenzene for 1-bromo-4-(trifluoromethoxy)benzene in Step 1.

$^1$HNMR (300 MHz, CDCl$_3$) δ: 7.41 (d, J=8.7 Hz, 2H), 7.14-7.29 (m, 5H), 7.01 (d, J=8.1 Hz, 2H), 6.89-6.93 (m, 1H), 6.04 (s, 1H), 4.01-4.06 (m, 2H), 3.20-3.32 (m, 3H), 1.98-2.14 (m, 4H). LC/MS (ES, m/z): 568 [M+H]$^+$.

Example PH-6

5-((4-chlorophenyl)(3,4-dichlorophenyl)methyl)-3-(1-(trifluoromethylsulfonyl)piperidin-4-yl)-1H-indazole

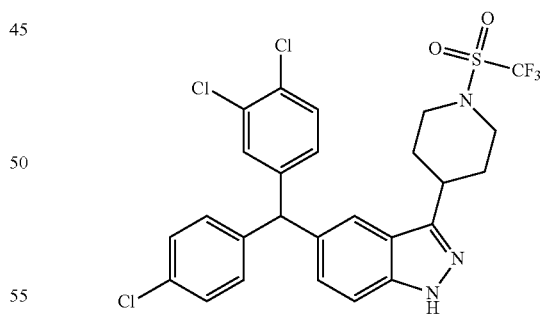

The title compound was prepared according to the procedure as described in Example PH-2 above substituting 4-bromo-1,2-dichlorobenzene for 1-bromo-4-(trifluoromethoxy)benzene in Step 1.

$^1$HNMR (400 MHz, CDCl$_3$) δ: 7.29-7.46 (m, 5H), 7.15-7.20 (m, 2H), 7.05 (d, J=8.4 Hz, 2H), 6.96 (d, J=8.4 Hz, 1H), 5.61 (s, 1H), 4.06-4.09 (m, 2H), 3.25-3.42 (m, 3H), 2.04-2.17 (m, 4H). LC/MS (ES, m/z): 602 [M+H]$^+$.

Example PH-7

2-((4-chlorophenyl)(3-(1-(trifluoromethylsulfonyl)piperidin-4-yl)-1H-indazol-5-yl)methyl)thiazole

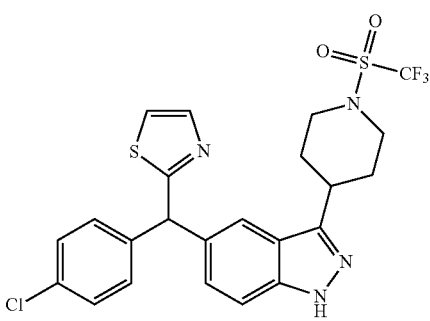 [SMILES: O=S(=O)(N1CCC(c2n[nH]c3ccc(C(c4ccc(Cl)cc4)c4nccs4)cc23)CC1)C(F)(F)F]

The title compound was prepared according to the procedure as described in Example PH-2 above substituting 2-bromo-1,3-thiazole for 1-bromo-4-(trifluoromethoxy)benzene in Step 1.

$^1$HNMR (300 MHz, CDCl$_3$) δ: 7.82 (d, J=3.3 Hz, 1H), 7.70 (s, 1H), 7.44 (d, J=8.9 Hz, 1H), 7.19-7.34 (m, 6H), 5.96 (s, 1H), 4.03-4.16 (m, 2H), 3.18-3.38 (m, 3H), 2.00-2.25 (m, 4H). LC/MS (ES, m/z): 541 [M+H]$^+$.

Example PH-8

2-((4-chlorophenyl)(3-(1-(trifluoromethylsulfonyl)piperidin-4-yl)-1H-indazol-5-yl)methyl)-5-methyl-thiazole

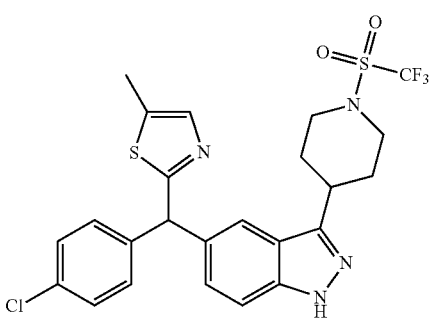 [SMILES: Cc1cnc(C(c2ccc(Cl)cc2)c2ccc3[nH]nc(C4CCN(S(=O)(=O)C(F)(F)F)CC4)c3c2)s1]

The title compound was prepared according to the procedure as described in Example PH-2 above substituting 2-bromo-5-methyl-1,3-thiazole for 1-bromo-4-(trifluoromethoxy)benzene in Step 1.

$^1$HNMR (300 MHz, CD$_3$OD) δ: 7.63 (s, 1H), 7.45-7.49 (m, 2H), 7.31-7.37 (m, 3H), 7.23-7.29 (m, 2H), 5.95 (s, 1H), 4.01-4.06 (m, 2H), 3.32-3.36 (m, 3H), 2.46 (s, 3H), 1.94-2.14 (m, 4H). LC/MS (ES, m/z): 555 [M+H]$^+$.

Example PH-9

5-(bis(4-methoxyphenyl)methyl)-3-(1-(trifluoromethylsulfonyl)piperidin-4-yl)-1H-indazole

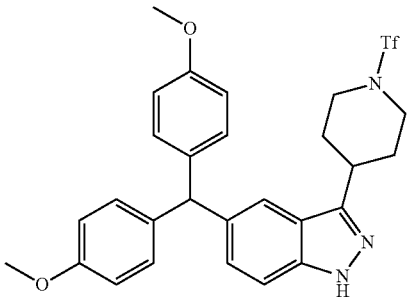

The title compound was prepared according to the procedure as described in Example PH-2 above substituting bis(4-methoxyphenyl)methanone for (4-chlorophenyl)[4-(trifluoromethoxy)phenyl]methanone in Step 2.

$^1$HNMR (400 MHz, CDCl$_3$) δ: 7.39 (d, J=8.8 Hz, 2H), 7.24 (d, J=8.8 Hz, 1H), 7.05 (d, J=8.4 Hz, 4H), 6.86 (d, J=8.4 Hz, 4H), 5.60 (s, 1H), 4.04-4.07 (m, 2H), 3.82 (s, 6H), 3.22-3.33 (m, 3H), 2.06-2.16 (m, 4H). LC/MS (ES, m/z): 560 [M+H]$^+$.

Example PH-10

5-(bis(4-chlorophenyl)methyl)-1-cyclopropyl-3-(1-(trifluoromethylsulfonyl)piperidin-4-yl)-1H-indazole

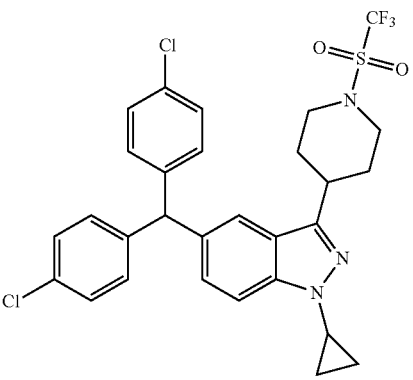 [SMILES: O=S(=O)(N1CCC(c2nn(C3CC3)c3ccc(C(c4ccc(Cl)cc4)c4ccc(Cl)cc4)cc23)CC1)C(F)(F)F]

Step 1: Synthesis of methyl 3-[1-[(tert-butoxy)carbonyl]-1,2,3,6-tetrahydropyridin-4-yl]-1H-indazole-5-carboxylate Into a 250-mL 3-necked round-bottom flask purged and maintained under nitrogen, were placed a solution of methyl 3-bromo-1H-indazole-5-carboxylate (5 g, 19.6 mmol) in 1,4-dioxane (210 mL), tert-butyl 4-(tetramethyl-1,3,2-dioxaborolan-2-yl)-1,2,3,6-tetrahydropyridine-1-carboxylate (9.2 g, 29.7 mmol), Pd(OAc)$_2$ (442 mg, 1.97 mmol), S-Phos (1.62 g, 3.94 mmol) and a solution of K$_3$PO$_4$ (16.72 g, 78.77 mmol) in water (31 mL). The resulting mixture was stirred overnight at 90° C. in an oil bath, and then concentrated under vacuum. The residue was purified on a silica gel column eluted with ethyl acetate/petroleum ether (0:100-1:1) to yield methyl 3-[1-[(tert-butoxy)carbonyl]-1,2,3,6-tetrahydropyridin-4-yl]-1H-indazole-5-carboxylate as a white solid.

LC/MS (ES, m/z): 358 [M+H]$^+$.

Step 2: Synthesis of methyl 3-[1-[(tert-butoxy)carbonyl]piperidin-4-yl]-1H-indazole-5-carboxylate Into a 250-mL round-bottom flask, were placed a solution of methyl 3-[1-[(tert-butoxy)carbonyl]-1,2,3,6-tetrahydropyridin-4-yl]-1H-indazole-5-carboxylate (3.2 g, 8.95 mmol) in methanol (200 mL), HCOONH$_4$ (8 g, 126.86 mmol) and 10% palladium on carbon (960 mg, 0.90 mmol). The resulting mixture was stirred for 1 h at 75° C. in an oil bath. The precipitate was filtered out and the filtrate was concentrated under vacuum. The residue was dissolved in ethyl acetate (200 mL), and then washed with water (3×100 mL). The organic layer was dried over anhydrous sodium sulfate and concentrated under vacuum to yield methyl 3-[1-[(tert-butoxy)carbonyl]piperidin-4-yl]-1H-indazole-5-carboxylate as a white solid. LC/MS (ES, m/z): 360 [M+H]$^+$.

Step 3: Synthesis of methyl 3-[1-[(tert-butoxy)carbonyl]piperidin-4-yl]-1-cyclopropyl-1H-indazole-5-carboxylate Into a 500-mL round-bottom flask, were placed a solution of methyl 3-[1-[(tert-butoxy)carbonyl]piperidin-4-yl]-1H-indazole-5-carboxylate (4.0 g, 11.13 mmol) in DCE (200 mL), cyclopropylboronic acid (4.8 g, 55.78 mmol), Cu(OAc)$_2$ (6.0 g, 33.30 mmol), sodium carbonate (4.4 g, 41.51 mmol) and pyridine (5.9 g, 74.59 mmol). The resulting mixture was stirred under nitrogen overnight at 70° C. in an oil bath. The precipitate was filtered out, and the filtrate was concentrated under vacuum. The residue was purified on a silica gel column eluted with ethyl acetate/petroleum ether (0:100-1:1) to yield methyl 3-[1-[(tert-butoxy)carbonyl]piperidin-4-yl]-1-cyclopropyl-1H-indazole-5-carboxylate as a white solid. LC/MS (ES, m/z): 400 [M+H]$^+$.

Step 4: Synthesis of tert-butyl 4-[5-[bis(4-chlorophenyl)(hydroxy)methyl]-1-cyclopropyl-1H-indazol-3-yl]piperidine-1-carboxylate Into a 500-mL oven-dried round-bottom flask, was placed a solution of methyl 3-[1-[(tert-butoxy)carbonyl]piperidin-4-yl]-1-cyclopropyl-1H-indazole-5-carboxylate (4 g, 9.51 mmol) in tetrahydrofuran (200 mL), followed by dropwise addition of a 1.0 M solution of bromo(4-chlorophenyl)magnesium in diethyl ether (50 mL, 50.0 mmol). The resulting solution was heated to reflux under nitrogen for 3 h in an oil bath, and then water (100 mL) was added, and extracted with ethyl acetate (2×100 mL). The combined organic layer was dried over anhydrous sodium sulfate and concentrated under vacuum to yield tert-butyl 4-[5-[bis(4-chlorophenyl)(hydroxy)methyl]-1-cyclopropyl-1H-indazol-3-yl]piperidine-1-carboxylate as yellow oil. LC/MS (ES, m/z): 593 [M+H]$^+$.

Step 5: Synthesis of 5-[bis(4-chlorophenyl)methyl]-1-cyclopropyl-3-(piperidin-4-yl)-1H-indazole Into a 250-mL round-bottom flask, were placed a solution of tert-butyl 4-[5-[bis(4-chlorophenyl)(hydroxy)methyl]-1-cyclopropyl-1H-indazol-3-yl]piperidine-1-carboxylate (6.0 g, 9.62 mmol) in dichloromethane (100 mL), Et$_3$SiH (4.9 g, 42.14 mmol) and trifluoroacetic acid (8.2 g, 72.54 mmol). The resulting solution was stirred overnight at room temperature, and then concentrated under vacuum. The residue was purified on a silica gel column eluted with dichloromethane/methanol (100:0-20:1) to yield 5-[bis(4-chlorophenyl)methyl]-1-cyclopropyl-3-(piperidin-4-yl)-1H-indazole as a light yellow solid. LC/MS (ES, m/z):476 [M+H]$^+$.

Step 6: Synthesis of 5-[bis(4-chlorophenyl)methyl]-1-cyclopropyl-3-[1-(trifluoromethane)sulfonylpiperidin-4-yl]-1H-indazole Into a 25-mL oven-dried round-bottom flask, were placed a solution of 5-[bis(4-chlorophenyl)methyl]-1-cyclopropyl-3-(piperidin-4-yl)-1H-indazole (100 mg, 0.21 mmol) in dichloromethane (10 mL), triethylamine (106 mg, 1.05 mmol) followed by dropwise addition of Tf$_2$O (65 mg, 0.23 mmol, 1.10 equiv) at −78° C. The resulting solution was allowed to warm to room temperature and stirred overnight, then dichloromethane (15 mL) was added, and washed with water (2×15 mL). The organic layer was dried over anhydrous sodium sulfate and concentrated under vacuum. The residue was purified by as Prep-HPLC described in Step 3 of Example PH-2. The title compound 5-[bis(4-chlorophenyl)methyl]-1-cyclopropyl-3-[1-(trifluoromethane)sulfonylpiperidin-4-yl]-1H-indazole was obtained as a white solid.

$^1$HNMR (400 MHz, CDCl$_3$) δ: 7.52 (d, J=8.4 Hz, 1H), 7.28-7.31 (m, 5H), 7.15 (d, J=8.8 Hz, 1H), 7.05 (d, J=8.4 Hz, 4H), 5.62 (s, 1H), 4.04-4.07 (m, 2H), 3.51-3.54 (m, 1H), 3.18-3.27 (m, 3H), 2.05-2.10 (m, 4H), 1.15-1.20 (m, 4H). LC/MS (ES, m/z): 608 [M+H]$^+$.

Example PH-11

4-(4-(5-(bis(4-chlorophenyl)methyl)-1-cyclopropyl-1H-indazol-3-yl)piperidine-1-carbonyl)benzamide 2,2,2-trifluoroacetate

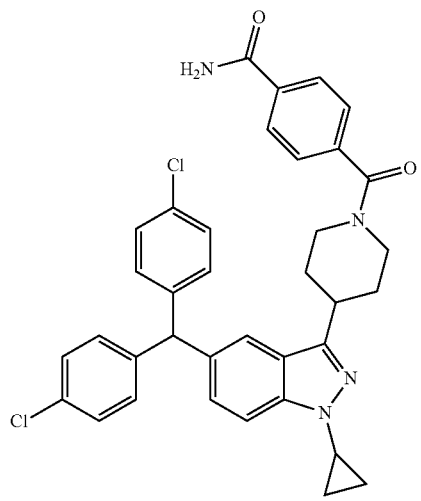 [SMILES: NC(=O)c1ccc(C(=O)N2CCC(c3nn(C4CC4)c4ccc(C(c5ccc(Cl)cc5)c5ccc(Cl)cc5)cc34)CC2)cc1]

Step 1: Synthesis of methyl 4-[(4-[5-[bis(4-chlorophenyl)methyl]-1-cyclopropyl-1H-indazol-3-yl]piperidin-1-yl)carbonyl]benzoate Into a 8-mL seal tube, were placed a solution of 4-(methoxycarbonyl)benzoic acid (83.4 mg, 0.46 mmol) in N,N-dimethylformamide (4 mL), HATU (319.5 mg, 0.84 mmol), DIEA (162.5 mg, 1.26 mmol). In 10 min 5-[bis(4-chlorophenyl)methyl]-1-cyclopropyl-3-(piperidin-4-yl)-1H-indazole (200.1 mg, 0.42 mmol) was added, and the resulting solution was stirred overnight at room temperature and then water (30 mL) was added. The precipitate formed was collected by filtration to yield methyl 4-[(4-[5-[bis(4-chlorophenyl)methyl]-1-cyclopropyl-1H-indazol-3-yl]piperidin-1-yl)carbonyl]benzoate as a yellow solid. LC/MS (ES, m/z): 638 [M+H]$^+$

Step 2: Synthesis of 4-[(4-[5-[bis(4-chlorophenyl)methyl]-1-cyclopropyl-1H-indazol-3-yl]piperidin-1-yl)carbonyl]benzoic acid Into a 50-mL round-bottom flask, were placed a solution of methyl 4-[(4-[5-[bis(4-chlorophenyl)methyl]-1-cyclopropyl-1H-indazol-3-yl]piperidin-1-yl)carbonyl]benzoate (166.0 mg, 0.26 mmol) in tetrahydrofuran (20 mL) and a solution of LiOH.H$_2$O (108 mg, 2.57 mmol) in methanol/H$_2$O (5/5 mL). The resulting mixture was stirred overnight at room temperature and then concentrated under vacuum to remove organic solvent. The mixture was acidified to pH 3-4 with 1 N HCl solution, and then extracted with DCM (3×20 mL). The combined organic layer was dried over anhydrous sodium sulfate and concentrated under vacuum. The residue was purified by Prep-HPLC as described in step 3 of Example PH-2. The title compound 4-[(4-[5-[bis(4-chlorophenyl)methyl]-1-cyclopropyl-1H-indazol-3-yl]piperidin-1-yl)carbonyl]benzoic acid was obtained as a light yellow solid. LC/MS (ES, m/z): 624 [M+H]$^+$

Step 3: Synthesis of 4-[(4-[5-[bis(4-chlorophenyl)methyl]-1-cyclopropyl-1H-indazol-3-yl]piperidin-1-yl)carbonyl]benzamide Into a 8-mL seal tube, were placed a solution of 4-[(4-[5-[bis(4-chlorophenyl)methyl]-1-cyclopropyl-1H-indazol-3-yl]piperidin-1-yl)carbonyl]benzoic acid (74.9 mg, 0.12 mmol) in N,N-dimethylformamide (3 mL), HATU (58.5 mg, 0.15 mmol), DIEA (49.5 mg, 0.38 mmol). After 10 min NH$_4$Cl (34.2 mg, 0.64 mmol) was added, and the resulting solution was stirred overnight at room temperature, and then water (25 mL) was added. The precipitate formed was collected by filtration, and purified by Prep-HPLC as described in Step 3 of Example PH-2. The title compound 4-[(4-[5-[bis(4-chlorophenyl)methyl]-1-cyclopropyl-1H-indazol-3-yl]piperidin-1-yl)carbonyl]benzamide was obtained as a white solid.

$^1$HNMR (400 MHz, CDCl$_3$) δ: 7.88 (d, J=8.4 Hz, 2H), 7.52 (d, J=8.0 Hz, 3H), 7.28-7.34 (m, 5H), 7.14 (d, J=8.4 Hz, 1H), 7.06 (d, J=8.4 Hz, 4H), 6.21 (br.s, 1H), 5.77 (br.s, 1H), 5.63 (s, 1H), 4.80 (m, 1H), 3.79-3.81 (m, 1H), 3.50-3.55 (m, 1H), 3.16-3.26 (m, 2H), 3.05-3.09 (m, 1H), 2.03-2.10 (m, 1H), 4H), 1.13-1.20 (m, 4H). LC/MS (ES, m/z): 623 [M+H]$^+$.

Example PH-12

1-(4-(5-(bis(4-chlorophenyl)methyl)-1-cyclopropyl-1H-indazol-3-yl)piperidin-1-yl)-2-hydroxyethanone

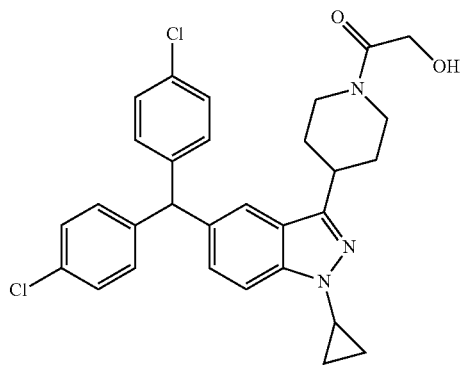 [SMILES: O=C(CO)N1CCC(c2nn(C3CC3)c3ccc(C(c4ccc(Cl)cc4)c4ccc(Cl)cc4)cc23)CC1]

The title compound was prepared according to the procedure as described in Example PH-11 substituting 2-hydroxyacetic acid for 4-(methoxycarbonyl)benzoic acid in Step 1.

$^1$HNMR (400 MHz, CDCl$_3$) δ 7.51 (d, J=8.8 Hz, 1H), 7.28-7.34 (m, 5H), 7.14 (d, J=8.8 Hz, 1H), 7.05 (d, J=8.0 Hz, 4H), 5.62 (s, 1H), 4.62-4.65 (m, 1H), 4.23 (s, 2H), 3.63-3.66 (m, 1H), 3.50-3.53 (m, 1H), 3.14-3.29 (m, 2H), 2.95-3.00 (m, 1H), 2.03-2.06 (m, 2H), 1.91-1.96 (m, 2H), 1.16-1.19 (m, 4H). LC/MS (ES, m/z): 534 [M+H]$^+$.

Example PH-13

1-(4-(5-(bis(4-chlorophenyl)methyl)-1-cyclopropyl-1H-indazol-3-yl)piperidin-1-yl)-3-hydroxypropan-1-one

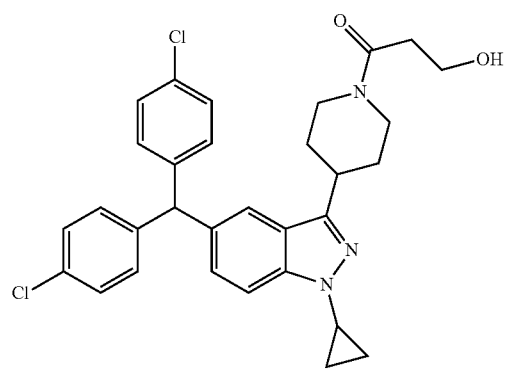 [SMILES: O=C(CCO)N1CCC(c2nn(C3CC3)c3ccc(C(c4ccc(Cl)cc4)c4ccc(Cl)cc4)cc23)CC1]

Step 1: Synthesis of methyl 3-(4-[5-[bis(4-chlorophenyl)methyl]-1-cyclopropyl-1H-indazol-3-yl]piperidin-1-yl)-3-oxopropanoate Into a 25-mL oven-dried round-bottom flask, were placed a solution of 5-[bis(4-chlorophenyl)methyl]-1-cyclopropyl-3-(piperidin-4-yl)-1H-indazole (100.1 mg, 0.21 mmol) in dichloromethane (10 mL), triethylamine (106 mg, 1.05 mmol) and methyl 3-chloro-3-oxopropanoate (34.4 mg, 0.25 mmol). The resulting solution was stirred for 3 h at room temperature, and then concentrated under vacuum to yield methyl 3-(4-[5-[bis(4-chlorophenyl)methyl]-1-cyclopropyl-1H-indazol-3-yl]piperidin-1-yl)-3-oxopropanoate as yellow oil. LC/MS (ES, m/z): 576 [M+H]$^+$ Step 2: Synthesis of 1-(4-[5-[bis(4-chlorophenyl)methyl]-1-cyclopropyl-1H-indazol-3-yl]piperidin-1-yl)-3-hydroxypropan-1-one Into a 25-mL round-bottom flask, was placed a solution of methyl 3-(4-[5-[bis(4-chlorophenyl)methyl]-1-cyclopropyl-1H-indazol-3-yl]piperidin-1-yl)-3-oxopropanoate (92.2 mg, 0.16 mmol) in tetrahydrofuran/H$_2$O (10/0.2 mL), followed by addition of LiBH$_4$ (34.6 mg, 1.59 mmol) in portions. The reaction mixture was stirred for 3 h at room temperature, and then acidified to pH to 4-5 with 1N HCl solution. After addition of water (20 mL), the reaction mixture was extracted with DCM (3×50 mL). The combined organic layer was dried over anhydrous sodium sulfate and concentrated under vacuum. The residue was purified by Prep-HPLC as described in Step 3 of Example PH-2. The title compound 1-(4-[5-[bis(4-chlorophenyl)methyl]-1-cyclopropyl-1H-indazol-3-yl]piperidin-1-yl)-3-hydroxypropan-1-one was obtained as a white solid.

$^1$HNMR (400 MHz, CD$_3$OD) δ: 7.58 (d, J=8.8 Hz, 1H), 7.45 (s, 1H), 7.32 (d, J=8.4 Hz, 4H), 7.21 (d, J=8.8 Hz, 1H), 7.11 (d, J=8.4 Hz, 4H), 5.73 (s, 1H), 4.59-4.63 (m, 1H), 4.09-4.13 (m, 1H), 3.87 (t, J=6.0 Hz, 2H), 3.52-3.57 (m, 1H), 3.25-3.28 (m, 2H), 2.86 (t, J=13.8 Hz, 1H), 2.66 (t, J=6.4 Hz, 2H), 1.82-2.02 (m, 4H), 1.10-1.16 (m, 4H). LC/MS (ES, m/z): 548 [M+H]$^+$.

Example PH-14

4-(4-(5-(bis(4-chlorophenyl)methyl)-1-cyclopropyl-1H-indazol-3-yl)piperidin-1-yl)-4-oxobutanamide 2,2,2-trifluoroacetate

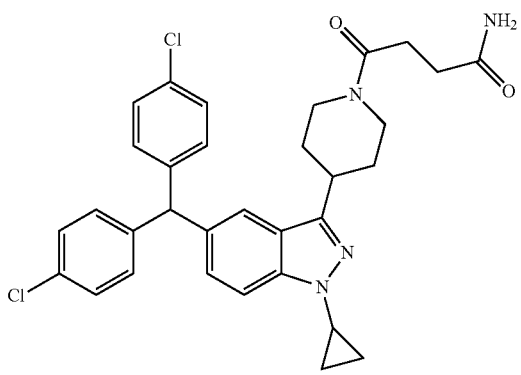 [SMILES: NC(=O)CCC(=O)N1CCC(c2nn(C3CC3)c3ccc(C(c4ccc(Cl)cc4)c4ccc(Cl)cc4)cc23)CC1]

Step 1: Synthesis of ethyl 4-(4-[5-[bis(4-chlorophenyl)methyl]-1-cyclopropyl-1H-indazol-3-yl]piperidin-1-yl)-4-oxobutanoate Into a 8-mL seal tube, was placed a solution of 5-[bis(4-chlorophenyl)methyl]-1-cyclopropyl-3-(piperidin-4-yl)-1H-indazole (200.1 mg, 0.42 mmol) in dichloromethane (4 mL), triethylamine (127.6 mg, 1.26 mmol) and ethyl 4-chloro-4-oxobutanoate (82.9 mg, 0.50 mmol). The resulting solution was stirred overnight at room temperature, and then concentrated under vacuum to yield ethyl 4-(4-[5-[bis(4-chlorophenyl)methyl]-1-cyclopropyl-1H-indazol-3-yl]piperidin-1-yl)-4-oxobutanoate as a yellow solid. LC/MS (ES, m/z): 605 [M+H]$^+$ Step 2: Synthesis of 4-(4-[5-[bis(4-chlorophenyl)methyl]-1-cyclopropyl-1H-indazol-3-yl]piperidin-1-yl)-4-oxobutanoic acid Into a 50-mL round-bottom flask, were placed a solution of ethyl 4-(4-[5-[bis(4-chlorophenyl)methyl]-1-cyclopropyl-1H-indazol-3-yl]piperidin-1-yl)-4-oxobutanoate (190 mg, 0.25 mmol) in tetrahydrofuran (20 mL) and a solution of LiOH.H$_2$O (106 mg, 2.53 mmol) in methanol/H$_2$O (5/5 mL). The resulting mixture was stirred for 4 h at room temperature, and then acidified to pH 3-4 with 1N HCl solution, followed by extraction with DCM (3×20 mL). The combined organic layer was dried over anhydrous sodium sulfate, and then concentrated under vacuum to yield 4-(4-[5-[bis(4-chlorophenyl)methyl]-1-cyclopropyl-1H-indazol-3-yl]piperidin-1-yl)-4-oxobutanoic acid. The residue was purified by Prep-HPLC as described in Step 3 of Example PH-2. The title compound 4-(4-[5-[bis(4-chlorophenyl)methyl]-1-cyclopropyl-1H-indazol-3-yl]piperidin-1-yl)-4-oxobutanoic acid as a light yellow solid. LC/MS (ES, m/z): 576 [M+H]$^+$ Step 3: Synthesis of 4-(4-[5-[bis(4-chlorophenyl)methyl]-1-cyclopropyl-1H-indazol-3-yl]piperidin-1-yl)-4-oxobutanamide; trifluoroacetic acid Into a 8-mL seal tube, were placed a solution of 4-(4-[5-[bis(4-chlorophenyl)methyl]-1-cyclopropyl-1H-indazol-3-yl]piperidin-1-yl)-4-oxobutanoic acid (86.3 mg, 0.15 mmol) in N,N-dimethylformamide (5 mL), HATU (79.8 mg, 0.21 mmol) and DIEA (67.1 mg, 0.52 mmol). After 10 min NH$_4$Cl (45.8 mg, 0.86 mmol) was added. The resulting mixture was stirred overnight at room temperature, and then water (25 mL) was added. The precipitate formed was collected by filtration and purified by Prep-HPLC as described in Step 3 of Example PH-2. The title compound 4-(4-[5-[bis(4-chlorophenyl)methyl]-1-cyclopropyl-1H-indazol-3-yl]piperidin-1-yl)-4-oxobutanamide was obtained as a white solid.

$^1$HNMR (400 MHz, CDCl$_3$) δ 7.51 (d, J=8.8 Hz, 1H), 7.36 (s, 1H), 7.28-7.30 (m, 4H), 7.14 (d, J=8.8 Hz, 1H), 7.06 (d, J=8.4 Hz, 4H), 6.68 (br.s, 1H), 6.06 (br.s, 1H), 5.63 (s, 1H), 4.62-4.66 (m, 1H), 4.02-4.05 (m, 1H), 3.51-3.52 (m, 1H), 3.26-3.28 (m, 2H), 2.87-2.93 (m, 1H), 2.80 (m, 2H), 2.69 (m, 2H), 1.88-2.04 (m, 4H), 1.13-1.19 (m, 4H). LC/MS (ES, m/z): 575 [M+H]$^+$.

Example PH-15

4-(4-(5-(bis(4-chlorophenyl)methyl)-1-cyclopropyl-1H-indazol-3-yl)piperidin-1-yl)benzamide 2,2,2-trifluoroacetate

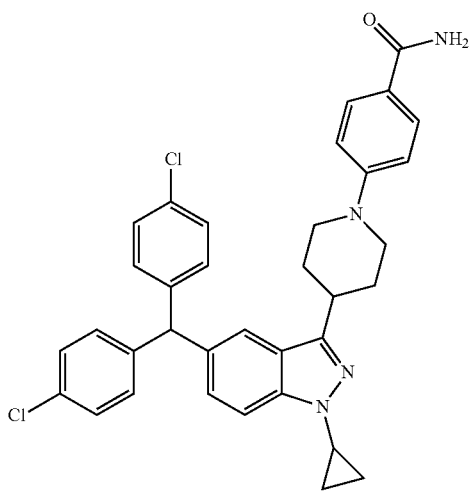 [SMILES: NC(=O)c1ccc(N2CCC(c3nn(C4CC4)c4ccc(C(c5ccc(Cl)cc5)c5ccc(Cl)cc5)cc34)CC2)cc1]

Step 1: Synthesis of methyl 4-(4-[5-[bis(4-chlorophenyl)methyl]-1-cyclopropyl-1H-indazol-3-yl]piperidin-1-yl)benzoate Into a 50-mL 3-necked round-bottom flask purged and maintained under nitrogen, were placed a solution of 5-[bis(4-chlorophenyl)methyl]-1-cyclopropyl-3-(piperidin-4-yl)-1H-indazole (162.0 mg, 0.34 mmol) in toluene (25 mL), methyl 4-bromobenzoate (97.3 mg, 0.45 mmol), $Pd_2(dba)_3$ (34.6 mg, 0.04 mmol), X-phos (54 mg, 0.11 mmol) and $Cs_2CO_3$ (246.5 mg, 0.76 mmol). The resulting mixture was stirred overnight at 95° C. in an oil bath, and then concentrated under vacuum. The residue was purified on a silica gel column with ethyl acetate/petroleum ether (0:100-1:3) to yield methyl 4-(4-[5-[bis(4-chlorophenyl)methyl]-1-cyclopropyl-1H-indazol-3-yl]piperidin-1-yl)benzoate as a light yellow solid. LC/MS (ES, m/z): 611 [M+H]$^+$

Step 2: Synthesis of 4-(4-[5-[bis(4-chlorophenyl)methyl]-1-cyclopropyl-1H-indazol-3-yl]piperidin-1-yl)benzoic acid Into a 100-mL round-bottom flask, were placed a solution of methyl 4-(4-[5-[bis(4-chlorophenyl)methyl]-1-cyclopropyl-1H-indazol-3-yl]piperidin-1-yl)benzoate (115.9 mg, 0.19 mmol) in tetrahydrofuran (20 mL) and a solution of $LiOH \cdot H_2O$ (80 mg, 1.91 mmol) in methanol/$H_2O$ (5/5 mL). The reaction mixture was stirred overnight at room temperature, concentrated to remove organic solvents, and then acidified to pH 3-4 with 1N HCl solution. The precipitate formed was collected by filtration and purified by Prep-HPLC as described in Step 3 of Example PH-2. The intermediate 4-(4-[5-[bis(4-chlorophenyl)methyl]-1-cyclopropyl-1H-indazol-3-yl]piperidin-1-yl)benzoic acid was obtained as an orange solid. LC/MS (ES, m/z): 596 [M+H]$^+$

Step 3: Synthesis of 4-(4-[5-[bis(4-chlorophenyl)methyl]-1-cyclopropyl-1H-indazol-3-yl]piperidin-1-yl)benzamide Into a 25-mL round-bottom flask, was placed a solution of 4-(4-[5-[bis(4-chlorophenyl)methyl]-1-cyclopropyl-1H-indazol-3-yl]piperidin-1-yl)benzoic acid (65.6 mg, 0.11 mmol) in N,N-dimethylformamide (3 mL), HATU (83.6 mg, 0.22 mmol), DIEA (42.6 mg, 0.33 mmol). After 10 min $NH_4Cl$ (11.2 mg, 0.21 mmol) was added, and the resulting solution was stirred overnight at room temperature, and then water (10 mL) was added. The precipitate formed was collected by filtration and purified by Prep-HPLC as described in Step 3 of Example PH-2. The title compound 4-(4-[5-[bis(4-chlorophenyl)methyl]-1-cyclopropyl-1H-indazol-3-yl]piperidin-1-yl)benzamide was obtained as an orange solid.

$^1$HNMR (300 MHz, $CDCl_3$) δ 7.76 (d, J=8.7 Hz, 2H), 7.51 (d, J=8.4 Hz, 1H), 7.39 (s, 1H), 7.27-7.28 (m, 4H), 7.02-7.15 (m, 7H), 5.60 (s, 1H), 3.99-4.03 (m, 2H), 3.49-3.55 (m, 1H), 3.11-3.31 (m, 3H), 2.16-2.17 (m, 4H), 1.14-1.27 (m, 4H). LC/MS (ES, m/z): 595 [M+H]$^+$.

Example PH-16

3-((4-(5-(bis(4-chlorophenyl)methyl)-1-cyclopropyl-1H-indazol-3-yl)piperidin-1-yl)methyl)benzoic acid

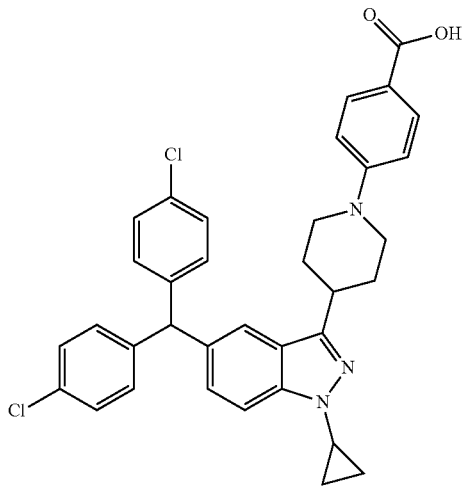 [SMILES: O=C(O)c1ccc(N2CCC(c3nn(C4CC4)c4ccc(C(c5ccc(Cl)cc5)c5ccc(Cl)cc5)cc34)CC2)cc1]

Step 1: Synthesis of methyl 3-[(4-[5-[bis(4-chlorophenyl)methyl]-1-cyclopropyl-1H-indazol-3-yl]piperidin-1-yl)methyl]benzoate Into a 100-mL round-bottom flask, were placed a solution of 5-[bis(4-chlorophenyl)methyl]-1-cyclopropyl-3-(piperidin-4-yl)-1H-indazole (1.5 g, 3.15 mmol) in dichloromethane (50 mL), methyl 3-formylbenzoate (569.8 mg, 3.47 mmol), triethylamine (478.2 mg, 4.73 mmol). After the solution was stirred overnight at room temperature, NaHB(OAc)$_3$ (1.47 g, 6.93 mmol) was added, and the resulting mixture was stirred for 3 h at room temperature, and then concentrated under vacuum. The residue was purified on a silica gel column eluted with ethyl acetate/petroleum ether (0:100-1:10) to yield methyl 3-[(4-[5-[bis(4-chlorophenyl)methyl]-1-cyclopropyl-1H-indazol-3-yl]piperidin-1-yl)methyl]benzoate as a white solid. LC/MS (ES, m/z): 625 [M+H]$^+$ Step 2: Synthesis of 3-[(4-[5-[bis(4-chlorophenyl)methyl]-1-cyclopropyl-1H-indazol-3-yl]piperidin-1-yl)methyl]benzoic acid Into a 100-mL round-bottom flask, were placed a solution of methyl 3-[(4-[5-[bis(4-chlorophenyl)methyl]-1-cyclopropyl-1H-indazol-3-yl]piperidin-1-yl)methyl]benzoate (499.7 mg, 0.80 mmol) in tetrahydrofuran (24 mL) and a solution of LiOH.H$_2$O (337 mg, 8.03 mmol) in methanol/H$_2$O (6/6 mL). The resulting mixture was stirred overnight at room temperature, and then concentrated under vacuum to remove organic solvents. The mixture was acidified to pH 3-4 with 1N HCl solution, precipitate was formed and collected by filtration. The residue was purified by Prep-HPLC as described in Step 3 of Example PH-2. The title compound 3-[(4-[5-[bis(4-chlorophenyl)methyl]-1-cyclopropyl-1H-indazol-3-yl]piperidin-1-yl)methyl]benzoic acid was obtained as an off-white solid.

$^1$HNMR (400 MHz, CD$_3$OD) δ: 8.06 (d, J=8.7 Hz, 2H), 7.59 (d, J=8.4 Hz, 2H), 7.48-7.53 (m, 2H), 7.30-7.32 (m, 4H), 7.21 (d, J=8.8 Hz, 1H), 7.10 (d, J=8.4 Hz, 4H), 5.71 (s, 1H), 4.26 (s, 2H), 3.48-3.59 (m, 3H), 2.91-3.15 (m, 2H), 2.15-2.24 (m, 4H), 1.12-1.18 (m, 4H). LC/MS (ES, m/z): 610 [M+H]$^+$.

Example PH-17

3-[(4-[5-[bis(4-chlorophenyl)methyl]-1-cyclopropyl-1H-indazol-3-yl]piperidin-1-yl)methyl]benzamide trifluoroacetic acid

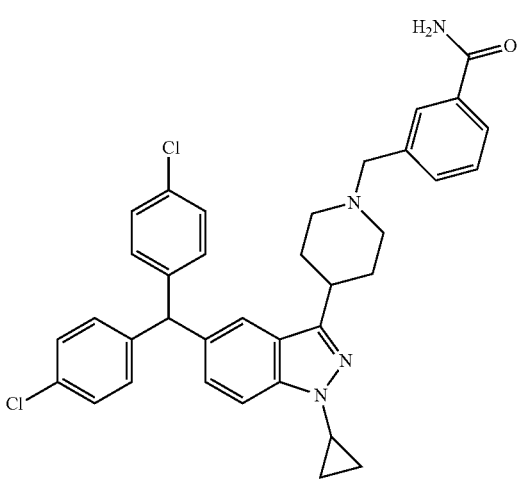 [SMILES: NC(=O)c1cccc(CN2CCC(c3nn(C4CC4)c4ccc(C(c5ccc(Cl)cc5)c5ccc(Cl)cc5)cc34)CC2)c1]

The title compound was prepared according to the procedure as described in Example PH-11, substituting 3-[(4-[5-[bis(4-chlorophenyl)methyl]-1-cyclopropyl-1H-indazol-3-yl]piperidin-1-yl)methyl]benzoic acid for 4-[(4-[5-[bis(4-chlorophenyl)methyl]-1-cyclopropyl-1H-indazol-3-yl]piperidin-1-yl)carbonyl]benzoic acid in Step 3.

$^1$HNMR (300 MHz, CD$_3$OD) δ: 7.99-8.05 (m, 2H), 7.72 (d, J=8.1 Hz, 1H), 7.58-7.66 (m, 2H), 7.43 (s, 1H), 7.31 (d, J=8.4 Hz, 4H), 7.22 (d, J=9.0 Hz, 1H), 7.10 (d, J=8.7 Hz, 4H), 5.72 (s, 2H), 4.43 (s, 2H), 3.54-3.64 (m, 3H), 3.19-3.27 (m, 2H), 2.11-2.26 (m, 4H), 1.08-1.15 (m, 4H). LC/MS (ES, m/z): 609 [M+H]$^+$.

Example PH-18

5-((4-(5-(bis(4-chlorophenyl)methyl)-1-cyclopropyl-1H-indazol-3-yl)piperidin-1-yl)methyl)furan-2-carboxylic acid

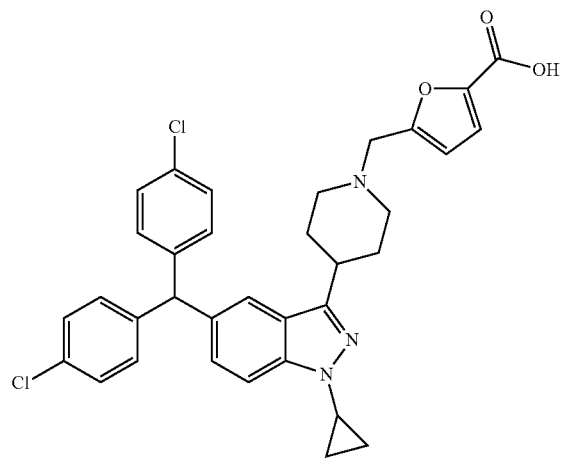 [SMILES: O=C(O)c1ccc(CN2CCC(c3nn(C4CC4)c4ccc(C(c5ccc(Cl)cc5)c5ccc(Cl)cc5)cc34)CC2)o1]

The title compound was prepared according to the procedure as described in Example PH-16 substituting 5-formylfuran-2-carboxylic acid for methyl 3-formylbenzoate in Step 1.

$^1$HNMR (400 MHz, CDCl$_3$) δ 7.47 (d, J=8.8 Hz, 2H), 7.22-7.24 (m, 4H), 7.10 (d, J=9.2 Hz, 1H), 7.01 (d, J=8.8 Hz, 5H), 6.54 (s, 1H), 5.55 (s, 1H), 4.15-4.24 (m, 2H), 3.44-3.50 (m, 3H), 3.22 (m, 1H), 2.92 (m, 2H), 2.24-2.35 (m, 4H), 1.07-1.17 (m, 4H). LC/MS (ES, m/z): 600 [M+H]$^+$.

Example PH-19

5-((4-(5-(bis(4-chlorophenyl)methyl)-1-cyclopropyl-1H-indazol-3-yl)piperidin-1-yl)methyl)thiophene-2-carboxamide

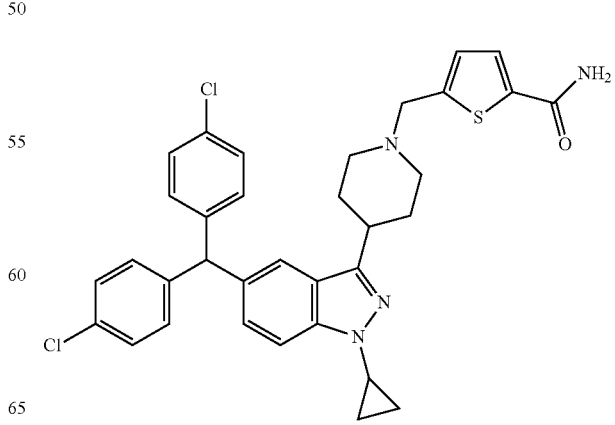

Step 1: Synthesis of 5-[(4-[5-[bis(4-chlorophenyl) methyl]-1-cyclopropyl-1H-indazol-3-yl]piperidin-1-yl)methyl]thiophene-2-carboxylic acid This intermediate was prepared according to the procedure as described in Example PH-16 substituting 5-formylthiophene-2-carboxylic acid for methyl 3-formylbenzoate in Step 1.

Step 2: Synthesis of 5-[(4-[5-[bis(4-chlorophenyl) methyl]-1-cyclopropyl-1H-indazol-3-yl]piperidin-1-yl)methyl]thiophene-2-carboxamide ethanol This intermediate was prepared according to the procedure as described in Example PH-11, substituting 5-[(4-[5-[bis(4-chlorophenyl)methyl]-1-cyclopropyl-1H-indazol-3-yl]piperidin-1-yl)methyl]thiophene-2-carboxylic acid for 4-[(4-[5-[bis(4-chlorophenyl)methyl]-1-cyclopropyl-1H-indazol-3-yl]piperidin-1-yl)carbonyl]benzoic acid in Step 3.
$^1$HNMR (400 MHz, CD$_3$OD) δ: 7.74 (s, 1H), 7.61 (d, J=8.4 Hz, 1H), 7.46 (s, 1H), 7.31-7.38 (m, 5H), 7.23 (d, J=8.8 Hz, 1H), 7.11 (d, J=8.8 Hz, 4H), 5.74 (s, 1H), 4.64 (s, 2H), 3.55-3.69 (m, 3H), 3.11-3.26 (m, 3H), 2.15-2.34 (m, 4H), 1.10-1.13 (m, 4H). LC/MS (ES, m/z): 615 [M+H]$^+$.

Example PH-20

5-((4-(5-(bis(4-chlorophenyl)methyl)-1-cyclopropyl-1H-indazol-3-yl)piperidin-1-yl)methyl)thiophene-3-carboxamide

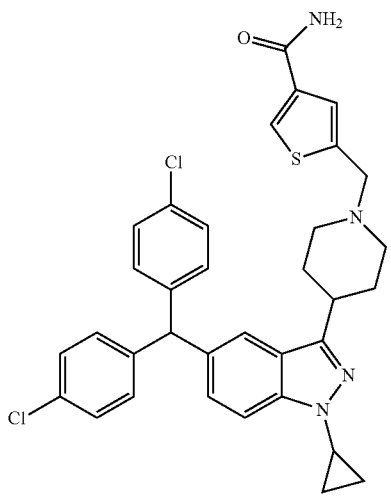 [SMILES: NC(=O)c1csc(CN2CCC(c3nn(C4CC4)c4ccc(C(c5ccc(Cl)cc5)c5ccc(Cl)cc5)cc34)CC2)c1]

Step 1: Synthesis of 5-[(4-[5-[bis(4-chlorophenyl) methyl]-1-cyclopropyl-1H-indazol-3-yl]piperidin-1-yl)methyl]thiophene-3-carboxylic acid This intermediate was prepared according to the procedure as described in Example PH-16 substituting methyl 5-formylthiophene-3-carboxylate for methyl 3-formylbenzoate in Step 1.

Step 2: Synthesis of 5-[(4-[5-[bis(4-chlorophenyl) methyl]-1-cyclopropyl-1H-indazol-3-yl]piperidin-1-yl)methyl]thiophene-3-carboxamide The intermediate was prepared according to the procedure as described in Example PH-11, substituting 5-[(4-[5-[bis(4-chlorophenyl)methyl]-1-cyclopropyl-1H-indazol-3-yl]piperidin-1-yl)methyl]thiophene-3-carboxylic acid for 4-[(4-[5-[bis(4-chlorophenyl)methyl]-1-cyclopropyl-1H-indazol-3-yl]piperidin-1-yl)carbonyl]benzoic acid in Step 3.
$^1$HNMR (400 MHz, CDCl$_3$+D$_2$O) δ: 7.99 (s, 1H), 7.45-7.64 (m, 3H), 7.21-7.28 (m, 4H), 7.12 (m, 1H), 7.01 (d, J=7.6 Hz, 4H), 5.60 (s, 1H), 4.44 (s, 2H), 2.82-3.81 (m, 6H), 2.05-2.31 (m, 4H), 0.81-1.27 (m, 4H). LC/MS (ES, m/z): 615 [M+H]$^+$.

Example PH-21

5-(bis(4-chlorophenyl)methyl)-2-cyclopropyl-3-(1-(trifluoromethylsulfonyl)piperidin-4-yl)-2H-indazole

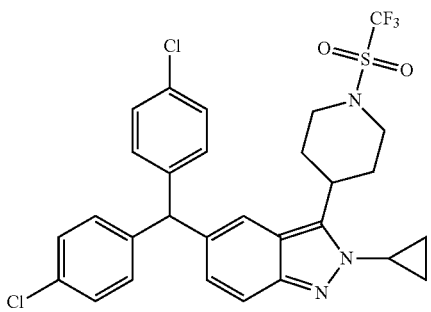 [SMILES: O=S(=O)(N1CCC(c2c3cc(C(c4ccc(Cl)cc4)c4ccc(Cl)cc4)ccc3nn2C2CC2)CC1)C(F)(F)F]

Step 1: Synthesis of methyl 3-(bromomethyl)-4-nitrobenzoate

Into a 2000-mL oven-dried round-bottom flask, were placed a solution of methyl 3-methyl-4-nitrobenzoate (199.6 g, 1.02 mol) in CCl$_4$ (1500 mL) and NBS (199.4 g, 1.12 mol), BPO (24.7 g, 96.39 mmol). The resulting mixture was stirred overnight at 80° C. under nitrogen in an oil bath. After the precipitate was filtered out, the filtrate was concentrated under vacuum. The residue was purified on a silica gel column eluted with ethyl acetate/petroleum ether (1:20) to yield methyl 3-(bromomethyl)-4-nitrobenzoate as a light yellow solid.

Step 2: Synthesis of methyl 3-[(cyclopropylamino)methyl]-4-nitrobenzoate

Into a 1000-mL oven-dried round-bottom flask, were placed a solution of methyl 3-(bromomethyl)-4-nitrobenzoate (40.0 g, 145.9 mmol) in CH$_3$CN (800 mL), cyclopropylamine (12.5 g, 218.9 mmol) and potassium carbonate (60 g, 434.1 mmol). The resulting mixture was stirred for 2 h at room temperature. After the precipitate was filtered out, the filtrate was concentrated under vacuum. The residue was dissolved in DCM (500 mL) and washed with water (3×200 mL). The organic layer was dried over anhydrous sodium sulfate and concentrated under vacuum to yield methyl 3-[(cyclopropylamino)methyl]-4-nitrobenzoate as yellow oil. LC/MS (ES, m/z): 251 [M+H]$^+$.

Step 3: Synthesis of 2-cyclopropyl-2H-indazole-5-carboxylic acid

Into a 2000-mL round-bottom flask, were placed a solution of methyl 3-[(cyclopropylamino)methyl]-4-nitrobenzoate (36 g, 143.9 mmol) in 1,4-dioxane (800 mL), Zn (37.4 g, 576.0 mmol), followed by dropwise addition of a solution of sodium hydroxide (57.6 g, 1.44 mol) in water (800 mL). The resulting mixture was stirred for 4 h at room temperature. The precipitate formed was filtered out, the filtrate was concentrated under vacuum. The product was precipitated by the addition of hydrogen chloride (12 M), and collected by filtration to yield 2-cyclopropyl-2H-indazole-5-carboxylic acid as a yellow solid. LC/MS (ES, m/z): 203 [M+H]$^+$.

Step 4: Synthesis of methyl 2-cyclopropyl-2H-indazole-5-carboxylate

Into a 500-mL oven-dried round-bottom flask, were placed a solution of 2-cyclopropyl-2H-indazole-5-carboxylic acid (14.8 g, 73.2 mmol) in N,N-dimethylformamide (200 mL) and potassium carbonate (30.3 g, 219.2 mmol) followed by dropwise addition CH$_3$I (15.6 g, 109.9 mmol). The resulting mixture was stirred overnight at room temperature, and then water (1000 mL) was added. The precipitate formed was collected by filtration to yield methyl 2-cyclopropyl-2H-indazole-5-carboxylate as a yellow solid. LC/MS (ES, m/z): 217 [M+H]$^+$ Step 5: Synthesis of methyl 3-bromo-2-cyclopropyl-2H-indazole-5-carboxylate Into a 250-mL oven-dried round-bottom flask, was placed a solution of methyl 2-cyclopropyl-2H-indazole-5-carboxylate (15.8 g, 73.1 mmol) in HOAc (148 mL) and NBS (12.9 g, 72.8 mmol). The resulting mixture was stirred overnight at room temperature, and then water (2000 mL) was added. The precipitate formed was collected by filtration to yield methyl 3-bromo-2-cyclopropyl-2H-indazole-5-carboxylate as a yellow solid. LC/MS (ES, m/z): 295 [M+H]$^+$.

Step 6: Synthesis of methyl 3-[1-[(tert-butoxy)carbonyl]-1,2,3,6-tetrahydropyridin-4-yl]-2-cyclopropyl-2H-indazole-5-carboxylate Into a 500-mL oven-dried 3-necked round-bottom flask purged and maintained with nitrogen, were placed a solution of methyl 3-bromo-2-cyclopropyl-2H-indazole-5-carboxylate (5.0 g, 16.9 mmol) in 1,4-dioxane/H$_2$O (210/25 mL), tert-butyl 4-(tetramethyl-1,3,2-dioxaborolan-2-yl)-1,2,3,6-tetrahydropyridine-1-carboxylate (9.18 g, 29.7 mmol), Pd(OAc)$_2$ (442 mg, 1.97 mmol), S-phos (1.62 g, 3.94 mmol) and K$_3$PO$_4$ (16.7 g, 78.8 mmol). The resulting mixture was stirred overnight at 90° C. in an oil bath under nitrogen, and then concentrated under vacuum. The residue was purified on a silica gel column eluted with ethyl acetate/petroleum ether (1:4) to yield methyl 3-[1-[(tert-butoxy)carbonyl]-1,2,3,6-tetrahydropyridin-4-yl]-2-cyclopropyl-2H-indazole-5-carboxylate as yellow oil. LC/MS (ES, m/z): 398 [M+H]$^+$.

Step 7: Synthesis of methyl 3-[1-[(tert-butoxy)carbonyl]piperidin-4-yl]-2-cyclopropyl-2H-indazole-5-carboxylate Into a 250-mL oven-dried round-bottom flask, were placed a solution of methyl 3-[1-[(tert-butoxy)carbonyl]-1,2,3,6-tetrahydropyridin-4-yl]-2-cyclopropyl-2H-indazole-5-carboxylate (4.1 g, 10.1 mmol) in methanol (100 mL), HCOONH$_4$ (9.4 g, 149.8 mmol) and 10% Palladium on carbon (1.07 g, 1.01 mmol). The resulting mixture was heated to reflux under nitrogen for 3.5 hr. The precipitate was filtered out, and the filtrate was concentrated under vacuum. The residue was dissolved in ethyl acetate (100 mL), and washed with water (2×50 mL). The organic layer was dried over anhydrous sodium sulfate and concentrated under vacuum to yield 3 methyl 3-[1-[(tert-butoxy)carbonyl] piperidin-4-yl]-2-cyclopropyl-2H-indazole-5-carboxylate as light yellow oil. LC/MS (ES, m/z): 400 [M+H]$^+$.

Step 8: Synthesis of tert-butyl 4-[5-[bis(4-chlorophenyl)(hydroxy)methyl]-2-cyclopropyl-2H-indazol-3-yl]piperidine-1-carboxylate Into a 250-mL round-bottom flask, was placed a solution of methyl 3-[1-[(tert-butoxy)carbonyl]piperidin-4-yl]-2-cyclopropyl-2H-indazole-5-carboxylate (3.5 g, 7.89 mmol) in tetrahydrofuran (50 mL), followed by dropwise addition of 1M solution of bromo(4-chlorophenyl)magnesium in diethyl ether (25 mL, 25.0 mmol). The resulting solution was heated to reflux under nitrogen overnight, and then concentrated under vacuum. The residue was then dissolved in DCM (100 mL) and washed with water (2×50 mL). The organic layer was dried over sodium sulfate and concentrated under vacuum to yield tert-butyl 4-[5-[bis(4-chlorophenyl)(hydroxy)methyl]-2-cyclopropyl-2H-indazol-3-yl]piperidine-1-carboxylate as a yellow solid. LC/MS (ES, m/z): 592 [M+H]$^+$.

Step 9: Synthesis of 5-[bis(4-chlorophenyl)methyl]-2-cyclopropyl-3-(piperidin-4-yl)-2H-indazole Into a 250-mL round-bottom flask, were placed a solution of tert-butyl 4-[5-[bis(4-chlorophenyl)(hydroxy)methyl]-2-cyclopropyl-2H-indazol-3-yl]piperidine-1-carboxylate (2.34 g, 3.95 mmol) in dichloromethane (100 mL), Et$_3$SiH (10 mL), and trifluoroacetic acid (10 mL). The resulting solution was stirred for 5 h at room temperature and then washed with NaHCO$_3$ (aq.) (3×100 mL). The organic layer was dried over sodium sulfate and concentrated under vacuum. The residue was purified on a silica gel column eluted with DCM/MeOH (20:1) to yield 5-[bis(4-chlorophenyl)methyl]-2-cyclopropyl-3-(piperidin-4-yl)-2H-indazole as a light yellow solid.

$^1$HNMR (300 MHz, CD$_3$OD) δ: 7.62 (s, 1H), 7.48-7.52 (m, 1H), 7.30-7.31 (m, 4H), 7.05-7.14 (m, 5H), 5.51 (s, 1H), 3.85-3.95 (m, 2H), 3.55-3.67 (m, 2H), 3.22-3.33 (m, 2H), 2.19-2.36 (m, 4H), 1.22-1.38 (m, 4H). LC/MS (ES, m/z): 476 [M+H]$^+$.

Step 10: Synthesis of 5-[bis(4-chlorophenyl) methyl]-2-cyclopropyl-3-[1-(trifluoromethane)sulfonylpiperidin-4-yl]-2H-indazole Into a 50-mL oven-dried round-bottom flask, were placed a solution of 5-[bis(4-chlorophenyl)methyl]-2-cyclopropyl-3-(piperidin-4-yl)-2H-indazole (100.1 mg, 0.21 mmol) in dichloromethane (10 mL) and triethylamine (63.6 mg, 0.63 mmol), followed by dropwise addition of Tf$_2$O (89.1 mg, 0.32 mmol) at −78° C. The resulting solution was stirred overnight at room temperature, and then water (10 mL) was added. The organic layer was washed with water (3×10 mL), and then dried over anhydrous sodium sulfate and concentrated under vacuum. The residue was purified by Prep-HPLC as described in Step 3 of Example PH-2. The title compound 5-[bis(4-chlorophenyl)methyl]-2-cyclopropyl-3-[1-(trifluoromethane)sulfonylpiperidin-4-yl]-2H-indazole was obtained as a white solid.

$^1$HNMR (400 MHz, CD$_3$OD) δ: 7.49 (d, J=9.2 Hz, 1H), 7.33 (d, J=8.0 Hz, 5H), 7.09-7.13 (m, 5H), 5.67 (s, 1H), 4.06-4.09 (m, 2H), 3.89-3.90 (m, 1H), 3.70-3.80 (m, 1H), 2.03 (m, 4H), 1.31-1.32 (m, 2H), 1.26-1.29 (m, 2H). LC/MS (ES, m/z): 608 [M+H]$^+$.

Example PH-22

5-((4-(5-(bis(4-chlorophenyl)methyl)-2-cyclopropyl-2H-indazol-3-yl)piperidin-1-yl)methyl)furan-2-carboxylic acid

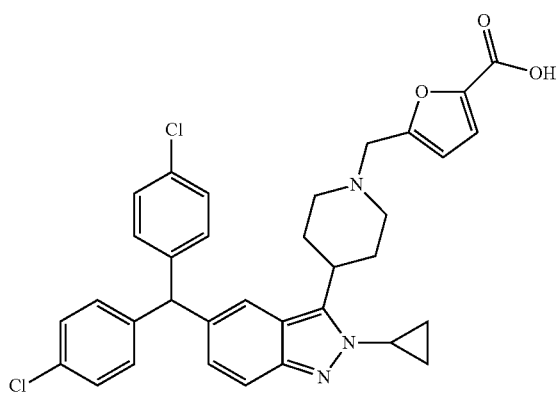 [SMILES: O=C(O)c1ccc(CN2CCC(c3c4cc(C(c5ccc(Cl)cc5)c5ccc(Cl)cc5)ccc4nn3C3CC3)CC2)o1]

The title compound was prepared according to the procedure as described in Example PH-16 substituting 5-formylfuran-2-carboxylic acid for methyl 3-formylbenzoate, and substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole in Step 1.

$^1$HNMR (300 MHz, CDCl$_3$) δ: 7.70 (s, 1H), 7.56 (d, J=9.0 Hz, 1H), 7.15-7.18 (m, 4H), 7.03-7.09 (m, 6H), 6.73 (s, 1H), 5.48 (s, 1H), 4.35 (s, 2H), 3.89 (m, 2H), 3.50-3.80 (m, 2H), 2.90-3.10 (m, 2H), 2.70-2.90 (m, 2H), 2.07-2.11 (m, 2H), 1.13-1.31 (m, 4H). LC/MS (ES, m/z): 600 [M+H]$^+$.

Example PH-23

5-((4-(5-(bis(4-chlorophenyl)methyl)-2-cyclopropyl-2H-indazol-3-yl)piperidin-1-yl)methyl)thiophene-2-carboxylic acid

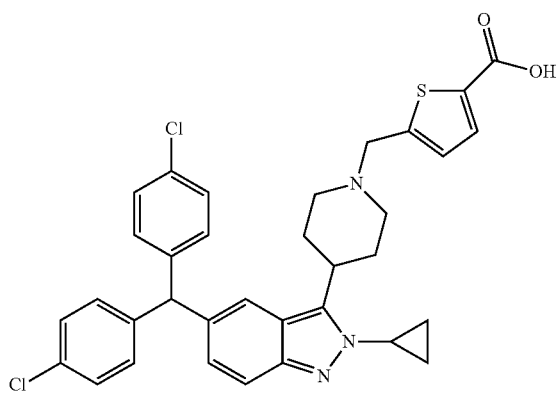

The title compound was prepared according to the procedure as described in Example PH-19 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole in Step 1.

$^1$HNMR (300 MHz, CD$_3$OD) δ: 7.75 (s, 1H), 7.53 (s, 1H), 7.46 (d, J=9.0 Hz, 1H), 7.35 (d, J=3.9 Hz, 1H), 7.26 (d, J=8.4 Hz, 4H), 7.00-7.08 (m, 5H), 5.58 (s, 1H), 4.84 (s, 2H), 3.78-3.90 (m, 2H), 3.67-3.71 (m, 2H), 3.24-3.30 (m, 2H), 2.20-2.42 (m, 4H), 1.18-1.33 (m, 4H). LC/MS (ES, m/z): 616 [M+H]$^+$.

Example PH-24

5-((4-(5-(bis(4-chlorophenyl)methyl)-2-cyclopropyl-2H-indazol-3-yl)piperidin-1-yl)methyl)thiophene-3-carboxylic acid

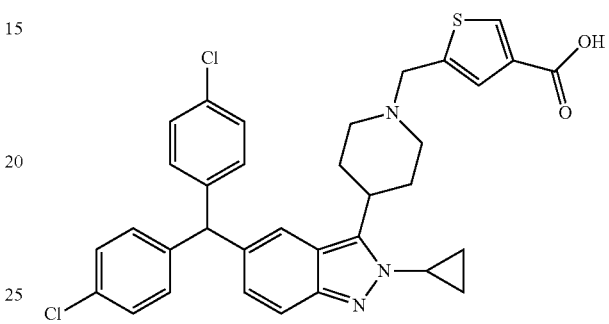

The title compound was prepared according to the procedure as described in Example PH-20 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole in Step 1.

$^1$HNMR (300 MHz, CDCl$_3$) δ: 8.15 (s, 1H), 7.45-7.77 (m, 3H), 7.20 (d, J=8.7 Hz, 4H), 6.94-7.08 (m, 5H), 5.53 (s, 1H), 4.50 (s, 2H), 3.88 (m, 2H), 3.63-3.78 (m, 2H), 2.80-3.10 (m, 4H), 2.01-2.27 (m, 2H), 1.12-1.43 (m, 4H). LC/MS (ES, m/z): 616 [M+H]$^+$.

Example PH-25

5-((4-(5-(bis(4-chlorophenyl)methyl)-2-cyclopropyl-2H-indazol-3-yl)piperidin-1-yl)methyl)thiophene-3-carboxamide

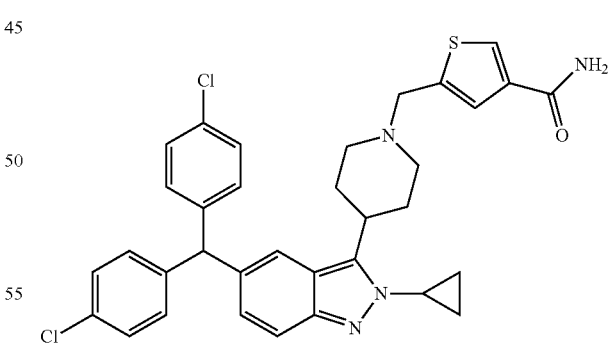

The title compound was prepared according to the procedure as described in Example PH-20 substituting 5-((4-(5-(bis(4-chlorophenyl)methyl)-2-cyclopropyl-2H-indazol-3-yl)piperidin-1-yl)methyl)thiophene-3-carboxylic acid for 5-((4-(5-(bis(4-chlorophenyl)methyl)-1-cyclopropyl-1H-indazol-3-yl)piperidin-1-yl)methyl)thiophene-3-carboxylic acid in Step 2.

$^1$HNMR (400 MHz, CDCl$_3$) δ: 8.15 (s, 1H), 8.06 (s, 1H), 7.51-7.65 (m, 2H), 7.25 (d, J=8.0 Hz, 4H), 7.04-7.06 (m,

5H), 5.54 (s, 1H), 4.58 (s, 2H), 3.62-3.94 (m, 5H), 2.85-3.07 (m, 3H), 2.03-2.14 (m, 2H), 1.25-1.39 (m, 4H). LC/MS (ES, m/z): 615 [M+H]+.

Example PH-26

6-((4-(5-(bis(4-chlorophenyl)methyl)-2-cyclopropyl-2H-indazol-3-yl)piperidin-1-yl)methyl)picolinic acid

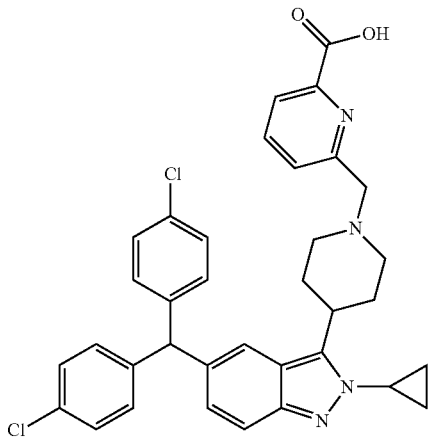 [SMILES: O=C(O)c1cccc(CN2CCC(c3c4cc(C(c5ccc(Cl)cc5)c5ccc(Cl)cc5)ccc4nn3C3CC3)CC2)n1]

The title compound was prepared according to the procedure as described in Example PH-16 substituting methyl 6-formylpyridine-2-carboxylate for methyl 3-formylbenzoate, and substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole in Step 1.

¹HNMR (400 NHz, CD₃OD) δ: 8.10 (d, J=7.2 Hz, 1H), 8.00 (t, J=7.6 Hz, 1H), 7.78 (s, 1H), 7.53 (t, J=7.2 Hz, 2H), 7.33 (d, J=8.8 Hz, 4H), 7.15 (d, J=8.4 Hz, 4H), 7.08 (d, J=8.8 Hz, 1H), 5.69 (s, 1H), 4.53 (s, 2H), 3.88-3.95 (m, 2H), 3.63-3.67 (m, 2H), 3.15-3.20 (m, 2H), 2.55-2.60 (m, 2H), 2.21-2.25 (m, 2H), 1.25-1.36 (m, 4H). LC/MS (ES, m/z): 611 [M+H]+.

Example PH-27

3-((4-(5-((4-chlorophenyl)(phenyl)methyl)-1-cyclopropyl-1H-indazol-3-yl)piperidin-1-yl)methyl)benzoic acid

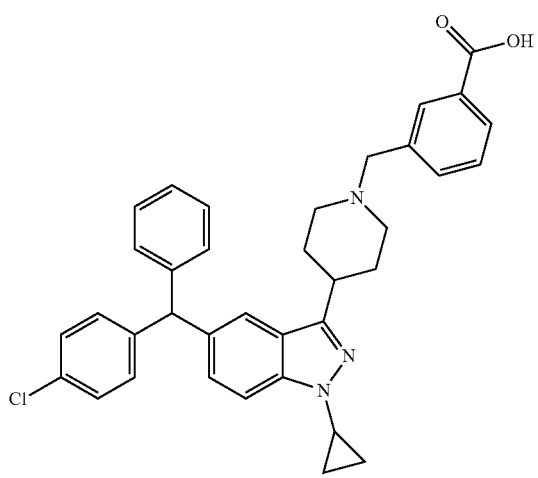 [SMILES: O=C(O)c1cccc(CN2CCC(c3nn(C4CC4)c4ccc(C(c5ccccc5)c5ccc(Cl)cc5)cc34)CC2)c1]

Step 1: Synthesis of tert-butyl 4-[1-cyclopropyl-5-[methoxy(methyl)carbamoyl]-1H-indazol-3-yl]piperidine-1-carboxylate Into a 250-mL oven-dried round-bottom flask, were placed a solution of methyl 3-[1-[(tert-butoxy)carbonyl]piperidin-4-yl]-1-cyclopropyl-1H-indazole-5-carboxylate (9.0 g, 22.53 mmol) in tetrahydrofuran (80 mL) and methoxy(methyl)amine hydrochloride (2.63 g, 26.96 mmol), followed by dropwise addition of 1M solution of LiHMDS in THF (56.3 mL, 56.3 mmol). The resulting solution was stirred for 10 min at room temperature and then saturated sodium bicarbonate solution (300 mL) was added. The reaction mixture was extracted with ethyl acetate (3×200 mL). The combined organic extract was dried over sodium sulfate and concentrated under vacuum. The residue was purified on a silica gel column eluted with ethyl acetate/petroleum ether (30%) to yield tert-butyl 4-[1-cyclopropyl-5-[methoxy(methyl)carbamoyl]-1H-indazol-3-yl]piperidine-1-carboxylate as a yellow solid. LC/MS (ES, m/z): 429 [M+H]+

Step 2: Synthesis of tert-butyl 4-[5-[(4-chlorophenyl)carbonyl]-1-cyclopropyl-1H-indazol-3-yl]piperidine-1-carboxylate Into a 250-mL oven-dried round-bottom flask, was placed a solution of tert-butyl 4-[1-cyclopropyl-5-[methoxy(methyl)carbamoyl]-1H-indazol-3-yl]piperidine-1-carboxylate (8.0 g, 18.67 mmol) in tetrahydrofuran (80 ml) followed by dropwise addition of a 1 M solution of bromo(4-chlorophenyl)magnesium in THF (37.3 mL, 37.3 mmol). The resulting solution was stirred under nitrogen for 2 h at room temperature and then saturated sodium bicarbonate solution (200 mL) was added. The reaction mixture was extracted with ethyl acetate (3×200 mL). The combined organic extract was dried over sodium sulfate and concentrated under vacuum. The residue was purified on a silica gel column eluted with ethyl acetate/petroleum ether (20%) to yield tert-butyl 4-[5-[(4-chlorophenyl)carbonyl]-1-cyclopropyl-1H-indazol-3-yl]piperidine-1-carboxylate as a white solid. LC/MS (ES, m/z): 480 [M+H]+

Step 3: Synthesis of tert-butyl 4-[5-[(4-chlorophenyl)(hydroxy)benzyl]-1-cyclopropyl-1H-indazol-3-yl]piperidine-1-carboxylate Into a 50-mL oven-dried round-bottom flask, were placed a solution of iodobenzene (2.13 g, 10.44 mmol) in tetrahydrofuran (8 mL), Mg (300 mg, 12.50 mmol). To the mixture was then added a solution of tert-butyl 4-[5-[(4-chlorophenyl)carbonyl]-1-cyclopropyl-1H-indazol-3-yl]piperidine-1-carboxylate 1.0 g, 2.08 mmol) in tetrahydrofuran (2 mL) dropwise. The resulting mixture was stirred under nitrogen for 2 h at room temperature, and then saturated NHCl₄ solution (10 mL) was added. The mixture was extracted with ethyl acetate (3×20 mL). The combined organic layer was washed with brine (1×30 mL), and then dried over anhydrous sodium sulfate and concentrated under vacuum to yield tert-butyl 4-[5-[(4-chlorophenyl) (hydroxy)benzyl]-1-cyclopropyl-1H-indazol-3-yl]piperidine-1-carboxylate as a yellow oil.

Step 4: Synthesis of 5-[(4-chlorophenyl) (phenyl)methyl]-1-cyclopropyl-3-(piperidin-4-yl)-1H-indazole Into a 50-mL oven-dried round-bottom flask, were placed a solution of tert-butyl 4-[5-[(4-chlorophenyl)(hydroxy)benzyl]-1-cyclopropyl-1H-indazol-3-yl]piperidine-1-carboxylate (1.5 g, 2.69 mmol) in dichloromethane (8 mL), trifluoroacetic acid (5 mL) and Et₃SiH (3 mL). The resulting solution was stirred for 3 h at room temperature and then concentrated under vacuum. The residue was purified on a silica gel column eluted with dichloromethane/methanol (100:12) to yield 5-[(4-chlorophenyl) (phenyl)methyl]-1-cyclopropyl-3-(piperidin-4-yl)-1H-indazole as a light yellow solid. LC/MS (ES, m/z): 442 [M+H]⁺

Step 5: Synthesis of methyl 3-[(4-[5-[(4-chlorophenyl) (phenyl)methyl]-1-cyclopropyl-1H-indazol-3-yl]piperidin-1-yl)methyl]benzoate Into a 50-mL round-bottom flask, were placed a solution of 5-[(4-chlorophenyl)(phenyl)methyl]-1-cyclopropyl-3-(piperidin-4-yl)-1H-indazole (397.8 mg, 0.90 mmol) in dichloromethane (10 mL), methyl 3-formylbenzoate (149.4 mg, 0.91 mmol) and TEA (1 mL). The solution was stirred for overnight at room temperature, and then NaBH(AcO)₃ (479.0 mg, 2.26 mmol) was added. The resulting mixture was stirred overnight at room temperature and then concentrated under vacuum. The residue was purified on a silica gel column eluted with dichloromethane/methanol (100:3) to yield methyl 3-[(4-[5-[(4-chlorophenyl) (phenyl)methyl]-1-cyclopropyl-1H-indazol-3-yl]piperidin-1-yl)methyl]benzoate as a light yellow solid. LC/MS (ES, m/z): 590 [M+H]⁺

Step 6: Synthesis of 3-[(4-[5-[(4-chlorophenyl)(phenyl)methyl]-1-cyclopropyl-1H-indazol-3-yl]piperidin-1-yl)carbonyl]benzoic acid hydrochloride Into a 50-mL round-bottom flask, were placed a solution of methyl 3-[(4-[5-[(4-chlorophenyl)(phenyl)methyl]-1-cyclopropyl-1H-indazol-3-yl]piperidin-1-yl)carbonyl]benzoate (295.1 mg, 0.50 mmol) in tetrahydrofuran/MeOH/H₂O (16/4/4 ml), LiOH.H₂O (1.0 g, 23.83 mmol). The resulting mixture was stirred overnight at room temperature, and concentrated under vacuum to remove organic solvents. After acidification to pH 4-5 with 2% HCl solution, precipitate formed was collected by filtration to yield 3-[(4-[5-[(4-chlorophenyl)(phenyl)methyl]-1-cyclopropyl-1H-indazol-3-yl]piperidin-1-yl)carbonyl]benzoic acid hydrochloride as an off-white solid.

¹HNMR (400 Hz, CD₃OD) δ: 8.26 (s, 1H), 8.19 (d, J=7.6 Hz, 1H), 7.79 (d, J=8.0 Hz, 1H), 7.64-7.68 (m, 1H), 7.59 (d, J=9.2 Hz, 1H), 7.49 (s, 1H), 7.31 (d, J=7.2 Hz, 4H), 7.23-7.29 (m, 2H), 7.11 (d, J=7.2 Hz, 4H), 5.73 (s, 1H), 4.45 (s, 2H), 3.54-3.63 (m, 2H), 3.45-3.50 (m, 1H), 3.15-3.38 (m, 4H), 2.13-2.26 (m, 3H), 1.10-1.17 (m, 4H). LC/MS (ES, m/z): 576 [M+H]⁺.

Example PH-28

3-((4-(5-((4-chlorophenyl)(4-fluorophenyl)methyl)-1-cyclopropyl-1H-indazol-3-yl)piperidin-1-yl)methyl)benzoic acid

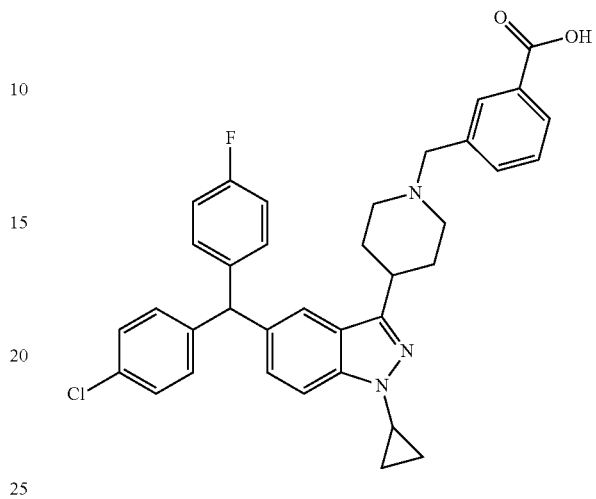

The title compound was prepared according to the procedure as described in Example PH-27 substituting 1-fluoro-4-iodobenzene for iodobenzene in Step 3.

¹HNMR (400 MHz, CD₃OD) δ: 8.25 (s, 1H), 8.19 (d, J=7.6 Hz, 1H), 7.80 (d, J=7.6 Hz, 1H), 7.64-7.68 (m, 1H), 7.60 (d, J=8.8 Hz, 1H), 7.46 (s, 1H), 7.30-7.32 (m, 2H), 7.24 (d, J=8.8 Hz, 1H), 7.10-7.15 (m, 4H), 7.02-7.07 (m, 2H), 5.74 (s, 1H), 4.46 (s, 2H), 3.45-3.64 (m, 3H), 3.22-3.38 (m, 4H), 2.11-2.25 (m, 3H), 1.09-1.19 (m, 4H). LC/MS (ES, m/z): 594 [M+H]⁺.

Example PH-29

3-((4-(5-((4-chlorophenyl)(p-tolyl)methyl)-1-cyclopropyl-1H-indazol-3-yl)piperidin-1-yl)methyl)benzoic acid

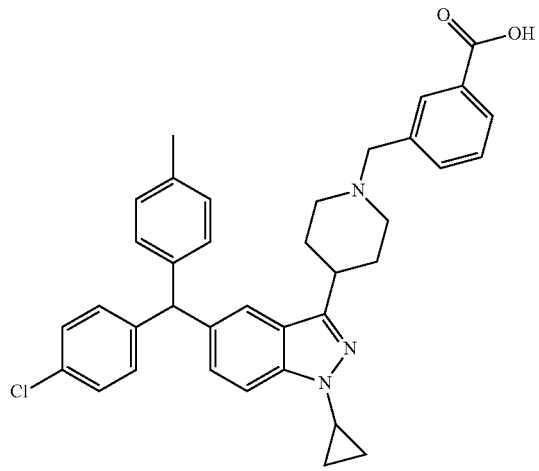 [SMILES: Cc1ccc(C(c2ccc(Cl)cc2)c2ccc3c(c2)c(C2CCN(Cc4cccc(C(=O)O)c4)CC2)nn3C2CC2)cc1]

The title compound was prepared according to the procedure as described in Example PH-27 substituting 1-bromo-4-methylbenzene for iodobenzene in Step 3.

¹HNMR (400 MHz, CD₃OD) δ: 8.25 (s, 1H), 8.19 (d, J=8.0 Hz, 1H), 7.80 (d, J=7.6 Hz, 1H), 7.64-7.68 (m, 1H), 7.58 (d, J=8.8 Hz, 1H), 7.46 (s, 1H), 7.22-7.30 (m, 3H), 7.08-7.13 (m, 4H), 6.99 (d, J=8.0 Hz, 2H), 5.69 (s, 1H), 4.46 (s, 2H), 3.45-3.63 (m, 3H), 3.22-3.38 (m, 4H), 2.31 (s, 3H), 2.11-2.25 (m, 3H), 1.10-1.16 (m, 4H). LC/MS (ES, m/z): 590 [M+H]$^+$.

Example PH-30

3-((4-(5-((4-chlorophenyl)(4-(trifluoromethyl)phenyl)methyl)-1-cyclopropyl-1H-indazol-3-yl)piperidin-1-yl)methyl)benzoic acid

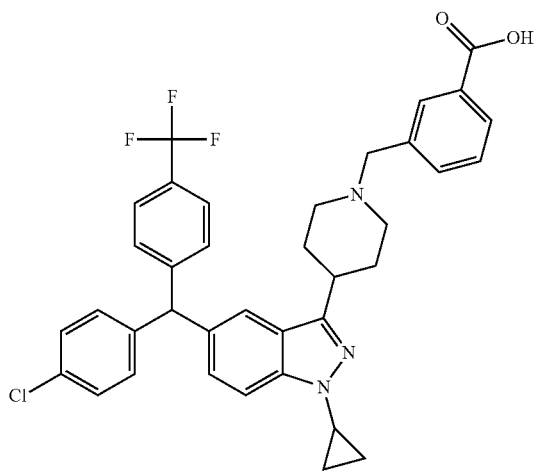 [SMILES: O=C(O)c1cccc(CN2CCC(c3nn(C4CC4)c4ccc(C(c5ccc(Cl)cc5)c5ccc(C(F)(F)F)cc5)cc34)CC2)c1]

The title compound was prepared according to the procedure as described in Example PH-27 substituting 1-iodo-4-(trifluoromethyl)benzene for iodobenzene in Step 3.

$^1$HNMR (400 MHz, CD$_3$OD) δ: 8.27 (s, 1H), 8.19 (d, J=7.6 Hz, 1H), 7.79 (d, J=7.6 Hz, 1H), 7.61-7.70 (m, 4H), 7.50 (s, 1H), 7.29-7.35 (m, 4H), 7.25 (d, J=8.8 Hz, 1H), 7.13 (d, J=8.4 Hz, 2H), 5.85 (s, 1H), 4.56 (s, 2H), 3.46-3.64 (m, 3H), 3.15-3.38 (m, 4H), 2.13-2.30 (m, 3H), 1.10-1.17 (m, 4H). LC/MS (ES, m/z): 644 [M−HCl+H]$^+$.

Example PH-31

3-((4-(1-cyclopropyl-5-(dip-tolylmethyl)-1H-indazol-3-yl)piperidin-1-yl)methyl)benzoic acid

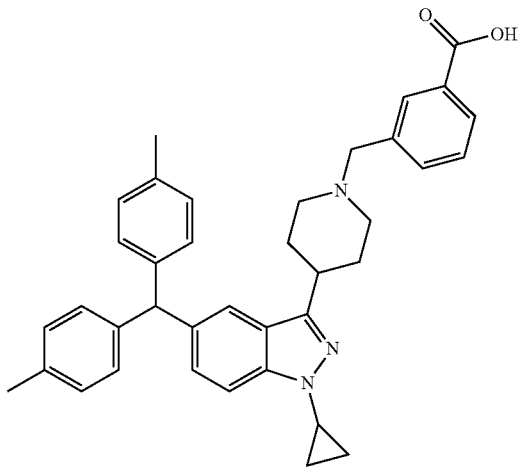 [SMILES: Cc1ccc(C(c2ccc(C)cc2)c2ccc3c(c2)c(C2CCN(Cc4cccc(C(=O)O)c4)CC2)nn3C2CC2)cc1]

The title compound was prepared according to the procedure as described in Example PH-27 substituting bromo(4-methylphenyl)magnesium for bromo(4-chlorophenyl)magnesium in Step 2, and substituting 1-bromo-4-methylbenzene for iodobenzene in Step 3.

$^1$HNMR (300 MHz, CDCl$_3$) δ: 8.59 (s, 1H), 8.08-8.10 (m, 1H), 7.35-7.45 (m, 4H), 7.17 (d, J=8.7 Hz, 1H), 6.86-7.05 (m, 8H), 5.50 (s, 1H), 3.98 (s, 2H), 3.34-3.48 (m, 4H), 2.92-3.03 (m, 2H), 2.29-2.38 (m, 10H), 1.09-1.15 (m 4H). LC/MS (ES, m/z): 570 [M+H]$^+$.

Example PH-32

Methyl 5-(4-(5-(bis(4-chlorophenyl)methyl)-1H-indazol-3-yl)piperidin-1-ylsulfonyl)furan-2-carboxylate

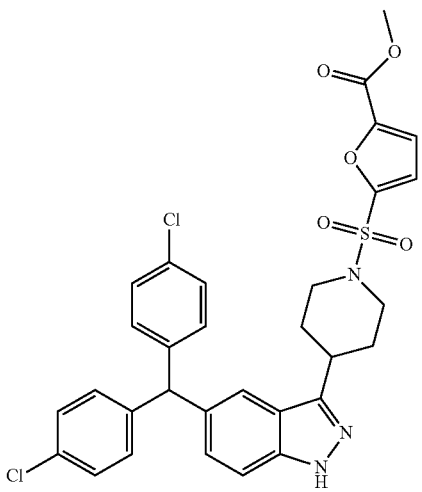 [SMILES: COC(=O)c1ccc(S(=O)(=O)N2CCC(c3n[nH]c4ccc(C(c5ccc(Cl)cc5)c5ccc(Cl)cc5)cc34)CC2)o1]

Step 1: Synthesis of tert-butyl 4-[5-[bis(4-chlorophenyl)(hydroxy)methyl]-1H-indazol-3-yl]piperidine-1-carboxylate Into a 500-mL oven-dried round-bottom flask, was placed a solution of methyl 3-[1-[(tert-butoxy)carbonyl]piperidin-4-yl]-1H-indazole-5-carboxylate (3.0 g, 8.35 mmol) in tetrahydrofuran (150 mL) followed by dropwise addition of a 1M solution of bromo(4-chlorophenyl)magnesium in THF (4.17 mL, 4.17 mmol). The resulting solution was stirred overnight at 65° C. under nitrogen and then saturated sodium bicarbonate solution (200 mL) was added. The mixture was extracted with ethyl acetate (3×200 mL), the combined organic extract was dried over sodium sulfate and concentrated under vacuum. The residue was purified on a silica gel column eluted with ethyl acetate/petroleum ether (1:3) to yield tert-butyl 4-[5-[bis(4-chlorophenyl)(hydroxy)methyl]-1H-indazol-3-yl]piperidine-1-carboxylate as a yellow solid. LC/MS (ES, m/z): 553 [M+H]$^+$ Step 2: Synthesis of 5-[bis(4-chlorophenyl)methyl]-3-(piperidin-4-yl)-1H-indazole Into a 1000-mL round-bottom flask, were placed a solution of tert-butyl 4-[5-[bis(4-chlorophenyl)(hydroxy)methyl]-1H-indazol-3-yl]piperidine-1-carboxylate (15.0 g, 27.15 mmol) in dichloromethane (500 mL), trifluoroacetic acid (63.1 g, 548.5 mmol) and Et$_3$SiH (63.2 g, 543.5 mmol). The resulting solution was stirred for 4 h at room temperature and then concentrated under vacuum. The residue was purified on a silica gel column eluted with dichloromethane/ methanol (100:0-20:1) to yield 5-[bis(4-chlorophenyl)methyl]-3-(piperidin-4-yl)-1H-indazole as a light yellow solid. LC/MS (ES, m/z): 437 [M+H]+

Step 3: Synthesis of methyl 5-(4-[5-[bis(4-chlorophenyl)methyl]-1H-indazol-3-yl]piperidine-1-sulfonyl)furan-2-carboxylate Into a 50-mL round-bottom flask, were placed a solution of 5-[bis(4-chlorophenyl)methyl]-3-(piperidin-4-yl)-1H-indazole (200.7 mg, 0.46 mmol) in dichloromethane (20 mL), triethylamine (232.3 mg, 2.30 mmol) and methyl 5-(chlorosulfonyl)furan-2-carboxylate (112.3 mg, 0.50 mmol). The resulting solution was stirred for 2 h at room temperature and then concentrated under vacuum. The residue was purified on a silica gel column eluted with ethyl acetate/petroleum ether (0:100-2:1), and then further purified by Prep-HPLC as described in Step 3 of Example PH-2. The title compound methyl 5-(4-[5-[bis(4-chlorophenyl)methyl]-1H-indazol-3-yl]piperidine-1-sulfonyl)furan-2-carboxylate was obtained as a white solid.

$^1$HNMR (300 MHz, DMSO-$d_6$) δ: 12.66 (br.s, 1H), 7.52 (d, J=8.4 Hz, 2H), 7.36-7.46 (m, 6H), 7.05-7.14 (m, 5H), 5.75 (s, 1H), 3.87 (s, 3H), 3.74-3.78 (m, 2H), 3.08-3.15 (m, 1H), 2.86 (t, J=9.9 Hz, 2H), 1.96-2.03 (m, 2H), 1.74-1.83 (m, 2H). LC/MS (ES, m/z): 624 [M+H]+.

Example PH-33

3-[(4-[5-[bis(4-chlorophenyl)methyl]-1H-indazol-3-yl]piperidin-1-yl)methyl]benzamide

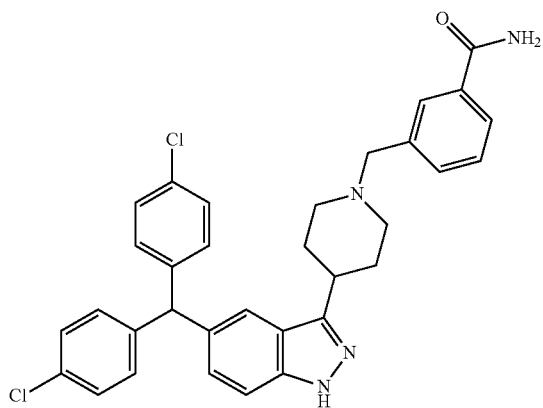 [SMILES: NC(=O)c1cccc(CN2CCC(c3n[nH]c4ccc(C(c5ccc(Cl)cc5)c5ccc(Cl)cc5)cc34)CC2)c1]

Step 1: Synthesis of tert-butyl 4-[1-(benzenesulfonyl)-5-[bis(4-chlorophenyl)(hydroxy)methyl]-1H-indazol-3-yl]piperidine-1-carboxylate Into a 100-mL oven-dried round-bottom flask, were placed a solution of tert-butyl 4-[5-[bis(4-chlorophenyl)(hydroxy)methyl]-1H-indazol-3-yl]piperidine-1-carboxylate (2.40 g, 4.34 mmol) in dichloromethane (50 mL), pyridine (10 mL) and triethylamine (4.39 g, 43.38 mmol), followed by slow addition of benzenesulfonyl chloride (1.53 g, 8.66 mmol) at 0° C. The resulting solution was stirred under nitrogen overnight at room temperature, and then washed with 3×30 mL of 1 N HCl solution. The organic layer was dried over anhydrous sodium sulfate and concentrated under vacuum to yield tert-butyl 4-[1-(benzenesulfonyl)-5-[bis(4-chlorophenyl)(hydroxy)methyl]-1H-indazol-3-yl]piperidine-1-carboxylate as a red oil. LC/MS (ES, m/z): 693 [M+H]+

Step 2: Synthesis of 1-(benzenesulfonyl)-5-[bis(4-chlorophenyl)methyl]-3-(piperidin-4-yl)-1H-indazole Into a 250-mL round-bottom flask, were placed a solution of tert-butyl 4-[1-(benzenesulfonyl)-5-[bis(4-chlorophenyl)(hydroxy)methyl]-1H-indazol-3-yl]piperidine-1-carboxylate (2.0 g, 2.89 mmol) in dichloromethane (100 mL), trifluoroacetic acid (10 mL) and triethylsilane (10 mL). The resulting solution was stirred overnight at room temperature and then concentrated. The residue was purified on a silica gel column eluted with ethyl acetate/petroleum ether (1:1) to yield 1-(benzenesulfonyl)-5-[bis(4-chlorophenyl)methyl]-3-(piperidin-4-yl)-1H-indazole as a red solid. LC/MS (ES, m/z): 577 [M+H]+

Step 3: Synthesis of methyl 3-([4-[1-(benzenesulfonyl)-5-[bis(4-chlorophenyl)methyl]-1H-indazol-3-yl]piperidin-1-yl]methyl)benzoate Into a 100-mL round-bottom flask, were placed a solution of 1-(benzenesulfonyl)-5-[bis(4-chlorophenyl)methyl]-3-(piperidin-4-yl)-1H-indazole (351.7 mg, 0.61 mmol) in dichloromethane (50 mL), methyl 3-formylbenzoate (99.6 mg, 0.61 mmol), triethylamine (92.4 mg, 0.91 mmol). To the mixture was then added sodium triacetoxyhydroborate (324.3 mg, 1.53 mmol) in 1 hr. The resulting mixture was stirred overnight at room temperature and then concentrated. The residue was purified on a silica gel column eluted with ethyl acetate/petroleum ether (1:3) to yield methyl 3-([4-[1-(benzenesulfonyl)-5-[bis(4-chlorophenyl)methyl]-1H-indazol-3-yl]piperidin-1-yl]methyl)benzoate as yellow oil. LC/MS (ES, m/z): 725 [M+H]+

Step 4: Synthesis of 3-[(4-[5-[bis(4-chlorophenyl)methyl]-1H-indazol-3-yl]piperidin-1-yl)methyl]benzoic acid Into a 100-mL round-bottom flask, were placed a solution of methyl 3-([4-[1-(benzenesulfonyl)-5-[bis(4-chlorophenyl)methyl]-1H-indazol-3-yl]piperidin-1-yl]methyl)benzoate (159.5 mg, 0.22 mmol) in tetrahydrofuran (40 mL), and a solution of LiOH.H$_2$O (556.4 mg, 13.26 mmol) in water (10 mL) and methanol (10 mL). The resulting mixture was stirred overnight at room temperature and then concentrated under vacuum to remove organic solvents. The mixture was acidified to pH 4-5 with 1N HCl solution. The precipitate formed was collected by filtration and purified by Prep-HPLC as described in Step 3 of Example PH-2. The title compound 3-[(4-[5-[bis(4-chlorophenyl)methyl]-1H-indazol-3-yl]piperidin-1-yl)methyl]benzoic acid was obtained as a white solid. LC/MS (ES, m/z): 570 [M+H]+

Step 5: Synthesis of 3-[(4-[5-[bis(4-chlorophenyl)methyl]-1H-indazol-3-yl]piperidin-1-yl)methyl]benzamide Into a 8-mL sample vial, were placed a solution of 3-[(4-[5-[bis(4-chlorophenyl)methyl]-1H-indazol-3-yl]piperidin-1-yl)methyl]benzoic acid (83.4 mg, 0.15 mmol) in N,N-dimethylformamide (3 mL), DIEA (57.6 mg, 0.45 mmol) and NH$_4$Cl (15.8 mg, 0.30 mmol), followed by addition of HATU (113.2 mg, 0.30 mmol) in 5 min. The resulting mixture was stirred overnight at room temperature and then water (5 mL) was added. The mixture was extracted with ethyl acetate (2×10 mL). The combined organic layer was washed with brine (2×10 mL), and dried over anhydrous sodium sulfate and concentrated under vacuum. The residue was purified by Prep-HPLC as described in Step 3 of Example PH-2. The title compound 3-[(4-[5-[bis(4-chlorophenyl)methyl]-1H-indazol-3-yl]piperidin-1-yl)methyl]benzamide was obtained as a white solid.

¹HNMR (300 MHz, CD₃OD): δ: 7.99-8.05 (m, 2H). 7.59-7.74 (m, 2H), 7.44-7.49 (m, 2H), 7.31 (d, J=8.4 Hz, 4H), 7.19 (d, J=8.7 Hz, 1H), 7.11 (d, J=8.7 Hz, 4H), 5.73 (s, 1H), 4.38-4.46 (m, 2H), 3.60-3.64 (m, 2H), 3.31-3.33 (m, 3H), 2.07-2.28 (m, 4H). LC/MS (ES, m/z): 569 [M+H]⁺.

Example PH-34

Cyclopentyl 4-(5-(bis(4-chlorophenyl)methyl)-1H-indazol-3-yl)piperidine-1-carboxylate

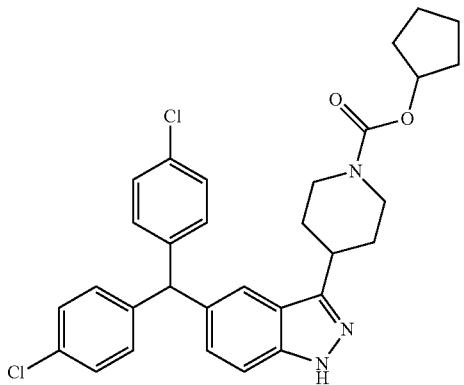 [SMILES: O=C(OC1CCCC1)N1CCC(c2n[nH]c3ccc(C(c4ccc(Cl)cc4)c4ccc(Cl)cc4)cc23)CC1]

The title compound was prepared according to the procedure as described in Example PH-32 substituting cyclopentyl chloroformate for methyl 5-(chlorosulfonyl)furan-2-carboxylate in Step 3.

¹HNMR (300 MHz, DMSO-d₆) δ: 12.64 (s, 1H), 7.49 (s, 1H), 7.32-7.39 (m, 5H), 7.10 (d, J=8.4 Hz, 4H), 7.02 (d, J=8.7 Hz, 1H), 5.73 (s, 1H), 4.93-4.97 (m, 1H), 3.95-3.99 (m, 2H), 3.09-3.17 (m, 1H), 2.80-2.99 (m, 2H), 1.59-1.86 (m, 12H). LC/MS (ES, m/z): 548 [M+H]⁺.

Example PH-35

Ethyl 4-(5-(bis(4-chlorophenyl)methyl)-1H-indazol-3-yl)piperidine-1-carboxylate

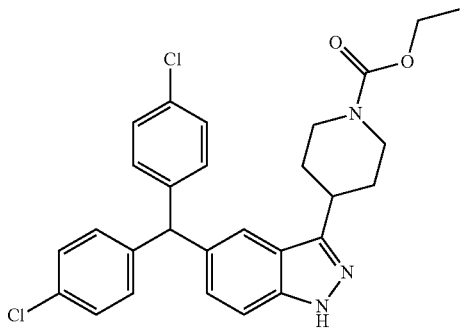 [SMILES: CCOC(=O)N1CCC(c2n[nH]c3ccc(C(c4ccc(Cl)cc4)c4ccc(Cl)cc4)cc23)CC1]

The title compound was prepared according to the procedure as described in Example PH-32, substituting ethyl chloroformate for methyl 5-(chlorosulfonyl)furan-2-carboxylate in Step 3.

¹HNMR (300 MHz, DMSO-d₆) δ: 12.68 (s, 1H), 7.54 (s, 1H), 7.36-7.44 (m, 5H), 7.13 (d, J=8.4 Hz, 4H), 7.07 (d, J=8.7 Hz, 5H), 5.77 (s, 1H), 4.01-4.08 (m, 4H), 3.15-3.22 (m, 1H), 2.96-2.98 (m, 2H), 1.88-1.92 (m, 2H), 1.61-1.73 (m, 2H), 1.19 (t, J=7.2 Hz, 3H). LC/MS (ES, m/z): 508 [M+H]⁺.

Example PH-36

3-(4-(5-(bis(4-chlorophenyl)methyl)-2-cyclopropyl-2H-indazol-3-yl)piperidin-1-ylsulfonyl)benzoic acid

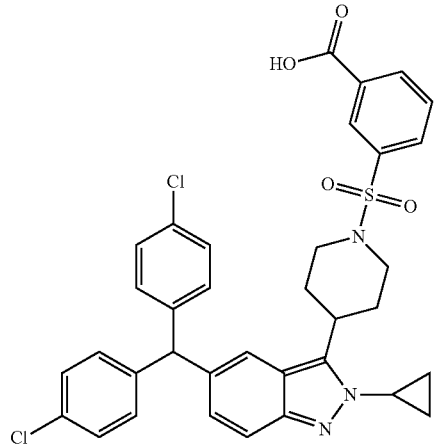 [SMILES: O=C(O)c1cccc(S(=O)(=O)N2CCC(c3c4cc(C(c5ccc(Cl)cc5)c5ccc(Cl)cc5)ccc4nn3C3CC3)CC2)c1]

The title compound was prepared according to the procedure as described in Example PH-21 substituting 3-(chlorosulfonyl)benzoic acid for trifluoromethanesulfonic anhydride in Step 10.

¹HNMR (400 MHz, CD₃OD) δ: 8.45 (s, 1H), 8.33 (d, J=7.6 Hz, 1H), 8.08 (d, J=8.0 Hz, 1H), 7.78 (t, J=8.0 Hz, 1H), 7.47 (d, J=9.2 Hz, 2H), 7.34 (d, J=8.4 Hz, 4H), 7.07-7.15 (m, 5H), 5.65 (s, 1H), 4.01-4.04 (m, 2H), 3.77-3.82 (m, 1H), 3.45-3.51 (m, 1H), 2.57 (t, J=12.4 Hz, 2H), 2.11-2.15 (m, 2H), 1.96-2.01 (m, 2H), 1.20-1.26 (m, 4H). LC/MS (ES, m/z): 660 [M+H]⁺.

Example PH-37

3-(4-(5-(bis(4-chlorophenyl)methyl)-2-cyclopropyl-2H-indazol-3-yl)piperidin-1-ylsulfonyl)benzamide

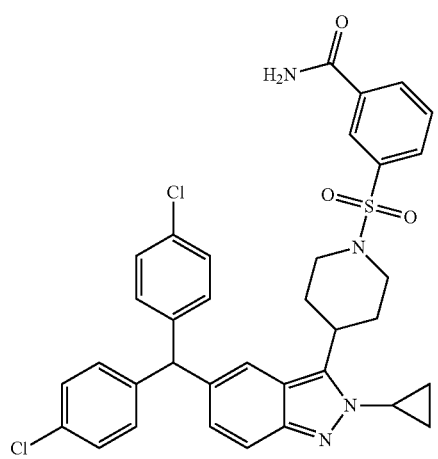 [SMILES: NC(=O)c1cccc(S(=O)(=O)N2CCC(c3c4cc(C(c5ccc(Cl)cc5)c5ccc(Cl)cc5)ccc4nn3C3CC3)CC2)c1]

The title compound was prepared according to the procedure as described in Example PH-15 substituting 3-((4-(5-(bis(4-chlorophenyl)methyl)-2-cyclopropyl-2H-indazol-3-yl)piperidin-1-yl)sulfonyl)benzoic acid for 4-(4-[5-[bis(4-chlorophenyl)methyl]-1-cyclopropyl-1H-indazol-3-yl]piperidin-1-yl)benzoic acid for in Step 3.

¹HNMR (300 MHz, CD₃OD) δ: 8.34 (s, 1H), 8.18 (d, J=7.8 Hz, 1H), 8.01 (d, J=8.1 Hz, 1H), 7.74 (t, J=7.8 Hz, 1H), 7.45 (d, J=8.7 Hz, 2H), 7.32 (d, J=6.6 Hz, 4H), 7.06-7.14 (m, 5H), 5.64 (s, 1H), 4.02 (d, J=11.7 Hz, 2H), 3.76-3.80 (m, 1H), 3.41-3.53 (m, 1H), 2.52-2.60 (m, 2H), 2.10-2.15 (m, 2H), 1.96-2.00 (m, 2H), 1.16-1.25 (m, 4H). LC/MS (ES, m/z): 659 [M+H]⁺.

Example PH-38

4-(4-(5-(bis(4-chlorophenyl)methyl)-2-cyclopropyl-2H-indazol-3-yl)piperidin-1-ylsulfonyl)benzoic acid

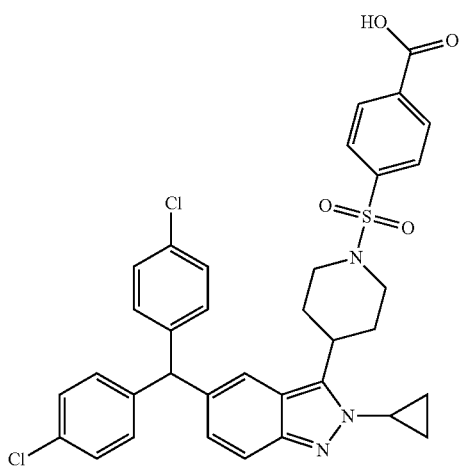 [SMILES: O=C(O)c1ccc(S(=O)(=O)N2CCC(c3c4cc(C(c5ccc(Cl)cc5)c5ccc(Cl)cc5)ccc4nn3C3CC3)CC2)cc1]

The title compound was prepared according to the procedure as described in Example PH-21 substituting 4-(chlorosulfonyl)benzoic acid for trifluoromethanesulfonic anhydride in Step 10.

1HNMR (400 MHz, CD3OD) δ: 8.29 (d, J=8.4 Hz, 2H), 7.97 (d, J=8.4 Hz, 2H), 7.43-7.47 (m, 2H), 7.33 (d, J=8.4 Hz, 4H), 7.05-7.15 (m, 5H), 5.63 (s, 1H), 4.00-4.03 (m, 2H), 3.77-3.81 (m, 1H), 3.48-3.51 (m, 1H), 2.58 (t, J=12.4 Hz, 2H), 2.05-2.14 (m, 2H), 1.97-2.00 (m, 2H), 1.24-1.28 (m, 2H), 1.16-1.19 (m, 2H). LC/MS (ES, m/z): 660 [M+H]+.

Example PH-39

4-(4-(5-(bis(4-chlorophenyl)methyl)-2-cyclopropyl-2H-indazol-3-yl)piperidin-1-ylsulfonyl)benzamide

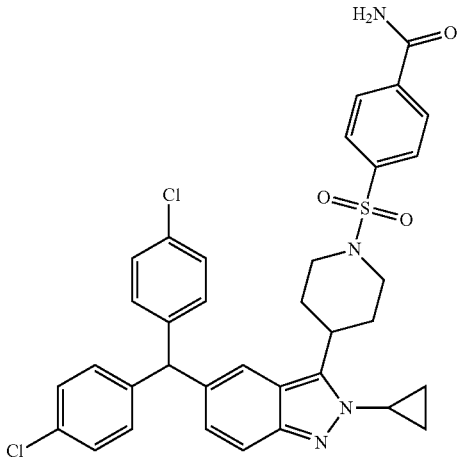 [SMILES: NC(=O)c1ccc(S(=O)(=O)N2CCC(c3c4cc(C(c5ccc(Cl)cc5)c5ccc(Cl)cc5)ccc4nn3C3CC3)CC2)cc1]

The title compound was prepared according to the procedure as described in Example PH-15 substituting 4-((4-(5-(bis(4-chlorophenyl)methyl)-2-cyclopropyl-2H-indazol-3-yl)piperidin-1-yl)sulfonyl)benzoic acid for 4-(4-[5-[bis(4-chlorophenyl)methyl]-1-cyclopropyl-1H-indazol-3-yl]piperidin-1-yl)benzoic acid in Step 3.

¹HNMR (400 MHz, CD₃OD) δ: 8.13 (d, J=8.4 Hz, 2H), 7.95 (d, J=8.4 Hz, 2H), 7.48-7.52 (m, 2H), 7.34 (d, J=8.4 Hz, 4H), 7.14 (d, J=7.6 Hz, 5H), 5.68 (s, 1H), 3.99-4.02 (m, 2H), 3.80-3.84 (m, 1H), 3.48-3.51 (m, 1H), 2.53-2.58 (m, 2H), 2.13-2.17 (m, 2H), 1.99-2.05 (m, 2H), 1.22-1.30 (m, 4H). LC/MS (ES, m/z): 659 [M+H]⁺.

Example PH-40

4-((4-chlorophenyl)(3-(1-(trifluoromethylsulfonyl)piperidin-4-yl)-1H-indazol-5-yl)methyl)phenol

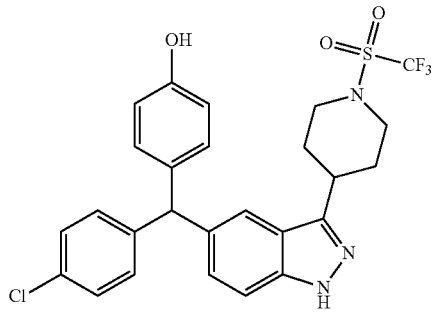 [SMILES: O=S(=O)(N1CCC(c2n[nH]c3ccc(C(c4ccc(O)cc4)c4ccc(Cl)cc4)cc23)CC1)C(F)(F)F]

Step 1: Synthesis of 3-[1-[(tert-butoxy)carbonyl]piperidin-4-yl]-1H-indazole-5-carboxylic acid Into a 250-mL round-bottom flask, were placed a solution of methyl 3-[1-[(tert-butoxy)carbonyl]piperidin-4-yl]-1H-indazole-5-carboxylate (7.4 g, 20.59 mmol) in tetrahydrofuran (80 mL) and a solution of LiOH.H₂O (8.7 g, 207.1 mmol) in water (80 mL). The resulting mixture was stirred for 2 days at 45° C. under nitrogen, and concentrated under vacuum to remove organic solvent. The mixture was then acidified to pH 4-5 with 1N HCl solution, and cool to 0° C., and the precipitate formed was collected by filtration to yield 3-[1-[(tert-butoxy)carbonyl]piperidin-4-yl]-1H-indazole-5-carboxylic acid as a white solid. LC/MS (ES, m/z): 345 [M+H]$^+$.

Step 2: Synthesis of tert-butyl 4-[5-[methoxy(methyl)carbamoyl]-1H-indazol-3-yl]piperidine-1-carboxylate Into a 250-mL oven-dried round-bottom flask, were placed methoxy(methyl)amine hydrochloride (2.95 g, 30.24 mmol), a solution of DIEA (12.9 g, 99.81 mmol) in N,N-dimethylformamide (100 mL). After 5 min, 3-[1-[(tert-butoxy)carbonyl]piperidin-4-yl]-1H-indazole-5-carboxylic acid (6.97 g, 20.27 mmol), HATU (9.12 g, 23.99 mmol) were added successively, and the resulting solution was stirred overnight at room temperature, then ethyl acetate (300 mL) was added. The organic layer was washed with water (3×200 mL), and dried over anhydrous sodium sulfate and concentrated under vacuum to yield tert-butyl 4-[5-[methoxy(methyl)carbamoyl]-1H-indazol-3-yl]piperidine-1-carboxylate as a white solid. LC/MS (ES, m/z): 389 [M+H]$^+$.

Step 3: Synthesis of tert-butyl 4-[5-[(4-chlorophenyl)carbonyl]-1H-indazol-3-yl]piperidine-1-carboxylate Into a 250-mL oven-dried round-bottom flask purged and maintained nitrogen, was placed a solution of tert-butyl 4-[5-[methoxy(methyl)carbamoyl]-1H-indazol-3-yl]piperidine-1-carboxylate (3.73 g, 9.60 mmol, 1.00 equiv) in tetrahydrofuran (50 mL), followed by dropwise addition of a 1M solution of bromo(4-chlorophenyl)magnesium in diethyl ether (22.0 mL, 22.0 mmol) at −20° C. The resulting solution was stirred overnight at room temperature, and then saturated NH$_4$Cl (aq) solution (20 mL) ethyl acetate (300 mL) were added successively. The organic layer was washed with water (3×200 mL), then dried over anhydrous sodium sulfate and concentrated under vacuum. The residue was purified on a silica gel column eluted with a gradient of EA/PE=5/100 to EA/PE=40/100 over 60 min to yield tert-butyl 4-[5-[(4-chlorophenyl)carbonyl]-1H-indazol-3-yl]piperidine-1-carboxylate was obtained as a white solid. LC/MS (ES, m/z): 440 [M+H]$^+$.

Step 4: Synthesis of 5-[(4-chlorophenyl)carbonyl]-3-(piperidin-4-yl)-1H-indazole Into a 500-mL round-bottom flask, were placed a solution of tert-butyl 4-[5-[(4-chlorophenyl)carbonyl]-1H-indazol-3-yl]piperidine-1-carboxylate (3.4 g, 7.73 mmol) in dichloromethane (100 mL), and then trifluoroacetic acid (10 mL). The resulting solution was stirred for 4 h at room temperature, and then concentrated under vacuum to remove organic solvents. The residue was dissolved in ethyl acetate (200 mL) and water (100 mL), and then basified to pH 9-10 with 1N sodium hydroxide solution. The organic layer was washed with sodium carbonate (2×200 mL), and dried over anhydrous sodium sulfate and concentrated under vacuum to yield 5-[(4-chlorophenyl)carbonyl]-3-(piperidin-4-yl)-1H-indazole as a yellow oil. LC/MS (ES, m/z): 340 [M+H]$^+$.

Step 5: Synthesis of 5-[(4-chlorophenyl)carbonyl]-3-[1-(trifluoromethane)sulfonylpiperidin-4-yl]-1H-indazole Into a 250-mL oven-dried round-bottom flask, were placed a solution of 5-[(4-chlorophenyl)carbonyl]-3-(piperidin-4-yl)-1H-indazole (2.0 g, 5.89 mmol) in dichloromethane (150 mL) and triethylamine (3.03 g, 29.94 mmol), followed by dropwise addition of trifluoromethanesulfonic anhydride (1.66 g, 5.88 mmol) at −15- to −20° C. The resulting solution was stirred under nitrogen overnight at room temperature and concentrated under vacuum. The residue was purified on a silica gel column eluted with a gradient of ethyl acetate/petroleum 5/100 to 30/100 over 60 min to yield 5-[(4-chlorophenyl)carbonyl]-3-[1-(trifluoromethane)sulfonylpiperidin-4-yl]-1H-indazole was obtained as a light yellow solid. LC/MS (ES, m/z): 472 [M+H]$^+$.

Step 6: Synthesis of (4-chlorophenyl)(4-methoxyphenyl)[3-[1-(trifluoromethane)sulfonylpiperidin-4-yl]-1H-indazol-5-yl]methanol Into a 50-mL oven-dried round-bottom flask, was placed a solution of 5-[(4-chlorophenyl)carbonyl]-3-[1-(trifluoromethane)sulfonylpiperidin-4-yl]-1H-indazole (235.5 mg, 0.50 mmol) in tetrahydrofuran (10 mL), followed by dropwise addition of a 0.5 M solution of bromo(4-methoxyphenyl)magnesium (14.2 mL, 7.10 mmol). The resulting solution was stirred under nitrogen overnight at room temperature, and then saturated sodium bicarbonate solution (30 mL) was added. The mixture was extracted with ethyl acetate (3×30 mL), the combined organic extract was dried over sodium sulfate and concentrated under vacuum. The residue was purified on a silica gel column eluted with ethyl acetate/petroleum ether (1:3) to yield (4-chlorophenyl)(4-methoxyphenyl)[3-[1-(trifluoromethane)sulfonylpiperidin-4-yl]-1H-indazol-5-yl]methanol as yellow oil. LC/MS (ES, m/z): 581 [M+H]$^+$.

Step 7: Synthesis of 5-[(4-chlorophenyl)(4-methoxyphenyl)methyl]-3-[1-(trifluoromethane)sulfonylpiperidin-4-yl]-1H-indazole Into a 25-mL oven-dried round-bottom flask, were placed a solution of (4-chlorophenyl)(4-methoxyphenyl)[3-[1-(trifluoromethane)sulfonylpiperidin-4-yl]-1H-indazol-5-yl]methanol (179.8 mg, 0.31 mmol) in dichloromethane (10 mL), trifluoroacetic acid (172.5 mg, 1.50 mmol) and Et$_3$SiH (176.8 mg, 1.52 mmol). The resulting solution was stirred under nitrogen for 3 h at room temperature and then concentrated under vacuum. The residue was purified on a silica gel column eluted with ethyl acetate/petroleum ether (1:3) to yield 5-[(4-chlorophenyl)(4-methoxyphenyl)methyl]-3-[1-(trifluoromethane)sulfonylpiperidin-4-yl]-1H-indazole as yellow oil. LC/MS (ES, m/z): 564 [M+H]$^+$.

Step 8: Synthesis of 4-[(4-chlorophenyl)([3-[1-(trifluoromethane)sulfonylpiperidin-4-yl]-1H-indazol-5-yl])methyl]phenol Into a 25-mL oven-dried round-bottom flask, was placed a solution of 5-[(4-chlorophenyl)(4-methoxyphenyl)methyl]-3-[1-(trifluoromethane)sulfonylpiperidin-4-yl]-1H-indazole (56.4 mg, 0.10 mmol) in dichloromethane (10 mL), followed by dropwise addition of BBr$_3$ (251 mg, 1.00 mmol) at 0° C. The resulting solution was stirred under nitrogen for 2 h at room temperature and concentrated under vacuum. After residue was suspended in water, the mixture was basified to pH 8 with aqueous sodium bicarbonate, and extracted with ethyl acetate (3×50 mL). The combined organic layer was dried over anhydrous sodium sulfate and concentrated under vacuum. The residue was purified by Prep-HPLC as described in Step 3 of Example PH-2. The title compound 4-[(4-chlorophenyl)([3-[1-(trifluoromethane)sulfonylpiperidin-4-yl]-1H-indazol-5-yl])methyl]phenol was obtained as an off-white solid.

$^1$H NMR (300 MHz, CD3OD) δ: 7.36-7.39 (m, 2H), 7.22-7.25 (m, 2H), 7.12-7.15 (m, 1H), 7.05 (d, J=8.4 Hz, 2H), 6.88 (d, J=8.4 Hz, 2H), 6.66-6.71 (m, 2H), 5.57 (s, 1H), 3.94-3.99 (m, 2H), 3.20-3.32 (m, 3H), 1.86-2.07 (m, 4H). LC/MS (ES, m/z): 550 [M+H]$^+$.

Example PH-41

4-((4-chlorophenyl)(3-(1-(trifluoromethylsulfonyl)piperidin-4-yl)-1H-indazol-5-yl)methyl)benzoic acid

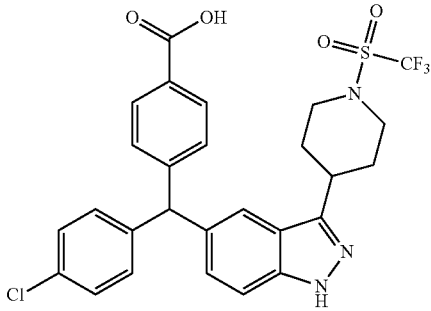 [SMILES: O=C(O)c1ccc(C(c2ccc(Cl)cc2)c2ccc3[nH]nc(C4CCN(S(=O)(=O)C(F)(F)F)CC4)c3c2)cc1]

Step 1: Synthesis of 5-bromo-1-(oxan-2-yl)-3-[1-(trifluoromethane) sulfonylpiperidin-4-yl]-1H-indazole Into a 100-mL round-bottom flask, were placed 5-bromo-3-[1-(trifluoromethane) sulfonylpiperidin-4-yl]-1H-indazole (12.3 g, 29.84 mmol), 3,4-dihydro-2H-pyran (3.8 g, 45.18 mmol), dichloromethane (50 mL) and TsOH (0.26 g, 1.5 mmol). The resulting solution was stirred under nitrogen for 5 h at room temperature and then concentrated under vacuum. The residue was purified by recrystallization from petroleum ether-ethyl acetate to yield 5-bromo-1-(oxan-2-yl)-3-[1-(trifluoromethane) sulfonylpiperidin-4-yl]-1H-indazole as a light yellow solid.

Step 2: Synthesis of 5-[(4-chlorophenyl) carbonyl]-1-(oxan-2-yl)-3-[1-(trifluoromethane) sulfonylpiperidin-4-yl]-1H-indazole Into a 100-mL oven-dried round-bottom flask under nitrogen, was placed a solution of 5-bromo-1-(oxan-2-yl)-3-[1-(trifluoromethane) sulfonylpiperidin-4-yl]-1H-indazole (4.96 g, 9.99 mmol) in tetrahydrofuran (30 mL), followed by dropwise addition of a 2.5 M solution of BuLi in hexanes (4.4 mL, 11.0 mmol) at −78° C. After 30 min at −78° C., a solution of 4-chloro-N-methoxy-N-methylbenzamide (2.0 g, 10.02 mmol) in tetrahydrofuran (5 mL) was added dropwise, and the resulting solution was stirred under nitrogen overnight at room temperature. After addition of water (100 mL), the mixture was extracted with ethyl acetate (3×50 mL). The combined organic layer was dried over anhydrous sodium sulfate and concentrated under vacuum. The residue was purified by recrystallization from petroleum ether-Et$_2$O to yield 5-[(4-chlorophenyl) carbonyl]-1-(oxan-2-yl)-3-[1-(trifluoromethane) sulfonylpiperidin-4-yl]-1H-indazole as a white solid. LC/MS (ES, m/z): 556 [M+H]$^+$.

Step 3: Synthesis of (4-bromophenyl)(4-chlorophenyl)[1-(oxan-2-yl)-3-[1-(trifluoromethane)sulfonylpiperidin-4-yl]-1H-indazol-5-yl]methanol Into a 50-mL oven-dried round-bottom flask under nitrogen, was placed a solution of 1,4-dibromobenzene (2.36 g, 10.00 mmol) in tetrahydrofuran (20 mL), followed by dropwise addition of a 2.5M solution BuLi in hexanes (3.8 mL, 9.50 mmol) at −78° C. After 30 min at −78° C., a solution of 5-[(4-chlorophenyl)carbonyl]-1-(oxan-2-yl)-3-[1-(trifluoromethane)sulfonylpiperidin-4-yl]-1H-indazole (1.12 g, 2.01 mmol) in tetrahydrofuran (3 mL) was added dropwise, and the resulting solution was allowed to warm to −30° C. and stirred for additional 2 h. After addition of water (100 mL), the mixture was extracted with ethyl acetate (3×50 mL). The combined organic layer was dried over anhydrous sodium sulfate and concentrated under vacuum to yield (4-bromophenyl)(4-chlorophenyl)[1-(oxan-2-yl)-3-[1-(trifluoromethane)sulfonylpiperidin-4-yl]-1H-indazol-5-yl]methanol.

Step 4: Synthesis of 4-[(4-chlorophenyl) (hydroxy) [1-(oxan-2-yl)-3-[1-(trifluoromethane) sulfonylpiperidin-4-yl]-1H-indazol-5-yl]methyl]benzoic acid Into a 25-mL oven-dried round-bottom flask under nitrogen, was placed a solution of (4-bromophenyl) (4-chlorophenyl) [1-(oxan-2-yl)-3-[1-(trifluoromethane) sulfonylpiperidin-4-yl]-1H-indazol-5-yl]methanol (71.3 mg, 0.10 mmol) in tetrahydrofuran (10 mL), followed by dropwise addition of a 2.5 M solution BuLi in hexanes (0.22 mL, 0.55 mmol) at −78° C. The reaction mixture was stirred for 30 min at −78° C., and then CO$_2$ was bubbled through for 30 min, and the resulting mixture was allowed to warm to room temperature and stirred overnight. After addition of water (30 mL), the mixture was extracted with EtOAc (3×30 mL). The combined organic layer was dried over sodium sulfate and then concentrated under vacuum to yield 4-[(4-chlorophenyl) (hydroxy) [1-(oxan-2-yl)-3-[1-(trifluoromethane) sulfonylpiperidin-4-yl]-1H-indazol-5-yl]methyl]benzoic acid as yellow oil. LC/MS (ES, m/z): 579 [M+H]$^+$.

Step 5: Synthesis of 4-[(4-chlorophenyl) (hydroxy) [3-[1-(trifluoromethane) sulfonylpiperidin-4-yl]-1H-indazol-5-yl]methyl]benzoic acid Into a 50-mL round-bottom flask, were placed 4-[(4-chlorophenyl) (hydroxy) [1-(oxan-2-yl)-3-[1-(trifluoromethane) sulfonylpiperidin-4-yl]-1H-indazol-5-yl]methyl]benzoic acid (508.6 mg, 0.88 mmol), dichloromethane (20 mL), trifluoroacetic acid (3 mL). The resulting solution was stirred overnight at room temperature, and then concentrated under vacuum to yield 4-[(4-chlorophenyl) (hydroxy) [3-[1-(trifluoromethane) sulfonylpiperidin-4-yl]-1H-indazol-5-yl]methyl]benzoic acid as yellow oil. LC/MS (ES, m/z): 594 [M+H]$^+$.

Step 6: Synthesis of 4-[(4-chlorophenyl) ([3-[1-(trifluoromethane) sulfonylpiperidin-4-yl]-1H-indazol-5-yl]) methyl]benzoic acid Into a 50-mL round-bottom flask, was placed 4-[(4-chlorophenyl) (hydroxy) [3-[1-(trifluoromethane)sulfonylpiperidin-4-yl]-1H-indazol-5-yl]methyl]benzoic acid (521.8 mg, 0.88 mmol), dichloromethane (20 mL), trifluoroacetic acid (3 mL) and Et₃SiH (3 mL). The resulting solution was stirred for 30 min at room temperature and then concentrated under vacuum. The residue was purified by Prep-HPLC as described in Step 3 of Example PH-2. The title compound 4-[(4-chlorophenyl) ([3-[1-(trifluoromethane) sulfonylpiperidin-4-yl]-1H-indazol-5-yl]) methyl]benzoic acid was obtained as an off-white solid.

$^1$H NMR (400 MHz, CDCl₃) δ: 8.07 (d, J=8.0 Hz, 2H), 7.51-7.54 (m, 5H), 7.31-7.37 (m, 3H), 7.02-7.09 (m, 2H), 5.74 (s, 1H), 4.06-4.15 (m, 2H), 3.23-3.33 (m, 3H), 2.03-2.16 (m, 4H). LC/MS (ES, m/z): 578 [M+H]$^+$.

The title compound (4-[(4-chlorophenyl) ([3-[1-(trifluoromethane) sulfonylpiperidin-4-yl]-1H-indazol-5-yl]) methyl]benzoic acid) was resolved to yield the corresponding R*- and S* enantiomers using the following conditions: Supercritical Fluid Chromatography: Column: AD-H 5 um, 20×250 mm, 40° C.; Detection wavelength: 235 nm, 32 min for each run; 15% Methanol as a cosolvent; CO₂ flow rate: 42.5 ml/min, co-solvent flow rate: 7.5 ml/min, 150 bar. The first product to come off the column was assigned as the R* enentiomer, whereas the second product peak was assigned as the S* enantiomer.

Example PH-42

4-((4-chlorophenyl)(3-(1-(trifluoromethylsulfonyl)piperidin-4-yl)-1H-indazol-5-yl)methyl)benzamide

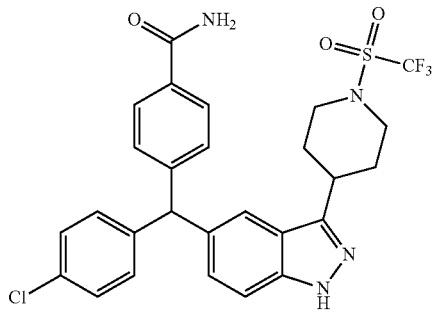 [SMILES: NC(=O)c1ccc(C(c2ccc(Cl)cc2)c2ccc3[nH]nc(C4CCN(S(=O)(=O)C(F)(F)F)CC4)c3c2)cc1]

The title compound was prepared according to the procedure as described in Example PH-11 substituting 4-((4-chlorophenyl)(3-(1-((trifluoromethyl)sulfonyl)piperidin-4-yl)-1H-indazol-5-yl)methyl)benzoic acid for 4-(4-(5-(bis(4-chlorophenyl)methyl)-1-cyclopropyl-1H-indazol-3-yl)piperidine-1-carbonyl)benzoic acid in Step 3.

$^1$H NMR (400 MHz, CDCl₃) δ: 7.73-7.79 (m, 2H), 7.44 (d, J=8.8 Hz, 1H), 7.17-7.36 (m, 6H), 7.02-7.07 (m, 2H), 6.08-6.13 (br.s, 1H), 5.71 (s, 1H), 4.05-4.08 (m, 2H), 3.23-3.42 (m, 3H), 2.03-2.09 (m, 4H). LC/MS (ES, m/z): 577 [M+H]$^+$.

Example PH-43

4-((4-chlorophenyl)(3-(1-(trifluoromethylsulfonyl)piperidin-4-yl)-1H-indazol-5-yl)methyl)-N-(2-hydroxyethyl)benzamide

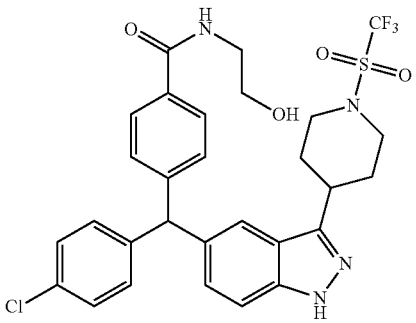 [SMILES: O=C(NCCO)c1ccc(C(c2ccc(Cl)cc2)c2ccc3[nH]nc(C4CCN(S(=O)(=O)C(F)(F)F)CC4)c3c2)cc1]

The title compound was prepared according to the procedure as described in Example PH-11 substituting 2-aminoethanol for ammonium chloride, and substituting 4-((4-chlorophenyl)(3-(1-((trifluoromethyl)sulfonyl)piperidin-4-yl)-1H-indazol-5-yl)methyl)benzoic acid for 4-(4-(5-(bis(4-chlorophenyl)methyl)-1-cyclopropyl-1H-indazol-3-yl)piperidine-1-carbonyl)benzoic acid in Step 3.

$^1$H NMR (400 MHz, CD₃COCD₃) δ: 7.86 (d, J=8.0 Hz, 2H), 7.70-7.74 (m, 1H), 7.64 (m, 1H), 7.51 (d, J=10.8 Hz, 1H), 7.20-7.50 (m, 4H), 7.18-7.27 (m, 3H), 5.84 (s, 1H), 3.80-4.09 (m, 2H), 3.50-3.69 (m, 2H), 3.38-3.41 (m, 5H), 1.80-2.20 (m, 4H). LC/MS (ES, m/z): 621 [M+H]$^+$.

Example PH-44

4-(4-(5-(bis(4-chlorophenyl)methyl)-2-cyclopropyl-2H-indazol-3-yl)piperidin-1-ylsulfonyl)-2-fluorobenzoic acid

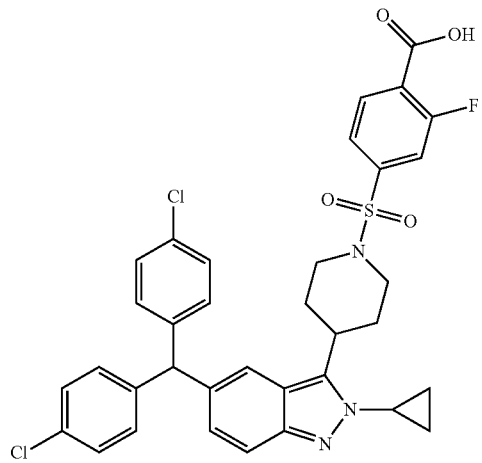 [SMILES: O=C(O)c1ccc(S(=O)(=O)N2CCC(c3c4cc(C(c5ccc(Cl)cc5)c5ccc(Cl)cc5)ccc4nn3C3CC3)CC2)cc1F]

Step 1: Synthesis of methyl 4-(4-[5-[bis(4-chlorophenyl)methyl]-2-cyclopropyl-2H-indazol-3-yl]piperidine-1-sulfonyl)-2-fluorobenzoate Into a 8-mL seal tube, were placed a solution of 5-[bis(4-chlorophenyl)methyl]-2-cyclopropyl-3-(piperidin-4-yl)-2H-indazole (247.7 mg, 0.52 mmol) in dichloromethane (5 mL), methyl 4-(chlorosulfonyl)-2-fluorobenzoate (197.1 mg, 0.78 mmol) and triethylamine (158.9 mg, 1.57 mmol). The resulting solution was stirred overnight at room temperature, and then concentrated under vacuum to yield methyl 4-(4-[5-[bis(4-chlorophenyl)methyl]-2-cyclopropyl-2H-indazol-3-yl]piperidine-1-sulfonyl)-2-fluorobenzoate as a yellow solid. LC/MS (ES, m/z): 692 [M+H]$^+$.

Step 2: Synthesis of 4-(4-[5-[bis(4-chlorophenyl)methyl]-2-cyclopropyl-2H-indazol-3-yl]piperidine-1-sulfonyl)-2-fluorobenzoic acid Into a 100-mL round-bottom flask, were placed a solution of methyl 4-(4-[5-[bis(4-chlorophenyl)methyl]-2-cyclopropyl-2H-indazol-3-yl]piperidine-1-sulfonyl)-2-fluorobenzoate (310.9 mg, 0.45 mmol) in tetrahydrofuran (32 mL) and a solution of LiOH.H$_2$O (195.4 mg, 4.65 mmol) in methanol/H$_2$O (8/8 mL). The resulting mixture was stirred for 4 h at room temperature, and then concentrated under vacuum to remove organic solvent. Acidification to pH 3-4 with 1 N HCl solution resulted in formation of precipitate. The solid was collected by filtration and purified by Prep-HPLC as described in Step 3 of Example PH-2. The title compound 4-(4-[5-[bis(4-chlorophenyl) methyl]-2-cyclopropyl-2H-indazol-3-yl]piperidine-1-sulfonyl)-2-fluorobenzoic acid was obtained as an off-white solid.

$^1$H NMR (300 MHz, CDCl$_3$) δ: 8.20-8.23 (m, 1H), 7.61-7.71 (m, 3H), 7.45 (s, 1H), 7.29-7.30 (m, 2H), 7.06 (d, J=8.1 Hz, 5H), 5.55 (s, 1H), 4.08 (d, J=11.4 Hz, 2H), 3.60-3.67 (m, 1H), 3.31-3.39 (m, 1H), 2.47-2.55 (m, 2H), 2.21-2.30 (m, 2H), 1.98-2.02 (m, 2H), 1.18-1.37 (m, 4H). LC/MS (ES, m/z): 678 [M+H]$^+$.

Example PH-45

4-(4-(5-(bis(4-chlorophenyl)methyl)-2-cyclopropyl-2H-indazol-3-yl)piperidin-1-ylsulfonyl)-2-fluorobenzamide

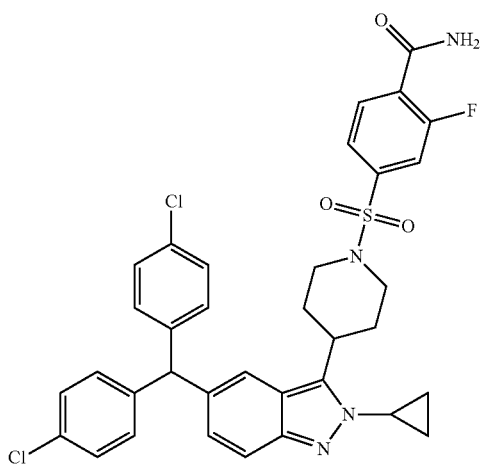 [SMILES: NC(=O)c1ccc(S(=O)(=O)N2CCC(c3c4cc(C(c5ccc(Cl)cc5)c5ccc(Cl)cc5)ccc4nn3C3CC3)CC2)cc1F]

Into a 25-mL round-bottom flask, were placed a solution of 4-(4-[5-[bis(4-chlorophenyl)methyl]-2-cyclopropyl-2H-indazol-3-yl]piperidine-1-sulfonyl)-2-fluorobenzoic acid (74.5 mg, 0.11 mmol) in N, N-dimethylformamide (3 mL), HATU (89.7 mg, 0.24 mmol), DIEA (45.7 mg, 0.35 mmol). After stirring for 10 min, NH$_4$Cl (9.4 mg, 0.18 mmol) was added, and the resulting mixture was stirred overnight at room temperature. Additional water (10 mL) was added, precipitate was formed and collected by filtration. The solid was purified by Prep-HPLC as described in Step 3 of Example PH-2. The title compound 4-(4-[5-[bis(4-chlorophenyl)methyl]-2-cyclopropyl-2H-indazol-3-yl]piperidine-1-sulfonyl)-2-fluorobenzamide trifluoroacetic acid was obtained as an off-white solid.

$^1$H NMR (400 MHz, CDCl$_3$) δ: 8.34 (t, J=7.8 Hz, 1H), 7.70-7.73 (m, 1H), 7.66 (t, J=11.8 Hz, 2H), 7.47 (s, 1H), 7.24-7.30 (m, 2H), 7.04-7.10 (m, 5H), 6.74 (d, J=9.3 Hz, 1H), 6.25 (s, 1H), 5.55 (s, 1H), 8.06 (d, J=11.8 Hz, 2H), 3.64 (s, 1H), 3.25-3.38 (m, 1H), 2.48 (t, J=12.0 Hz, 2H), 2.23-2.38 (m, 2H), 1.97-2.09 (m, 2H), 1.21-1.32 (m, 4H). LC/MS (ES, m/z): 677 [M+H]$^+$.

Example PH-46

4-(4-(5-(bis(4-chlorophenyl)methyl)-2-cyclopropyl-2H-indazol-3-yl)piperidin-1-ylsulfonyl)-2-fluoro-N-methylbenzamide

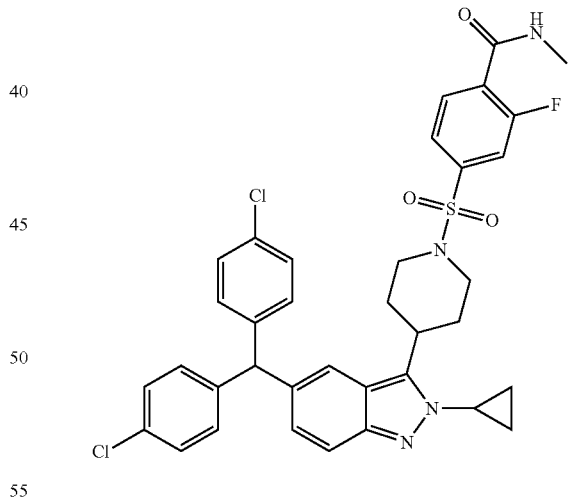

The title compound was prepared according to the procedure as described in Example PH-45 substituting methylamine hydrochloride for ammonium chloride.

$^1$H NMR (400 MHz, CDCl$_3$) δ: 8.31 (t, J=7.5 Hz, 1H), 7.69 (d, J=8.7 Hz, 1H), 7.58-7.62 (m, 2H), 7.45 (s, 1H), 7.27-7.34 (m, 4H), 7.02-7.11 (m, 5H), 6.72-6.76 (m, 1H), 5.54 (s, 1H), 4.05 (d, J=12.4 Hz, 2H), 3.62 (s, 1H), 3.28-3.35 (m, 1H), 3.05-3.10 (m, 3H), 2.46 (t, J=12.3 Hz, 2H), 2.23-2.30 (m, 2H), 1.97-2.06 (m, 2H), 1.13-1.33 (m, 4H). LC/MS (ES, m/z): 691 [M+H]$^+$.

Example PH-47

4-(4-(5-(bis(4-chlorophenyl)methyl)-2-cyclopropyl-2H-indazol-3-yl)piperidin-1-ylsulfonyl)-2-chlorobenzoic acid

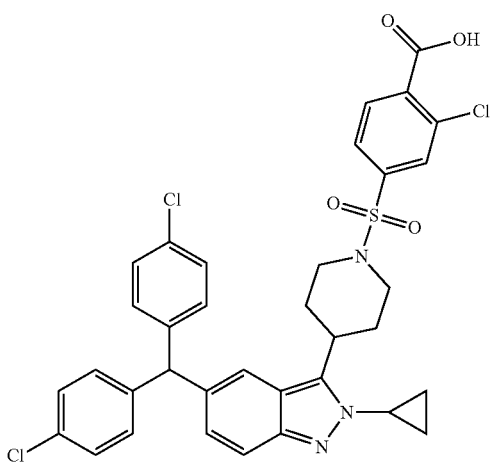 [SMILES: O=C(O)c1ccc(S(=O)(=O)N2CCC(c3c4cc(C(c5ccc(Cl)cc5)c5ccc(Cl)cc5)ccc4nn3C3CC3)CC2)cc1Cl]

The title compound was prepared according to the procedure as described in Example PH-44 substituting methyl 2-chloro-4-(chlorosulfonyl)benzoate for methyl 4-(chlorosulfonyl)-2-fluorobenzoate in Step 1.

$^1$H NMR (300 MHz, CD$_3$COCD$_3$) δ: 8.14 (d, J=8.1 Hz, 1H), 7.87-7.93 (m, 2H), 7.71 (s, 1H), 7.46 (d, J=9.0 Hz, 1H), 7.33-7.37 (m, 4H), 7.20-7.23 (m, 4H), 7.00-7.03 (m, 1H), 5.75 (s, 1H), 3.89-4.00 (m, 3H), 3.52-3.67 (m, 1H), 2.58-2.67 (m, 2H), 2.18-2.24 (m, 4H), 1.28-1.32 (m, 2H), 1.06-1.09 (m, 2H). LC/MS (ES, m/z): 694 [M+H]$^+$.

Example PH-48

4-(4-(5-(bis(4-chlorophenyl)methyl)-2-cyclopropyl-2H-indazol-3-yl)piperidin-1-ylsulfonyl)-2-chlorobenzamide

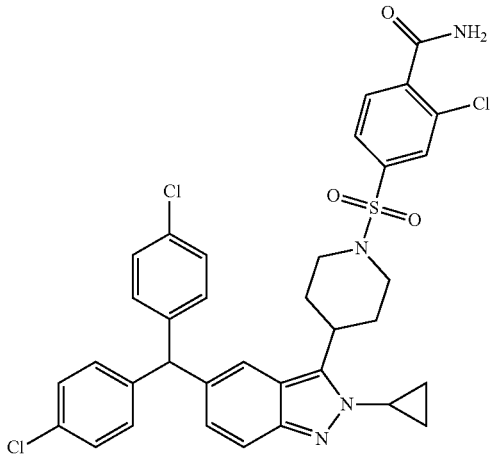 [SMILES: NC(=O)c1ccc(S(=O)(=O)N2CCC(c3c4cc(C(c5ccc(Cl)cc5)c5ccc(Cl)cc5)ccc4nn3C3CC3)CC2)cc1Cl]

The title compound was prepared according to the procedure as described in Example PH-45 substituting 4-((4-(5-(bis(4-chlorophenyl)methyl)-2-cyclopropyl-2H-indazol-3-yl)piperidin-1-yl)sulfonyl)-2-chlorobenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CD$_3$COCD$_3$) δ: 7.83 (d, J=13.8 Hz, 3H), 7.71 (s, 1H), 7.46 (d, J=9.0 Hz, 1H), 7.35 (d, J=8.4 Hz, 4H), 7.22 (d, J=8.4 Hz, 4H), 7.02 (d, J=6.0 Hz, 1H), 5.76 (s, 1H), 3.87-3.99 (m, 3H), 3.54-3.62 (m, 1H), 2.55-2.64 (m, 2H), 2.14-2.26 (m, 2H), 2.05-2.12 (m, 4H), 1.29-1.34 (m, 2H), 1.03-1.13 (m, 2H). LC/MS (ES, m/z): 693 [M+H]$^+$.

Example PH-49

4-(4-(5-(bis(4-chlorophenyl)methyl)-2-cyclopropyl-2H-indazol-3-yl)piperidin-1-ylsulfonyl)-2-chloro-N-methylbenzamide

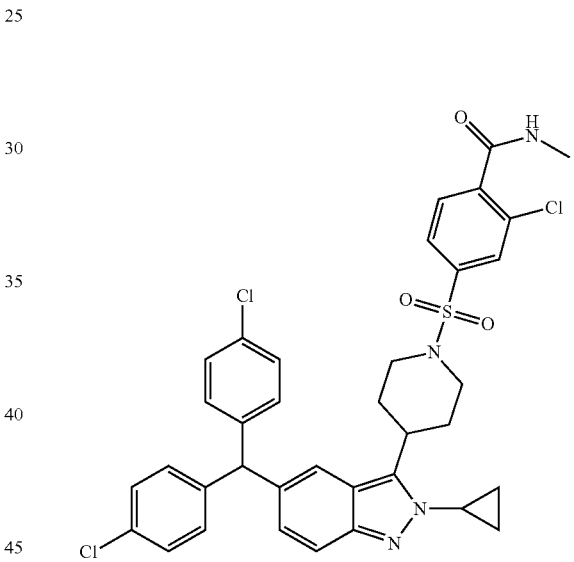

The title compound was prepared according to the procedure as described in Example PH-45 substituting methylamine hydrochloride for ammonium chloride, and substituting 4-((4-(5-(bis(4-chlorophenyl)methyl)-2-cyclopropyl-2H-indazol-3-yl)piperidin-1-yl)sulfonyl)-2-chlorobenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CD$_3$COCD$_3$) δ: 7.72-7.84 (m, 4H), 7.64 (s, 1H), 7.35 (d, J=8.4 Hz, 4H), 7.22 (d, J=8.4 Hz, 4H), 7.02 (d, J=8.7 Hz, 1H), 5.76 (s, 1H), 3.88-3.98 (m, 3H), 3.54-3.62 (m, 1H), 2.95-2.96 (m, 3H), 2.58 (t, J=12.0 Hz, 2H), 2.09-2.26 (m, 4H), 1.29-1.34 (m, 2H), 1.10-1.12 (m, 2H). LC/MS (ES, m/z): 707 [M+H]$^+$.

Example PH-50

4-(4-(5-(bis(4-chlorophenyl)methyl)-2-cyclopropyl-2H-indazol-3-yl)piperidin-1-ylsulfonyl)-2-methoxybenzoic acid

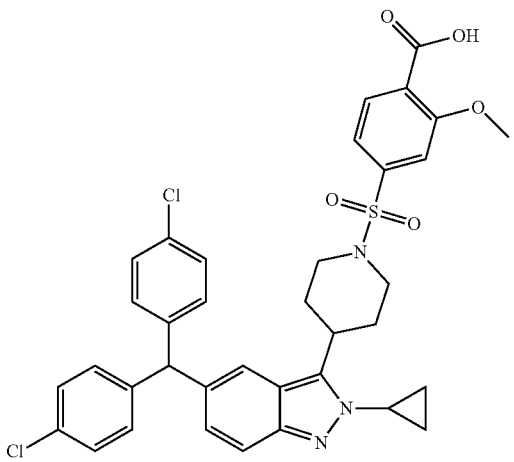 [SMILES: COc1cc(S(=O)(=O)N2CCC(c3c4cc(C(c5ccc(Cl)cc5)c5ccc(Cl)cc5)ccc4nn3C3CC3)CC2)ccc1C(=O)O]

The title compound was prepared according to the procedure as described in Example PH-44 substituting methyl 4-(chlorosulfonyl)-2-methoxybenzoate for methyl 4-(chlorosulfonyl)-2-fluorobenzoate in STEP 1.

$^1$H NMR (300 MHz, CD$_3$OD): δ 7.98 (d, J=6.0 Hz, 1H), 7.45-7.48 (m, 4H), 7.32 (d, J=8.4 Hz, 4H), 7.06-7.14 (m, 5H), 5.64 (s, 1H), 3.98-4.02 (m, 5H), 3.76-3.83 (m, 1H), 3.44-3.54 (m, 1H), 2.59 (t, J=12.0 Hz, 2H), 1.96-2.19 (m, 4H), 1.14-1.29 (m, 4H). LC/MS (ES, m/z): 690 [M+H]$^+$.

Example PH-51

4-(4-(5-(bis(4-chlorophenyl)methyl)-2-cyclopropyl-2H-indazol-3-yl)piperidin-1-ylsulfonyl)-2-methoxybenzamide

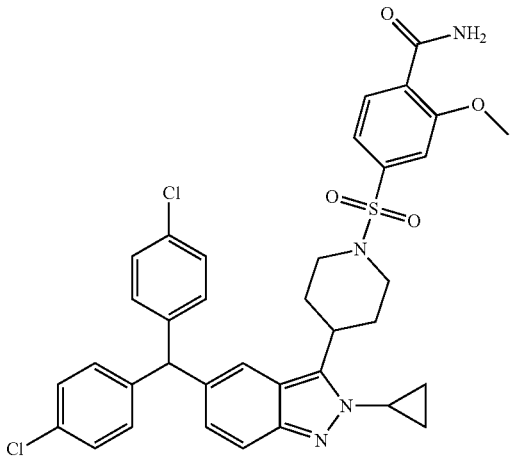 [SMILES: COc1cc(S(=O)(=O)N2CCC(c3c4cc(C(c5ccc(Cl)cc5)c5ccc(Cl)cc5)ccc4nn3C3CC3)CC2)ccc1C(N)=O]

The title compound was prepared according to the procedure as described in Example PH-45 substituting 4-((4-(5-(bis(4-chlorophenyl)methyl)-2-cyclopropyl-2H-indazol-3-yl)piperidin-1-yl)sulfonyl)-2-methoxybenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (400 MHz, CD$_3$COCD$_3$) δ: 8.28 (d, J=8.4 Hz, 1H), 7.78 (s, 1H), 7.70 (s, 1H), 7.46-7.52 (m, 3H), 7.35-7.38 (m, 4H), 7.22-7.24 (m, 4H), 7.02-7.04 (m, 1H), 5.76 (s, 1H), 4.15 (s, 3H), 3.91-4.00 (m, 2H), 3.88-3.90 (m, 1H), 3.54-3.60 (m, 2H), 2.56-2.62 (m, 2H), 2.10-2.22 (m, 2H), 1.30-1.33 (m, 2H), 1.06-1.11 (m, 2H). LC/MS (ES, m/z): 689 [M+H]$^+$.

Example PH-52

4-(4-(5-(bis(4-chlorophenyl)methyl)-2-cyclopropyl-2H-indazol-3-yl)piperidin-1-ylsulfonyl)-2-methoxy-N-methylbenzamide

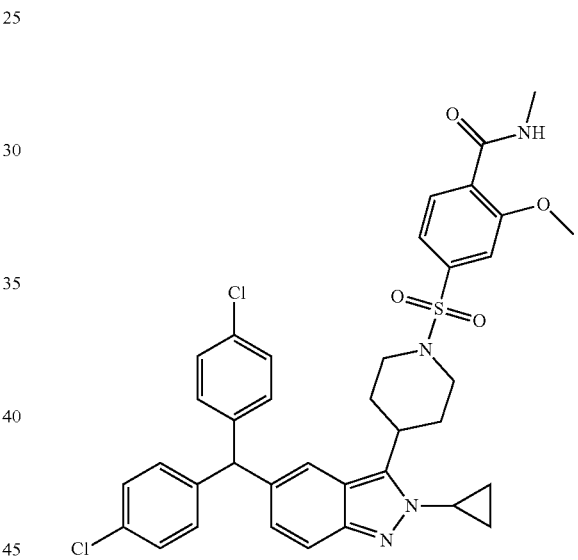

The title compound was prepared according to the procedure as described in Example PH-45 substituting methylamine hydrochloride for ammonium chloride, and substituting 4-((4-(5-(bis(4-chlorophenyl)methyl)-2-cyclopropyl-2H-indazol-3-yl)piperidin-1-yl)sulfonyl)-2-methoxybenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (400 MHz, CD$_3$COCD$_3$) δ: 8.28 (d, J=7.6 Hz, 1H), 8.16 (br, 1H), 7.68 (s, 1H), 7.46-7.53 (m, 3H), 7.36-7.38 (m, 3H), 7.21-7.24 (m, 4H), 7.01-7.04 (m, 1H), 5.75 (s, 1H), 4.11 (s, 3H), 3.97-4.00 (m, 2H), 3.88-3.91 (m, 1H), 3.48-3.59 (m, 2H), 2.94 (s, 3H), 2.56-2.59 (m, 2H), 2.10-2.20 (m, 2H), 1.29-1.32 (m, 2H), 1.07-1.09 (m, 2H). LC/MS (ES, m/z): 703 [M+H]$^+$.

Example PH-53

5-(4-(5-(bis(4-chlorophenyl)methyl)-2-cyclopropyl-2H-indazol-3-yl)piperidin-1-ylsulfonyl)-2-fluorobenzoic acid

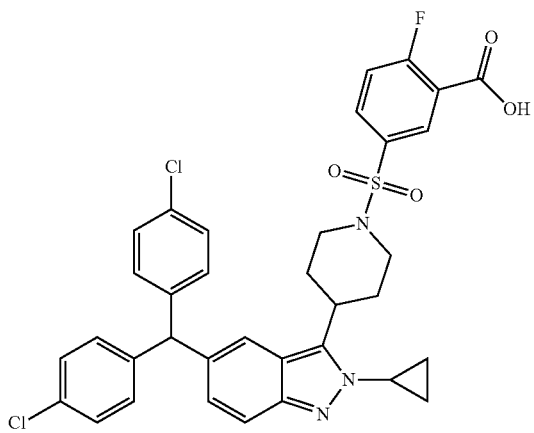 [SMILES: O=C(O)c1cc(S(=O)(=O)N2CCC(c3c4cc(C(c5ccc(Cl)cc5)c5ccc(Cl)cc5)ccc4nn3C3CC3)CC2)ccc1F]

The title compound was prepared according to the procedure as described in Example PH-44 substituting 5-(chlorosulfonyl)-2-fluorobenzoic acid for methyl 4-(chlorosulfonyl)-2-fluorobenzoate in Step 1.

1H NMR (300 MHz, CD3OD) δ: 8.36-8.39 (m, 1H), 8.06-8.10 (m, 1H), 7.48-7.54 (m, 3H), 7.31-7.34 (m, 4H), 7.04-7.15 (m, 5H), 5.64 (s, 1H), 3.97-4.01 (m, 2H), 3.78-3.81 (m, 1H), 3.42-3.48 (m, 1H), 2.52-2.59 (m, 2H), 2.11-2.16 (m, 2H), 1.98-2.05 (m, 2H), 1.16-1.26 (m, 4H). LC/MS (ES, m/z): 678 [M+H]+.

Example PH-54

5-(4-(5-(bis(4-chlorophenyl)methyl)-2-cyclopropyl-2H-indazol-3-yl)piperidin-1-ylsulfonyl)-2-fluorobenzamide

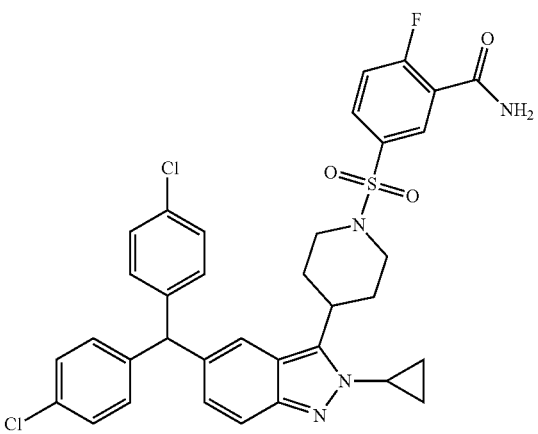 [SMILES: NC(=O)c1cc(S(=O)(=O)N2CCC(c3c4cc(C(c5ccc(Cl)cc5)c5ccc(Cl)cc5)ccc4nn3C3CC3)CC2)ccc1F]

The title compound was prepared according to the procedure as described in Example PH-45 substituting 5-((4-(5-(bis(4-chlorophenyl)methyl)-2-cyclopropyl-2H-indazol-3-yl)piperidin-1-yl)sulfonyl)-2-fluorobenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CD$_3$COCD$_3$) δ: 8.29-8.32 (m, 1H), 8.01-8.02 (m, 1H), 7.71 (s, 1H), 7.53-7.59 (m, 1H), 7.44-7.47 (m, 1H), 7.33-7.37 (m, 4H), 7.20-7.23 (m, 4H), 7.00-7.03 (m, 1H), 5.760 (s, 1H), 3.89-3.98 (m, 3H), 3.47-3.56 (m, 1H), 2.50-2.55 (m, 2H), 2.08-2.23 (m, 4H), 1.30-1.34 (m, 2H), 1.06-1.09 (m, 2H). LC/MS (ES, m/z): 677 [M+H]+.

Example PH-55

5-(4-(5-(bis(4-chlorophenyl)methyl)-2-cyclopropyl-2H-indazol-3-yl)piperidin-1-ylsulfonyl)-2-chlorobenzoic acid

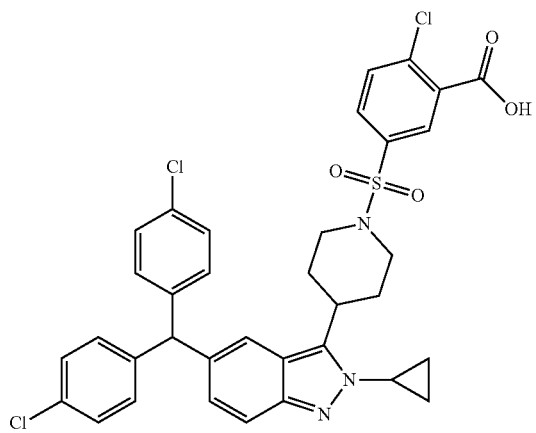 [SMILES: O=C(O)c1cc(S(=O)(=O)N2CCC(c3c4cc(C(c5ccc(Cl)cc5)c5ccc(Cl)cc5)ccc4nn3C3CC3)CC2)ccc1Cl]

The title compound was prepared according to the procedure as described in Example PH-44 substituting methyl 2-chloro-5-(chlorosulfonyl)benzoate for methyl 4-(chlorosulfonyl)-2-fluorobenzoate in Step 1.

$^1$H NMR (400 MHz, CDCl$_3$) δ: 3.39 (d, J=2.0 Hz, 1H), 7.88-7.90 (m, 1H), 7.71-7.73 (m, 1H), 7.63-7.68 (m, 1H), 7.47 (s, 1H), 7.27-7.29 (m, 4H), 7.03-7.08 (m, 5H), 5.55 (s, 1H), 4.05-4.08 (m, 2H), 3.62-3.66 (m, 1H), 3.31-3.37 (m, 1H), 2.47 (t, J=11.6 Hz, 2H), 2.28-2.35 (m, 2H), 1.98-2.03 (m, 2H), 1.33-1.38 (m, 2H), 1.18-1.23 (m, 2H). LC/MS (ES, m/z): 694 [M+H]+.

Example PH-56

5-(4-(5-(bis(4-chlorophenyl)methyl)-2-cyclopropyl-2H-indazol-3-yl)piperidin-1-ylsulfonyl)-2-chlorobenzamide

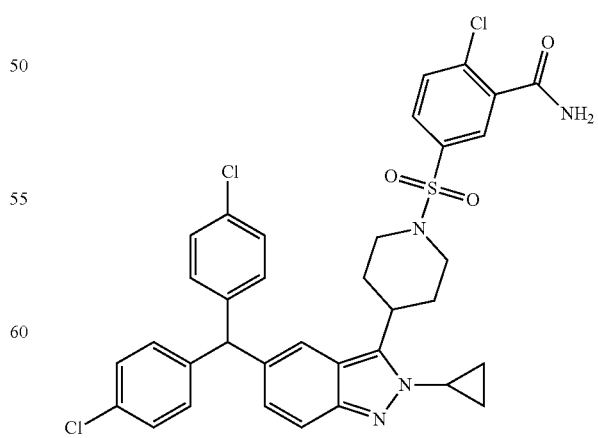

The title compound was prepared according to the procedure as described in Example PH-45 substituting 5-((4-

(5-(bis(4-chlorophenyl)methyl)-2-cyclopropyl-2H-indazol-3-yl)piperidin-1-yl)sulfonyl)-2-chlorobenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CDCl3) δ: 8.12 (s, 1H), 7.83 (d, J=8.4 Hz, 1H), 7.54-7.67 (m, 3H), 7.27-7.30 (m, 2H), 7.17 (d, J=9.3 Hz, 1H), 7.05 (d, J=8.4 Hz, 4H), 6.33-6.46 (m, 2H), 5.58 (s, 1H), 4.01-4.25 (m, 3H), 3.71-3.72 (m, 1H), 3.38-3.49 (m, 1H), 2.40-2.53 (m, 2H), 2.24-2.27 (m, 2H), 1.91-2.01 (m, 2H), 1.31-1.32 (m, 4H). LC/MS (ES, m/z): 693 [M+H]$^+$.

Example PH-57

5-(4-(5-(bis(4-chlorophenyl)methyl)-2-cyclopropyl-2H-indazol-3-yl)piperidin-1-ylsulfonyl)-2-chloro-N-methylbenzamide

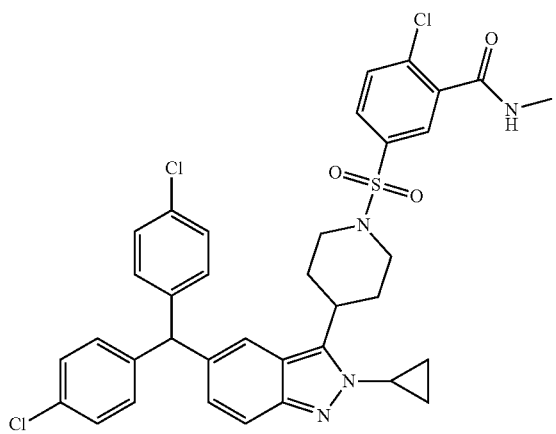 [SMILES: CNC(=O)c1cc(S(=O)(=O)N2CCC(c3c4cc(C(c5ccc(Cl)cc5)c5ccc(Cl)cc5)ccc4nn3C3CC3)CC2)ccc1Cl]

The title compound was prepared according to the procedure as described in Example PH-45 substituting methylamine hydrochloride for ammonium chloride, and substituting 5-((4-(5-(bis(4-chlorophenyl)methyl)-2-cyclopropyl-2H-indazol-3-yl)piperidin-1-yl)sulfonyl)-2-chlorobenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (400 MHz, CDCl3) δ: 8.00 (s, 1H), 7.75-7.78 (m, 1H), 7.62-7.69 (m, 2H), 7.51 (s, 1H), 7.27-7.30 (m, 4H), 7.04-7.14 (m, 5H), 6.27 (s, 1H), 5.56 (s, 1H), 4.00-4.03 (m, 2H), 3.55 (m 1H), 3.35 (m, 1H), 3.08 (s, 3H), 2.09-2.49 (m, 4H), 1.86-1.96 (m, 2H), 1.27-1.31 (m, 4H). LC/MS (ES, m/z): 707 [M+H]$^+$.

Example PH-58

5-(4-(5-(bis(4-chlorophenyl)methyl)-2-cyclopropyl-2H-indazol-3-yl)piperidin-1-ylsulfonyl)-2-methoxybenzoic acid

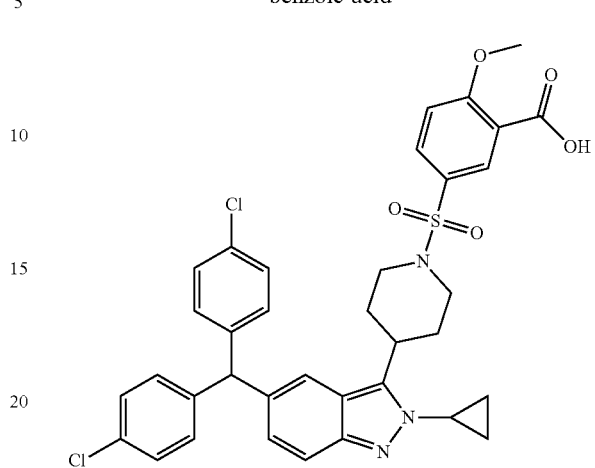

The title compound was prepared according to the procedure as described in Example PH-44 substituting 5-(chlorosulfonyl)-2-methoxybenzoic acid for methyl 4-(chlorosulfonyl)-2-fluorobenzoate in Step 1.

$^1$H NMR (300 MHz, CDCl$_3$) δ: 8.22 (d, J=2.4 Hz, 1H), 7.97-8.01 (m, 1H). 7.44-7.47 (m, 2H), 7.31-7.36 (m, 5H), 7.04-7.15 (m, 5H), 5.63 (s, 1H), 3.94-4.00 (m, 5H), 3.76-3.81 (m, 1H), 3.32-3.45 (m, 1H), 2.51 (t, J=11.7 Hz, 2H), 1.96-2.16 (m, 4H), 1.15-1.28 (m, 4H). LC/MS (ES, m/z): 690 [M+H]$^+$.

Example PH-59

5-(4-(5-(bis(4-chlorophenyl)methyl)-2-cyclopropyl-2H-indazol-3-yl)piperidin-1-ylsulfonyl)-2-methoxybenzamide

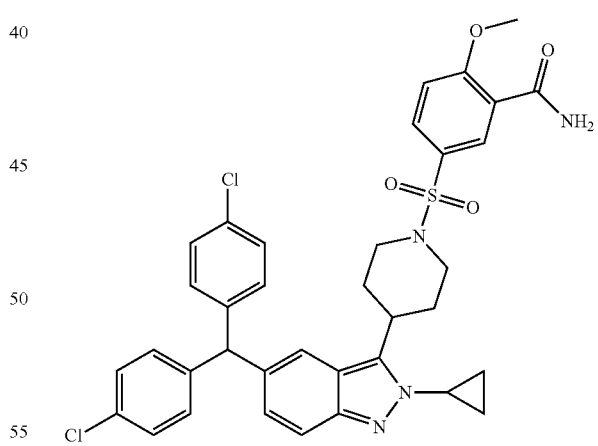

The title compound was prepared according to the procedure as described in Example PH-45 substituting 5-((4-(5-(bis(4-chlorophenyl)methyl)-2-cyclopropyl-2H-indazol-3-yl)piperidin-1-yl)sulfonyl)-2-methoxybenzoic acid for 4-((4-(5-(bis(4-chlorophenyl)methyl)-2-cyclopropyl-2H-indazol-3-yl)piperidin-1-yl)sulfonyl)-2-fluorobenzoic acid.

0 $^1$H NMR (300 MHz, CDCl$_3$+D$_2$O) δ: 8.60-8.63 (m, 1H), 7.95-8.09 (m, 1H), 7.46-7.63 (m, 2H), 7.22-7.34 (m, 4H), 6.96-7.18 (m, 5H), 5.53-5.60 (m, 1H), 4.78-4.85 (m, 4H), 3.64-3.67 (m, 1H), 3.30-3.33 (m, 1H), 2.30-2.61 (m, 3H), 2.00-2.04 (m, 2H), 1.15-1.39 (m, 4H). LC/MS (ES, m/z): 689 [M+H]$^+$.

Example PH-60

5-(4-(5-(bis(4-chlorophenyl)methyl)-2-cyclopropyl-2H-indazol-3-yl)piperidin-1-ylsulfonyl)-2-methoxy-N-methylbenzamide

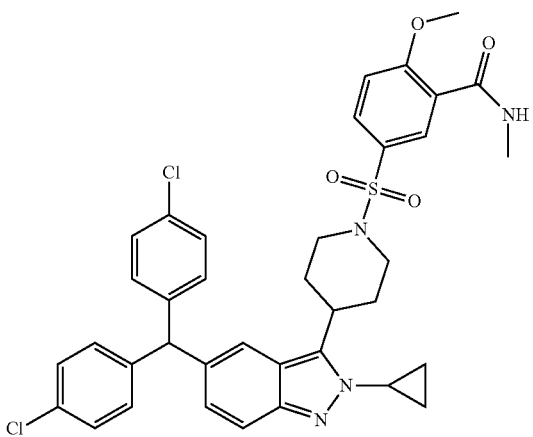 [SMILES: CNC(=O)c1cc(S(=O)(=O)N2CCC(c3c4cc(C(c5ccc(Cl)cc5)c5ccc(Cl)cc5)ccc4nn3C3CC3)CC2)ccc1OC]

The title compound was prepared according to the procedure as described in Example PH-45 substituting methylamine hydrochloride for ammonium chloride, and substituting 5-((4-(5-(bis(4-chlorophenyl)methyl)-2-cyclopropyl-2H-indazol-3-yl)piperidin-1-yl)sulfonyl)-2-methoxybenzoic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CDCl$_3$) δ: 8.62 (s, 1H), 7.94 (d, J=8.1 Hz, 1H), 7.71 (s, 1H), 7.60 (d, J=9.0 Hz, 1H), 7.52 (s, 1H), 7.27-7.29 (m, 2H), 7.15 (d, J=8.7 Hz, 1H), 7.06 (d, J=8.4 Hz, 5H), 5.56 (s, 1H), 4.04-4.09 (m, 5H), 3.18-3.61 (m, 6H), 3.05 (s, 3H), 2.23-2.50 (m, 4H), 1.94-1.98 (m, 2H), 1.21-1.32 (m, 4H). LC/MS (ES, m/z): 703 [M+H]$^+$.

Example PH-61

5-(4-(5-(bis(4-chlorophenyl)methyl)-2-cyclopropyl-2H-indazol-3-yl)piperidin-1-ylsulfonyl)picolinic acid

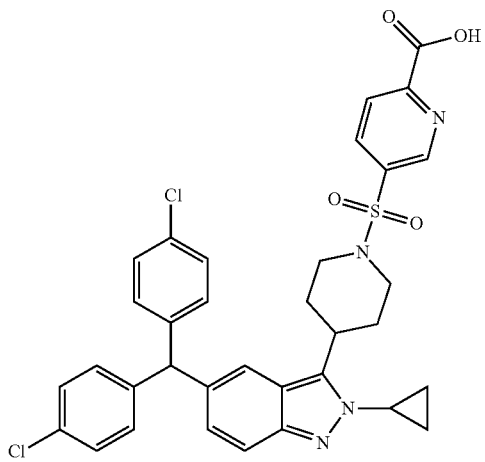 [SMILES: O=C(O)c1ccc(S(=O)(=O)N2CCC(c3c4cc(C(c5ccc(Cl)cc5)c5ccc(Cl)cc5)ccc4nn3C3CC3)CC2)cn1]

The title compound was prepared according to the procedure as described in Example PH-44 substituting methyl 5-(chlorosulfonyl)pyridine-2-carboxylate for methyl 4-(chlorosulfonyl)-2-fluorobenzoate in Step 1.

$^1$H NMR (300 MHz, CD$_3$OD) δ: 9.08 (s, 1H), 8.37-8.45 (m, 2H), 7.46-7.49 (m, 2H), 7.31-7.34 (m, 4H), 7.10-7.14 (m, 5H), 5.66 (s, 1H), 4.04 (d, J=12.0 Hz, 2H), 3.79-3.81 (m, 1H), 3.51-3.55 (m, 1H), 2.64 (t, J=12.0 Hz, 2H), 1.94-2.18 (m, 4H), 1.18-1.30 (m, 4H). LC/MS (ES, m/z): 661 [M+H]$^+$.

Example PH-62

5-(4-(5-(bis(4-chlorophenyl)methyl)-2-cyclopropyl-2H-indazol-3-yl)piperidin-1-ylsulfonyl)picolinamide

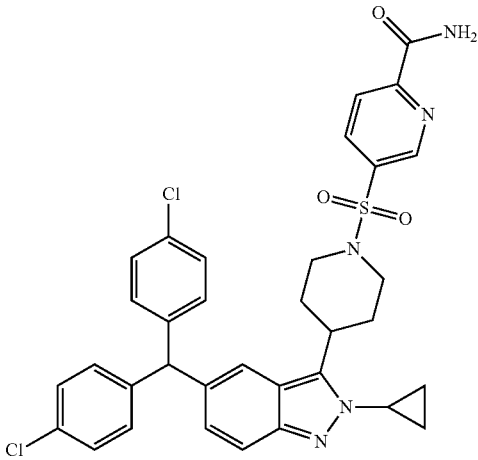 [SMILES: NC(=O)c1ccc(S(=O)(=O)N2CCC(c3c4cc(C(c5ccc(Cl)cc5)c5ccc(Cl)cc5)ccc4nn3C3CC3)CC2)cn1]

The title compound was prepared according to the procedure as described in Example PH-45 substituting 5-((4-(5-(bis(4-chlorophenyl)methyl)-2-cyclopropyl-2H-indazol-3-yl)piperidin-1-yl)sulfonyl)picolinic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CD$_3$OD) δ: 8.94-8.95 (m, 1H), 8.23-8.31 (m, 2H), 7.34-7.36 (m, 2H), 7.19-7.24 (m, 4H), 6.64-7.04 (m, 5H), 5.53 (s, 1H), 3.90-3.94 (m, 2H), 3.66-3.69 (m, 1H), 3.32-3.39 (m, 1H), 2.46-2.56 (m, 2H), 1.87-2.06 (m, 4H), 1.05-1.14 (m, 4H). LC/MS (ES, m/z): 660 [M+H]$^+$.

Example PH-63

5-(4-(5-(bis(4-chlorophenyl)methyl)-2-cyclopropyl-2H-indazol-3-yl)piperidin-1-ylsulfonyl)-N-methylpicolinamide

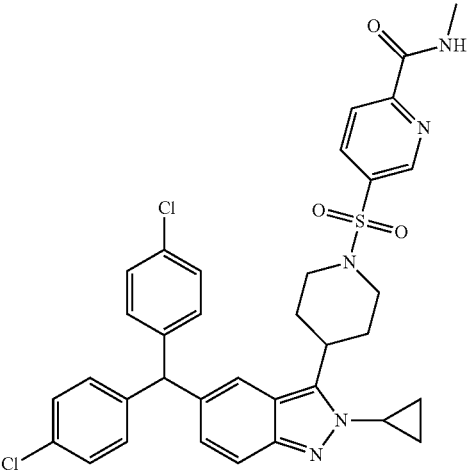 [SMILES: CNC(=O)c1ccc(S(=O)(=O)N2CCC(c3c4cc(C(c5ccc(Cl)cc5)c5ccc(Cl)cc5)ccc4nn3C3CC3)CC2)cn1]

The title compound was prepared according to the procedure as described in Example PH-45 substituting methylamine hydrochloride for ammonium chloride, and substituting 5-((4-(5-(bis(4-chlorophenyl)methyl)-2-cyclopropyl-2H-indazol-3-yl)piperidin-1-yl)sulfonyl)picolinic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (300 MHz, CDCl$_3$) δ: 8.96 (d, J=1.5 Hz, 1H), 8.40-8.43 (m, 1H), 8.23-8.26 (m, 1H), 8.07-8.09 (m, 1H), 7.63 (d, J=9.0 Hz, 1H), 7.47 (s, 1H), 7.26-7.31 (m, 4H), 7.13-7.16 (m, 1H), 7.02-7.05 (m, 4H), 5.56 (s, 1H), 4.07-4.11 (m, 2H), 3.62-3.66 (m, 1H), 3.31-3.35 (m, 1H), 3.09-3.35 (m, 3H), 2.47 (t, J=12.3 Hz, 2H), 2.22-2.34 (m, 2H), 1.97-2.01 (m, 2H), 1.25-1.30 (m, 4H). LC/MS (ES, m/z): 674 [M+H]$^+$.

Example PH-64

5-(bis(4-chlorophenyl)methyl)-2-cyclopropyl-3-(1-(2-methoxyphenylsulfonyl)piperidin-4-yl)-2H-indazole

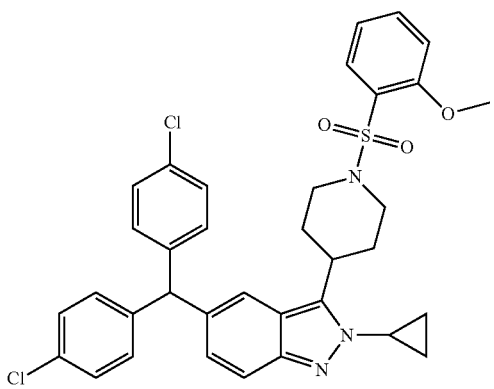 [SMILES: COc1ccccc1S(=O)(=O)N1CCC(c2c3cc(C(c4ccc(Cl)cc4)c4ccc(Cl)cc4)ccc3nn2C2CC2)CC1]

The title compound was prepared according to the procedure as described in Example PH-44 substituting 2-methoxybenzene-1-sulfonyl chloride for methyl 4-(chlorosulfonyl)-2-fluorobenzoate in Step 1.

$^1$H NMR (300 MHz, CDCl$_3$) δ: 7.96 (d, J=7.8 Hz, 1H), 7.66 (d, J=8.7 Hz, 1H), 7.55-7.62 (m, 2H), 7.28-7.31 (m, 4H), 7.21 (d, J=8.7 Hz, 1H), 7.03-7.20 (m, 6H), 5.57 (s, 1H), 4.13-4.16 (m, 2H), 3.94 (s, 3H), 3.46-3.74 (m, 2H), 2.81 (br.s, 2H), 2.22 (br.s, 2H), 1.94-2.02 (m, 2H), 1.37 (br.s, 4H). LC/MS (ES, m/z): 646 [M+H]$^+$.

Example PH-65

2-(4-(5-(bis(4-chlorophenyl)methyl)-2-cyclopropyl-2H-indazol-3-yl)piperidin-1-ylsulfonyl)phenol

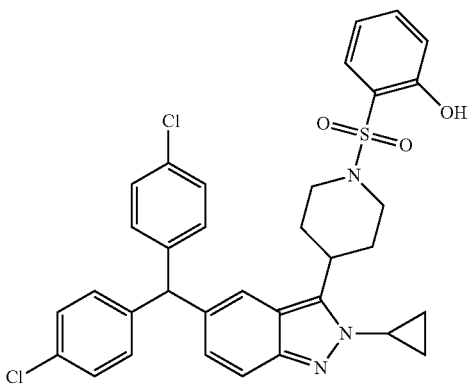 [SMILES: O=S(=O)(c1ccccc1O)N1CCC(c2c3cc(C(c4ccc(Cl)cc4)c4ccc(Cl)cc4)ccc3nn2C2CC2)CC1]

Into a 50-mL oven-dried round-bottom flask under nitrogen, was placed a solution of 5-[bis(4-chlorophenyl)methyl]-2-cyclopropyl-3-[1-[(2-methoxybenzene)sulfonyl]piperidin-4-yl]-2H-indazole (90.3 mg, 0.14 mmol) in dichloromethane (10 mL), followed by dropwise addition of BBr$_3$ (100.8 mg, 0.41 mmol) at 0° C., and the resulting solution was stirred for 2.5 h at room temperature, and concentrated under vacuum. The mixture was dissolved in DCM (20 mL), then washed with saturated NaHCO$_3$ (aq.) (2×20 mL). The organic layer was dried over anhydrous sodium sulfate and concentrated under vacuum. The residue was purified by Prep-HPLC as described in Step 3 of Example PH-2. The title compound 2-(4-[5-[bis(4-chlorophenyl)methyl]-2-cyclopropyl-2H-indazol-3-yl]piperidine-1-sulfonyl)phenol was obtained as a white solid.

$^1$H NMR (300 MHz, CDCl$_3$) δ: 7.51-7.66 (m, 3H), 7.48 (s, 1H), 7.27-7.31 (m, 4H), 7.18 (d, J=9.0 Hz, 1H), 7.03-7.12 (m, 6H), 5.57 (s, 1H), 4.05 (m, 2H), 3.67 (br.s, 1H), 3.39 (t, J=12.9 Hz, 1H), 2.58 (t, J=11.7 Hz, 2H), 2.19-2.31 (m, 2H), 1.96-2.01 (m, 2H), 1.32 (br.s, 4H). LC/MS (ES, m/z): 632 [M+H]$^+$.

Example PH-66

5-(bis(4-chlorophenyl)methyl)-2-cyclopropyl-3-(1-(3-methoxyphenylsulfonyl)piperidin-4-yl)-2H-indazole

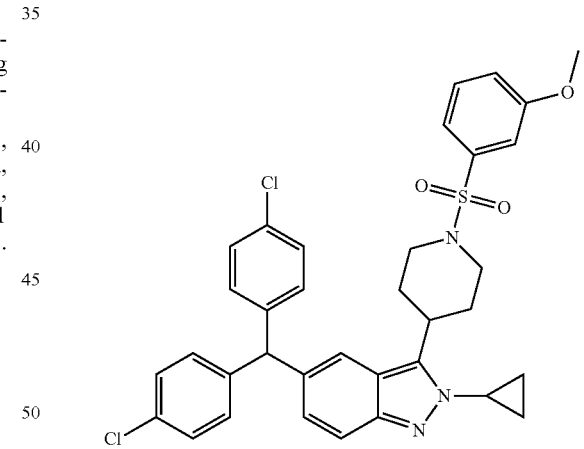

The title compound was prepared according to the procedure as described in Example PH-44 substituting 3-methoxybenzene-1-sulfonyl chloride for methyl 4-(chlorosulfonyl)-2-fluorobenzoate in Step 1.

$^1$H NMR (400 MHz, CDCl$_3$) δ: 7.65 (d, J=8.8 Hz, 1H), 7.49-7.54 (m, 2H), 7.40-7.42 (m, 1H), 7.28-7.34 (m, 5H), 7.19 (d, J=8.4 Hz, 2H), 7.05-7.07 (m, 4H), 5.58 (s, 1H), 4.06-4.09 (m, 2H), 3.91 (s, 3H), 3.67 (br.s, 1H), 3.32-3.39 (m, 1H), 2.45-2.51 (m, 2H), 2.24-2.33 (m, 2H), 1.96-1.99 (m, 2H), 1.28-1.33 (m, 4H). LC/MS (ES, m/z): 646 [M+H]$^+$.

Example PH-67

3-(4-(5-(bis(4-chlorophenyl)methyl)-2-cyclopropyl-2H-indazol-3-yl)piperidin-1-ylsulfonyl)phenol

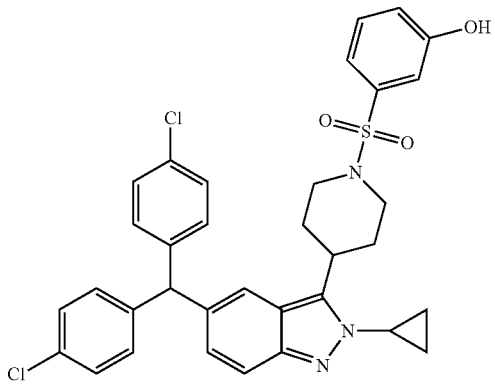 [SMILES: O=S(=O)(c1cccc(O)c1)N1CCC(c2c3cc(C(c4ccc(Cl)cc4)c4ccc(Cl)cc4)ccc3nn2C2CC2)CC1]

The title compound was prepared according to the procedure as described in Example PH-65 substituting 5-(bis(4-chlorophenyl)methyl)-2-cyclopropyl-3-(1-((3-methoxyphenyl)sulfonyl)piperidin-4-yl)-2H-indazole for 5-(bis(4-chlorophenyl)methyl)-2-cyclopropyl-3-(1-((2-methoxyphenyl)sulfonyl)piperidin-4-yl)-2H-indazole.

$^1$H NMR (300 MHz, CDCl$_3$) δ: δ 7.63 (d, J=11.7 Hz, 1H), 7.52 (s, 1H), 7.31-7.43 (m, 6H), 7.21 (d, J=9.0 Hz, 1H), 7.02-7.09 (m, 5H), 5.57 (s, 1H), 4.00-4.03 (m, 2H), 3.68 (br.s, 1H), 3.34 (br.s, 1H), 2.43-2.51 (m, 2H), 2.21-2.25 (m, 2H), 1.93-1.97 (m, 2H), 1.33 (br.s, 4H). LC/MS (ES, m/z): 632[M+H]$^+$.

Example PH-68

5-(bis(4-chlorophenyl)methyl)-2-cyclopropyl-3-(1-(4-methoxyphenylsulfonyl)piperidin-4-yl)-2H-indazole

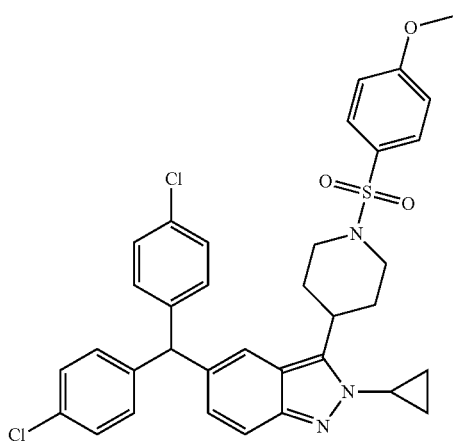 [SMILES: COc1ccc(S(=O)(=O)N2CCC(c3c4cc(C(c5ccc(Cl)cc5)c5ccc(Cl)cc5)ccc4nn3C3CC3)CC2)cc1]

The title compound was prepared according to the procedure as described in Example PH-44 substituting 4-methoxybenzene-1-sulfonyl chloride for ethyl 4-(chlorosulfonyl)-2-fluorobenzoate in Step 1.

$^1$H NMR (400 MHz, CDCl$_3$) δ: 7.78 (d, J=8.4 Hz, 2H), 7.65 (d, J=8.8 Hz, 1H), 7.55 (s, 1H), 7.28-7.32 (m, 4H), 7.20 (d, J=8.8 Hz, 1H), 7.00-7.08 (m, 6H), 5.58 (s, 1H), 4.03-4.06 (m, 2H), 3.92 (s, 3H), 3.68 (brs, 1H), 3.31-3.36 (m, 1H), 2.24-2.46 (m, 4H), 1.95-1.99 (m, 2H), 1.30-1.34 (m, 4H). LC/MS (ES, m/z): 646 [M+H]$^+$.

Example PH-69

5-(4-(5-(bis(4-chlorophenyl)methyl)-2-cyclopropyl-2H-indazol-3-yl)piperidin-1-ylsulfonyl)furan-2-carboxylic acid

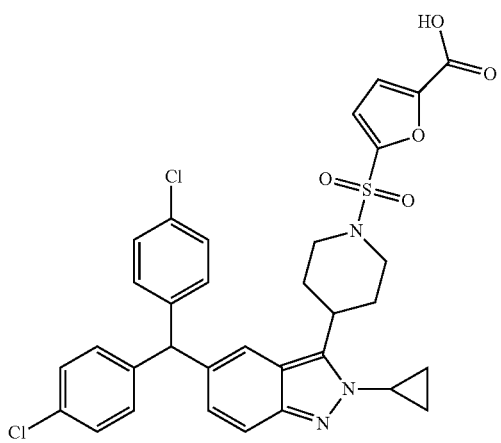 [SMILES: O=C(O)c1ccc(S(=O)(=O)N2CCC(c3c4cc(C(c5ccc(Cl)cc5)c5ccc(Cl)cc5)ccc4nn3C3CC3)CC2)o1]

The title compound was prepared according to the procedure as described in Example PH-44 substituting 5-(chlorosulfonyl)furan-2-carboxylic acid for methyl 4-(chlorosulfonyl)-2-fluorobenzoate in Step 1.

$^1$H NMR (400 MHz, CDCl$_3$) δ: 7.66 (d, J=8.8 Hz, 1H), 7.54 (s, 1H), 7.24-7.38 (m, 5H), 7.13-7.19 (m, 2H), 7.02-7.06 (m, 4H), 5.58 (s, 1H), 4.16-4.18 (m, 2H), 3.75 (br.s, 1H), 3.48-3.55 (m, 1H), 2.87-3.05 (m, 2H), 2.21-2.28 (m, 2H), 2.03-2.11 (m, 2H), 1.32-1.38 (m, 4H). LC/MS (ES, m/z): 650 [M+H]$^+$.

Example PH-70

5-(4-(5-(bis(4-chlorophenyl)methyl)-2-cyclopropyl-2H-indazol-3-yl)piperidin-1-ylsulfonyl)furan-2-carboxamide

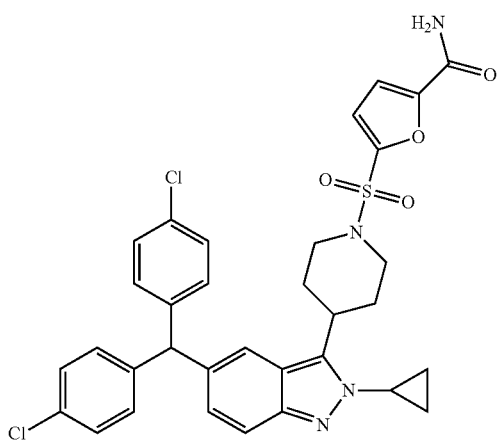 [SMILES: NC(=O)c1ccc(S(=O)(=O)N2CCC(c3c4cc(C(c5ccc(Cl)cc5)c5ccc(Cl)cc5)ccc4nn3C3CC3)CC2)o1]

The title compound was prepared according to the procedure as described in Example PH-45 substituting 5-((4-(5-(bis(4-chlorophenyl)methyl)-2-cyclopropyl-2H-indazol-3-yl)piperidin-1-yl)sulfonyl)furan-2-carboxylic acid for 4-((4-(5-(bis(4-chlorophenyl)methyl)-2-cyclopropyl-2H-indazol-3-yl)piperidin-1-yl)sulfonyl)-2-fluorobenzoic acid.

$^1$H NMR (400 MHz, CDCl$_3$) δ: 7.64 (d, J=8.8 Hz, 1H), 7.55 (s, 1H), 7.28-7.31 (m, 5H), 7.11-7.14 (m, 2H), 7.05-7.07 (m, 4H), 6.46 (br.s, 1H), 6.08 (br.s, 1H), 5.57 (s, 1H), 4.12 (m, 2H), 3.72 (m, 1H), 3.465 (m, 1H), 2.75 (m, 2H), 2.27 (m, 2H), 1.92-2.06 (m, 2H), 1.18-1.36 (m, 4H). LC/MS (ES, m/z): 649 [M+H]$^+$.

Example PH-71

4-((4-chlorophenyl)(2-cyclopropyl-3-(1-(trifluoromethylsulfonyl)piperidin-4-yl)-2H-indazol-5-yl)methyl)benzamide

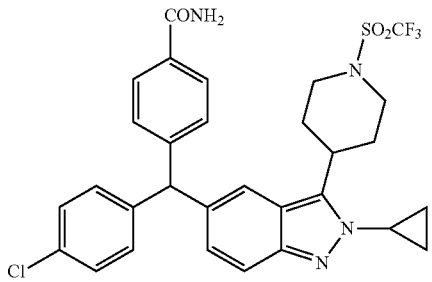

Step 1: Synthesis of methyl 2-cyclopropyl-3-(piperidin-4-yl)-2H-indazole-5-carboxylate Into a 100-mL round-bottom flask, were placed a solution of methyl 3-[1-[(tert-butoxy)carbonyl]piperidin-4-yl]-2-cyclopropyl-2H-indazole-5-carboxylate (5.0 g, 12.52 mmol) in dichloromethane (25 mL), CF$_3$COOH (5 mL). The resulting solution was stirred overnight at room temperature and concentrated under vacuum to yield methyl 2-cyclopropyl-3-(piperidin-4-yl)-2H-indazole-5-carboxylate as a brown solid. LC/MS (ES, m/z): 300 [M+H]$^+$ Step 2: Synthesis of methyl 2-cyclopropyl-3-[1-(trifluoromethane)sulfonylpiperidin-4-yl]-2H-indazole-5-carboxylate This intermediate was prepared according to the procedure as described in Example PH-40 substituting methyl 2-cyclopropyl-3-(piperidin-4-yl)-2H-indazole-5-carboxylate for (4-chlorophenyl)(3-(piperidin-4-yl)-1H-indazol-5-yl)methanone in Step 7. LC/MS (ES, m/z): 432 [M+H]$^+$ Step 3: Synthesis of 2-cyclopropyl-N-methoxy-N-methyl-3-[1-(trifluoromethane)sulfonylpiperidin-4-yl]-2H-indazole-5-carboxamide This intermediate was prepared according to the procedure as described in Example PH-27 substituting methyl 2-cyclopropyl-3-(1-((trifluoromethyl)sulfonyl)piperidin-4-yl)-2H-indazole-5-carboxylate for methyl 3-(1-(tert-butoxycarbonyl)piperidin-4-yl)-1-cyclopropyl-1H-indazole-5-carboxylate in Step 1. LC/MS (ES, m/z): 461 [M+H]$^+$ Step 4: Synthesis of 5-[(4-chlorophenyl)carbonyl]-2-cyclopropyl-3-[1-(trifluoromethane)sulfonylpiperidin-4-yl]-2H-indazole This intermediate was prepared according to the procedure as described in Example PH-27 substituting 2-cyclopropyl-N-methoxy-N-methyl-3-(1-((trifluoromethyl)sulfonyl)piperidin-4-yl)-2H-indazole-5-carboxamide for tert-butyl 4-(1-cyclopropyl-5-(methoxy(methyl)carbamoyl)-1H-indazol-3-yl)piperidine-1-carboxylate in Step 2. LC/MS (ES, m/z): 512 [M+H]$^+$ Step 5: Synthesis of 4-[(4-chlorophenyl) ([2-cyclopropyl-3-[1-(trifluoromethane)sulfonylpiperidin-4-yl]-2H-indazol-5-yl])hydroxymethyl]benzoic acid Into a 100-mL oven-dried round-bottom flask under nitrogen, was placed a solution of 1,4-dibromobenzene (2.34 g, 9.92 mmol) in tetrahydrofuran (20 mL), followed by dropwise addition of a 2.5 M solution of n-BuLi in hexanes (3.6 mL, 9.0 mmol at −78° C. After 30 min, a solution of 5-[(4-chlorophenyl)carbonyl]-2-cyclopropyl-3-[1-(trifluoromethane)sulfonylpiperidin-4-yl]-2H-indazole (1.02 g, 1.99 mmol,) in tetrahydrofuran (10 mL) was added, and the mixture was kept at the same temperature for 30 min. To the reaction solution was then added additional 2.5 M solution of n-BuLi in hexanes (4.4 mL, 11.0 mmol) dropwise at −78° C. After 20 min, carbon dioxide was bubbled through for 30 min, and the resulting solution was allowed to warm to room temperature and stirred overnight. After water (100 mL) was added, the mixture extracted with EtOAc (3×100). The combined organic extract was dried over Na$_2$SO$_4$ and concentrated under vacuum. The residue was purified on a silica gel column eluted with dichloromethane/methanol (1:5) to yield 4-[(4-chlorophenyl) ([2-cyclopropyl-3-[1-(trifluoromethane)sulfonylpiperidin-4-yl]-2H-indazol-5-yl])hydroxymethyl]benzoic acid as a light yellow solid. LC/MS (ES, m/z): 634 [M+H]$^+$ Step 6: Synthesis of 4-[(4-chlorophenyl) ([2-cyclopropyl-3-[1-(trifluoromethane)sulfonylpiperidin-4-yl]-2H-indazol-5-yl])methyl]benzoic acid This intermediate was prepared according to the procedure as described in Example PH-41 substituting 4-((4-chlorophenyl)(2-cyclopropyl-3-(1-((trifluoromethyl)sulfonyl)piperidin-4-yl)-2H-indazol-5-yl)(hydroxy)methyl)benzoic acid for 4-((4-chlorophenyl)(hydroxy)(3-(1-((trifluoromethyl)sulfonyl)piperidin-4-yl)-1H-indazol-5-yl)methyl)benzoic acid in Step 6. LC/MS (ES, m/z): 618 [M+H]$^+$ Step 7: Synthesis of 4-[(4-chlorophenyl)([2-cyclopropyl-3-[1-(trifluoromethane)sulfonylpiperidin-4-yl]-2H-indazol-5-yl])methyl]benzamide trifluoroacetic acid The title compound was prepared according to the procedure as described in Example PH-11 substituting 4-((4-chlorophenyl)(2-cyclopropyl-3-(1-((trifluoromethyl)sulfonyl)piperidin-4-yl)-2H-indazol-5-yl)methyl)benzoic acid for 4-(4-(5-(bis(4-chlorophenyl)methyl)-1-cyclopropyl-1H-indazol-3-yl)piperidine-1-carbonyl)benzoic acid in Step 3.

$^1$HNMR (300 MHz, CD$_3$OD) δ: 7.84 (d, J=8.1 Hz, 2H), 7.49 (d, J=9.0 Hz, 1H), 7.25-7.47 (m, 5H), 7.09-7.14 (m, 3H), 5.73 (s, 1H), 4.03-4.13 (m, 2H), 3.88-3.89 (m, 1H), 3.74-3.77 (m, 1H), 3.32-3.46 (m, 2H), 1.90-2.04 (m, 4H), 1.24-1.31 (m, 4H). LC/MS (ES, m/z): 617 [M+H]$^+$.

Example PH-72

4-(4-(5-(bis(4-chlorophenyl)methyl)-1H-indazol-3-ylamino)piperidin-1-ylsulfonyl)phenol

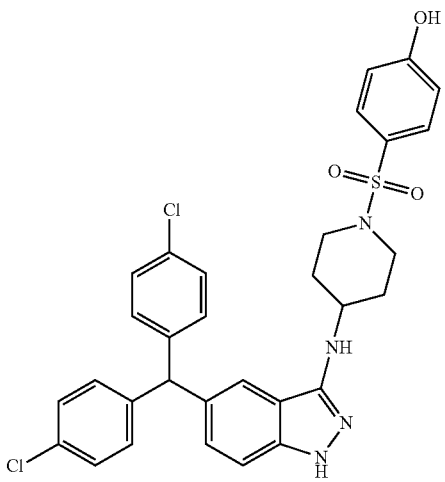 [SMILES: O=S(=O)(c1ccc(O)cc1)N1CCC(Nc2n[nH]c3ccc(C(c4ccc(Cl)cc4)c4ccc(Cl)cc4)cc23)CC1]

Step 1 Synthesis of methyl 3-bromo-1-(oxan-2-yl)-1H-indazole-5-carboxylate

Into a 100-mL round-bottom flask, were placed a solution of methyl 3-bromo-1H-indazole-5-carboxylate (3.0 g, 11.76 mmol) in dichloromethane (50 mL), 3,4-dihydro-2H-pyran (1.98 g, 23.54 mmol) and p-TsOH*H$_2$O (245 mg, 1.18 mmol). The resulting solution was stirred overnight at room temperature, and then concentrated under vacuum. The residue was recrystallized from DCM-Hexane (1:20) to yield methyl 3-bromo-1-(oxan-2-yl)-1H-indazole-5-carboxylate as a yellow solid. LC/MS (ES, m/z): 339 [M+H]$^+$.

Step 2: Synthesis of methyl 3-([1-[(tert-butoxy)carbonyl]piperidin-4-yl]amino)-1-(oxan-2-yl)-1H-indazole-5-carboxylate Into a 50-mL oven-dried round-bottom flask, were placed methyl 3-bromo-1-(oxan-2-yl)-1H-indazole-5-carboxylate (1.69 g, 4.98 mmol), tert-butyl 4-aminopiperidine-1-carboxylate (1.2 g, 5.99 mmol), Pd(OAc)$_2$ (56.1 mg, 0.25 mmol), BINAP (155.7 mg, 0.25 mmol) and a suspension of Cs$_2$CO$_3$ (5.7 g, 17.49 mmol, 3.51 equiv) in toluene (15 mL). The resulting mixture was stirred overnight at 95° C. under nitrogen, and then concentrated under vacuum. The residue was purified on a silica gel column eluted with ethyl acetate/petroleum ether (1:2) to yield methyl 3-([1-[(tert-butoxy)carbonyl]piperidin-4-yl]amino)-1-(oxan-2-yl)-1H-indazole-5-carboxylate as a yellow oil. LC/MS (ES, m/z): 460 [M+H]$^+$.

Step 3: Synthesis of 6-([5-[bis(4-chlorophenyl)(hydroxy)methyl]-1-(oxan-2-yl)-1H-indazol-3-yl]amino)-1-tert-butyl-1ˆ[3],3-oxazocan-2-one Into a 250-mL oven-dried round-bottom flask, was placed a solution of methyl 3-([1-[(tert-butoxy)carbonyl]piperidin-4-yl]amino)-1-(oxan-2-yl)-1H-indazole-5-carboxylate (4.59 g, 10.01 mmol) in tetrahydrofuran (50 mL), followed by dropwise addition of a 1 M solution of bromo(4-chlorophenyl)magnesium in THF (50 mL, 50.0 mmol). The resulting solution was stirred under nitrogen overnight at room temperature, and then quenched with water (50 mL), and extracted with ethyl acetate (3×50 mL). The combined organic extract was dried over anhydrous sodium sulfate and concentrated under vacuum. The residue was purified on a silica gel column with ethyl acetate/petroleum ether (1:2) to yield 6-([5-[bis(4-chlorophenyl)(hydroxy)methyl]-1-(oxan-2-yl)-1H-indazol-3-yl]amino)-1-tert-butyl-1ˆ[3],3-oxazocan-2-one as a yellow oil. LC/MS (ES, m/z): 653 [M+H]$^+$.

Step 4: Synthesis of bis(4-chlorophenyl)([3-[(piperidin-4-yl)amino]-1H-indazol-5-yl])methanol Into a 100-mL round-bottom flask, were placed 6-([5-[bis(4-chlorophenyl)(hydroxy)methyl]-1-(oxan-2-yl)-1H-indazol-3-yl]amino)-1-tert-butyl-1ˆ[3],3-oxazocan-2-one (6.0 g, 9.19 mmol) and a solution of trifluoroacetic acid (5 mL) in dichloromethane (50 mL). The resulting solution was stirred for 3 h at room temperature, and then concentrated to yield bis(4-chlorophenyl)([3-[(piperidin-4-yl)amino]-1H-indazol-5-yl])methanol as a yellow oil. LC/MS (ES, m/z): 467 [M+H]$^+$.

Step 5: Synthesis of 5-[bis(4-chlorophenyl)methyl]-N-(piperidin-4-yl)-1H-indazol-3-amine Into a 100-mL round-bottom flask, were placed bis(4-chlorophenyl)([3-[(piperidin-4-yl)amino]-1H-indazol-5-yl])methanol (3.99 g, 8.56 mmol), trifluoroacetic acid (5 mL) and a solution of Et$_3$SiH (2 mL) in dichloromethane (50 mL). The resulting solution was stirred for 2 h at room temperature, and then concentrated under vacuum. The residue was purified on a silica gel column eluted with dichloromethane/methanol (15:1) to yield 5-[bis(4-chlorophenyl)methyl]-N-(piperidin-4-yl)-1H-indazol-3-amine as a yellow oil. LC/MS (ES, m/z): 451 [M+H]$^+$.

Step 6: Synthesis of 5-[bis(4-chlorophenyl)methyl]-N-[1-[(4-methoxybenzene) sulfonyl]piperidin-4-yl]-1H-indazol-3-amine Into a 25-mL oven-dried round-bottom flask, were placed 5-[bis(4-chlorophenyl)methyl]-N-(piperidin-4-yl)-1H-indazol-3-amine (45.1 mg, 0.10 mmol), 4-methoxybenzene-1-sulfonyl chloride (22.7 mg, 0.11 mmol) and a solution of triethylamine (30.4 mg, 0.30 mmol) in dichloromethane (5 mL). The resulting solution was stirred under nitrogen for 3 h at room temperature, and then concentrated under vacuum to yield 5-[bis(4-chlorophenyl)methyl]-N-[1-[(4-methoxybenzene) sulfonyl]piperidin-4-yl]-1H-indazol-3-amine as a yellow oil. LC/MS (ES, m/z): 621 [M+H]$^+$.

Step 7: Synthesis of 4-[4-([5-[bis(4-chlorophenyl)methyl]-1H-indazol-3-yl]amino)piperidine-1-sulfonyl]phenol trifluoroacetic acid Into a 25-mL oven-dried round-bottom flask, was placed a solution of 5-[bis(4-chlorophenyl)methyl]-N-[1-[(4-methoxybenzene)sulfonyl]piperidin-4-yl]-1H-indazol-3-amine (49.7 mg, 0.08 mmol) in dichloromethane (10 mL), followed by dropwise addition of BBr$_3$ (200.4 mg, 0.80 mmol) at 0° C. The resulting solution was stirred under nitrogen for 3 h at room temperature and then concentrated under vacuum. The residue was purified by Prep-HPLC as described in Step 3 of Example PH-2. The title compound 4-[4-([5-[bis(4-chlorophenyl)methyl]-1H-indazol-3-yl]

amino)piperidine-1-sulfonyl]phenol trifluoroacetic acid was obtained as an off-white solid.

¹H NMR (400 MHz, DMSO-d₆) δ: 11.61-11.64 (brs, 1H), 10.52 (brs, 1H), 7.58 (d, J=8.4 Hz, 2H), 7.45 (s, 1H), 7.37-7.39 (m, 4H), 7.20-7.22 (m, 1H), 7.11-7.13 (m, 5H), 6.95-6.98 (m, 2H), 5.70 (s, 1H), 3.54-3.64 (m, 3H), 2.33-2.39 (m, 3H), 2.05-2.08 (m, 2H), 1.47-1.55 (m, 2H). LC/MS (ES, m/z): 607 [M+H]⁺.

Example PH-73

3-(4-(5-(bis(4-chlorophenyl)methyl)-2-cyclopropyl-2H-indazol-3-yl)piperidin-1-yl)benzamide

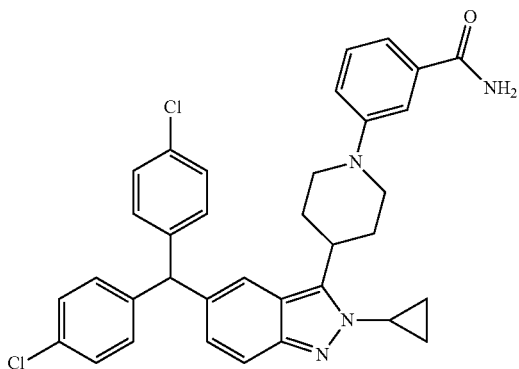 [SMILES: NC(=O)c1cccc(N2CCC(c3c4cc(C(c5ccc(Cl)cc5)c5ccc(Cl)cc5)ccc4nn3C3CC3)CC2)c1]

The title compound was prepared according to the procedure as described in Example PH-15 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole, and substituting methyl 3-bromobenzoate for methyl 4-bromobenzoate in Step 1.

¹H NMR (400 MHz, CDCl₃) δ: 8.12 (s, 1H), 7.50-7.64 (m, 4H), 7.42-7.44 (m, 1H), 7.26-7.28 (m, 4H), 7.05-7.09 (m, 5H), 6.69 (brs, 1H), 6.15 (brs, 1H), 5.56 (s, 1H), 3.92-3.95 (m, 2H), 3.77-3.83 (m, 1H), 3.60-3.67 (m, 1H), 3.21 (t, J=10.8 Hz, 2H), 2.59-2.68 (m, 2H), 2.11-2.14 (m, 2H), 1.42-1.46 (m, 2H), 1.27-1.33 (m, 2H). LC/MS (ES, m/z): 595 [M+H]⁺.

Example PH-74

4-(4-(5-(bis(4-chlorophenyl)methyl)-2-cyclopropyl-2H-indazol-3-yl)piperidin-1-yl)benzamide

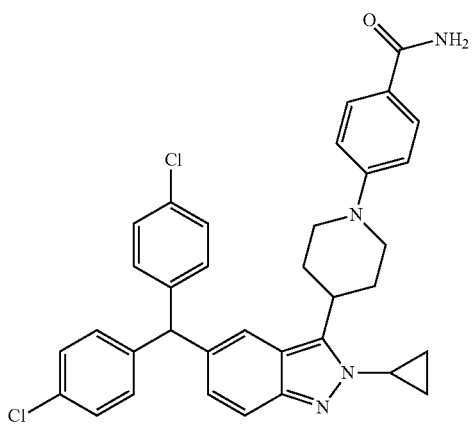 [SMILES: NC(=O)c1ccc(N2CCC(c3c4cc(C(c5ccc(Cl)cc5)c5ccc(Cl)cc5)ccc4nn3C3CC3)CC2)cc1]

The title compound was prepared according to the procedure as described in Example PH-15 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole in Step 1.

¹H NMR (300 MHz, CDCl₃) δ: 7.79 (d, J=8.4 Hz, 2H), 7.61 (d, J=9.0 Hz, 1H), 7.36 (s, 1H), 7.22-7.27 (m, 4H), 6.98-7.11 (m, 7H), 5.49 (s, 1H), 4.03-4.07 (m, 2H), 3.56-3.75 (m, 2H), 3.05 (t, J=12.0 Hz, 2H), 2.20-2.27 (m, 2H), 2.01-2.05 (m, 2H), 1.41 (br.s, 2H), 1.21-1.34 (m, 2H). LC/MS (ES, m/z): 595 [M+H]⁺.

Example PH-75

2-(3-(4-(5-(bis(4-chlorophenyl)methyl)-2-cyclopropyl-2H-indazol-3-yl)piperidin-1-yl)phenoxy)acetamide

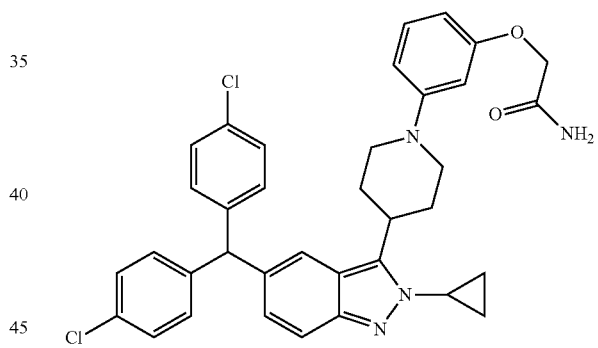

The title compound was prepared according to the procedure as described in Example PH-15 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole, and substituting ethyl 2-(3-bromophenoxy)acetate for methyl 4-bromobenzoate in Step 1.

¹H NMR (300 MHz, CDCl₃) δ: 7.57-7.79 (m, 2H), 7.38 (t, J=8.4 Hz, 1H), 7.24-7.30 (m, 4H), 6.97-7.09 (m, 7H), 6.76-6.79 (m, 1H), 6.69 (br.s, 1H), 6.11 (br.s, 1H), 5.54 (s, 1H), 4.57 (s, 2H), 3.59-3.93 (m, 4H), 3.20 (t, J=11.7 Hz, 2H), 2.63-2.74 (m, 2H), 2.02-2.13 (m, 2H), 1.26-1.42 (m, 4H). LC/MS (ES, m/z): 625[M+H]⁺.

Example PH-76

2-(4-(4-(5-(bis(4-chlorophenyl)methyl)-2-cyclopropyl-2H-indazol-3-yl)piperidin-1-yl)phenoxy)acetamide

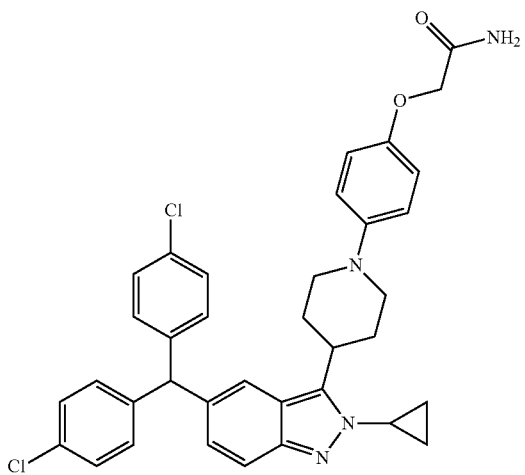 [SMILES: NC(=O)COc1ccc(N2CCC(c3c4cc(C(c5ccc(Cl)cc5)c5ccc(Cl)cc5)ccc4nn3C3CC3)CC2)cc1]

The title compound was prepared according to the procedure as described in Example PH-15 substituting 5-(bis(4-chlorophenyl)methyl)-2-cyclopropyl-3-(piperidin-4-yl)-2H-indazole for 5-(bis(4-chlorophenyl)methyl)-1-cyclopropyl-3-(piperidin-4-yl)-1H-indazole, and substituting ethyl 2-(4-bromophenoxy)acetate for methyl 4-bromobenzoate in Step 1.

$^1$H NMR (300 MHz, CDCl$_3$) δ: 7.58-7.63 (m, 4H), 7.24-7.27 (m, 4H), 7.05-7.08 (m, 7H), 6.55 (br.s, 1H), 5.96 (br.s, 1H), 5.57 (s, 1H), 4.55 (s, 2H), 3.80-3.93 (m, 2H), 3.64-3.79 (m, 2H), 3.37 (t, J=11.4 Hz, 2H), 2.97-3.01 (m, 2H), 2.15-2.19 (m, 2H), 1.40-1.42 (m, 2H), 1.25-1.31 (m, 2H). LC/MS (ES, m/z): 625 [M+H]$^+$.

Example PH-77

5-((4-(5-(bis(4-chlorophenyl)methyl)-2-cyclopropyl-2H-indazol-3-yl)piperidin-1-yl)methyl)nicotinic acid

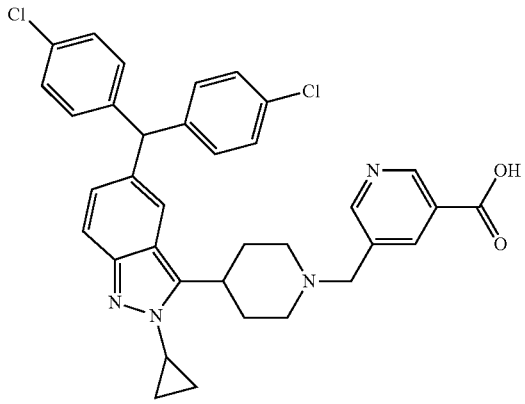 [SMILES: O=C(O)c1cncc(CN2CCC(c3c4cc(C(c5ccc(Cl)cc5)c5ccc(Cl)cc5)ccc4nn3C3CC3)CC2)c1]

Step 1: Synthesis of methyl 5-[(4-[5-[bis(4-chlorophenyl)methyl]-2-cyclopropyl-2H-indazol-3-yl]piperidin-1-yl)methyl]pyridine-3-carboxylate Into a 25-mL round-bottom flask, were placed a solution of 5-[bis(4-chlorophenyl)methyl]-2-cyclopropyl-3-(piperidin-4-yl)-2H-indazole (247.7 mg, 0.52 mmol) in dichloromethane (5 mL), methyl 5-formylpyridine-3-carboxylate (87.5 mg, 0.53 mmol) and AcOH (0.1 mL). After the solution was stirred for 2 h at room temperature, NaBH(OAc)$_3$ (279 mg, 1.32 mmol) was added, and the resulting mixture was stirred under nitrogen overnight at room temperature, and then concentrated under vacuum. The residue was purified on a silica gel column eluted with dichloromethane/methanol (100:5) to yield methyl 5-[(4-[5-[bis(4-chlorophenyl)methyl]-2-cyclopropyl-2H-indazol-3-yl]piperidin-1-yl)methyl]pyridine-3-carboxylate as a yellow solid. LC/MS (ES, m/z): 625 [M+H]$^+$.

Step 2: Synthesis of 5-[(4-[5-[bis(4-chlorophenyl)methyl]-2-cyclopropyl-2H-indazol-3-yl]piperidin-1-yl)methyl]pyridine-3-carboxylic acid The title compound was prepared according to the procedure as described in Example PH-11 substituting methyl 5-((4-(5-(bis(4-chlorophenyl)methyl)-2-cyclopropyl-2H-indazol-3-yl)piperidin-1-yl)methyl)nicotinate for methyl 4-(4-(5-(bis(4-chlorophenyl)methyl)-1-cyclopropyl-1H-indazol-3-yl)piperidine-1-carbonyl)benzoate in Step 2.

$^1$H NMR (300 MHz, DMSO-d$_6$) δ: 9.29 (s, 1H), 8.96 (s, 1H), 8.64 (s, 1H), 7.50-7.56 (m, 2H), 7.30-7.40 (m, 4H), 7.05-7.12 (m, 5H), 5.67 (s, 1H), 4.67 (s, 2H), 3.86-3.91 (m, 2H), 3.70-3.73 (m, 2H), 3.33-3.43 (m, 2H), 2.26-2.43 (m, 4H), 1.28-1.35 (m, 2H), 1.25-1.27 (m, 2H). LC/MS (ES, m/z): 611 [M+H]$^+$.

Example PH-78

3-((4-(5-(bis(4-chlorophenyl)methyl)-2-cyclopropyl-2H-indazol-3-yl)piperidin-1-yl)methyl)benzoic acid

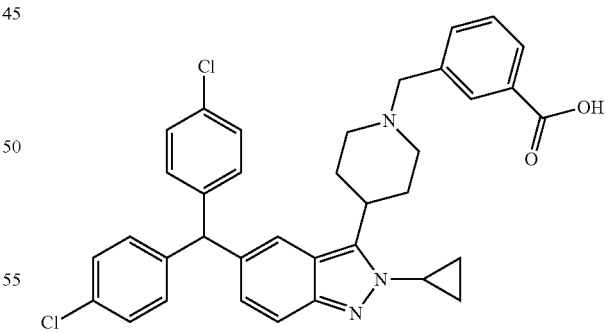

The title compound was prepared according to the procedure as described in Example PH-77 substituting methyl 3-formylbenzoate for methyl 5-formylpyridine-3-carboxylate in Step 1.

1H NMR (300 MHz, DMSO-d6) δ: 7.84-7.94 (m, 2H), 7.61-7.63 (m, 1H), 7.37-7.52 (m, 7H), 7.13-7.15 (m, 4H), 6.90-6.94 (m, 1H), 5.72 (s, 1H), 3.93-4.00 (m, 1H), 3.65 (brs, 2H), 3.00-3.09 (m, 2H), 1.89-2.27 (m, 5H), 1.22-1.23 (m, 2H), 1.08-1.17 (m, 2H). LC/MS (ES, m/z): 610 [M+H]$^+$.

Example PH-79

4-((4-(5-(bis(4-chlorophenyl)methyl)-2-cyclopropyl-2H-indazol-3-yl)piperidin-1-yl)methyl)benzoic acid

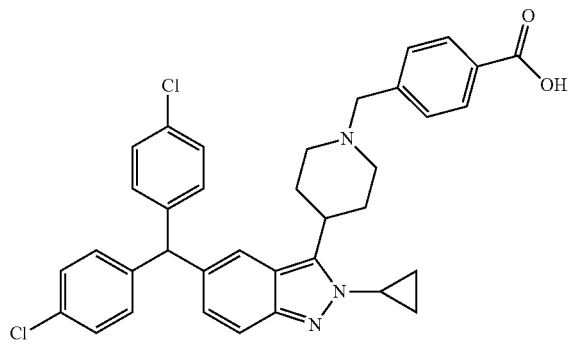 [SMILES: O=C(O)c1ccc(CN2CCC(c3c4cc(C(c5ccc(Cl)cc5)c5ccc(Cl)cc5)ccc4nn3C3CC3)CC2)cc1]

The title compound was prepared according to the procedure as described in Example PH-77 substituting methyl 4-formylbenzoate for methyl 5-formylpyridine-3-carboxylate, in Step 1.

$^1$H NMR (300 MHz, CD$_3$OD) δ: 8.16-8.19 (m, 2H), 7.66-7.68 (m, 2H), 7.57 (s, 2H), 7.48-7.51 (m, 2H), 7.29-7.36 (m, 4H), 7.04-7.11 (m, 5H), 5.61 (s, 1H), 4.48 (s, 2H), 3.86-3.92 (m, 2H), 3.66-3.70 (m, 2H), 2.22-2.45 (m, 4H), 1.22-1.37 (m, 4H). LC/MS (ES, m/z): 610 [M+H]$^+$.

Example PH-80

5-((4-chlorophenyl)(cyclopropyl)methyl)-3-(1-(trifluoromethylsulfonyl)piperidin-4-yl)-1H-indazole

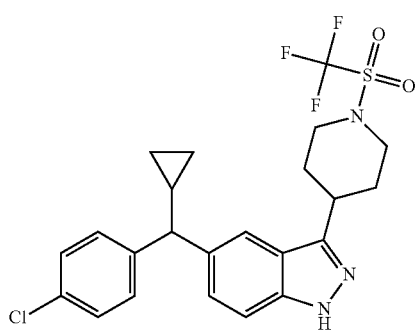 [SMILES: O=S(=O)(N1CCC(c2n[nH]c3ccc(C(c4ccc(Cl)cc4)C4CC4)cc23)CC1)C(F)(F)F]

Step 1: Synthesis of (4-chlorophenyl)[1-(oxan-2-yl)-3-[1-(trifluoromethane)sulfonylpiperidin-4-yl]-1H-indazol-5-yl]methanol Into a 250-mL oven-dried round-bottom flask, were placed a solution of 5-[(4-chlorophenyl)carbonyl]-1-(oxan-2-yl)-3-[1-(trifluoromethane)sulfonylpiperidin-4-yl]-1H-indazole (3.0 g, 5.40 mmol) in C$_2$H$_5$OH (100 mL) and NaBH$_4$ (410.2 mg, 10.84 mmol), and the resulting solution was stirred under nitrogen for 3 h at room temperature and then concentrated under vacuum. The residue was dissolved in DCM (100 mL), and then washed with water (3×50 mL). The organic layer was dried over anhydrous sodium sulfate and concentrated under vacuum to yield (4-chlorophenyl)[1-(oxan-2-yl)-3-[1-(trifluoromethane)sulfonylpiperidin-4-yl]-1H-indazol-5-yl]methanol as a white solid. LC/MS (ES, m/z): 582 [M+Na]$^+$

Step 2: Synthesis of 5-[chloro(4-chlorophenyl)methyl]-1-(oxan-2-yl)-3-[1-(trifluoromethane)sulfonylpiperidin-4-yl]-1H-indazole Into a 25-mL oven-dried round-bottom flask, were placed a solution of (4-chlorophenyl)[1-(oxan-2-yl)-3-[1-(trifluoromethane)sulfonylpiperidin-4-yl]-1H-indazol-5-yl]methanol (209.2 mg, 0.36 mmol) in dichloromethane (10 mL) and thionyl chloride (2 mL). The resulting solution was stirred for 2 h at 45° C. under nitrogen, and then concentrated under vacuum to yield 5-[chloro(4-chlorophenyl)methyl]-1-(oxan-2-yl)-3-[1-(trifluoromethane)sulfonylpiperidin-4-yl]-1H-indazole as a white solid. LC/MS (ES, m/z): 576 [M+H]$^+$

Step 3: Synthesis of 5-[(4-chlorophenyl)(cyclopropyl)methyl]-1-(oxan-2-yl)-3-[1-(trifluoromethane)sulfonylpiperidin-4-yl]-1H-indazole Into a 25-mL oven-dried round-bottom flask purged and maintained under nitrogen, were placed 1M solution of bromo(cyclopropyl)magnesium (2 mL, 2 mmol) in tetrahydrofuran (5 mL), 1M solution of ZnCl$_2$ in THF (2 mL, 2.0 mmol), and the solution was stirred for 10 min at 50° C. A solution of 5-[chloro(4-chlorophenyl)methyl]-1-(oxan-2-yl)-3-[1-(trifluoromethane)sulfonylpiperidin-4-yl]-1H-indazole (97.8 mg, 0.17 mmol) in tetrahydrofuran (10 mL) was then added. After stirred overnight at room temperature, the mixture was concentrated under vacuum. The residue was purified on a silica gel column eluted with ethyl acetate/petroleum ether (0:100-1:5) to yield 5-[(4-chlorophenyl)(cyclopropyl)methyl]-1-(oxan-2-yl)-3-[1-(trifluoromethane)sulfonylpiperidin-4-yl]-1H-indazole as a colorless oil. LC/MS (ES, m/z): 582 [M+H]$^+$

Step 4: Synthesis of 5-[(4-chlorophenyl)(cyclopropyl)methyl]-3-[1-(trifluoromethane)sulfonylpiperidin-4-yl]-1H-indazole Into a 25-mL round-bottom flask, were placed a solution of 5-[(4-chlorophenyl)(cyclopropyl)methyl]-1-(oxan-2-yl)-3-[1-(trifluoromethane)sulfonylpiperidin-4-yl]-1H-indazole (81.4 mg, 0.14 mmol) in dichloromethane (10 mL) and trifluoroacetic acid (1 mL). The resulting solution was stirred overnight at room temperature, and then concentrated under vacuum. The residue (120 mg) was purified by Prep-HPLC as described in Step 3 of Example PH-2. The title compound 5-[(4-chlorophenyl)(cyclopropyl)methyl]-3-[1-(trifluoromethane)sulfonylpiperidin-4-yl]-1H-indazole was obtained as a white solid.

$^1$H NMR (300 MHz, CD$_3$OD) δ: 7.74 (s, 1H), 7.40-7.43 (m, 1H), 7.24-7.33 (m, 5H), 4.05-4.10 (m, 2H), 3.33-3.40 (m, 4H), 2.03-2.21 (m, 4H), 1.45-1.50 (m, 1H), 0.68-0.74 (m, 2H), 0.32-0.37 (m, 2H). LC/MS (ES, m/z): 498 [M+H]$^+$.

Example PH-81

4-((4-chlorophenyl)(3-(4-(trifluoromethylsulfonyl)piperazin-1-yl)-1H-indazol-5-yl)methyl)benzamide

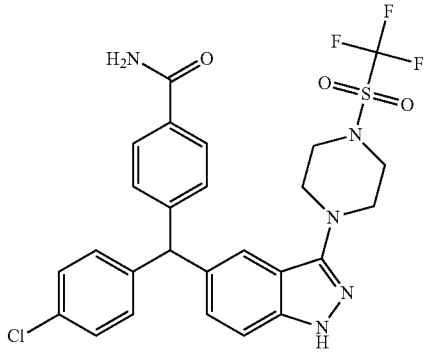 [SMILES: NC(=O)c1ccc(C(c2ccc(Cl)cc2)c2ccc3[nH]nc(N4CCN(S(=O)(=O)C(F)(F)F)CC4)c3c2)cc1]

Step 1: Synthesis of methyl 3-bromo-1-(triphenylmethyl)-1H-indazole-5-carboxylate Into a 250-mL oven-dried round-bottom flask, were placed a solution of methyl 3-bromo-1H-indazole-5-carboxylate (5.0 g, 19.60 mmol) in CH$_3$CN (150 mL), (chlorodiphenylmethyl)benzene (21.9 g, 78.56 mmol) and potassium carbonate (13.6 g, 98.40 mmol). The resulting mixture was stirred under nitrogen for 4 h at room temperature, and the precipitate formed was collected by filtration. The residue was suspended in DCM (200 mL), and filtered to remove the insoluble material. The filtrate was concentrated under vacuum to yield methyl 3-bromo-1-(triphenylmethyl)-1H-indazole-5-carboxylate as a white solid.

Step 2: Synthesis of methyl 3-[4-(trifluoromethane)sulfonylpiperazin-1-yl]-1-(triphenylmethyl)-1H-indazole-5-carboxylate Into a 50-mL oven-dried 3-necked round-bottom flask purged and maintained under nitrogen, were placed a solution of methyl 3-bromo-1-(triphenylmethyl)-1H-indazole-5-carboxylate (8.0 g, 16.08 mmol) in toluene (25 mL), 1-(trifluoromethane)sulfonylpiperazine hydrochloride (5.33 g, 20.93 mmol,), Pd(OAc)$_2$ (361.4 mg, 1.61 mol), BINAP (2.0 g, 3.21 mmol) and Cs$_2$CO$_3$ (15.8 g, 48.49 mmol). The resulting mixture was stirred overnight at 90° C., and then concentrated under vacuum. The residue was purified on a silica gel column eluted with ethyl acetate/petroleum ether (0:100-1:10) to yield of methyl 3-[4-(trifluoromethane)sulfonylpiperazin-1-yl]-1-(triphenylmethyl)-1H-indazole-5-carboxylate as a white solid. LC/MS (ES, m/z): 635 [M+H]$^+$.

Step 3: Synthesis of N-methoxy-N-methyl-3-[4-(trifluoromethane)sulfonylpiperazin-1-yl]-1-(triphenylmethyl)-1H-indazole-5-carboxamide Into a 250-mL oven-dried round-bottom flask purged and maintained under nitrogen, were placed a solution of methyl 3-[4-(trifluoromethane)sulfonylpiperazin-1-yl]-1-(triphenylmethyl)-1H-indazole-5-carboxylate (7.5 g, 11.82 mmol) in tetrahydrofuran (100 mL), and methoxy(methyl)amine hydrochloride (1.38 g, 14.15 mmol). To the mixture was then added 1M solution of LiHMDS in THF (29.6 mL, 29.6 mmol) dropwise. The reaction was stirred for 1 h at room temperature, and then quenched with water (100 mL), and extracted with ethyl acetate (3×100 mL). The combined organic extract was dried over sodium sulfate and concentrated under vacuum. The residue was purified on a silica gel column eluted with EA/PE (0:100-2:1) to yield N-methoxy-N-methyl-3-[4-(trifluoromethane)sulfonylpiperazin-1-yl]-1-(triphenylmethyl)-1H-indazole-5-carboxamide as a yellow solid. LC/MS (ES, m/z): 650 [M+H]$^+$.

Step 4: Synthesis of 5-[(4-chlorophenyl)carbonyl]-3-[4-(trifluoromethane)sulfonylpiperazin-1-yl]-1-(triphenylmethyl)-1H-indazole Into a 100-mL oven-dried round-bottom flask, was placed a solution of N-methoxy-N-methyl-3-[4-(trifluoromethane)sulfonylpiperazin-1-yl]-1-(triphenylmethyl)-1H-indazole-5-carboxamide (7.8 g, 11.75 mmol) in tetrahydrofuran (100 mL). To the solution was then added 1M solution of bromo(4-chlorophenyl)magnesium in THF (23.6 mL, 23.6 mmol) dropwise with stirring at 0° C. The reaction was stirred overnight at 40° C., and then quenched with water (200 mL), and extracted with ethyl acetate (3×150 mL). The combined organic extract was dried over sodium sulfate and concentrated under vacuum. The residue was purified on a silica gel column eluted with ethyl acetate/petroleum ether (0:100-1:5) to yield 5-[(4-chlorophenyl)carbonyl]-3-[4-(trifluoromethane)sulfonylpiperazin-1-yl]-1-(triphenylmethyl)-1H-indazole as a light yellow solid. LC/MS (ES, m/z): 715 [M+H]$^+$.

Step 5: Synthesis of 4-[(4-chlorophenyl)(hydroxy)[3-[4-(trifluoromethane)sulfonylpiperazin-1-yl]-1-(triphenylmethyl)-1H-indazol-5-yl]methyl]benzoic acid Into a 250-mL oven-dried round-bottom flask purged and maintained under nitrogen, was placed a solution of 1,4-dibromobenzene (4.92 g, 20.86 mmol) in tetrahydrofuran (50 mL). To the mixture was then added 2.5 M solution of n-BuLi in hexanes (7.56 mL, 18.90 mmol) dropwise with stirring at −78° C. After 45 min, a solution of 5-[(4-chlorophenyl)carbonyl]-3-[4-(trifluoromethane)sulfonylpiperazin-1-yl]-1-(triphenylmethyl)-1H-indazole (3.0 g, 4.19 mmol) in tetrahydrofuran (25 mL) was added, and the solution was stirred for 30 min at room temperature. To the mixture was then added additional 2.5 M solution of n-BuLi in hexanes (9.24 mL, 23.1 mmol) dropwise with stirring. The solution was stirred for 30 min, then CO$_2$ was bubbled through for 20 min. The resulting solution was allowed to warm to room temperature and stirred overnight. After water (150 mL) was added, the mixture was extracted with ethyl acetate (3×150 mL). The combined organic extract was dried over sodium sulfate and concentrated under vacuum. The residue was purified on a silica gel column eluted with dichloromethane/methanol (100:0-10:1) to yield 4-[(4-chlorophenyl)(hydroxy)[3-[4-(trifluoromethane)sulfonylpiperazin-1-yl]-1-(triphenylmethyl)-1H-indazol-5-yl]methyl]benzoic acid as red oil. LC/MS (ES, m/z): 837 [M+H]$^+$.

Step 6: Synthesis of 4-[(4-chlorophenyl)([3-[4-(trifluoromethane)sulfonylpiperazin-1-yl]-1H-indazol-5-yl])methyl]benzoic acid Into a 100-mL round-bottom flask, were placed a solution of 4-[(4-chlorophenyl)(hydroxy)[3-[4-(trifluoromethane)sulfonylpiperazin-1-yl]-1-(triphenylmethyl)-1H-indazol-5-yl]methyl]benzoic acid (2.4 g, 2.84 mmol) in dichloromethane (50 mL), trifluoroacetic acid (8 mL) and Et₃SiH (4 mL). The resulting solution was stirred for 4 h at room temperature and then concentrated under vacuum. The residue was purified on a silica gel column eluted with dichloromethane/methanol (100:0-10:1) to yield product, which was further purified by Prep-HPLC as described in Step 3 of Example PH-2. The title compound 4-[(4-chlorophenyl)([3-[4-(trifluoromethane)sulfonylpiperazin-1-yl]-1H-indazol-5-yl])methyl]benzoic acid was obtained as a white solid. LC/MS (ES, m/z): 579 [M+H]⁺

Step 7: Synthesis of 4-[(4-chlorophenyl)([3-[4-(trifluoromethane)sulfonylpiperazin-1-yl]-1H-indazol-5-yl])methyl]benzamide; trifluoroacetic acid Into a 25-mL round-bottom flask, were placed a solution of 4-[(4-chlorophenyl)([3-[4-(trifluoromethane)sulfonylpiperazin-1-yl]-1H-indazol-5-yl])methyl]benzoic acid (346.8 mg, 0.60 mmol) in N,N-dimethylformamide (5 mL), HATU (460.1 mg, 1.21 mmol), DIEA (234 mg, 1.81 mmol) and the solution was stirred for 10 min at room temperature. To the reaction mixture was then added NH₄Cl (64.2 mg, 1.20 mmol). The resulting mixture was stirred overnight at room temperature, then the product was precipitated out with H₂O (10 mL). The solid was collected by filtration and purified by Prep-HPLC as described in Step 3 of Example PH-2. The title compound 4-[(4-chlorophenyl)([3-[4-(trifluoromethane)sulfonylpiperazin-1-yl]-1H-indazol-5-yl])methyl]benzamide was obtained as a white solid.
¹H NMR (300 MHz, CDCl₃) δ: 7.77 (d, J=8.1 Hz, 2H), 7.13-7.36 (m, 7H), 7.02-7.05 (m, 2H), 6.25-6.28 (m, 2H), 6.16 (s, 1H), 3.69 (m, 4H), 3.48 (m, 4H). LC/MS (ES, m/z): 578 [M+H]⁺.

Example PH-82

5-((4-chlorophenyl)(3-(1-(trifluoromethylsulfonyl)piperidin-4-yl)-1H-indazol-5-yl)methyl)picolinamide compound

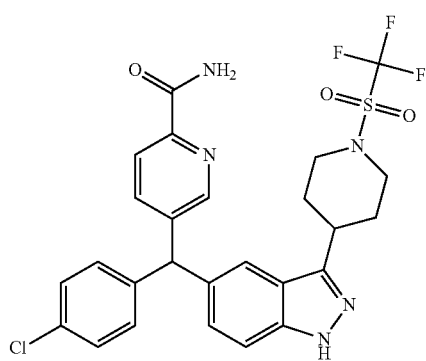 [SMILES: NC(=O)c1ccc(C(c2ccc(Cl)cc2)c2ccc3[nH]nc(C4CCN(S(=O)(=O)C(F)(F)F)CC4)c3c2)cn1]

Step 1: Synthesis of 5-[(6-chloropyridin-3-yl)carbonyl]-1-(oxan-2-yl)-3-[1-(trifluoromethane)sulfonylpiperidin-4-yl]-1H-indazole Into a 100-mL oven-dried round-bottom flask purged and maintained under nitrogen, was placed a solution of 5-bromo-1-(oxan-2-yl)-3-[1-(trifluoromethane)sulfonylpiperidin-4-yl]-1H-indazole (3.0 g, 6.04 mmol) in tetrahydrofuran (40 mL), followed by dropwise addition of 2.5 M solution of n-BuLi in hexanes (2.9 mL, 7.25 mmol) with stirring at −78° C. After the solution was stirred for 40 min, a solution of 6-chloro-N-methoxy-N-methylnicotinamide (1.21 g, 6.07 mmol) in tetrahydrofuran (10 mL) was added, and the resulting solution was stirred overnight at room temperature. After water (150 mL) was added, the mixture was extracted with ethyl acetate (3×150 mL). The combined organic extract was dried over sodium sulfate and concentrated under vacuum. The residue was purified on a silica gel column with EA/PE (0:100-2:1) to yield 5-[(6-chloropyridin-3-yl)carbonyl]-1-(oxan-2-yl)-3-[1-(trifluoromethane)sulfonylpiperidin-4-yl]-1H-indazole as a yellow solid. LC/MS (ES, m/z): 557 [M+H]⁺

Step 2: Synthesis of (4-chlorophenyl)(6-chloropyridin-3-yl)[1-(oxan-2-yl)-3-[1-(trifluoromethane)sulfonylpiperidin-4-yl]-1H-indazol-5-yl]methanol Into a 100-mL oven-dried round-bottom flask purged and maintained under nitrogen, was placed a solution of 5-[(6-chloropyridin-3-yl)carbonyl]-1-(oxan-2-yl)-3-[1-(trifluoromethane)sulfonylpiperidin-4-yl]-1H-indazole (2.4 g, 4.27 mmol) in tetrahydrofuran (25 mL). To the mixture was then added 1M solution of bromo(4-chlorophenyl)magnesium in THF (10.7 mL, 10.7 mmol) dropwise with stirring. The resulting solution was stirred overnight at 60° C., then water (100 mL) was added, and the mixture was extracted with ethyl acetate (3×100 mL). The combined organic extract was dried over sodium sulfate and concentrated under vacuum. The residue was purified on a silica gel column eluted with EA/PE (0:100-100:0) to yield (4-chlorophenyl)(6-chloropyridin-3-yl)[1-(oxan-2-yl)-3-[1-(trifluoromethane)sulfonylpiperidin-4-yl]-1H-indazol-5-yl]methanol as a white solid. LC/MS (ES, m/z): 669 [M+H]⁺

Step 3: Synthesis of ethyl 5-[(4-chlorophenyl)(hydroxy)[1-(oxan-2-yl)-3-[1-(trifluoromethane)sulfonylpiperidin-4-yl]-1H-indazol-5-yl]methyl]pyridine-2-carboxylate Into a 250-mL oven-dried 3-necked round-bottom flask purged and maintained under CO, were placed a solution of (4-chlorophenyl)(6-chloropyridin-3-yl)[1-(oxan-2-yl)-3-[1-(trifluoromethane)sulfonylpiperidin-4-yl]-1H-indazol-5-yl]methanol (995.3 mg, 1.49 mmol) in ethanol (50 mL), Pd(dppf)Cl₂ (58.5 mg, 0.08 mmol) and triethylamine (454.5 mg, 4.49 mmol,). The resulting solution was stirred overnight at 50° C., and concentrated under vacuum. The residue was purified on a silica gel column eluted with ethyl acetate/petroleum ether (0:100-100:0) to yield ethyl 5-[(4-chlorophenyl)(hydroxy)[1-(oxan-2-yl)-3-[1-(trifluoromethane)sulfonylpiperidin-4-yl]-1H-indazol-5-yl]methyl]pyridine-2-carboxylate as a white solid. LC/MS (ES, m/z): 707 [M+H]⁺

Step 4: Synthesis of 5-[(4-chlorophenyl)(hydroxy)[1-(oxan-2-yl)-3-[1-(trifluoromethane)sulfonylpiperidin-4-yl]-1H-indazol-5-yl]methyl]pyridine-2-carboxylic acid Into a 100-mL round-bottom flask, were placed a solution of ethyl 5-[(4-chlorophenyl)(hydroxy)[1-(oxan-2-yl)-3-[1-(trifluoromethane)sulfonylpiperidin-4-yl]-1H-indazol-5-yl]methyl]pyridine-2-carboxylate (896.6 mg, 1.27 mmol) in tetrahydrofuran (36 mL) and a solution of LiOH.H₂O (534.2 mg, 12.73 mmol,) in methanol/H₂O (9/9 mL). The resulting mixture was stirred overnight at room temperature, and concentrated under vacuum to remove organic solvent. After the mixture was acidification to pH 3-4 with 1N HCl solution, precipitate was formed and collected by filtration to yield 5-[(4-chlorophenyl)(hydroxy)[1-(oxan-2-yl)-3-[1-(trifluoromethane)sulfonylpiperidin-4-yl]-1H-indazol-5-yl] methyl]pyridine-2-carboxylic acid as a white solid. LC/MS (ES, m/z): 679 [M+H]$^+$.

Step 5: Synthesis of 5-[(4-chlorophenyl)(hydroxy) [3-[1-(trifluoromethane)sulfonylpiperidin-4-yl]-1H-indazol-5-yl]methyl]pyridine-2-carboxylic acid This intermediate was prepared according to the procedure as described in Example PH-41 substituting 5-((4-chlorophenyl)(hydroxy)(1-(tetrahydro-2H-pyran-2-yl)-3-(1-((trifluoromethyl)sulfonyl)piperidin-4-yl)-1H-indazol-5-yl) methyl)picolinic acid for 4-((4-chlorophenyl)(hydroxy)(1-(tetrahydro-2H-pyran-2-yl)-3-(1-((trifluoromethyl)sulfonyl) piperidin-4-yl)-1H-indazol-5-yl)methyl)benzoic acid in Step 5.

Step 6: Synthesis of yield 4-[(4-chlorophenyl)([3-[1-(trifluoromethane)sulfonylpiperidin-4-yl]-1H-indazol-5-yl])methyl]benzoic acid This intermediate was prepared according to the procedure as described in Example PH-41 substituting 5-((4-chlorophenyl)(hydroxy)(3-(1-((trifluoromethyl)sulfonyl)piperidin-4-yl)-1H-indazol-5-yl)methyl)picolinic acid for 4-((4-chlorophenyl)(hydroxy)(3-(1-((trifluoromethyl)sulfonyl)piperidin-4-yl)-1H-indazol-5-yl)methyl)benzoic acid in Step 6. LC/MS (ES, m/z): 579 [M+H]$^+$ Step 7: Synthesis of 5-[(4-chlorophenyl)([3-[1-(trifluoromethane)sulfonylpiperidin-4-yl]-1H-indazol-5-yl])methyl]pyridine-2-carboxamide; ethanol The title compound was prepared according to the procedure as described in Example PH-11 substituting 5-((4-chlorophenyl)(3-(1-((trifluoromethyl)sulfonyl)piperidin-4-yl)-1H-indazol-5-yl)methyl)picolinic acid for 4-(4-(5-(bis (4-chlorophenyl)methyl)-1-cyclopropyl-1H-indazol-3-yl) piperidine-1-carbonyl)benzoic acid in Step 3.

$^1$H NMR (400 MHz, CD3OD) δ: 8.46 (d, J=2.0 Hz, 1H), 8.06-8.08 (m, 1H), 7.69-7.71 (m, 1H), 7.48-7.52 (m, 2H), 7.35-7.37 (m, 2H), 7.16-7.23 (m, 3H), 5.90 (s, 1H), 4.00-4.04 (m, 2H), 3.14-3.26 (m, 3H), 1.94-2.12 (m, 4H), 1.32 (t, J=8.8 Hz, 3H). LC/MS (ES, m/z): 578 [M+H]$^+$.

Example PH-83

5-(bis(4-chlorophenyl)methyl)-3-(4-(trifluoromethylsulfonyl)piperazin-1-yl)-1H-indazole

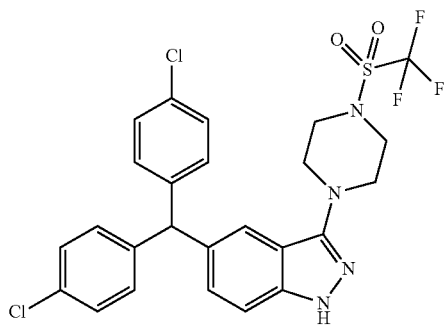 [SMILES: O=S(=O)(N1CCN(c2n[nH]c3ccc(C(c4ccc(Cl)cc4)c4ccc(Cl)cc4)cc23)CC1)C(F)(F)F]

Step 1: Synthesis of bis(4-chlorophenyl)([3-[4-(trifluoromethane)sulfonylpiperazin-1-yl]-1-(triphenylmethyl)-1H-indazol-5-yl])methanol Into a 1000-mL oven-dried round-bottom flask purged and maintained under nitrogen, was placed a solution of methyl 3-[4-(trifluoromethane)sulfonylpiperazin-1-yl]-1-(triphenylmethyl)-1H-indazole-5-carboxylate (15.9 g, 23.63 mmol) in tetrahydrofuran (300 mL), followed by dropwise addition of 1M solution of bromo(4-chlorophenyl)magnesium in THF (118 mL, 118.0 mmol) with stirring. The resulting solution was stirred overnight at 60° C. in an oil bath. After water (200 mL) was added, the mixture was extracted with ethyl acetate (3×200 mL). The combined organic extract was dried over sodium sulfate and concentrated under vacuum. The residue was purified on a silica gel column with ethyl acetate/petroleum ether (0:100-1:3) to yield bis(4-chlorophenyl)([3-[4-(trifluoromethane)sulfonylpiperazin-1-yl]-1-(triphenylmethyl)-1H-indazol-5-yl]) methanol as yellow oil. LC/MS (ES, m/z): 828 [M+H]$^+$ Step 2: Synthesis of 5-[bis(4-chlorophenyl)methyl]-3-[4-(trifluoromethane)sulfonylpiperazin-1-yl]-1H-indazole Into a 250-mL round-bottom flask, were placed a solution of bis(4-chlorophenyl)([3-[4-(trifluoromethane)sulfonylpiperazin-1-yl]-1-(triphenylmethyl)-1H-indazol-5-yl])methanol (15.0 g, 18.12 mmol) in dichloromethane (100 mL), trifluoroacetic acid (15 mL) and Et$_3$SiH (10 mL). The resulting solution was stirred overnight at room temperature and then concentrated under vacuum. The residue was purified on a silica gel column with EA:PE (0:100-1:1) to yield 5-[bis(4-chlorophenyl)methyl]-3-[4-(trifluoromethane)sulfonylpiperazin-1-yl]-1H-indazole as an off-white solid.

1H NMR (300 MHz, DMSO-d$_6$) δ: 9.23-9.29 (brs, 1H), 7.26-7.34 (m, 6H), 7.04-7.15 (m, 5H), 7.41-7.44 (m, 4H), 5.61 (s, 1H), 3.70-3.80 (m, 4H), 3.40-3.53 (m, 4H). LC/MS (ES, m/z): 569 [M+H]$^+$ Example PH-84

4-((4-chlorophenyl)(3-(4-((trifluoromethyl)sulfonyl) piperazin-1-yl)-1H-indazol-5-yl)methyl)benzoic acid

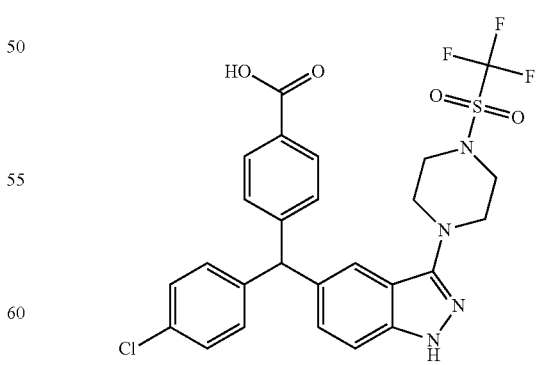

The title compound was prepared according to the procedure as described in Step 6 of Example PH-81.

$^1$H NMR (400 MHz, DMSO-d$_6$) b=12.19 (s, 1H), 7.87 (br d, J=8.1 Hz, 2H), 7.59 (s, 1H), 7.41-7.32 (m, 3H), 7.21 (br d, J=7.8 Hz, 2H), 7.14 (d, J=8.6 Hz, 2H), 7.07 (br d, J=8.8 Hz, 1H), 5.79 (s, 1H), 3.66 (br s, 4H), 3.37 (br s, 4H). LC/MS (ES, m/z): 579 [M+H]+.

The title compound, 4-((4-chlorophenyl)(3-(4-((trifluoromethyl)sulfonyl)piperazin-1-yl)-1H-indazol-5-yl)methyl) benzoic acid, was resolved to yield the corresponding R*- and S* enantiomers using the following conditions: Supercritical Fluid Chromatography: Column: AD-H 5 um, 20×250 mm, 40° C.; Detection wavelength: 235 nm, 32 min for each run; 15% Methanol as a cosolvent; CO$_2$ flow rate: 42.5 ml/min, co-solvent flow rate: 7.5 ml/min, 150 bar. The first product to come off the column was assigned as the R* enentiomer, whereas the second product peak was assigned as the S* enantiomer.

Example RZ-1

5-(bis(4-chlorophenyl)methyl)-1-methyl-3-(4-((trifluoromethyl)sulfonyl)piperazin-1-yl)-1H-indazole

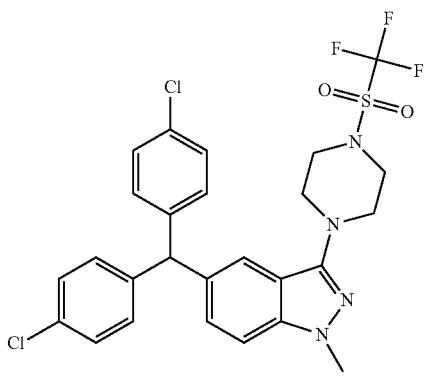 [SMILES: Cn1nc(N2CCN(S(=O)(=O)C(F)(F)F)CC2)c2cc(C(c3ccc(Cl)cc3)c3ccc(Cl)cc3)ccc21]

Step 1: methyl 3-iodo-1-((2-(trimethylsilyl)ethoxy) methyl)-1H-indazole-5-carboxylate A solution of methyl 3-iodo-1H-indazole-5-carboxylate (2.30 g, 7.61 mmol) and (2-(chloromethoxy)ethyl)trimethylsilane (1.61 mL, 9.14 mmol) was cooled to 0° C., 60% NaH in mineral oil (0.36 g, 9.14 mmol) was added in portions. The reaction mixture was allowed to gradually warm to room temperature, and stirred under argon for 2 h. The reaction was then quenched with saturated NaHCO$_3$ solution (100 mL), and extracted with diethyl ether (3×100 mL). The combined organic extract was dried over Na$_2$SO$_4$ and concentrated. The residue was purified by flash chromatography, eluted with a gradient of 100% heptane to 1:1 heptane-EtOAc over 20 min, to yield methyl 3-iodo-1-((2-(trimethylsilyl)ethoxy)methyl)-1H-indazole-5-carboxylate as an off-white solid. LCMS (ES, m/z): 433 [M+H]+.

Step 2: methyl 3-(4-((trifluoromethyl)sulfonyl)piperazin-1-yl)-1-((2-(trimethylsilyl)ethoxy)methyl)-1H-indazole-5-carboxylate A mixture of methyl 3-iodo-1-((2-(trimethylsilyl)ethoxy) methyl)-1H-indazole-5-carboxylate (408.2 mg, 0.94 mmol), 1-((trifluoromethyl)sulfonyl)piperazine (267.8 mg, 1.23 mmol), Pd(OAc)$_2$ (21.2 mg, 0.09 mmol), BINAP (117.6 mg, 0.19 mmol) and Cs$_2$CO$_3$ (922.9 mg, 2.83 mmol) in toluene (10 mL) was evacuated and then refilled with argon for three times. The reaction was then heated overnight at 95° C. under argon. After EtOAc (50 mL) was added, the mixture was washed with H$_2$O (50 mL) and brine (50 mL). The organic layer was dried over Na$_2$SO$_4$ and concentrated. The residue was purified by flash chromatography, eluted with a gradient of 100% heptane to 100% EtOAc over 20 min, to yield methyl 3-(4-((trifluoromethyl)sulfonyl)piperazin-1-yl)-1-((2-(trimethylsilyl)ethoxy)methyl)-1H-indazole-5-carboxylate as a light yellow oil. LCMS (ES, m/z): 523 [M+H]+.

Step 3: bis(4-chlorophenyl)(3-(4-((trifluoromethyl) sulfonyl)piperazin-1-yl)-1-((2-(trimethylsilyl) ethoxy)methyl)-1H-indazol-5-yl)methanol A solution of 4-chloro-iodobenzene in THF (3 mL) was cooled to −78° C. under argon, 1.6M solution of n-BuLi in hexane (4.27 mL, 6.83 mmol) was added slowly. After stirring for 15 min, a solution of methyl 3-(4-((trifluoromethyl)sulfonyl)piperazin-1-yl)-1-((2-(trimethylsilyl)ethoxy) methyl)-1H-indazole-5-carboxylate (830.2 mg, 1.59 mmol) in THF (3 mL) was added, and the resultant mixture was allowed to warm to room temperature gradually. The reaction was then quenched with saturated NaHCO$_3$ solution (50 mL), and extracted with diethyl ether (3×50 mL). The combined organic extract was dried over Na$_2$SO$_4$ and concentrated. The residue was purified by flash chromatography, eluted with a gradient of 100% heptane to 100% EtOAc over min, to yield bis(4-chlorophenyl)(3-(4-((trifluoromethyl)sulfonyl)piperazin-1-yl)-1-((2-(trimethylsilyl)ethoxy) methyl)-1H-indazol-5-yl)methanol as a white solid. LCMS (ES, m/z): 715 [M+H]+.

Step 4: 5-(bis(4-chlorophenyl)methyl)-1-methyl-3- (4-((trifluoromethyl)sulfonyl)piperazin-1-yl)-1H- indazole A solution of bis(4-chlorophenyl)(3-(4-((trifluoromethyl) sulfonyl)piperazin-1-yl)-1-((2-(trimethylsilyl)ethoxy) methyl)-1H-indazol-5-yl)methanol (35.0 mg, 0.05 mmol) in DCM (10 mL) was cooled to 0° C., and triethylsilane (0.03 mL, 0.20 mmol) was added, followed by slow addition of TFA (0.015 mL, 0.20 mmol). The reaction mixture was maintained at 0° C. for 30 min under argon, then allowed to gradually warm to room temperature, and stirred for additional 1 h (reaction became colorless solution from the beginning deep blue color). The mixture was basified with 0.5M K$_2$CO$_3$ solution (10 mL), and then extracted with DCM (3×10 mL). The organic extract was dried over Na$_2$SO$_4$ and concentrated. The residue was purified by flash chromatography, eluted with a gradient of 100% heptane to 100% EtOAc over 20 min, to yield 5-(bis(4-chlorophenyl) methyl)-1-methyl-3-(4-((trifluoromethyl)sulfonyl)piperazin-1-yl)-1H-indazole as a white solid.

$^1$H NMR (400 MHz, CHLOROFORM-d) δ=7.30-7.24 (m, 5H), 7.21 (br. d, J=8.8 Hz, 1H), 7.09 (br. d, J=8.6 Hz, 1H), 7.02 (br. d, J=8.3 Hz, 4H), 5.58 (s, 1H), 3.89 (s, 3H), 3.67 (m, 4H), 3.42 (m, 4H). LCMS (ES, m/z): 583 [M+H]+.

Example RZ-2

4-((4-(5-(bis(4-chlorophenyl)methyl)-1-methyl-1H-indazol-3-yl)piperidin-1-yl)sulfonyl)benzamide

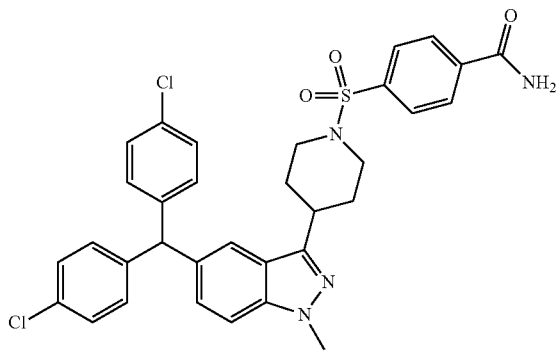 [SMILES: Cn1nc(C2CCN(S(=O)(=O)c3ccc(C(N)=O)cc3)CC2)c2cc(C(c3ccc(Cl)cc3)c3ccc(Cl)cc3)ccc21]

Step 1: methyl 4-((4-(5-(bis(4-chlorophenyl)methyl)-1H-indazol-3-yl)piperidin-1-yl)sulfonyl)benzoate A solution of 5-(bis(4-chlorophenyl)methyl)-3-(piperidin-4-yl)-1H-indazole (61.3 mg, 0.14 mmol) and Et₃N (0.06 mL, 0.42 mmol) in DCM (2 mL) was cooled to 0° C., 4-methoxycarbonylphenylsulfonyl chloride (39.6 mg, 0.17 mmol) was added. After stirred at 0° C. for 1 h, the reaction mixture was concentrated. The residue was purified by flash chromatography, eluted with a gradient of 100% heptane to 100% EtOAc over 20 min, to yield methyl 4-((4-(5-(bis(4-chlorophenyl)methyl)-1H-indazol-3-yl)piperidin-1-yl)sulfonyl)benzoate as a white solid. LCMS (ES, m/z): 634 [M+H]⁺.

Step 2: methyl 4-((4-(5-(bis(4-chlorophenyl)methyl)-1H-indazol-3-yl)piperidin-1-yl)sulfonyl)benzoate A mixture of methyl 4-((4-(5-(bis(4-chlorophenyl)methyl)-1H-indazol-3-yl)piperidin-1-yl)sulfonyl)benzoate (36.5 mg, 0.058 mmol), MeI (5.4 µL, 0.086 mmol) and Cs₂CO₃ (37.5 mg, 0.12 mmol) in DMF (2 mL) was stirred at room temperature for 1 h, then Et₂O (20 mL) was added. The organic layer was separated and washed with H₂O (20 mL) and brine (20 mL), then dried over Na₂SO₄ and concentrated. The residue was purified by flash chromatography, eluted with a gradient of 100% heptane to 100% EtOAc over 20 min, to yield methyl 4-((4-(5-(bis(4-chlorophenyl)methyl)-1H-indazol-3-yl)piperidin-1-yl)sulfonyl)benzoate as a white solid. LCMS (ES, m/z): 648 [M+H]⁺.

Step 3: 4-((4-(5-(bis(4-chlorophenyl)methyl)-1-methyl-1H-indazol-3-yl)piperidin-1-yl)sulfonyl)benzoic acid A solution of methyl 4-((4-(5-(bis(4-chlorophenyl)methyl)-1H-indazol-3-yl)piperidin-1-yl)sulfonyl)benzoate (31.7 mg, 0.049 mmol) in 2:1 mixture of THF-MeOH (1.5 mL) was treated with 3N NaOH solution (82 µL, 0.24 mmol) at room temperature for 1 h under argon. The mixture was acidified to pH 3-4 with 1N HCl solution, and then extracted with EtOAc (3×20 mL). The combined extract was dried over Na₂SO₄ and concentrated. C18 HPLC purification of the residue (Phenomenex Luna 5u, 100×30 mm, flow rate: 30 mL/min) eluted with a gradient of 10% to 95% of MeCN/H₂O both with 0.1% TFA over 15 min yielded 4-((4-(5-(bis(4-chlorophenyl)methyl)-1-methyl-1H-indazol-3-yl)piperidin-1-yl)sulfonyl)benzoic acid as a white solid after lyophilization. LCMS (ES, m/z): 634 [M+H]⁺.

Step 4: 4-((4-(5-(bis(4-chlorophenyl)methyl)-1-methyl-1H-indazol-3-yl)piperidin-1-yl)sulfonyl)benzamide A mixture of 4-((4-(5-(bis(4-chlorophenyl)methyl)-1-methyl-1H-indazol-3-yl)piperidin-1-yl)sulfonyl)benzoic acid (14.8 mg, 0.023 mmol), 0.5 M NH₃ solution in 1,4-dioxane (0.47 mL, 0.23 mmol), HATU (13.3 mg, 0.035 mmol) and diisopropylethylamine (0.012 mL, 0.07 mmol) in DMF (2 mL) was stirred at room temperature overnight under argon, then concentrated to remove organic solvents. The residue was purified by C18 HPLC as described in Step 3 to yield 4-((4-(5-(bis(4-chlorophenyl)methyl)-1-methyl-1H-indazol-3-yl)piperidin-1-yl)sulfonyl)benzamide as a white solid after lyophilization.

¹H NMR (400 MHz, CHLOROFORM-d) δ=7.98 (d, J=8.3 Hz, 2H), 7.88 (d, J=8.3 Hz, 2H), 7.30-7.23 (m, 6H), 7.09 (d, J=8.8 Hz, 1H), 7.01 (d, J=8.3 Hz, 4H), 6.19 (br. s, 1H), 5.91 (br. s, 1H), 5.57 (s, 1H), 3.96 (s, 3H), 3.89 (m, 2H), 2.92 (m, 1H), 2.52 (dt, J=2.9, 11.0 Hz, 2H), 2.15-1.90 (m, 4H). LCMS (ES, m/z): 633 [M+H]⁺.

Example RZ-3

3-((4-(5-(bis(4-chlorophenyl)methyl)-1-methyl-1H-indazol-3-yl)piperidin-1-yl)sulfonyl)benzamide

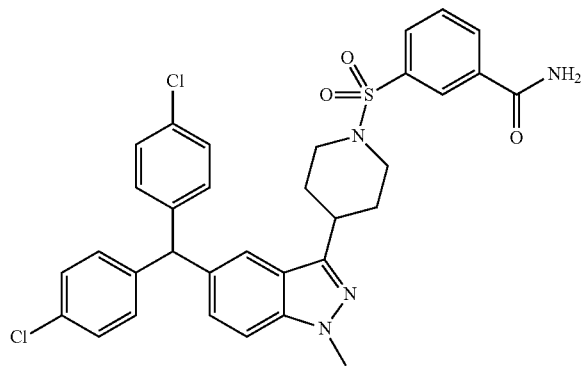 [SMILES: Cn1nc(C2CCN(S(=O)(=O)c3cccc(C(N)=O)c3)CC2)c2cc(C(c3ccc(Cl)cc3)c3ccc(Cl)cc3)ccc21]

The title compound was prepared according to the procedure as described in Example RZ-2 substituting 3-methoxycarbonylphenylsulfonyl chloride for 4-methoxycarbonylphenylsulfonyl chloride in Step 1.

¹H NMR (400 MHz, CHLOROFORM-d) δ=8.20 (t, J=1.6 Hz, 1H), 8.10 (d, J=8.0 Hz, 1H), 7.98 (d, J=8.0 Hz, 1H), 7.68 (t, J=7.8 Hz, 1H), 7.32-7.23 (m, 6H), 7.10 (dd, J=1.5, 8.8 Hz, 1H), 7.04-6.99 (m, 4H), 6.37 (br. s, 2H), 5.58 (s, 1H), 3.96 (s, 3H), 3.90 (m, 2H), 2.94 (m, 1H), 2.53 (dt, J=3.4, 11.2 Hz, 2H), 2.14-2.00 (m, 4H). LCMS (ES, m/z): 633 [M+H]⁺.

Example RZ-4

5-(bis(4-chlorophenyl)methyl)-3-(1-(cyclopropylsulfonyl)piperidin-4-yl)-1H-indazole

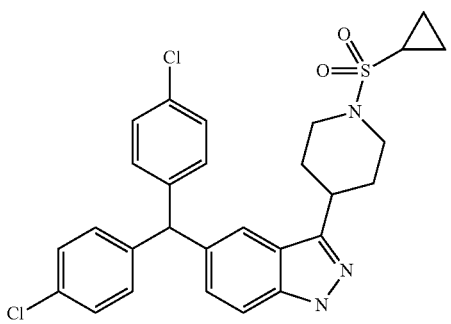 [SMILES: O=S(=O)(C1CC1)N1CCC(c2n[nH]c3ccc(C(c4ccc(Cl)cc4)c4ccc(Cl)cc4)cc23)CC1]

The title compound was prepared according to the procedure as described in Example PH-32 substituting cyclopropanesulfonyl chloride for methyl 5-(chlorosulfonyl)furan-2-carboxylate in Step 3.

$^1$H NMR (400 MHz, CHLOROFORM-d) δ=7.42 (d, J=8.7 Hz, 1H), 7.41 (s, 1H), 7.30-7.25 (m, 4H), 7.17 (dd, J=1.6, 8.7 Hz, 1H), 7.06-7.01 (m, 4H), 5.61 (s, 1H), 3.97-3.90 (m, 2H), 3.17 (m, 1H), 3.08-3.00 (m, 2H), 2.32 (m, 1H), 2.12-2.01 (m, 4H), 1.26-1.16 (m, 2H), 1.04-0.98 (m, 2H). LCMS (ES, m/z): 540 [M+H]$^+$.

Example RZ-5

5-(bis(4-chlorophenyl)methyl)-3-(1-((2,2,2-trifluoroethyl)sulfonyl)piperidin-4-yl)-1H-indazole

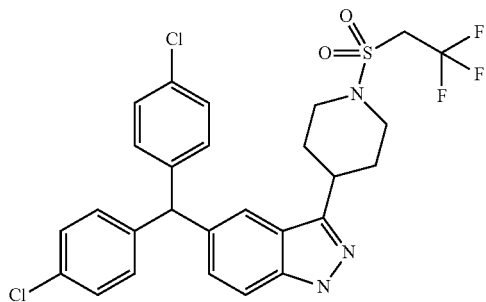 [SMILES: O=S(=O)(CC(F)(F)F)N1CCC(c2n[nH]c3ccc(C(c4ccc(Cl)cc4)c4ccc(Cl)cc4)cc23)CC1]

The title compound was prepared according to the procedure as described in Example PH-32 substituting 2,2,2-trifluoroethanesulfonyl chloride for methyl 5-(chlorosulfonyl)furan-2-carboxylate in Step 3.

$^1$H NMR (400 MHz, CHLOROFORM-d) δ=7.48-7.36 (m, 2H), 7.31-7.20 (m, 5H), 7.03 (d, J=7.7 Hz, 4H), 5.62 (s, 1H), 3.99 (m, 2H), 3.75 (q, J=9.5 Hz, 2H), 3.21 (m, 1H), 3.13-3.04 (m, 2H), 2.15-1.98 (m, 4H). LCMS (ES, m/z): 582 [M+H]$^+$.

Example RZ-6

5-(bis(4-chlorophenyl)methyl)-3-(1-((2-(trifluoromethyl)phenyl)sulfonyl)piperidin-4-yl)-1H-indazole

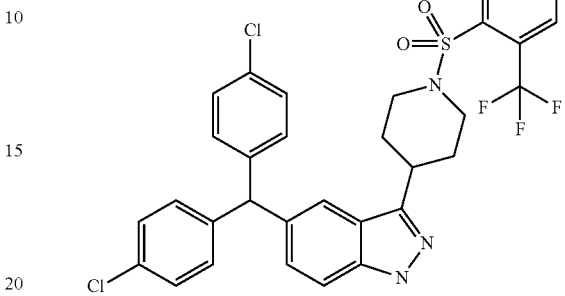

The title compound was prepared according to the procedure as described in Example PH-32 substituting 2-(trifluoromethyl)benzene-1-sulfonyl chloride for methyl 5-(chlorosulfonyl)furan-2-carboxylate in Step 3.

$^1$H NMR (400 MHz, CHLOROFORM-d) δ=8.17 (d, J=6.7 Hz, 1H), 7.90 (d, J=6.6 Hz, 1H), 7.74-7.67 (m, 2H), 7.40-7.34 (m, 2H), 7.29-7.23 (m, 4H), 7.11 (dd, J=1.6, 8.7 Hz, 1H), 7.06-7.00 (m, 4H), 5.59 (s, 1H), 5.30 (s, 1H), 3.96-3.88 (m, 2H), 3.11 (m, 1H), 3.00-2.89 (m, 2H), 2.17-2.00 (m, 4H). LCMS (ES, m/z): 644 [M+H]$^+$.

Example RZ-7

(4-(5-(bis(4-chlorophenyl)methyl)-1H-indazol-3-yl)piperidin-1-yl)(1H-1,2,3-triazol-4-yl)methanone

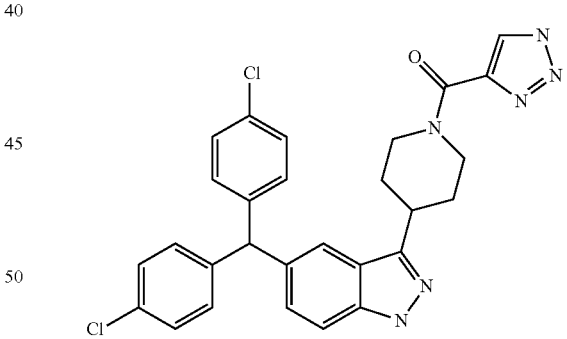

The title compound was prepared according to the procedure as described in Example PH-11 substituting 1H-1,2,3-triazole-4-carboxylic acide for 4-(methoxycarbonyl)benzoic acid, and substituting 5-(bis(4-chlorophenyl)methyl)-3-(piperidin-4-yl)-1H-indazole for 5-(bis(4-chlorophenyl)methyl)-1-cyclopropyl-3-(piperidin-4-yl)-1H-indazol in Step 1.

$^1$H NMR (400 MHz, MeOH) b=8.19 (br s, 1H), 7.47 (br. s, 1H), 7.43 (d, J=12.0 Hz, 1H) 2H), 7.29 (d, J=8.6 Hz, 4H), 7.16 (br. d, J=12.0 Hz, 1H), 7.10 (d, J=8.0 Hz, 4H), 5.71 (s, 1H), 4.74 (br t, J=14.8 Hz, 2H), 3.45-3.35 (m, 2H), 3.07 (br t, J=11.9 Hz, 1H), 2.13-1.88 (m, 4H). LCMS (ES, m/z): 531 [M+H]$^+$.

Example RZ-8

2-(5-(bis(4-chlorophenyl)methyl)-3-(4-((trifluoromethyl)sulfonyl)piperazin-1-yl)-1H-indazol-1-yl)ethanol

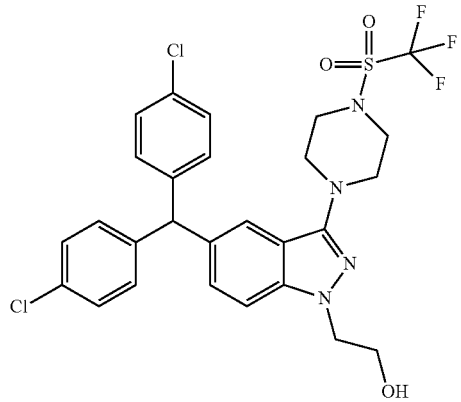 [SMILES: O=S(=O)(N1CCN(c2nn(CCO)c3ccc(C(c4ccc(Cl)cc4)c4ccc(Cl)cc4)cc23)CC1)C(F)(F)F]

Step 1: ethyl 2-(5-(bis(4-chlorophenyl)methyl)-3-(4-((trifluoromethyl)sulfonyl)piperazin-1-yl)-1H-indazol-1-yl)acetate A mixture of 5-(bis(4-chlorophenyl)methyl)-3-(4-((trifluoromethyl)sulfonyl)piperazin-1-yl)-1H-indazole (52.6 mg, 0.092 mmol), ethyl 2-bromocetate (13 µL, 0.11 mmol), and $Cs_2CO_3$ (143.4 mg, 0.44 mmol) in MeCN (2 mL) was stirred at room temperature for 1 h under argon, then $H_2O$ (15 mL) was added. The mixture was extracted with EtOAc (3×15 mL), and the combined extract was dried over $Na_2SO_4$ and concentrated. The residue was purified by flash chromatography, eluted with a gradient of 100% heptane to 100% EtOAc over 20 min, to yield ethyl 2-(5-(bis(4-chlorophenyl)methyl)-3-(4-((trifluoromethyl)sulfonyl)piperazin-1-yl)-1H-indazol-1-yl)acetate as a white solid. LC/MS (ES, m/z): 655 $[M+H]^+$.

Step 2: 2-(5-(bis(4-chlorophenyl)methyl)-3-(4-((trifluoromethyl)sulfonyl)piperazin-1-yl)-1H-indazol-1-yl)ethanol To a solution of ethyl 2-(5-(bis(4-chlorophenyl)methyl)-3-(4-((trifluoromethyl)sulfonyl)piperazin-1-yl)-1H-indazol-1-yl)acetate (63.6 mg, 0.096 mmol) in MeOH (2 mL), was added $NaBH_4$ (11.0 mg, 0.29 mmol), and the reaction was stirred at room temperature for 2 h. After quenched with saturated $NH_4Cl$ solution (10 mL), the reaction mixture was extracted with EtOAc (3×10 mL). The combined organic extract was dried over $Na_2SO_4$ and concentrated. The residue was purified by flash chromatography, eluted with a gradient of 100% heptane to 100% EtOAc, to yield 2-(5-(bis(4-chlorophenyl)methyl)-3-(4-((trifluoromethyl)sulfonyl)piperazin-1-yl)-1H-indazol-1-yl)ethanol as a white solid.
$^1$H NMR (400 MHz, CHLOROFORM-d) δ=7.31-7.22 (m, 6H), 7.11 (dd, J=1.5, 8.8 Hz, 1H), 7.02 (d, J=8.6 Hz, 4H), 5.58 (s, 1H), 4.33-4.25 (m, 2H), 4.10-4.01 (m, 2H), 3.67 (m, 4H), 3.43 (m, 3H), 2.94 (t, J=6.0 Hz, 1H). LC/MS (ES, m/z): 613 $[M+H]^+$.

Example RZ-9

2-(5-(bis(4-chlorophenyl)methyl)-3-(1-((trifluoromethyl)sulfonyl)piperidin-4-yl)-1H-indazol-1-yl)ethanol

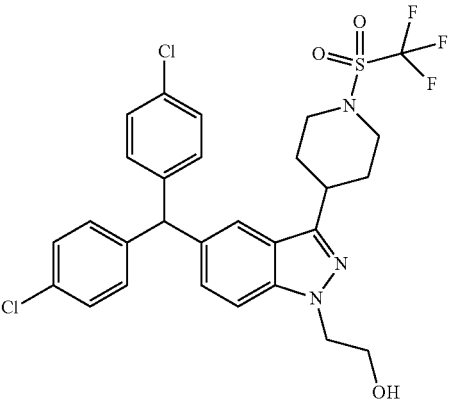 [SMILES: O=S(=O)(N1CCC(c2nn(CCO)c3ccc(C(c4ccc(Cl)cc4)c4ccc(Cl)cc4)cc23)CC1)C(F)(F)F]

The title compound was prepared according to the procedure as described in Example RZ-8 substituting 5-(bis(4-chlorophenyl)methyl)-3-(1-((trifluoromethyl)sulfonyl)piperidin-4-yl)-1H-indazole for 5-(bis(4-chlorophenyl)methyl)-3-(4-((trifluoromethyl)sulfonyl)piperazin-1-yl)-1H-indazole in Step 1.
$^1$H NMR (400 MHz, CHLOROFORM-d) δ=7.35-7.25 (m, 6H), 7.15 (dd, J=1.5, 8.8 Hz, 1H), 7.06-7.00 (m, 4H), 5.61 (s, 1H), 4.42-4.38 (m, 2H), 4.12-4.01 (m, 4H), 3.33-3.15 (m, 3H), 2.51 (br s, 1H), 2.13-1.98 (m, 4H). LC/MS (ES, m/z): 612 $[M+H]^+$.

Example RZ-10

4-((4-(5-(bis(4-chlorophenyl)methyl)-1-(2-hydroxyethyl)-1H-indazol-3-yl)piperidin-1-yl)sulfonyl)benzamide

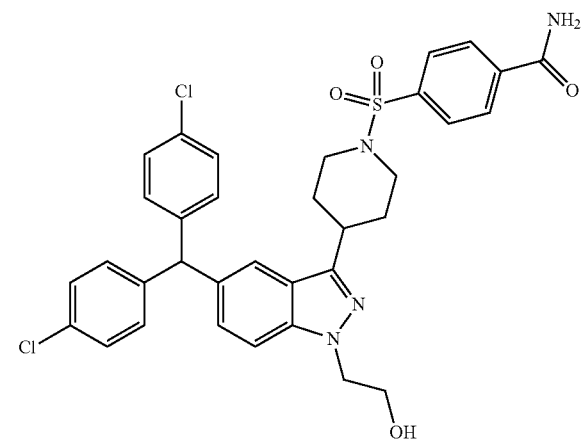 [SMILES: NC(=O)c1ccc(S(=O)(=O)N2CCC(c3nn(CCO)c4ccc(C(c5ccc(Cl)cc5)c5ccc(Cl)cc5)cc34)CC2)cc1]

Step 1: tert-butyl 4-(5-(bis(4-chlorophenyl)methyl)-1-(2-ethoxy-2-oxoethyl)-1H-indazol-3-yl)piperidine-1-carboxylate This intermediate was prepared according to the procedure as described in Example RZ-8 substituting tert-butyl 4-(5-(bis(4-chlorophenyl)methyl)-1H-indazol-3-yl)piperidine-1-carboxylate for 5-(bis(4-chlorophenyl)methyl)-3-(4-((trifluoromethyl)sulfonyl)piperazin-1-yl)-1H-indazole in Step 1.

Step 2: tert-butyl 4-(5-(bis(4-chlorophenyl)methyl)-1-(2-hydroxyethyl)-1H-indazol-3-yl)piperidine-1-carboxylate This intermediate was prepared according to the procedure as described in Example RZ-8 substituting tert-butyl 4-(5-(bis(4-chlorophenyl)methyl)-1-(2-ethoxy-2-oxoethyl)-1H-indazol-3-yl)piperidine-1-carboxylate for ethyl 2-(5-(bis(4-chlorophenyl)methyl)-3-(4-((trifluoromethyl)sulfonyl)piperazin-1-yl)-1H-indazol-1-yl)acetate in Step 2.

Step 3: tert-butyl 4-(1-(2-acetoxyethyl)-5-(bis(4-chlorophenyl)methyl)-1H-indazol-3-yl)piperidine-1-carboxylate A solution of tert-butyl 4-(5-(bis(4-chlorophenyl)methyl)-1-(2-hydroxyethyl)-1H-indazol-3-yl)piperidine-1-carboxylate (565.7 mg, 0.97 mmol) in DCM (6 mL) was cooled to OC, then acetyl chloride (84 uL, 1.17 mmol) and triethylamine (0.27 mL, 1.95 mmol) were added successively. The reaction mixture was allowed to warm to room temperature and stirred under argon for 1 h. After more DCM (10 mL) was added, the mixture was washed with saturated NaHCO3 (15 mL) and 1N HCl (15 mL) successively. The organic layer was dried over $Na_2SO_4$ and concentrated. The residue was purified by flash chromatography, eluted with a gradient of 100% heptane to 100% EtOAc, to yield tert-butyl 4-(1-(2-acetoxyethyl)-5-(bis(4-chlorophenyl)methyl)-1H-indazol-3-yl)piperidine-1-carboxylate as a white solid. LCMS (ES, m/z): 623 $[M+H]^+$.

Step 4: 2-(5-(bis(4-chlorophenyl)methyl)-3-(piperidin-4-yl)-1H-indazol-1-yl)ethyl acetate tert-Butyl 4-(1-(2-acetoxyethyl)-5-(bis(4-chlorophenyl)methyl)-1H-indazol-3-yl)piperidine-1-carboxylat (550.8 mg, 0.88 mmol) was treated with 1:1 DCM-TFA (8 mL). After stirred under argon at room temperature for 1 h, the reaction mixture was concentrated to yield 2-(5-(bis(4-chlorophenyl)methyl)-3-(piperidin-4-yl)-1H-indazol-1-yl)ethyl acetate. LCMS (ES, m/z): 522 $[M+H]^+$.

Step 5: 4-((4-(5-(bis(4-chlorophenyl)methyl)-1-(2-hydroxyethyl)-1H-indazol-3-yl)piperidin-1-yl)sulfonyl)benzamide A solution of 2-(5-(bis(4-chlorophenyl)methyl)-3-(piperidin-4-yl)-1H-indazol-1-yl)ethyl acetate (22.6 mg, 0.043 mmol) in DCM (2 mL) was cooled to 0° C., then 4-carbamoylbenzene-1-sulfonyl chloride (11.4 mg, 0.052 mmol) and triethylamine (9.0 μL, 0.065 mmol) were added successively. The reaction mixture was allowed to warm to room temperature and stirred for 1 h, and then concentrated. The residue was dissolved in THF (1 mL) and MeOH (0.5 mL), 3N solution of NaOH (58 μL, 0.17 mmol) was added. After stirred for 30 min, the reaction mixture was acidified with 1N HCl solution to pH 3-4, and then concentrated under reduced pressure to remove organic solvents. The residue was purified by C18 HPLC as described in Step 3 to yield 4-((4-(5-(bis(4-chlorophenyl)methyl)-1-(2-hydroxyethyl)-1H-indazol-3-yl)piperidin-1-yl)sulfonyl)benzamide as a white solid after lyophilization.

$^1$H NMR (400 MHz, CHLOROFORM-d) δ=7.99-7.89 (m, 4H), 7.30-7.23 (m, 6H), 7.13 (br.d, J=12.0 Hz, 1H), 7.03-6.97 (m, 4H), 6.71 (br.s, 1H), 6.53 (br.s, 1H), 5.57 (s, 1H), 4.40-4.31 (m, 2H), 4.10-3.95 (m, 2H), 3.90-3.82 (m, 2H), 3.00 (m, 1H), 2.80-2.68 (m, 2H), 2.09-1.87 (m, 4H). LC/MS (ES, m/z): 663 $[M+H]^+$.

Example RZ-11

4-(4-(5-(bis(4-chlorophenyl)methyl)-1-(2-hydroxyethyl)-1H-indazol-3-yl)piperidine-1-carbonyl)benzenesulfonamide

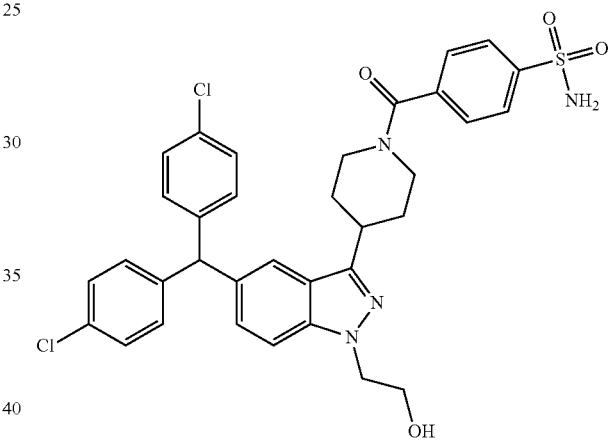

A solution of 4-sulfamoylbenzoic acid (9.8 mg, 0.049 mmol), HATU (20.3 mg, 0.053 and diisopropylethylamine (16 μL, 0.089 mmol) in DMF was stirred at room temperature for 5 min, then 2-(5-(bis(4-chlorophenyl)methyl)-3-(piperidin-4-yl)-1H-indazol-1-yl)ethyl acetate (28.3 mg, 0.044 mmol) was added. The reaction mixture was stirred under argon for 5 h, and then concentrated under vacuum. The residue was dissolved in THF (1 mL) and MeOH (1 mL), 3N solution of NaOH (0.10 mL, 0.30 mmol) was added. After stirred for 30 min, the reaction mixture was acidified with 1N HCl solution to pH 3-4, and then concentrated under reduced pressure to remove organic solvents. The residue was purified by C18 HPLC as described in Step 3 to yield 4-(4-(5-(bis(4-chlorophenyl)methyl)-1-(2-hydroxyethyl)-1H-indazol-3-yl)piperidine-1-carbonyl)benzenesulfonamide as a white solid after lyophilization.

$^1$H NMR (400 MHz, CHLOROFORM-d) δ=7.98 (d, J=7.8 Hz, 2H), 7.55 (d, J=7.8 Hz, 2H), 7.34 (m, 2H), 7.30-7.25 (m, 5H), 7.16 (br.d, J=8.8 Hz, 1H), 7.03 (br.d, J=7.6 Hz, 4H), 5.62 (s, 1H), 5.05 (br.s, 2H), 4.77 (br.d, J=13.2 Hz, 1H), 4.42 (m, 2H), 4.10 (m, 2H), 3.75 (br.d, J=12.5 Hz, 1H), 3.35-3.19 m, 2H), 3.07 (m, 1H), 2.15 (m, 1H), 2.07-1.84 (m, 3H). LC/MS (ES, m/z): 663 $[M+H]^+$.

Example RZ-12

1-(5-(bis(4-chlorophenyl)methyl)-3-(4-((trifluoromethyl)sulfonyl)piperazin-1-yl)-1H-indazol-1-yl)ethanone

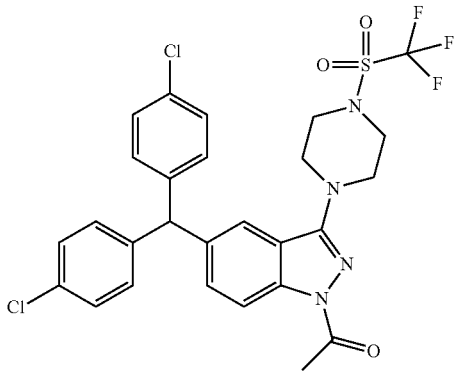 [SMILES: CC(=O)n1nc(N2CCN(S(=O)(=O)C(F)(F)F)CC2)c2cc(C(c3ccc(Cl)cc3)c3ccc(Cl)cc3)ccc21]

Into a solution of 5-(bis(4-chlorophenyl)methyl)-3-(4-((trifluoromethyl)sulfonyl)piperazin-1-yl)-1H-indazole (36.2 mg, 0.064 mmol) in DCM (2 mL), were added acetyl chloride (7.0 µL, 0.096 mmol), diisopropylethylamine (21.9 µL, 0.13 mmol) and DMAP (0.8 mg, 0.006 mmol). The reaction mixture was stirred overnight under argon at room temperature, and then concentrated. The residue was purified by flash chromatography eluted with a gradient of 100% heptane to 100% EtOAc over 20 min to yield 1-(5-(bis(4-chlorophenyl)methyl)-3-(4-((trifluoromethyl)sulfonyl)piperazin-1-yl)-1H-indazol-1-yl)ethanone as a white solid.

$^1$H NMR (400 MHz, CHLOROFORM-d) δ=8.39 (d, J=8.3 Hz, 1H), 7.32-7.23 (m, 7H), 7.00 (br. d, J=8.3 Hz, 4H), 5.62 (s, 1H), 3.68 (m, 4H), 3.56 (m, 4H), 2.65 (s, 3H). LC/MS (ES, m/z): 611 [M+H]$^+$.

BIOLOGICAL EXAMPLES $CB_1$ and $CB_2$ receptors are $G_i$-coupled GPCR. Activation of $CB_1$ and $CB_2$ receptors results in a decrease in cAMP production. An inverse agonist of the $CB_1$ or $CB_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+TBP-NHS Cryptate (supplied as part of the assay kit). The specific signal (i.e. energy transfer) is inversely proportional to the concentration of cAMP in the standard or sample.

Biological Example 1

CB-1 and CB-2 In Vitro Assay

Preparation of Cells

Human $CB_1R$ (Cannabanoid receptor 1) was stably transfected in HEK-293 cells (DiscoveRx, cat: 93-0200C1). Human $CB_2R$ (Cannabanoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/ml Hygromycin B (Invitrogen Cat#10687-010), 600 µg/mL G418 (Invitrogen Cat#10131-035), and 1× Penn/Strep (Invitrogen 15140-122). After cell expansion, aliquots were cryo-stored in media containing 5% DMSO (Pierce Cat#20684).

Plating Cells from Cryostore

One day prior to experiments media was warmed to 37° C. and the cryo-stored cells were thawed in a 37° C. water bath. The cells were then added to media (10× volume) and the mixture was centrifugated at 1000 RPM for 5 min. The supernate was removed and the cells were re-suspended in media. A sample of the cell suspension was evaluated on a Cedex XS automated cell counter (Innovatis Systems) to determine viable cells/ml. Additional media was added to the cells to achieve a final cell density of 4E5 cells/mL. The cells were then plated into 384 well PDL white solid bottom plates (Greiner, Cat#781945) at 20 µL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% $CO_2$, 95% humidity) overnight.

Preparation of Compound Plates

DMSO was added to all wells of 384 well V bottom polystyrene plate (Greiner, Cat#781280) except to columns 1 and 13, rows O and P and wells M13-M23 and N13-N23. Test compounds (60 µL, 10 mM) were added to Column 1 and 13 (A1 through N1 and A13 through L13). Test compounds were serially diluted 1/3 by transferring and mixing 20 µl sample with 40 µL DMSO. This process resulted in a plate of 26 compounds, 11 doses per compound, 10 mM to 0.5 µM.

Preparation of Control Plate

DMSO (40 µL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 µL, 10 mM) was added to O1; and 1-(2,4-dichlorophenyl)-7-[(4-fluorophenyl)methylene]-4,5,6,7-tetrahydro-N-1-piperidinyl-1H-indazole-3-carboxamide (60 µL, 10 mM) was added to N13. The control was serially diluted 1/3 by transferring and mixing 20 µl sample with 40 µL DMSO. This process resulted 11 doses per control, 10 mM to 0.5 µM.

cAMP Assay Protocol

Cells plated the day prior to the assay in clear bottom plates were viewed on an inverse microscope to ensure confluency in the range of 60-75%.

The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma 15879) in Buffer 1; (c) 1 µM cAMP Standard (50 µM stock, Perkin Elmer Cat#AD0262) diluted in Buffer 2 and serially diluted in Buffer 2, 12 doses @ ½ dilutions resulting in a dose range of 1 µM to 0.5 nM; (d) d2 labelled cAMP (CisBio HTRF Detection Kit Cat #62AM4PEB reconstituted with 6 ml dH$_2$0) diluted 1/20 with lysis buffer (CisBio HTRF Detection Kit Cat #62AM4PEB); (e) anti-cAMP (CisBio HTRF Detection Kit Cat #62AM4PEB reconstituted with 5 ml dH$_2$0) diluted 1/20 with lysis buffer (CisBio HTRF Detection Kit Cat #62AM4PEB); and (f) Forskolin (Sigma Cat#F6886, 10 mM in DMSO) diluted first in DMSO to 1 mM and then to 1.5 µM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 µl per well). Media as "dumped" from the cell plate and 30 µL Buffer 1 was added to each well using a Multidrop. The content of the cell plate was again "dumped" and 10 µL Buffer 2 was added to each well using a Flexdrop. 12.5 nL test compound dilutions or control compound dilutions (10 mM to 0.5 µM) were added to the cell plate using an ECHO 555 (Labcyte). The cell plate was mixed (Speed 6, Lab-Line Instruments Titer Plate Shaker) and centrifuged (1000 RPMs, 1 min). Using the Flexdrop, 2 µl additions were made into the cell plate: Buffer 2 was added to Column 24; and, 1.5 µM Forskolin was added to columns 1 through 23. Final volume of the cell plate was 12 µl with 250 nM Forskolin in all wells except column 12, and serial dilutions of test compound or control ranging from 10 µM to 0.5 nM. The cell plate was again mixed (speed 6) and centrifuged (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 µL d2 labelled cAMP and 6 µL of Anti-cAMP were added to all wells of the cell plate using a BioMek FX (Beckman Coulter). The cell plate was again mixed (speed 6) and centrifuged (1000 RPMs, 1 min) and was incubated for 60 minutes in the dark at room Temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence×10,000 (Normalized signal (NS)). Amount of cAMP in nM was calculated for each well (based on NS) from a cAMP standard curve located on each plate (at P1-12 and P13-24). $EC_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of formula (I) of the present invention were tested for activity against the CB-1 and CB-2 receptors, according to assay protocol as outlined in Biological Example 1, with $EC_{50}$ results (in micromolar) as listed in Tables 3, below. Where a compound was tested more than once, the result presented below represents a mean of the individual measurements.

TABLE 3

Biological Activity Against CB-1 and CB-2 Receptors

| ID No. | CB-1 (HEK_cAMP) $EC_{50}$ (µM) | CB-2 (HEK_cAMP) $EC_{50}$ (µM) |
|---|---|---|
| 17 | 0.006 | >10 |
| 19 | 0.084 | >10 |
| 20 | 0.165 | >10 |
| 21 | 0.170 | >10 |
| 22 | 0.249 | >10 |
| 23 | 2.149 | >10 |
| 24 | 0.151 | >10 |
| 25 | 1.233 | >10 |
| 26 | 0.005 | >10 |
| 27 | 0.410 | >10 |
| 28 | 0.134 | >10 |
| 29 | 1.488 | >10 |
| 30 | >10 | >10 |
| 31 | 0.128 | 2.34 |
| 32 | 0.071 | >10 |
| 33 | 0.049 | >10 |
| 34 | 6.033 | 7.50 |
| 35 | 0.005 | >10 |
| 37 | 0.008 | >10 |
| 38 | 0.012 | >10 |
| 39 | 0.144 | >10 |
| 40 | 0.297 | 10.20 |
| 41 | 1.653 | >10 |
| 42 | 0.006 | >10 |
| 43 | 0.169 | >10 |
| 44 | 0.014 | >10 |
| 45 | 0.941 | >10 |
| 46 | 0.040 | >10 |
| 47 | 0.041 | >10 |
| 48 | 0.031 | >10 |
| 49 | 0.018 | >10 |
| 50 | 0.059 | >10 |
| 51 | 0.152 | >10 |
| 52 | 0.499 | >10 |
| 53 | 0.049 | >10 |
| 54 | 0.027 | >10 |
| 55 | 0.649 | >10 |
| 56 | 0.072 | >10 |
| 57 | 0.474 | >10 |
| 58 | 0.013 | >10 |
| 59 | 0.374 | >10 |
| 60 | 0.065 | >10 |
| 61 | 0.191 | >10 |
| 62 | 0.845 | >10 |
| 63 | 0.066 | >10 |
| 64 | 0.024 | >10 |
| 65 | 0.025 | >10 |
| 66 | 0.160 | >10 |
| 67 | 0.002 | 5.20 |
| 68 | 0.085 | >10 |
| 69 | 0.026 | >10 |
| 70 | 0.428 | >10 |
| 71 | 0.068 | >10 |
| 72 | 0.039 | >10 |
| 73 | 0.762 | >10 |
| 74 | 0.162 | >10 |
| 75 | 3.925 | >10 |
| 76 | 0.112 | >10 |
| 77 | 0.060 | >10 |
| 78 | 0.179 | >10 |
| 79 | 0.014 | >10 |
| 80 | 0.374 | >10 |
| 81 | 7.320 | >10 |
| 82 | 0.082 | >10 |
| 83 | 1.569 | >10 |
| 86 | >10 | >10 |
| 87 | 6.745 | >10 |
| 88 | 0.115 | >10 |
| 89 | 0.339 | >10 |
| 90 | 0.716 | 3.10 |
| 91 | 0.039 | >10 |
| 92 | 0.029 | >10 |
| 93 | 0.533 | >10 |
| 94 | 0.065 | >10 |
| 95 | 0.063 | 6.50 |
| 96 | 2.245 | >10 |
| 97 | 0.478 | >10 |
| 98 | 0.064 | >10 |
| 99 | 0.345 | >10 |
| 100 | 0.428 | >10 |
| 101 | 0.293 | >10 |
| 102 | 0.477 | >10 |
| 103 | 6.006 | >10 |
| 104 | 0.007 | >10 |

TABLE 3-continued

Biological Activity Against CB-1 and CB-2 Receptors

| ID No. | CB-1 (HEK_cAMP) EC$_{50}$ (μM) | CB-2 (HEK_cAMP) EC$_{50}$ (μM) |
|---|---|---|
| 105 | 0.008 | >10 |
| 106 | 9.200 | >10 |
| 107 | 0.920 | >10 |
| 108 | 0.037 | >10 |
| 109 | 0.729 | >10 |
| 110 | 0.134 | >10 |
| 111 | 3.499 | >10 |
| 112 | 0.062 | >10 |
| 113 | 4.242 | >10 |
| 114 | 0.283 | 9.90 |
| 115 | 1.014 | >10 |
| 116 | 0.005 | 7.99 |
| 117 | 0.009 | 1.55 |
| 118 | 0.004 | >10 |
| 119 | 0.144 | >10 |
| 120 | 0.050 | >10 |
| 121 | 0.375 | >10 |
| 122 | 0.099 | >10 |
| 123 | 5.800 | >10 |
| 124 | 0.236 | >10 |
| 125 | 0.135 | >10 |
| 126 | 0.617 | >10 |
| 127 | 4.756 | >10 |
| 128 | 1.225 | >10 |
| 129 | 0.203 | >10 |
| 130 | 0.015 | >10 |
| 131 | 9.499 | >10 |
| 132 | 0.166 | >10 |
| 133 | 3.911 | >10 |
| 134 | 0.216 | >10 |
| 135 | 0.166 | >10 |
| 136 | 0.011 | >10 |
| 137 | 0.158 | >10 |
| 138 | 0.587 | >10 |
| 139 | 0.202 | >10 |
| 140 | 0.011 | >10 |
| 141 | 6.115 | >10 |
| 143 | 1.006 | >10 |
| 144 | 5.484 | >10 |
| 145 | 0.049 | >10 |
| 146 | 0.007 | >10 |
| 147 | 0.023 | >10 |
| 149 | 0.007 | >10 |
| 150 | 0.007 | >10 |
| 151 | 0.006 | >10 |
| 152 | 0.017 | >10 |
| 153 | 0.017 | >10 |
| 154 | 0.004 | >10 |
| 155 | 0.006 | >10 |
| 156 | 0.001 | >10 |
| 157 | 0.002 | 4.03 |
| 158 | 0.003 | >10 |
| 159 | 0.003 | >10 |
| 160 | 0.005 | 4.40 |
| 161 | 0.004 | 0.95 |
| 162 | 0.004 | 5.20 |
| 163 | 0.012 | >10 |
| 164 | 0.026 | >10 |
| 165 | 0.013 | >10 |
| 166 | 0.002 | 2.39 |
| 167 | 0.012 | >10 |
| 168 | 0.002 | 7.04 |
| 169 | 0.017 | >10 |
| 170 | 0.009 | >10 |
| 171 | 0.003 | >10 |
| 172 | 0.003 | >10 |
| 173 | 0.007 | 5.78 |
| 175 | 1.134 | >10 |
| 176 | 0.005 | >10 |
| 178 | 0.324 | >10 |
| 179 | 0.093 | >10 |
| 180 | 6.548 | >10 |
| 181 | 7.800 | >10 |
| 182 | 0.271 | >10 |
| 183 | 0.077 | >10 |
| 184 | 0.026 | >10 |
| 185 | 0.833 | >10 |
| 186 | 0.059 | >10 |
| 187 | 3.042 | >10 |
| 189 | 0.023 | >10 |
| 190 | 1.084 | >10 |
| 191 | 5.292 | >10 |
| 192 | 7.075 | >10 |
| 193 | 0.474 | 9.30 |
| 194 | 0.048 | >10 |
| 195 | 0.032 | 6.99 |
| 196 | 4.183 | >10 |
| 197 | 0.032 | 7.10 |
| 198 | 0.150 | >10 |
| 199 | 0.158 | >10 |
| 200 | 0.624 | >10 |
| 201 | 2.640 | >10 |
| 202 | 0.169 | >10 |
| 203 | 0.053 | >10 |
| 204 | 0.019 | >10 |
| 205 | 0.006 | 2.12 |
| 206 | 0.008 | >10 |
| 207 | 0.009 | 9.70 |
| 208 | 0.068 | >10 |
| 209 | 0.068 | >10 |
| 210 | 0.134 | >10 |
| 211 | 4.686 | >10 |
| 212 | 1.833 | >10 |
| 213 | 0.367 | >10 |
| 214 | 3.240 | >10 |
| 215 | 2.957 | >10 |
| 216 | 1.280 | >10 |
| 217 | 1.033 | 4.10 |
| 218 | 0.265 | >10 |
| 219 | 1.543 | >10 |
| 220 | 0.027 | >10 |
| 221 | 0.134 | >42 |
| 222 | 0.163 | >10 |
| 223 | 0.699 | >10 |
| 224 | 2.078 | >10 |
| 225 | 0.056 | 3.30 |
| 226 | 0.008 | 5.50 |
| 227 | 0.084 | >10 |
| 228 | 0.020 | >10 |
| 229 | 0.037 | >10 |
| 230 | 3.262 | >10 |
| 231 | 4.200 | >10 |
| 232 | 0.026 | >10 |
| 233 | 3.550 | >10 |
| 234 | 0.016 | >10 |
| 235 | 0.022 | >10 |
| 236 | 0.068 | >10 |
| 237 | 0.005 | >10 |
| 238 | 0.198 | >10 |
| 239 | 0.043 | >10 |
| 240 | >10 | >10 |
| 241 | 1.631 | >10 |
| 242 | 0.016 | >10 |
| 243 | 0.285 | >10 |
| 244 | 0.048 | >10 |
| 245 | 0.020 | >10 |
| 246 | 0.029 | >10 |
| 247 | 0.020 | >10 |
| 248 | 0.041 | >10 |
| 249 | 0.015 | >10 |
| 250 | 0.043 | >10 |
| 251 | 0.014 | >10 |
| 252 | 0.077 | >10 |
| 253 | 0.011 | 6.93 |
| 254 | 0.016 | >10 |
| 255 | 0.034 | >10 |
| 256 | 0.030 | >10 |
| 257 | 0.013 | >5 |
| 258 | 0.428 | >42 |
| 259 | 0.374 | >42 |

TABLE 3-continued

Biological Activity Against CB-1 and CB-2 Receptors

| ID No. | CB-1 (HEK_cAMP) $EC_{50}$ (μM) | CB-2 (HEK_cAMP) $EC_{50}$ (μM) |
|---|---|---|
| 260 | 0.025 | >42 |
| 261 | 0.271 | 6.82 |
| 262 | 0.672 | >10 |
| 263 | 0.234 | 2.33 |
| 264 | 0.199 | 4.27 |
| 265 | 0.208 | >10 |
| 267 | 0.079 | >2 |
| 268 | 0.032 | 12.37 |
| 269 | 0.590 | >10 |
| 270 | 9.601 | >10 |
| 271 | 0.040 | >10 |
| 272 | 0.333 | >10 |
| 273 | 6.800 | >10 |
| 275 | 0.024 | >10 |
| 276 | 0.698 | >42 |
| 277 | 1.549 | 7.00 |
| 278 | | |
| 279 | 0.785 | >42 |
| 280 | 0.565 | >42 |

Biological Example 2A

CB-1 Receptor Binding Assay

Into Greiner V bottom polypropylene plates, hCB1-CHO-K1 membranes (2 μg/well final concentration) in assay buffer (50 mM Tris-HCl pH 7.4, 5 mM $MgCl_2$ and 0.5 mg/ml (0.05%) Ultra fatty acid free BSA) were dispensed. Membranes were purchased from Perkin Elmer. Test compounds were then added to each well and then [$^3$H] CP 55, 940 (0.4 nM final well concentration) in assay buffer (50 mM Tris-HCl pH 7.4, 5 mM $MgCl_2$ and 0.5 mg/ml (0.05%) Ultra fatty acid free BSA) was added. Samples were mixed and incubated for 90 min at 30° C. in the Greiner V Bottom Polypropylene plate. After incubation, assay reagents were transferred to a blocked 384 well polypropylene filter plates. The binding reaction was stopped by filtration and washed seven times with ice cold rinse buffer. Filter plates were then dried overnight at room temperature. The next day, plate bottoms were sealed with plate tape and 15 μl MicroScint is added to each well. Plates were incubated for 2 h and radioactivity is measured by Topcount.

Total Binding:

Total Binding levels were achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):

Non-Specific Binding (NSB) levels were achieved by combining membrane, 10 μM final concentration WIN-55, 212 (also known as (R)-(+)-[2,3-dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H]CP-55,940 (also known as 5-(1,1-dimethylheptyl)-2-[(1R,2R,5R)-5-hydroxy-2-(3-hydroxypropyl)cyclohexyl]-phenol).

Data Analysis:

Top Count raw data files were used for data analysis as follows: Non-specific binding (NSB=10 μM WIN-55,212+ Membrane+[$^3$H] CP-55,940) was used as the negative control, while the Total Binding (TB=DMSO+Membrane+[$^3$H] CP-55,940) was used as the positive control. Excel data file reports were generated by the PE TopCount and imported into Excel for calculations or were imported into a macro driven Excel template.

$IC_{50}$ data was calculated using raw CPM values. Curves are fitted individually from singlet 11 point dosing curves+ 1% DMSO Control. $IC_{50}$ values re fit appropriately and calculated using the following equation:

$$v = V_{min} + \frac{V_0 - V_{min}}{1 + ([I]/IC_{50})^h}$$

$V_{min}$, CPM at maximum inhibition; $V_o$, CPM at zero inhibition; $IC_{50}$, inhibitor concentration at 50% inhibition; h, Hill coefficient.

Maximal compound % inhibition of control treated wells was also noted since some compounds may exhibit values suitable for calculating $IC_{50}$'s.

% Inhibition of Total Binding=(1−(CPM Compound Treated Well/CPM Control Treated Well))*100

Compound #18 was tested according to the procedure as described in Biological Example 2A above and measured to exhibit an $IC_{50}$ binding of 0.07 μM.

Biological Example 2B

CB-2 Receptor Binding Assay

Prophetic Example

Into Greiner V bottom polypropylene plates, hCB2-HEK293 membranes (2 μg/well final concentration) in assay buffer (50 mM Tris-HCl pH 7.4, 5 mM $MgCl_2$ and 0.5 mg/ml (0.05%) Ultra fatty acid free BSA) are dispensed. Membranes are prepared as described in FELDER, C. C., et al., Molecular Pharmacology, 1992, pp 838-845, Vol. 42. Test compounds are then added to each well and then [$^3$H] CP 55, 940 (0.5 nM final well concentration) in assay buffer (50 mM Tris-HCl pH 7.4, 5 mM $MgCl_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed nine times with ice cold rinse buffer. Filter plates are then dried overnight at room temperature. The next day, plate bottoms are sealed with plate tape and 15 μl MicroScint 20 is added to each well. Plates are incubated for 2 h and radioactivity is measured by Topcount.

Total Binding:

Total Binding levels are achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):

Non-Specific Binding (NSB) levels are achieved by combining membrane, 10 μM final concentration WIN-55,212 (also known as (R)-(+)-[2,3-dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H]CP-55,940 (also known as 5-(1,1-dimethylheptyl)-2-[(1R,2R,5R)-5-hydroxy-2-(3-hydroxypropyl)cyclohexyl]-phenol).

Data Analysis:

Top Count raw data files are used for data analysis as follows: Non-specific binding (NSB=10 μM WIN-55,212+

Membrane+[³H] CP-55,940) is used as the negative control, while the Total Binding (TB=DMSO+Membrane+[³H] CP-55,940) is used as the positive control. Excel data file reports are generated by the PE TopCount and imported into Excel for calculations or were imported into a macro driven Excel template.

IC$_{50}$ data is calculated using raw CPM values. Curves are fitted individually from singlet 11 point dosing curves+1% DMSO Control. IC$_{50}$ values re fit appropriately and calculated using the following equation:

$$v = V_{min} + \frac{V_0 - V_{min}}{1 + ([I]/IC_{50})^h}$$

$V_{min}$, CPM at maximum inhibition; $V_o$, CPM at zero inhibition; IC$_{50}$, inhibitor concentration at 50% inhibition; h, Hill coefficient.

Maximal compound % inhibition of control treated wells is also noted since some compounds may exhibit values suitable for calculating IC$_{50}$'s.

% Inhibition of Total Binding=(1−(CPM Compound Treated Well/CPM Control Treated Well))*100

In Vivo Biological Assays

General Information: Animals, Diets and Test Compound:

Male 14-20-week old diet-induced obese mice are ordered from Taconic. Mice were started on a 60% fat diet (D12492, Research Diets, New Brunswick, N.J.) at 6 weeks of age.

Mice are single-housed. Male Sprague Dawley rats are ordered from Charles River (225-250 gm upon arrival). They are fed standard chow diet (Purina 5001) and housed 2 per cage.

Male C57bl/6j mice were ordered from Charles River at 22-25 g and housed 3 per cage. They were fed standard chow (Purina 5001).

All animals were/are housed in a temperature-controlled room with 12-hour light/dark cycle. Animals were/are given food and water ad libitum, except as noted.

Test compounds were/are formulated in 10% PEG400 and 10% solutol. Test compounds are administered by oral gavage (5 ml kg$^{-1}$).

Biological Example 3

Mouse Fast PK/BBB

Male C57bl/6j mice were dosed with test compounds at 20 mg/kg or 30 mg/kg. Plasma was collected via retro-orbital bleeding at 1 hr and 4 hrs after dosing. Whole brain without cerebellum was collected at 4 hrs after dosing. Wet brain weight was recorded before freezing. Brains were homogenized in saline and sent for analysis for determination of concentration of test compound.

Representative compounds of the present invention were tested according to the procedure as described above, with results as listed in Table 4, below.

TABLE 4

Mouse Fast PK/BBB Results

| ID No. | Dose (mg/kg) | Time | PLASMA Mean Conc. (ng/mL) ± Std. Dev (ng/mL) | BRAIN Mean Conc. (ng/mL) ± Std. Dev (ng/mL) |
|---|---|---|---|---|
| 17 | 20 | 1 hr | 4478.2 ± 1576.9 | 51.8 ± 16.6 |
|  |  | 4 hr | 3444.4 ± 1058.9 | 103.2 ± 10.8 |
| 35 | 20 | 1 hr | 3613 ± 253 | BLOQ ± NA |
|  |  | 4 hr | 611 ± 125 | BLOQ ± NA |
| 151 | 30 | 1 hr | 2738 ± 160 | 41.8 ± 15.7 |
|  |  | 4 hr | 884 ± 584 | 31.4 ± 13.4 |
| 157 | 30 | 1 hr | 241 ± 117 | BLOQ ± NA |
|  |  | 4 hr | 13.0 ± 1.7 | BLOQ ± NA |
| 169 | 30 | 1 hr | 2461 ± 427 | 29.4 ± 3.9 |
|  |  | 4 hr | 2311 ± 554 | 54.8 ± 14.5 |
| 206 | 30 | 1 hr | 333.5 ± 70.5 | 21.5 ± NA |
|  |  | 4 hr | 532.8 ± 58.9 | 30.6 ± 6.5 |
| 207 | 30 | 1 hr | 7373 ± 867 | 516 ± 44.2 |
|  |  | 4 hr | 4317 ± 856 | 1180 ± 115 |
| 232 | 30 | 1 hr | 1763 ± 474 | BLOQ ± NA |
|  |  | 4 hr | 196 ± 88.0 | BLOQ ± NA |
| 234 | 30 | 1 hr | 8693 ± 499 | 11.2 ± 3.95 |
|  |  | 4 hr | 979 ± 376 | 8.31 ± 2.31 |

BLOQ = below level of quantitation,
NA = Not applicable

Biological Example 4

5-Day Sub-Chronic DIO Mouse Assay

Test compound was formulated in 10% PEG400 and 10% solutol. DIO mice (n=9) received vehicle or test compound daily for four days at 4 PM. Body weight and food weight were monitored daily at this time. On day 5, fed blood glucose, body weight, and food weight were measured at 9 AM and the mice were dosed at this time. Two hours later, mice were bled via the retro-orbital sinus under 70% CO$_2$/30% O$_2$ anesthesia. Plasma was used to determine insulin levels and compound concentration.

Three mice from each treatment group were anesthetized IP with 0.1 ml of a 4/1 mixture of Ketaset:AnaSed. (Prepared 10 ml Ketaset (100 mg/ml Ketamine)+2.5 ml AnaSed (20 mg/ml Xylazine) and then perfused with 60 ml heparinized saline through the left ventricle of the heart. The brains were removed and homogenized in PBS (4 ml/gm tissue). The samples were submitted for determination of plasma and brain compound levels.

Compound #17 was tested according to the procedure as described above, with results as listed in 5A through 5E, below.

TABLE 5A

Mean Daily Food Intake (in Grams (Std Err))

|  | Vehicle | 30 mg/kg |
|---|---|---|
| Day 1 | 2.4 (0.2) | 0.8 (0.3) |
| Day 2 | 3.1 (0.1) | 0.3 (0.1) |
| Day 3 | 3.0 (0.1) | 0.5 (0.1) |
| Day 4 | 2.6 (0.1) | 0.8 (0.1) |

TABLE 5B

Mean Body Weight (in Grams (Std Err))

|  | Vehicle | 30 mg/kg |
|---|---|---|
| Day 0 | 42.5 (0.9) | 42.3 (1.0) |
| Day 1 | 42.7 (1.0) | 40.2 (1.1) |

TABLE 5B-continued

Mean Body Weight (in Grams (Std Err))

|       | Vehicle    | 30 mg/kg   |
|-------|------------|------------|
| Day 2 | 42.7 (1.0) | 38.3 (1.0) |
| Day 3 | 42.9 (0.9) | 37.2 (1.1) |
| Day 4 | 42.7 (0.9) | 36.3 (1.0) |

TABLE 5C

Plasma Insulin (in ng/mL (Std Err))

|          | Plasma Insulin |
|----------|----------------|
| Vehicle  | 3.78 (0.95)    |
| 30 mg/kg | 1.24 (0.28)    |

TABLE 5D

Fed Blood Glucose (in mg/dL (Std Err))

|          | Day 0    | Day 4    |
|----------|----------|----------|
| Vehicle  | 179 (10) | 179 (6)  |
| 30 mg/kg | 174 (9)  | 150 (7)  |

TABLE 5E

Plasma and Brain Concentrations, 2 Hours Post Dose, Day 5

|          | Plasma ng/mL (Std Dev) | Brain ng/g (Std Dev) |
|----------|------------------------|----------------------|
| 30 mg/kg | 16237 (2427)           | 304 (28.6)           |

Biological Example 5

Chronic DIO Mouse

Prophetic Example

The test compound is formulated in 10% PEG400 and 10% solutol. DIO mice receive vehicle, test compound (@ 1, 3 and 10 mg/kg) daily for 26 days. At the end of the experiment, the mice are euthanized and blood and tissues are collected.

Body weight and food weight (food intake) are monitored daily for days 1-5 and twice weekly thereafter. Fed blood glucose is measured weekly. An insulin tolerance test (0.5 U/kg Humulin, ip) is performed on day 19 after a 4 hour food removal. Blood glucose is measured at 0, 15, 30, 60 and 120 minutes after insulin. After an overnight fast, an oral glucose tolerance test (2 g/kg glucose) is performed on day 23. Blood glucose is measured at 0, 30, 60 and 120 minutes after glucose challenge. Blood glucose is measured from the tail vein with a Lifescan glucometer. Plasma insulin is measured with an ELISA or HTRF kit (Cisbio). Plasma parameters are measured with an Olympus clinical chemistry analyzer.

Biological Example 6

Open Field Locomotor Activity in Rats (CNS Activity)

Prophetic Example

Male SD rats are weighed and transferred to the Activity Chambers with access to water. After a 2-hr acclimation period, the rats are dosed with vehicle or test compound (@ 3 and 10 mg/kg). The Activity Chamber monitoring software program is initiated and automatically records rat activity in each chamber for a period of 4 hours. At the end of the 4 hour monitoring period, the software is stopped and the rats are removed from the activity chambers. The rats are anesthetized and blood samples are obtained via retro-orbital puncture to determine plasma concentration of compounds. The rats are immediately euthanized with $CO_2$ and the brains are removed, washed with PBS, frozen on dry ice and stored at −80° C. for receptor occupancy (RO) analysis.

Satellite groups of 3 rats are dosed with test compound at 3 mg/kg and 10 mg/kg respectively. Four hours later, the rats are anesthetized. Blood is collected from these rats and then perfused with 400 ml heparinized saline through the left ventricle of the heart. The brains are removed and homogenized in PBS (4 ml/gm tissue). The samples are submitted for determination of plasma and brain compound levels.

Formulation Example 1

Solid, Oral Dosage Form

Prophetic Example

As a specific embodiment of an oral composition, 100 mg of the Compound #17 prepared as described in Example PH-1 above, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

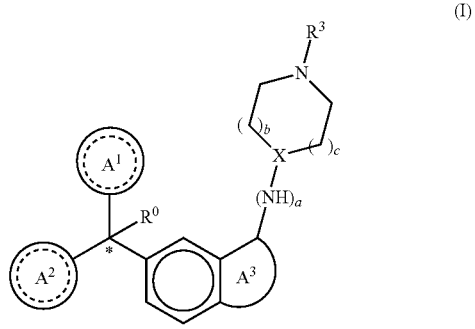

wherein
$R^0$ is selected from the group consisting of hydrogen and hydroxy;

is selected from the group consisting of cyclopropyl, cyclobutyl, cyclopentyl, cyclohexyl, phenyl, furyl, thienyl, pyridyl, thiazolyl, benzothiazolyl and benzo[d][1,3]dioxolyl;

wherein the phenyl, furyl, thienyl, pyridyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl, —C(O)NR$^A$R$^B$ and NR$^A$R$^B$; wherein R$^A$ and R$^B$ are each independently selected from the group consisting of hydrogen, $C_{1-2}$alkyl, hydroxy substituted $C_{1-2}$alkyl and carboxy substituted $C_{1-2}$alkyl; provided that each substituent is bound to a carbon atom of the ring;

is selected from the group consisting of cyclopropyl, cyclobutyl, cyclopentyl, cyclohexyl, phenyl, furyl, thienyl, pyridyl, thiazolyl, benzothiazolyl and benzo[d][1,3]dioxolyl;

wherein the phenyl, furyl, thienyl, pyridyl, thiazolyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl, —C(O)NR$^C$R$^D$ and NR$^C$R$^D$; wherein R$^C$ and R$^D$ are each independently selected from the group consisting of hydrogen, $C_{1-2}$alkyl, hydroxy substituted $C_{1-2}$alkyl and carboxy substituted $C_{1-2}$alkyl; provided that each substituent is bound to a carbon atom of the ring;

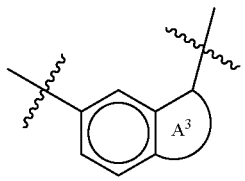

is selected from the group consisting of
(a)

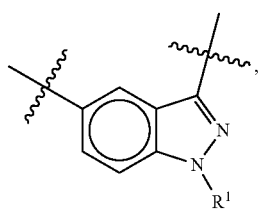

wherein $R^1$ is selected from the group consisting of hydrogen, $C_{1-4}$alkyl, hydroxy substituted $C_{1-4}$alkyl, —C(O)—($C_{1-4}$ alkyl), —($C_{1-2}$alkyl)-C(O)OH, —($C_{1-2}$alkyl)-C(O)—O—($C_{1-4}$alkyl), —($C_{1-2}$alkyl)-O—($C_{1-2}$alkyl)-C(O)OH, —($C_{1-2}$alkyl)-C(O)—NR$^E$R$^F$, —SO$_2$-(fluorinated $C_{1-2}$alkyl), $C_{3-6}$cycloalkyl and benzyl;

wherein the benzyl is optionally substituted with one substituent selected from the group consisting of —C(O)OH, —C(O)O—($C_{1-4}$alkyl) and —C(O)—NR$^E$R$^F$;

and wherein R$^E$ and R$^F$ are each independently selected from the group consisting of hydrogen and $C_{1-2}$alkyl;

and (b)

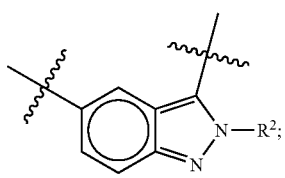

wherein $R^2$ is selected from the group consisting of $C_{3-6}$cycloalkyl and $C_{1-4}$alkyl;

a is an integer from 0 to 1;
b is an integer from 0 to 1; c is an integer from 0 to 1;
X is selected from the group consisting of CH and N;
provided that when one or both of b or c is 0, then X is CH;
such that

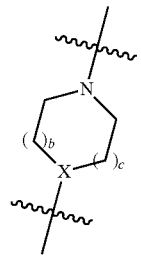

is selected from the group consisting of piperazin-1,4-diyl, piperidin-1,4-diyl, pyrroldin-1,3-diyl and azetidin-1,3-diyl;

$R^3$ is selected from the group consisting of $C_{1-4}$alkyl, halogenated $C_{1-4}$alkyl, —C(O)-(fluorinated $C_{1-2}$alkyl), —C(O)-(hydroxy substituted $C_{1-4}$alkyl), —C(O)—($C_{1-2}$ alkyl)-C(O)OH, —C(O)—($C_{1-2}$alkyl)-C(O)O—($C_{1-4}$alkyl), —C(O)—($C_{1-4}$alkyl)-C(O)—NR$^G$R$^H$, —C(O)O—($C_{1-4}$alkyl), —C(O)O—($C_{3-6}$cycloalkyl), —C(O)—NR$^G$R$^H$, —SO$_2$—($C_{1-4}$alkyl), —SO$_2$-(halogenated $C_{1-4}$alkyl), —SO$_2$—($C_{1-2}$alkyl)-C(O)OH, —SO$_2$—($C_{1-2}$alkyl)-C(O)O—($C_{1-4}$alkyl), —SO$_2$—NR$^G$R$^H$, —SO$_2$—($C_{1-2}$alkyl)-C(O)—NR$^G$R$^H$, phenyl, pyridyl (provided that the pyridyl is bound through a carbon atom) and -L$^1$-R$^4$;

wherein phenyl or pyridyl is optionally substituted with one or more (preferably one to two) substituents independently selected from the group consisting of halogen, $C_{1-4}$alkyl, halogenated $C_{1-2}$alkyl, $C_{1-4}$alkoxy, —($C_{1-2}$alkyl)-C(O)OH, —($C_{1-2}$alkyl)-C(O)O—($C_{1-4}$ alkyl), —($C_{1-2}$alkyl)-C(O)—NR$^J$R$^K$, —O—($C_{1-2}$ alkyl)-C(O)OH, —O—($C_{1-2}$alkyl)-C(O)O—($C_{1-4}$ alkyl), —O—($C_{1-2}$alkyl)-C(O)—NR$^J$R$^K$, —C(O)OH, —C(O)O—($C_{1-4}$alkyl) and —C(O)—NR$^J$R$^K$;

wherein R$^G$ and R$^H$ are each independently selected from the group consisting of hydrogen and C$_{1-4}$alkyl; and wherein R$^J$ and R$^K$ are each independently selected from the group consisting of hydrogen and C$_{1-2}$alkyl;

L$^1$ is selected from the group consisting of —CH$_2$—, —CH$_2$CH$_2$—, —CH(CH$_3$)—, —C(O)—, —C(O)—CH$_2$—, —C(O)O—, —C(O)O—CH$_2$—, —C(O)—NH—, —C(O)—NH—CH$_2$— and —SO$_2$—;

R$^4$ is selected from the group consisting of C$_{3-6}$cycloalkyl, phenyl, furanyl, thienyl, pyridyl, pyrazolyl, triazolyl, and tetrazolyl;

wherein the phenyl, furanyl, thienyl, pyridyl, pyrazolyl and triazolyl is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, —C(O)OH, —C(O)O—(C$_{1-4}$alkyl), —C(O)—NR$^L$R$^M$ and —SO$_2$—NR$^L$R$^M$; wherein R$^L$ and R$^M$ are each independently selected from the group consisting of hydrogen and C$_{1-2}$alkyl;

or a stereoisomer, tautomer or pharmaceutically acceptable salt thereof.

2. A compound as in claim 1, wherein

R$^0$ is selected from the group consisting of hydrogen and hydroxy;

is selected from the group consisting of cyclopropyl, cyclopentyl, cyclohexyl, phenyl, furyl, thienyl, pyridyl and thiazolyl;

wherein the phenyl, furyl, thienyl, pyridyl or thiazolyl is optionally substituted with one to three substituents independently selected from the group consisting of halogen, hydroxy, C$_{1-2}$alkyl, C$_{1-2}$alkoxy, fluorinated C$_{1-2}$alkyl, fluorinated C$_{1-2}$alkoxy, —C(O)OH, —C(O)O—C$_{1-4}$alkyl, —C(O)—NR$^A$R$^B$ and —NR$^A$R$^B$ wherein R$^A$ and R$^B$ are each independently selected from the group consisting of hydrogen, C$_{1-2}$alkyl, hydroxy substituted C$_{1-2}$alkyl and carboxy substituted C$_{1-2}$alkyl; provided that each substituent is bound to a carbon atom of the ring;

is selected from the group consisting of cyclopropyl, cyclopentyl, cyclohexyl, phenyl, furyl, thienyl, pyridyl and thiazolyl;

wherein the phenyl, furyl, thienyl, pyridyl or thiazolyl is optionally substituted with one to three substituents independently selected from the group consisting of halogen, hydroxy, C$_{1-2}$alkyl, C$_{1-2}$alkoxy, fluorinated C$_{1-2}$alkyl, fluorinated C$_{1-2}$alkoxy, —C(O)OH, —C(O)O—C$_{1-4}$alkyl, —C(O)—NR$^A$R$^B$ and —NR$^A$R$^B$ wherein R$^A$ and R$^B$ are each independently selected from the group consisting of hydrogen, C$_{1-2}$alkyl, hydroxy substituted C$_{1-2}$alkyl and carboxy substituted C$_{1-2}$alkyl; provided that each substituent is bound to a carbon atom of the ring;

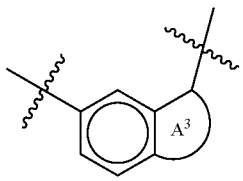

is selected from the group consisting of (a)

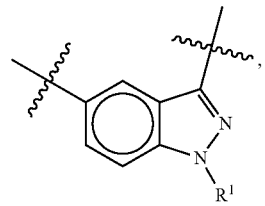

wherein R$^1$ is selected from the group consisting of hydrogen, C$_{1-4}$alkyl, hydroxy substituted C$_{1-4}$alkyl, —C(O)—(C$_{1-4}$ alkyl), —(C$_{1-2}$alkyl)-C(O)OH, —(C$_{1-2}$alkyl)-C(O)—O—(C$_{1-4}$alkyl), —(C$_{1-2}$alkyl)-O—(C$_{1-2}$alkyl)-C(O)OH, —(C$_{1-2}$alkyl)-C(O)—NR$^E$R$^F$, —SO$_2$-(fluorinated C$_{1-2}$alkyl) and benzyl;

wherein the benzyl is optionally substituted with one substituent selected from the group consisting of —C(O)OH, —C(O)O—(C$_{1-4}$alkyl) and —C(O)—NR$^E$R$^F$;

and wherein R$^E$ and R$^F$ are each independently selected from the group consisting of hydrogen and C$_{1-2}$alkyl; and (b)

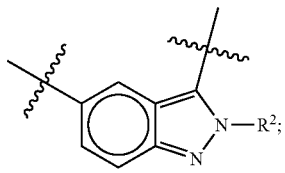

wherein R$^2$ is selected from the group consisting of C$_{3-6}$cycloalkyl and C$_{1-2}$alkyl;

a is an integer from 0 to 1;
b is an integer from 0 to 1; c is 1;
X is selected from the group consisting of CH and N; provided that when b 0, then X is C;
such that

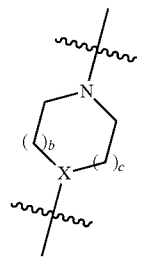

is selected from the group consisting of piperazin-1,4-diyl, piperidin-1,4-diyl and pyrroldin-1,3-diyl;

R³ is selected from the group consisting of C₁₋₄alkyl, halogenated C₁₋₂alkyl, —C(O)-(fluorinated C₁₋₂alkyl), —C(O)-(hydroxy substituted C₁₋₄alkyl), —C(O)—(C₁₋₂ alkyl)-C(O)OH, —C(O)—(C₁₋₂alkyl)-C(O)O—(C₁₋₄alkyl), —C(O)—(C₁₋₄alkyl)-C(O)—NR$^G$R$^H$, —C(O)O—(C₁₋₄alkyl), —C(O)—NR$^G$R$^H$, —SO₂—(C₁₋₄alkyl), —SO₂-(halogenated C₁₋₄alkyl), —SO₂—(C₁₋₂alkyl)-C(O)OH, —SO₂—(C₁₋₂alkyl)-C(O)O—(C₁₋₄alkyl), —SO₂—NR$^G$R$^H$, —SO₂—(C₁₋₂alkyl)-C(O)—NR$^G$R$^H$, phenyl and -L¹-R⁴;

wherein phenyl is optionally substituted with one to two substituents independently selected from the group consisting of halogen, C₁₋₂alkyl, halogenated C₁₋₂alkyl, C₁₋₂alkoxy, —(C₁₋₂alkyl)-C(O)OH, —(C₁₋₂alkyl)-C(O)O—(C₁₋₄alkyl), —(C₁₋₂alkyl)-C(O)—NR$^J$R$^K$, —O—(C₁₋₂alkyl)-C(O)OH, —O—(C₁₋₂alkyl)-C(O)O—(C₁₋₄alkyl), —O—(C₁₋₂alkyl)-C(O)—NR$^J$R$^K$, —C(O)OH, —C(O)O—(C₁₋₄alkyl) and —C(O)—NR$^J$R$^K$;

wherein R$^G$ and R$^H$ are each independently selected from the group consisting of hydrogen and C₁₋₄alkyl; and wherein R$^J$ and R$^K$ are each independently selected from the group consisting of hydrogen and C₁₋₂alkyl;

L¹ is selected from the group consisting of —CH₂—, —CH₂CH₂—, —CH(CH₃)—, —C(O)—, —C(O)O—, —C(O)—NH—, —C(O)—NH—CH₂— and —SO₂—;

R⁴ is selected from the group consisting of C₃₋₆cycloalkyl, phenyl, furanyl, thienyl, pyridyl, triazolyl, and tetrazolyl;

wherein the phenyl, furanyl, thienyl, pyridyl, pyrazolyl and triazolyl is optionally substituted with one to two substituents independently selected from the group consisting of halogen, hydroxy, C₁₋₂alkyl, fluorinated C₁₋₄alkyl, C₁₋₄alkoxy, fluorinated C₁₋₅alkoxy, —C(O)OH, —C(O)O—(C₁₋₄alkyl), —C(O)—NR$^L$R$^M$ and —SO₂—NR$^L$R$^M$; wherein R$^L$ and R$^M$ are each independently selected from the group consisting of hydrogen and C₁₋₂alkyl;

or a stereoisomer, tautomer or pharmaceutically acceptable salt thereof.

3. A compound as in claim 2, wherein

R⁰ is selected from the group consisting of hydrogen and hydroxy;

is phenyl; wherein the phenyl is substituted with a substituent selected from the group consisting of halogen, C₁₋₂alkyl and C₁₋₂alkoxy;

is selected from the group consisting of cyclopropyl, cyclopentyl, cyclohexyl, phenyl, pyridyl and thiazolyl;
wherein the phenyl, pyridyl or thiazolyl is optionally substituted with one to two substituents independently selected from the group consisting of halogen, C₁₋₂alkyl, C₁₋₂alkoxy, fluorinated C₁₋₂alkyl, fluorinated C₁₋₂alkoxy, —C(O)OH and —C(O)—NR$^A$R$^B$; wherein R$^A$ and R$^B$ are each independently selected from the group consisting of hydrogen, hydroxy substituted C₁₋₂alkyl and carboxy substituted C₁₋₂alkyl; provided that each substituent is bound to a carbon atom of the ring;

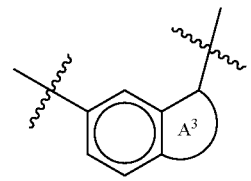

is selected from the group consisting of
(a)

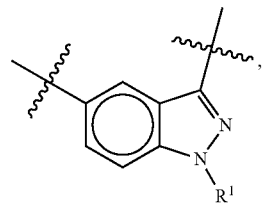

wherein R¹ is selected from the group consisting of hydrogen, C₁₋₄alkyl, hydroxy substituted C₁₋₄alkyl, —C(O)—(C₁₋₂ alkyl), —(C₁₋₂alkyl)-C(O)OH, —(C₁₋₂alkyl)-C(O)O—(C₁₋₂alkyl), —(C₁₋₂alkyl)-O—(C₁₋₂alkyl)-C(O)OH), —(C₁₋₂alkyl)-C(O)—NH₂, —SO₂-(fluorinated C₁₋₂alkyl) and benzyl;
wherein the benzyl is optionally substituted with one substituent selected from the group consisting of —C(O)OH, —C(O)O—(C₁₋₂alkyl) and —C(O)—NH₂;
and (b)

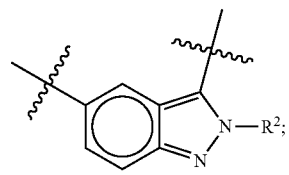

wherein R² is C₃₋₆cycloalkyl;
a is an integer from 0 to 1;
b is an integer from 0 to 1; c is 1;
X is selected from the group consisting of CH and N; provided that when b 0, then X is C;
such that

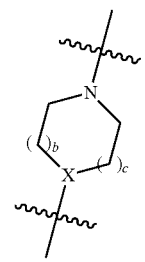

is selected from the group consisting of piperazin-1,4-diyl, piperidin-1,4-diyl and pyrroldin-1,3-diyl;

$R^3$ is selected from the group consisting of —C(O)-(fluorinated $C_{1-2}$alkyl), —C(O)-(hydroxy substituted $C_{1-2}$alkyl), —C(O)—($C_{1-2}$alkyl)-C(O)OH, —C(O)—($C_{1-2}$alkyl)-C(O)O—($C_{1-2}$alkyl), —C(O)—($C_{1-2}$alkyl)-C(O)—$NR^GR^H$, —C(O)O—($C_{1-4}$alkyl), —C(O)—$NR^GR^H$, —SO$_2$—($C_{1-4}$alkyl), —SO$_2$-(fluorinated $C_{1-2}$alkyl), —SO$_2$—($C_{1-2}$alkyl-C(O)OH, —SO$_2$—C(O)O—($C_{1-2}$alkyl), —SO$_2$—$NR^GR^H$, —SO$_2$—($C_{1-2}$alkyl)-C(O)—$NR^GR^H$, phenyl and -$L^1$-$R^4$;

wherein the phenyl is optionally substituted with a substituent selected from the group consisting of —C(O)OH, —($C_{1-2}$alkyl)-C(O)OH, —O—($C_{1-2}$alkyl)-C(O)OH, —C(O)—NH$_2$, —($C_{1-2}$alkyl)-C(O)—NH$_2$ and —O—($C_{1-2}$alkyl)-C(O)—NH$_2$;

wherein $R^G$ and $R^H$ are each independently selected from the group consisting of hydrogen and $C_{1-2}$alkyl;

wherein $L^1$ is selected from the group consisting of —CH$_2$—, —CH(CH$_3$)—, —C(O)—, —C(O)O—, —C(O)O—CH$_2$—, —C(O)—NH—, —C(O)—NH—CH$_2$— and —SO$_2$—;

$R^4$ is selected from the group consisting of cyclopropyl, cyclopentyl, phenyl, furan-2-yl, thien-2-yl, pyrid-2-yl, pyrid-3-yl, 1,2,3-triazol-4-yl, 1,3,4-triazol-2-yl, and 1,2,3,4-tetrazol-5-yl;

wherein the phenyl, furan-2-yl, thien-2-yl, pyrid-2-yl or pyrid-3-yl is optionally substituted with one to two substituents independently selected from the group consisting of halogen, hydroxy, $C_{1-2}$alkyl, fluorinated $C_{1-2}$alkyl, $C_{1-2}$alkoxy, fluorinated $C_{1-2}$alkoxy, —C(O)OH, —C(O)O—($C_{1-2}$alkyl), —C(O)—$NR^LR^M$ and —SO$_2$—$NR^LR^M$; and wherein $R^L$ and $R^M$ are each independently selected from the group consisting of hydrogen and $C_{1-2}$alkyl;

or a stereoisomer, tautomer or pharmaceutically acceptable salt thereof.

4. A compound as in claim 3, wherein $R^0$ is selected from the group consisting of hydrogen and hydroxy;

is selected from the group consisting of 4-chlorophenyl, 4-fluorophenyl, 4-methylphenyl and 4-methoxyphenyl;

is selected from the group consisting of cyclopropyl, cyclopentyl, cyclohexyl, phenyl, 2-chlorophenyl, 3-chlorophenyl, 4-chlorophenyl, 4-fluorophenyl, 3,4-dichlorophenyl, 4-methylphenyl, 4-methoxyphenyl, 3-trifluoromethylphenyl, 4-trifluoromethylphenyl, 4-trifluoromethoxyphenyl, 4-carboxyphenyl, S*-4-carboxyphenyl, R*-4-carboxyphenyl, 4-aminocarbonylphenyl, 4-(2-hydroxyethyl-aminocarbonyl)-phenyl, 4-(2-carboxyethyl-aminocarbonyl)-phenyl, 6-carboxy-pyrid-3-yl, 6-(aminocarbonyl)-pyrid-3-yl, thiazol-2-yl and 5-methyl-thiazol-2-yl;

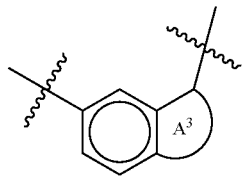

is selected from the group consisting of (a

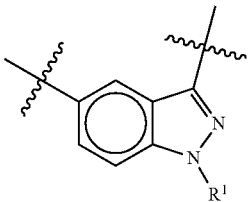

wherein $R^1$ is selected from the group consisting of hydrogen, methyl, 2-hydroxy-ethyl, 2-hydroxy-1-methyl-ethyl-, 2-hydoxy-1,1-dimethyl-ethyl-, 2-(carboxy-methoxy)-ethyl, —C(O)—CH$_3$, —CH$_2$—C(O)OH, —CH$_2$—C(O)O—CH$_2$CH$_3$, —CH$_2$—C(O)—NH$_2$, —SO$_2$—CF$_3$, cyclopropyl, 2-(methoxycarbonyl)-benzyl, 2-carboxy-benzyl and 2-(aminocarbonyl)-benzyl;

and (b)

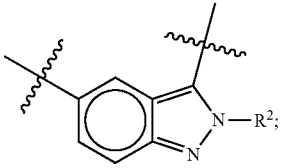

wherein $R^2$ is cyclopropyl;

a is an integer from 0 to 1;

b is an integer from 0 to 1; c is 1;

X is selected from the group consisting of CH and N;

provided that when b 0, then X is C;

such that

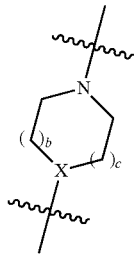

is selected from the group consisting of piperazin-1,4-diyl, piperidin-1,4-diyl and pyrroldin-1,3-diyl;

$R^3$ is selected from the group consisting of —C(O)—CH$_2$OH, —C(O)—CH$_2$CH$_2$OH, —C(O)—CH$_2$CF$_3$, —C(O)—CH$_2$—C(O)OH, —C(O)—CH$_2$CH$_2$—C(O)OH, —C(O)—CH$_2$—C(O)O—CH$_3$, —C(O)—CH$_2$—C(O)—NH$_2$, —C(O)—CH$_2$CH$_2$—C(O)—NH$_2$, —C(O)O—C(CH$_3$)$_3$, —C(O)O—CH$_2$CH$_3$, —C(O)—

NH—CH₂CH₃, —SO₂—CH₃, —SO₂—CH(CH₂)₂, —SO₂—CF₃, —SO₂—CH₂CF₃, —SO₂—CH₂—C(O)OH, —SO₂—CH₂—C(O)OH, —SO₂—CH₂—C(O)O—CH₂CH₃, —SO₂—NH₂, —SO₂—CH₃, —SO₂—C(O)—NH₂, —SO₂—CH₂CH₂—C(O)—NH₂, 3-carboxyphenyl, 4-carboxyphenyl, 3-(carboxymethyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;

wherein

L¹ is selected from the group consisting of —CH₂—, —CH(CH₃)—, —C(O)—, —C(O)O—, —C(O)O—CH₂—, —C(O)—NH—, —C(O)—NH—CH₂— and —SO₂—;

R⁴ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxycarbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 4-carboxy-pyrid-2-yl, 5-carboxy-pyrid-2-yl, 6-carboxy-pyrid-2-yl, 5-carboxy-pyrid-3-yl, 6-carboxy-pyrid-3-yl, 1,2,3-triazol-4-yl, 1,3,4-triazol-2-yl, and 1,2,3,4-tetrazol-5-yl;

or a stereoisomer, tautomer or pharmaceutically acceptable salt thereof.

5. A compound as in claim 4, wherein
R⁰ is hydrogen;

is selected from the group consisting of 4-chlorophenyl, 4-fluorophenyl, 4-methylphenyl and 4-methoxyphenyl;

is selected from the group consisting of cyclopropyl, phenyl, 2-chlorophenyl, 3-chlorophenyl, 4-chlorophenyl, 4-fluorophenyl, 3,4-dichlorophenyl, 4-methylphenyl, 4-methoxyphenyl, 3-trifluoromethylphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl;

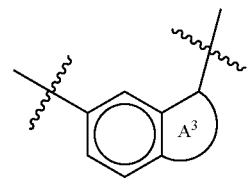

is selected from the group consisting of
(a)

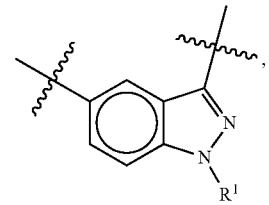

wherein R¹ is selected from the group consisting of hydrogen, methyl, 2-hydroxy-ethyl, 2-hydroxy-1-methyl-ethyl-, 2-(carboxy-methoxy)-ethyl, —C(O)—CH₃, —CH₂—C(O)O—CH₂CH₃, —CH₂—C(O)—NH₂ and cyclopropyl;
and (b)

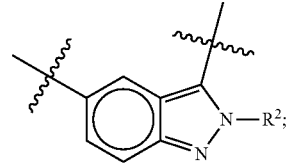

wherein R² is cyclopropyl;
a is an integer from 0 to 1;
b is an integer from 0 to 1; c is 1;
X is selected from the group consisting of CH and N;
provided that when b 0, then X is C;
such that

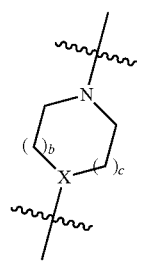

is selected from the group consisting of piperazin-1,4-diyl, piperidin-1,4-diyl and pyrrolidin-1,3-diyl;

R³ is selected from the group consisting of —C(O)—CH₂OH, —C(O)—CH₂CH₂OH, —C(O)—CH₂CF₃, —C(O)—CH₂—C(O)OH, —C(O)—CH₂—C(O)O—CH₃, —C(O)—CH₂—C(O)—NH₂, —C(O)—CH₂CH₂—C(O)—NH₂, —C(O)O—C(CH₃)₃, —C(O)O—CH₂CH₃, —C(O)—NH—CH₂CH₃, —SO₂—CH₃, —SO₂—CH(CH₂)₂, —SO₂—CF₃, —SO₂—CH₂CF₃, —SO₂—CH₂—C(O)OH, —SO₂—CH₂—C(O)O—CH₂CH₃, —SO₂—CH₂CH₂—C(O)—NH₂, 3-carboxyphenyl, 4-carboxyphenyl, 3-(carboxy-methyl)-phenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;
wherein
L¹ is selected from the group consisting of —CH₂—, —C(O)—, —C(O)O—, —C(O)O—CH₂—, —C(O)—NH— and —SO₂—;
R⁴ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-chloro-phenyl, 3-(methylaminocarbonyl)-4-methoxy-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl, 6-carboxy-pyrid-3-yl and 1,2,3-triazol-4-yl;
or a stereoisomer, tautomer or pharmaceutically acceptable salt thereof.

6. A compound as in claim 4, wherein
R⁰ is hydrogen;

is selected from the group consisting of 4-chlorophenyl, 4-fluorophenyl, 4-methylphenyl and 4-methoxyphenyl;

is selected from the group consisting of cyclopropyl, phenyl, 2-chlorophenyl, 3-chlorophenyl, 4-chlorophenyl, 4-fluorophenyl, 3,4-dichlorophenyl, 4-methylphenyl, 4-methoxyphenyl, 4-trifluoromethylphenyl, 4-trifluoromethoxyphenyl, 4-carboxyphenyl, S*-4-carboxyphenyl, 4-aminocarbonyl-phenyl, 4-(2-hydroxyethyl-aminocarbonyl)-phenyl, 6-(aminocarbonyl)-pyrid-3-yl, thiazol-2-yl and 5-methyl-thiazol-2-yl;

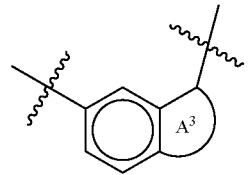

is selected from the group consisting of
(a)

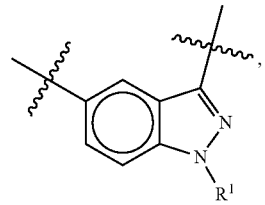

wherein R¹ is selected from the group consisting of hydrogen, methyl, 2-hydroxy-ethyl, —C(O)—CH₃, —CH₂—C(O)—NH₂ and cyclopropyl;
and (b)

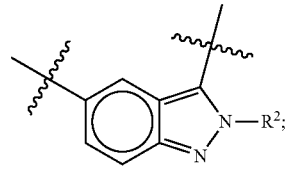

wherein R² is cyclopropyl;
a is an integer from 0 to 1;
b is 1; c is 1;
X is selected from the group consisting of CH and N;
such that

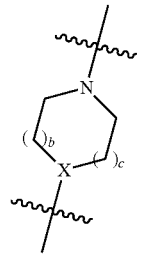

is selected from the group consisting of piperazin-1,4-diyl and piperidin-1,4-diyl;
R³ is selected from the group consisting of —C(O)—CH₂OH, —C(O)—CH₂CH₂OH, —C(O)O—CH₂CH₂—C(O)—NH₂, —C(O)—CH₂CF₃, —C(O)O—CH₂CH₃, —SO₂—CF₃, —SO₂—CH₂CF₃, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;
wherein
L¹ is selected from the group consisting of —CH₂—, —C(O)—, —C(O)O— and —SO₂—;

R⁴ is selected from the group consisting of cyclopropyl, cyclopentyl, phenyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 4-(trifluoromethyl)-phenyl, 3-(methoxycarbonyl)-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl, 6-carboxy-pyrid-3-yl and 1,2,3-triazol-4-yl;

or a stereoisomer, tautomer or pharmaceutically acceptable salt thereof.

7. A compound as in claim 4, wherein

R⁰ is hydrogen;

is selected from the group consisting of 4-chlorophenyl, 4-methylphenyl and 4-methoxyphenyl;

is selected from the group consisting of cyclopropyl, phenyl, 2-chlorophenyl, 4-chlorophenyl, 4-fluorophenyl, 3,4-dichlorophenyl, 4-methylphenyl, 4-methoxyphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl;

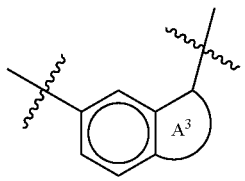

is selected from the group consisting of
(a)

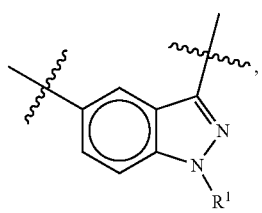

wherein R¹ is selected from the group consisting of hydrogen, methyl, 2-hydroxy-ethyl, —C(O)—CH₃ and cyclopropyl;

and (b)

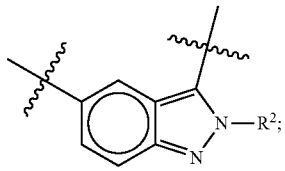

wherein R² is cyclopropyl;
a is an integer from 0 to 1;
b is 1; cis 1;
X is selected from the group consisting of CH and N;
such that

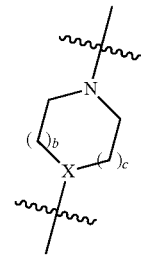

is selected from the group consisting of piperazin-1,4-diyl and piperidin-1,4-diyl;

R³ is selected from the group consisting of —C(O)—CH₂OH, —C(O)—CH₂CH₂OH, —C(O)O—CH₂CH₂—C(O)—NH₂, —C(O)O—CH₂CH₃, —SO₂—CF₃, —SO₂—CH₂CF₃, 4-(carboxy-methyl)-phenyl, 3-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;

wherein
L¹ is selected from the group consisting of —CH₂—, —C(O)—, —C(O)O— and —SO₂—;

R⁴ is selected from the group consisting of cyclopropyl, cyclopentyl, 2-hydroxyphenyl, 3-hydroxyphenyl, 4-hydroxyphenyl, 2-methoxyphenyl, 3-methoxyphenyl, 4-methoxyphenyl, 2-(trifluoromethyl)-phenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-methoxy-phenyl, 3-(aminocarbonyl)-4-chloro-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 4-(aminocarbonyl)-thien-2-yl, 5-(aminocarbonyl)-thien-2-yl, 6-(aminocarbonyl)-pyrid-3-yl, 6-(methylaminocarbonyl)-pyrid-3-yl, 6-carboxy-pyrid-2-yl, 5-carboxy-pyrid-3-yl, 6-carboxy-pyrid-3-yl and 1,2,3-triazol-4-yl;

or a stereoisomer, tautomer or pharmaceutically acceptable salt thereof.

8. A compound as in claim 4, wherein
R⁰ is hydrogen;

is selected from the group consisting of 4-chlorophenyl and 4-methoxyphenyl;

is selected from the group consisting of 4-chlorophenyl, 3,4-dichlorophenyl, 4-methoxyphenyl, 4-aminocarbonyl-phenyl, 6-(aminocarbonyl)-pyrid-3-yl, thiazol-2-yl and 5-methyl-thiazol-2-yl;

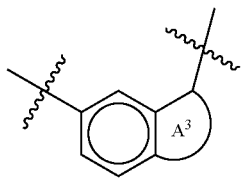

is selected from the group consisting of
(a)

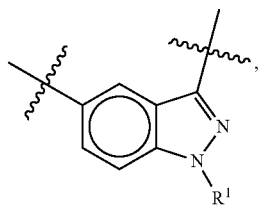

wherein R¹ is selected from the group consisting of hydrogen, methyl, 2-hydroxy-ethyl, —C(O)—CH₃ and cyclopropyl;
and (b)

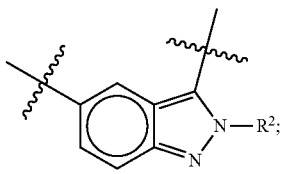

wherein R² is cyclopropyl;
a is an integer from 0 to 1;
b is 1; cis 1;
X is selected from the group consisting of CH and N;
such that

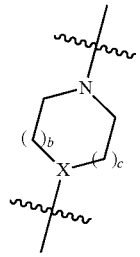

is selected from the group consisting of piperazin-1,4-diyl and piperidin-1,4-diyl;
R³ is selected from the group consisting of —SO₂—CF₃ and -L¹-R⁴;
wherein
L¹ is selected from the group consisting of —CH₂—, —C(O)—, and —SO₂—;
R⁴ is selected from the group consisting of 2-hydroxyphenyl, 3-hydroxyphenyl, 4-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-chloro-4-carboxy-phenyl, 3-chloro-4-(methylaminocarbonyl)-phenyl, 3-methoxy-4-(aminocarbonyl)-phenyl 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 5-carboxy-furan-2-yl, 5-(aminocarbonyl)-furan-2-yl, 4-(aminocarbonyl)-thien-2-yl, 6-(methylaminocarbonyl)-pyrid-3-yl, 6-carboxy-pyrid-2-yl, 6-carboxy-pyrid-3-yl and 6-(aminocarbonyl)-pyrid-3-yl;
or a stereoisomer, tautomer or pharmaceutically acceptable salt thereof.

9. A compound as in claim 4, wherein
R⁰ is selected from the group consisting of hydrogen and hydroxy;

is selected from the group consisting of 4-chlorophenyl, 4-fluorophenyl, 4-methylphenyl and 4-methoxyphenyl;

is selected from the group consisting of cyclopropyl, cyclopentyl, cyclohexyl, phenyl, 2-chlorophenyl, 3-chlorophenyl, 4-chlorophenyl, 4-fluorophenyl, 3,4-dichlorophenyl, 4-methylphenyl, 4-methoxyphenyl, 3-trifluoromethylphenyl, 4-trifluoromethylphenyl, 4-trifluoromethoxyphenyl, 4-carboxyphenyl, S*-4-carboxyphenyl, R*-4-carboxyphenyl, 4-aminocarbonyl-phenyl, 4-(2-hydroxyethyl-aminocarbonyl)-phenyl, 4-(2-carboxyethyl-aminocarbonyl)-phenyl, 6-carboxy-pyrid-3-yl, 6-(aminocarbonyl)-pyrid-3-yl, thiazol-2-yl and 5-methyl-thiazol-2-yl;

is

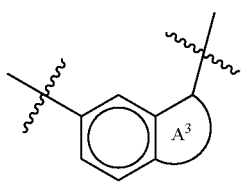

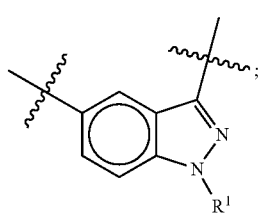

wherein R¹ is selected from the group consisting of hydrogen, methyl, 2-hydroxy-ethyl, 2-hydroxy-1-methyl-ethyl-, 2-hydoxy-1,1-dimethyl-ethyl-, 2-(carboxy-methoxy)-ethyl, —C(O)—CH₃, —CH₂—C(O)OH, —CH₂—C(O)O—CH₂CH₃, —CH₂—C(O)—NH₂, —SO₂—CF₃, cyclopropyl, 2-(methoxycarbonyl)-benzyl, 2-carboxy-benzyl and 2-(aminocarbonyl)-benzyl;
a is an integer from 0 to 1;
b is an integer from 0 to 1; c is 1;
X is selected from the group consisting of CH and N; provided that when b 0, then X is C;
such that

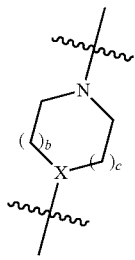

is selected from the group consisting of piperazin-1,4-diyl, piperidin-1,4-diyl and pyrroldin-1,3-diyl;
R³ is selected from the group consisting of —C(O)—CH₂OH, —C(O)—CH₂CH₂OH, —C(O)—CH₂CF₃, —C(O)—CH₂—C(O)OH, —C(O)—CH₂CH₂—C(O)OH, —C(O)—CH₂—C(O)O—CH₃, —C(O)—CH₂—C(O)—NH₂, —C(O)—CH₂CH₂—C(O)—NH₂, —C(O)O—C(CH₃)₃, —C(O)O—CH₂CH₃, —C(O)—NH—CH₂CH₃, —SO₂—CH₃, —SO₂—CF₃, —SO₂—CH₂CF₃, —SO₂—CH₂—C(O)OH, —SO₂—CH₂CH₂—C(O)OH, —SO₂—CH₂—C(O)O—CH₂CH₃, —SO₂—NH₂, —SO₂—CH₂—C(O)—NH₂, —SO₂—CH₂CH₂—C(O)—NH₂, 3-carboxyphenyl, 4-carboxyphenyl, 3-(carboxy-methyl)-phenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 3-(aminocarbonyl-methyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;

wherein
L¹ is selected from the group consisting of —CH₂—, —CH(CH₃)—, —C(O)—, —C(O)O—, —C(O)O—CH₂—, —C(O)—NH—, —C(O)—NH—CH₂— and —SO₂—;
R⁴ is selected from the group consisting of cyclopropyl, cyclopentyl, phenyl, 4-hydroxyphenyl, 2-methoxyphenyl, 3-methoxyphenyl, 4-methoxyphenyl, 2-(trifluoromethyl)-phenyl, 3-(trifluoromethyl)-phenyl, 4-(trifluoromethyl)-phenyl, 2-(methoxycarbonyl)-phenyl, 3-(methoxycarbonyl)-phenyl, 4-(methoxycarbonyl)-phenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-(aminosulfonyl)-phenyl, 4-(aminosulfonyl)-phenyl, 5-carboxy-furan-2-yl, 5-(aminocarbonyl)-furan-2-yl, 5-(methoxy-carbonyl)-furan-2-yl, 4-carboxy-thien-2-yl, 5-carboxy-thien-2-yl, 4-(aminocarbonyl)-thien-2-yl, 4-carboxy-pyrid-2-yl, 1,2,3-triazol-4-yl, 1,3,4-triazol-2-yl, and 1,2,3,4-tetrazol-5-yl;
or a stereoisomer, tautomer or pharmaceutically acceptable salt thereof.
10. A compound as in claim 9, wherein
R⁰ is hydrogen;

is selected from the group consisting of 4-chlorophenyl, 4-fluorophenyl, 4-methylphenyl and 4-methoxyphenyl;

is selected from the group consisting of cyclopropyl, phenyl, 2-chlorophenyl, 3-chlorophenyl, 4-chlorophenyl, 4-fluorophenyl, 3,4-dichlorophenyl, 4-methylphenyl, 4-methoxyphenyl, 4-trifluoromethylphenyl, 4-trifluoromethoxyphenyl, 4-carboxyphenyl, S*-4-carboxyphenyl, 4-aminocarbonylphenyl, 4-(2-hydroxyethyl-aminocarbonyl)-phenyl, 6-(aminocarbonyl)-pyrid-3-yl, thiazol-2-yl and 5-methyl-thiazol-2-yl;

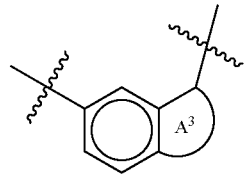

is

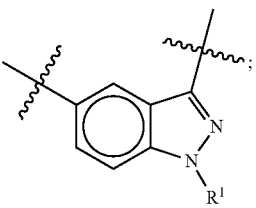

wherein R¹ is selected from the group consisting of hydrogen, methyl, 2-hydroxy-ethyl, —C(O)—CH₃, —CH₂—C(O)—NH₂ and cyclopropyl;

a is an integer from 0 to 1;
b is 1; c is 1;
X is selected from the group consisting of CH and N;
such that

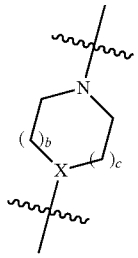

is selected from the group consisting of piperazin-1,4-diyl and piperidin-1,4-diyl;

R³ is selected from the group consisting of —C(O)—CH₂OH, —C(O)—CH₂CH₂OH, —C(O)O—CH₂CH₂—C(O)—NH₂, —C(O)—CH₂CF₃, —C(O)O—CH₂CH₃, —SO₂—CF₃, —SO₂—CH₂CF₃, 3-(aminocarbonyl)-phenyl, 4-(aminocarbonyl)-phenyl, and -L¹-R⁴;

wherein

L¹ is selected from the group consisting of —CH₂—, —C(O)—, —C(O)O— and —SO₂—;

R⁴ is selected from the group consisting of cyclopropyl, cyclopentyl, phenyl, 4-hydroxyphenyl 2-(trifluoromethyl)-phenyl, 4-(trifluoromethyl)-phenyl, 3-(methoxycarbonyl)-phenyl, 3-carboxy-phenyl, 4-carboxy-phenyl, 3-(aminocarbonyl)-phenyl, 4-(aminocarbonyl)-phenyl 4-(aminosulfonyl)-phenyl, 5-carboxy-furan-2-yl, 5-(methoxy-carbonyl)-furan-2-yl, 4-carboxy-thien-2-yl, 5-carboxy-thien-2-yl, 4-(aminocarbonyl)-thien-2-yl, 5-(aminocarbonyl)-thien-2-yl and 1,2,3-triazol-4-yl;

or a stereoisomer, tautomer or pharmaceutically acceptable salt thereof.

11. A compound as in claim 9, wherein

R⁰ is hydrogen;

is selected from the group consisting of 4-chlorophenyl and 4-methoxyphenyl;

is selected from the group consisting of 4-chlorophenyl, 3,4-dichlorophenyl, 4-methoxyphenyl, 4-aminocarbonylphenyl, 6-(aminocarbonyl)-pyrid-3-yl, thiazol-2-yl and 5-methyl-thiazol-2-yl;

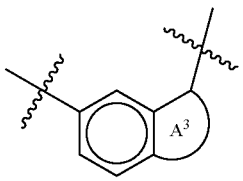

is

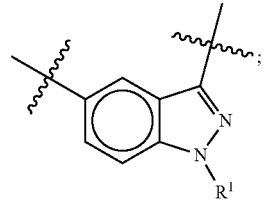

wherein R¹ is selected from the group consisting of hydrogen, methyl, 2-hydroxy-ethyl, —C(O)—CH₃ and cyclopropyl;

a is an integer from 0 to 1;
b is 1; c is 1;
X is selected from the group consisting of CH and N;
such that

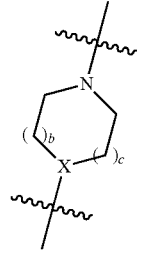

is selected from the group consisting of piperazin-1,4-diyl and piperidin-1,4-diyl;

R³ is selected from the group consisting of —SO₂—CF₃ and -L¹-R⁴;

wherein

L¹ is selected from the group consisting of —CH₂—, —C(O)—, and —SO₂—;

R⁴ is selected from the group consisting of 4-hydroxyphenyl, 3-carboxy-phenyl, 3-(aminocarbonyl)-phenyl and 4-(aminocarbonyl)-phenyl;

or a stereoisomer, tautomer or pharmaceutically acceptable salt thereof.

12. A compound as in claim 4, wherein

R⁰ is hydrogen;

is 4-chlorophenyl;

is selected from the group consisting of 4-chlorophenyl, 4-carboxyphenyl and 4-aminocarbonylphenyl;

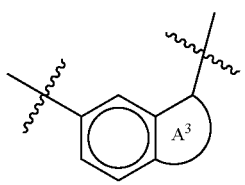

is

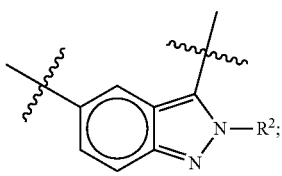

wherein R² is cyclopropyl;
a is 0;
b is 1; cis 1;
X is CH;
such that

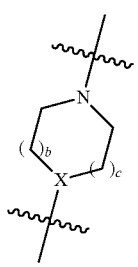

is piperidin-1,4-diyl;
R³ is selected from the group consisting of —C(O)—CH₂OH, —C(O)—CH₂CH₂OH, —C(O)—CH₂—C(O)OH, —C(O)—CH₂CH₂—C(O)OH, —C(O)—CH₂—C(O)—NH₂, —C(O)—CH₂CH₂—C(O)—NH₂, —SO₂—CF₃, —SO₂—CH₂—C(O)OH, —SO₂—CH₂CH₂—C(O)OH, —SO₂—CH₂—C(O)—NH₂, —SO₂—CH₂CH₂—C(O)—NH₂, 3-carboxyphenyl, 4-carboxyphenyl, 3-(carboxy-methoxy)-phenyl, 4-(carboxy-methyl)-phenyl, 4-(carboxy-methoxy)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;
wherein
L¹ is selected from the group consisting of —CH₂—, —C(O)— and —SO₂—;
R⁴ is selected from the group consisting of 2-hydroxyphenyl, 3-hydroxyphenyl, 2-methoxyphenyl, 3-methoxyphenyl, 4-methoxyphenyl, 2-carboxy-phenyl, 3-carboxy-phenyl, 4-carboxy-phenyl, 2-(aminocarbonyl)-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-(aminocarbonyl)-furan-2-yl, 5-carboxy-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl;
or a stereoisomer, tautomer or pharmaceutically acceptable salt thereof.

13. A compound as in claim 12, wherein
R⁰ is hydrogen;

is 4-chlorophenyl;

is selected from the group consisting of 4-chlorophenyl and 4-aminocarbonylphenyl;

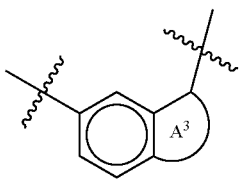

is

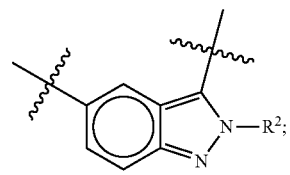

wherein R² is cyclopropyl;
a is 0;
b is 1; cis 1;
X is CH;
such that

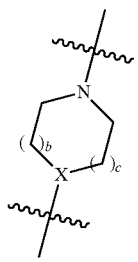

is piperidin-1,4-diyl;
R³ is selected from the group consisting of —SO₂—CF₃, 3-carboxyphenyl, 4-(carboxy-methyl)-phenyl, 3-(aminocarbonyl)-phenyl, 4-(aminocarbonyl)-phenyl, 4-(aminocarbonyl-methyl)-phenyl, 3-(aminocarbonyl-methoxy)-phenyl, 4-(aminocarbonyl-methoxy)-phenyl and -L¹-R⁴;

wherein

L¹ is selected from the group consisting of —CH₂—, —C(O)— and —SO₂—;

R⁴ is selected from the group consisting of 2-hydroxyphenyl, 3-hydroxyphenyl, 2-methoxyphenyl, 3-methoxyphenyl, 4-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(aminocarbonyl)-phenyl, 3-chloro-4-(methylaminocarbonyl)-phenyl, 3-methoxy-4-(aminocarbonyl)-phenyl, 3-methoxy-4-(methylaminocarbonyl)-phenyl, 3-methoxy-4-carboxy-phenyl, 3-(aminocarbonyl)-4-chloro-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 3-carboxy-4-methoxy-phenyl, 5-carboxy-furan-2-yl, 5-(aminocarbonyl)-furan-2-yl, 4-carboxy-thien-2-yl, 5-carboxy-thien-2-yl, 4-(aminocarbonyl)-thien-2-yl, 6-(aminocarbonyl)-pyrid-3-yl, 6-(methylaminocarbonyl)-pyrid-3-yl, 5-carboxy-pyrid-2-yl, 6-carboxy-pyrid-2-yl, 5-carboxy-pyrid-3-yl and 6-carboxy-pyrid-3-yl;

or a stereoisomer, tautomer or pharmaceutically acceptable salt thereof.

14. A compound as in claim 12, wherein

R⁰ is hydrogen;

is 4-chlorophenyl;

is 4-chlorophenyl;

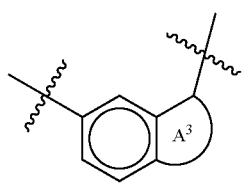

is

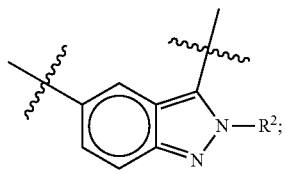

wherein R² is cyclopropyl;

a is 0;

b is 1; cis 1;

X is CH;

such that

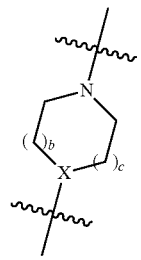

is piperidin-1,4-diyl;

R³ is selected from the group consisting of —SO₂—CF₃ and -L¹-R⁴;

wherein

L¹ is selected from the group consisting of —CH₂— and —SO₂—;

R⁴ is selected from the group consisting of 2-hydroxyphenyl, 3-hydroxyphenyl, 2-methoxyphenyl, 3-methoxyphenyl, 3-carboxy-phenyl, 4-carboxy-phenyl, 3-(aminocarbonyl)-phenyl, 4-(aminocarbonyl)-phenyl, 3-fluoro-4-carboxy-phenyl, 3-fluoro-4-(aminocarbonyl)-phenyl, 3-fluoro-4-(methylaminocarbonyl)-phenyl, 3-chloro-4-carboxy-phenyl, 3-chloro-4-(methylaminocarbonyl)-phenyl, 3-methoxy-4-(aminocarbonyl)-phenyl, 3-methoxy-4-carboxy-phenyl, 3-(aminocarbonyl)-4-methoxy-phenyl, 3-(methylaminocarbonyl)-4-methoxy-phenyl, 3-(methylaminocarbonyl)-4-chloro-phenyl, 3-(aminocarbonyl)-4-fluoro-phenyl, 3-carboxy-4-fluoro-phenyl, 3-carboxy-4-chloro-phenyl, 5-carboxy-furan-2-yl, 5-(aminocarbonyl)-furan-2-yl, 4-(aminocarbonyl)-thien-2-yl, 6-(aminocarbonyl)-pyrid-3-yl, 6-(methylaminocarbonyl)-pyrid-3-yl, 6-carboxy-pyrid-2-yl and 6-carboxy-pyrid-3-yl;

or a stereoisomer, tautomer or pharmaceutically acceptable salt thereof.

15. A compound as in claim 12, wherein

R⁰ is hydrogen;

is 4-chlorophenyl;

is 4-chlorophenyl;

is

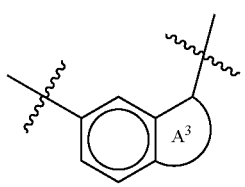

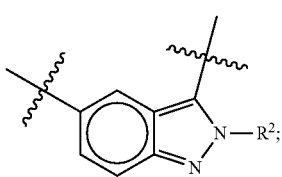

wherein R² is cyclopropyl;
a is 0;
b is 1; c is 1; X is CH; such that

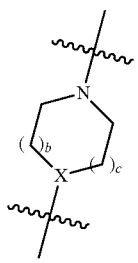

is piperidin-1,4-diyl;
R³ is -L¹-R⁴;
  wherein L¹ is selected from the group consisting of
    —CH₂— and —SO₂—;
  R⁴ is selected from the group consisting of 2-methoxy-phenyl, 4-(aminocarbonyl)-phenyl, 3-fluoro-4-carboxy-phenyl, 3-chloro-4-carboxy-phenyl, 3-chloro-4-(methylamninocarbonyl)-phenyl, 3-methoxy-4-carboxy-phenyl, 3-carboxy-4-fluoro-phenyl, 3-carboxy-4-chloro-phenyl, 3-(aminocarbonyl)-4-methoxy-phenyl, 3-(methylaminocabronyl)-4-methoxy-phenyl, 5-carboxy-furan-2-yl, 5-(aminocarbonyl)-furan-2-yl and 4-(aminocarbonyl)-thien-2-yl;
or a stereoisomer, tautomer or pharmaceutically acceptable salt thereof.

16. A compound as in claim 4, wherein
R⁰ is hydrogen;

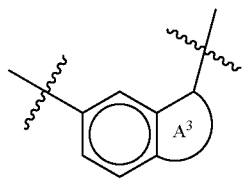

is 4-chlorophenyl;

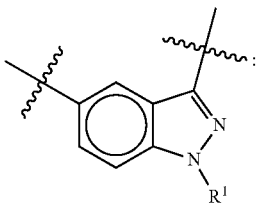

is selected from the group consisting of 4-chlorophenyl and S*-(3-carboxyphenyl);

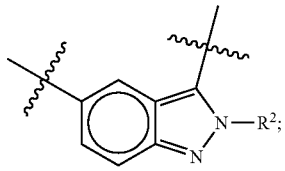

is selected from the group consisting of
(a)

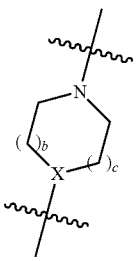

wherein R¹ is selected from the group consisting of hydrogen and cyclopropyl;
and (b)

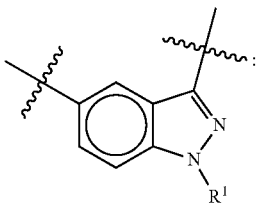

wherein R² is cyclopropyl;
a is 0;
b is 1; cis 1;
X is selected from the group consisting of CH and N; such that

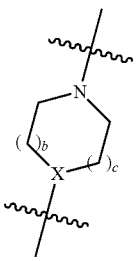

is selected from the group consisting of piperazin-1,4-diyl and piperidin-1,4-diyl;
R³ is selected from the group consisting of trifluoromethylsulfonyl, 3-(aminocarbonyl)-phenyl, 3-hydroxyphenyl-sulfonyl-, 3-methoxy-4-carboxyphenyl-sulfonyl-, 3-(aminocarbonyl)-4-chloro-phenyl-sulfonyl-, 3-(aminocarbonyl)-benzyl, 3-carboxy-benzyl and 4-(aminocarbonyl)-thien-2-yl-methyl-;
or a stereoisomer, tautomer or pharmaceutically acceptable salt thereof.

17. A compound as in claim 9, wherein R⁰ is hydrogen;

is 4-chlorophenyl;

is selected from the group consisting of 4-chlorophenyl and S*-(3-carboxyphenyl);

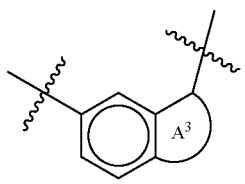

is (a)

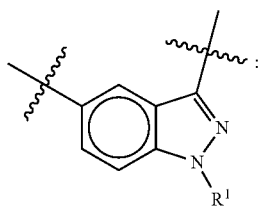

wherein R¹ is selected from the group consisting of hydrogen and cyclopropyl;
a is 0;
b is 1; c is 1;
X is selected from the group consisting of CH and N; such that

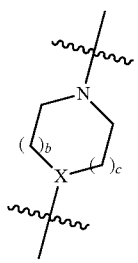

is selected from the group consisting of piperazin-1,4-diyl and piperidin-1,4-diyl;
R³ is selected from the group consisting of trifluoromethylsulfonyl 3-(aminocarbonyl)-benzyl and 3-carboxybenzyl;
or a stereoisomer, tautomer or pharmaceutically acceptable salt thereof.

18. A compound as in claim 12, wherein R⁰ is hydrogen;

is 4-chlorophenyl;

is 4-chlorophenyl;

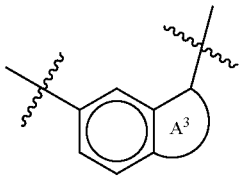

is

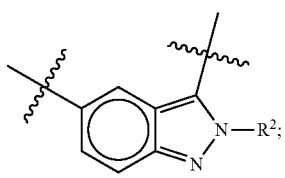

wherein R² is cyclopropyl;
a is 0;
b is 1; c is 1; X is CH; such that

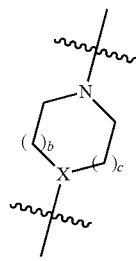

is piperidin-1,4-diyl;
R³ is selected from the group consisting of 3-(aminocarbonyl)-phenyl, 3-hydroxyphenyl-sulfonyl-, 3-methoxy-4-carboxyphenyl-sulfonyl-, 3-(aminocarbonyl)-4-chloro-phenyl-sulfonyl- and 4-(aminocarbonyl)-thien-2-yl-methyl-;
or a stereoisomer, tautomer or pharmaceutically acceptable salt thereof.

19. A pharmaceutical composition comprising a pharmaceutically acceptable carrier and a compound of claim 1.

20. A pharmaceutical composition made by mixing a compound of claim 1 and a pharmaceutically acceptable carrier.

21. A process for making a pharmaceutical composition comprising mixing a compound of claim 1 and a pharmaceutically acceptable carrier.

* * * * *